US008883783B2

(12) United States Patent
Bhagwat et al.

(10) Patent No.: US 8,883,783 B2
(45) Date of Patent: *Nov. 11, 2014

(54) SOLID FORMS COMPRISING N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL}UREA, COMPOSITIONS THEREOF, AND USES THEREWITH

(75) Inventors: Shripad S. Bhagwat, San Diego, CA (US); Wei Lai, West Lafayette, IN (US); Stephan D. Parent, West Lafayette, IN (US); Melanie J. Roe, Lafayette, IN (US); Alan Schwartz, Carlsbad, CA (US); Valeriya N. Smolenskaya, Lafayette, IN (US)

(73) Assignee: Ambit Biosciences Corporation, San Diego, CA (US)

( * ) Notice: Subject to any disclaimer, the term of this patent is extended or adjusted under 35 U.S.C. 154(b) by 1034 days.

This patent is subject to a terminal disclaimer.

(21) Appl. No.: 12/233,906

(22) Filed: Sep. 19, 2008

(65) Prior Publication Data

US 2009/0131426 A1 May 21, 2009

Related U.S. Application Data

(60) Provisional application No. 60/994,635, filed on Sep. 19, 2007.

(51) Int. Cl.
*A61K 31/535* (2006.01)
*C07D 415/00* (2006.01)
*C07D 417/00* (2006.01)
*C07D 513/04* (2006.01)

(52) U.S. Cl.
CPC .................................. *C07D 513/04* (2013.01)
USPC ........................ 514/233.2; 544/133

(58) Field of Classification Search
USPC ............... 514/366, 233.2; 548/151; 544/133
See application file for complete search history.

(56) References Cited

U.S. PATENT DOCUMENTS

| 3,210,370 | A | 10/1965 | Ursprung |
| 3,267,112 | A | 8/1966 | Iwai et al. |
| 3,507,854 | A | 4/1970 | Sumagawa et al. |
| 4,354,970 | A | 10/1982 | Fleischer et al. |
| 4,464,384 | A | 8/1984 | Murase et al. |
| 4,497,817 | A | 2/1985 | Murase et al. |
| 4,880,824 | A | 11/1989 | Press et al. |
| 5,236,952 | A | 8/1993 | Bernauer et al. |
| 5,466,706 | A | 11/1995 | George et al. |
| 5,623,073 | A | 4/1997 | Anisimova et al. |
| 5,639,756 | A | 6/1997 | Anisimova et al. |
| 5,919,799 | A | 7/1999 | Tasaka et al. |
| 6,696,441 | B1 | 2/2004 | Cottam et al. |
| 7,153,873 | B2 | 12/2006 | Gerlach et al. |
| 7,351,481 | B2 | 4/2008 | Lee et al. |
| 7,601,846 | B2 | 10/2009 | Cottam et al. |
| 2004/0067991 | A1 | 4/2004 | Greig et al. |
| 2004/0127719 | A1 | 7/2004 | Yang et al. |
| 2005/0075271 | A1* | 4/2005 | Linsell et al. ............ 514/1 |
| 2005/0165024 | A1 | 7/2005 | Milanov et al. |
| 2007/0232604 | A1 | 10/2007 | Bhagwat et al. |
| 2009/0123418 | A1 | 5/2009 | James et al. |
| 2009/0131426 | A1 | 5/2009 | Bhagwat et al. |

FOREIGN PATENT DOCUMENTS

| EP | 0 082 712 | | 6/1983 |
| EP | 524 055 | A1 | 1/1993 |
| EP | 0 607 076 | | 7/1994 |
| EP | 1 029 854 | A1 | 1/2000 |
| EP | 1 047 418 | B1 | 7/2005 |
| FR | 2699920 | | 7/1994 |
| FR | 2700546 | | 7/1994 |
| FR | 2722501 | | 1/1996 |
| FR | 2759698 | | 8/1998 |
| GB | 2 056 982 | | 3/1981 |
| JP | 56138196 | A | 10/1981 |
| JP | 57040492 | | 3/1982 |
| JP | 57149288 | | 9/1982 |
| JP | 05107705 | A | 4/1993 |
| JP | 7291976 | A | 11/1995 |
| JP | 11-106340 | | 4/1999 |
| JP | 2001048786 | | 2/2001 |
| JP | 2001192386 | A | 7/2001 |
| WO | WO 98/06724 | | 2/1998 |
| WO | WO 98/25469 | | 6/1998 |
| WO | WO 99/40094 | | 8/1999 |
| WO | WO 00/78726 | | 12/2000 |
| WO | WO 01/27119 | | 4/2001 |
| WO | WO 03/031587 | | 4/2003 |
| WO | WO 2004/048368 | | 6/2004 |
| WO | WO 2004/058758 | | 7/2004 |
| WO | WO2007109120 | A2 * | 9/2007 |

OTHER PUBLICATIONS

Berge et. al., Journal of Pharmaceutical Sciences, 1977, American Pharmaceutical Association, vol. 66, issue 1, pp. 1-19.*
Abignente, et al., "Research on Heterocyclic Compounds. XXIII., Phenyl Derivatives of Fused Imidazole Systems," *Journal of Heterocyclic Chemistry*, 1989, 26(6): 1875-80.
Abignente, et al., "Research on heterocyclic compounds-V," *Il Farmaco Edizione Scientifica*, 1976, 31(fasc. 12): 880-887.
Achen, et al., "Targeting lymphangiogenesis to prevent tumor metastasis," *British Journal of Cancer*, 2006, 94:1355-1360.
Anisimova, et al., "Synthesis and Properties of Alcohols of the Imidazo[1,2-a] Benzimidazole Series," *Khimiya Geterotsiklicheskikh Soedinenii*, 1976, 1: 126-134.
Anisimova, et al., "Synthethis of Haloketones in the Imidazo[1,2-a] Benzimidazole Series," *Khimiya Geterotsiklicheskikh Soedinenii*, 1986, 3: 339-45.

(Continued)

*Primary Examiner* — Sarah Pihonak
(74) *Attorney, Agent, or Firm* — Jones Day

(57) ABSTRACT

Solid forms comprising N-(5-tert-butyl-isoxazol-3-yl)-N'-{4-[7-(2-morpholin-4-yl-ethoxy)imidazo[2,1-b][1,3]benzothiazol-2-yl]phenyl}urea, compositions comprising the solid forms, methods of making the solid forms and methods of their use for the treatment of various diseases and/or disorders are disclosed.

23 Claims, 68 Drawing Sheets

(56) References Cited

OTHER PUBLICATIONS

Figure 1:
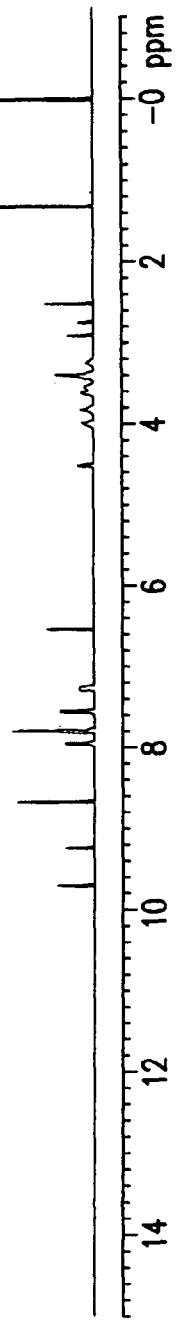

Anisimova, et al., "Nitration of 2,9-disubstituted imidazole [1,2-a] benzimidazoles," *Khimiya Geterotsiklicheskikh Soedinenii*, 1975, 2:258-62.

Balaban, T.S. and Balaban A.T., "Product Class 1: Pyrylium Salts," *Science of Synthesis*, 2003, 14:11-200.

Bergers, et al., "Benefits of targeting both pericytes and endothelial cells in the tumor vasculature with kinase inhibitors," (2003), *Journal of Clinical Investigation*, 2003, 111(9):1287-1295.

Blume-Jensen, et al., "Oncogenic kinase signalling," *Nature*, 2001, 411:355-365.

Buu-Hoi, et al., "La réaction des ω-bromocétophénones avec l'amino-2 thiazole et les amino-2 benzothiazoles," *Bulletin de la Societe Chimique de France*, 1966, 4:1277-9.

Carlomagno, et al., "BAY 43-9006 Inhibition of Oncogenic RET Mutants," *Journal of the National Cancer Institute*, 2006, 98(5):326-334.

Chernovyants, et al., Spectrochemical characteristics of symmetrical monomethinecyanines based on pyrrolo- and imidazo [1,2-a] benzimidazole, *Urainskii Khimicheskii Zhurnal*, 1992, 58(3):257-61.

Cools, et al., "A Tyrosine Kinase Created by Fusion of the PDGFRA and FIP1L1 Genes as a Therapeutic Target of Imatinib in Idiopathic Hypereosinophilic Syndrome," *The New England Journal of Medicine*, 2003, 348(13):1201-1214.

Curtin, et al., "Somatic Activation of KIT in Distinct Subtypes of Melanoma," *Journal of Clinical Oncology*, 2006, 24(26):4340-4346.

De Giorgi, et al., "Imatinib and gastrointestinal stromal tumors: Where do we go from here?," *Mol. Cancer Ther.*, 2005, 4(3):495-501.

Duensing, et al., "Biology of Gastrointestinal Stromal Tumors: KIT Mutations and Beyond," *Cancer Investigation*, 2004, 22(1):106-116.

Fabian, et al., "A small molecule-kinase interation map for clinical kinase inhibitors," *Nature Biotechnology*, 2005, 23(3):329-336.

Gazit, et al., "Tyrphostins. 5. Potent Inhibitors of Platelet-Drived Growth Factor Receptor Tyrosine Kinase: Structure-Activity Relationships in Quinoxalines, Quinolines, and Indole Tyrphostins," *J. Med. Chem*, 1996, 39:2170-2177.

Gilliland, et al., "The roles of FLT3 in hematopoiesis and leukemia," *Blood*, 2002, 100:1532-1542.

Glickman, et al., "A Comparison of ALPHAScreen, TR-FRET, and TRF as Assay Methods for FXR Nuclear Receptors," *Journal of Biomolecular Screening*, 2002, 7(1):3-10.

Grin, et al., "Investigations in the imidazole series LXXVIII. Reaction of 2-aminobenzothiazoles with α-Halo Ketones," *Khimiya Geterotsiklicheskii Soedinenii*, 1972, 9:1271-1274.

Haran-Ghera, et al., "Increased Circulating Colony-Stimulating Factor-1 (CSF-1) in SJL/J Mice with Radiation-Induced Acute Myeloid Leukemia (AML) is Associated With Autocrine Regulation of AML Cells by CSF-1," *Blood*, 1997, 89(7):2537-2545.

Heinrich, "Targeting FLT3 Kinase in Acute Myelogenous Leukemia: Progress, Perils, and Prospects," *Mini-Reviews in Medicinal Chemistry*, 2004, 4:255-271.

Heinrich, et al., "PDGFRA Activating Mutations in Gastrointestinal Stromal Tumors," *Science*, 2003, 299:708-710.

Kacinski, "CSF-1 and Its Receptor in Breast Carcinomas and Neoplasms of the Female Reproductive Tract," *Molecular Reproduction and Development*, 1997, 46:71-74.

Kandeel, "Synthetic Studies on Some New Diaryl Sulphides and Diaryl Sulphones with Fused Heterocyclic Rings," *Bulletin of the Polish Academy of Science, Chemistry*, 2002, 50(3):309-322.

Kandeel, "Synthesis and Biological Activity of Some New Diaryl Sulphones Containing Fused Thiazolo Pyrimidines," *Journal of Chinese Chemical Society*, 2001, 48(1):37-43.

Kelly, et al., "CT53518, a novel selective FLT3 antagonist for the treatment of acute myelogenous leukemia (AML)," *Cancer Cell*, 2002, 1:421-432.

Kiyoi, et al., "Clinical Significance of FLT3 in Leukemia," *International Journal of Hematology*, 2005, 82(2):85-92.

Kohn, et al., "Cell Cycle Control and Cancer Chemotherapy," *Journal of Cellular Biochemistry*, 1994, 54:440-452.

Krasovskii, et al., "Synthesis and properties of naphtha[1,2-d]thiazolo[3,2-a]imidazole derivatives," *Farmatsevtichnii Zhurnal (Kiev)*, 1977, (5):83-4.

Krause, et al., "Tyrosine Kinases as Targets for Cancer Therapy," *New England Journal of Medicine*, 2005, 353(2):172-187.

Kumabe, et al., "Amplification of α-platelet-derived growth factor receptor gene lacking an exon coding for a portion of the extracellular region in a primary brain tumor of glial origin," *Oncogene*, 1992, 7:627-633.

Levis, et al., "A FLT3-targeted tyrosine kinase inhibitor is cytotoxic to leukemia cells in vitro and in vivo," *Blood*, 2002, 99:3885-3891.

Levis, et al., "FLT3 Tyrosine Kinase Inhibitors," *International Journal of Hematology*, 2005, 82(2): 100-107.

Magnusson, et al., "Activity of STI571 in chronic myelomonocytic leukemia with a platelet-derived growth factor B receptor fusion oncogene," *Blood*, 2002, 100(3):1088-1091.

Malempati, et al., "Outcome after relapse among children with standard risk (SR) ALL treated on CCG-1952," *Blood* (*ASH Annual Meeting Abstracts*), 2004, 104(11):Abstract 520.

Mase, et al., "Nucleophilic Subsitution Reactions on Sulfur by n-Butyllithium 2," *Heterocycles*, 1987, 26(12):3159-3164.

Mase, et al., "Imidazo[2,1-b]benzothiazoles. 2. New Immunosuppressive Agents," *J. Med. Chem.*, 1986, 29:386-394.

Ostman, et al., "Involvement of Platelet-Derived Growth Factor in Disease: Development of Specific Antagonists," *Advances in Cancer Research*, 2001, 80:1-38.

Palagiano et al., "Synthesis and SAR Study of Imidazo[2,1-b]Benzothiazole Acids and Some Related Compounds with Anti-Inflammatory and Analgesic Activities," *Il Farmaco*, 1996, 51(7):483-491.

Patra, et al., "Derivatives of Imidazole," *J. Indian Chem. Soc.*, 1974, LI:1031-1034.

Paz, et al., "Development of Angiogenesis Inhibitors to Vascular Endothelial Growth Factor Receptor 2. Current Status and Future Perspective," *Fronters in Bioscience*, 2005, 10:1415-1439.

Pentimalli, "Substitution and addition reactions of benzo-substituted 2-phenylimidazo [2,1-b]benzothiazoles," *Gazzetta Chimica Italiana*, 1969, 99(4), 362-72, CODEN: GCITA9; ISSN: 0016-5603. English summary at the bottom of page 1.

Pietras, et al., "Inhibition of PDGF Receptor Signaling in Tumor Stroma Enhances Antitumor Effect of Chemotherapy," *Cancer Research*, 2002, 62:5476-5484.

Pietras, et al., "PDGF receptors as cancer drug targets," *Cancer Cell*, 2003, 3:439-443.

Plowman, et al., "Receptor Tyrosine Kinases as Targets for Drug Intervention," *Drug News and Perspectives*, 1994, 7(6):334-339.

Rached, et al., "Synthése et approche pharmacologique de nouveaux hétéocycles azotés et soufrés apparaentés au Fostedil," *European Journal of Medicinal Chemistry*, 1992, 27(4):425-429.

Rolland, et al., "Increased Blood Myeloid Dendritic Cells and Dendritic Cell-Poietins in Langerhans Cell Histiocytosis," *The Journal of Immunology*, 2005, 174: 3067-3071.

Saharinen, et al., "Double target for tumor mass destruction," *The Journal of Clinical Investigation*, 2003, 111(9):1277-1280.

Sawhney, et al., "Synthesis & Antiinflammatory Activity of Some Arylimidazo[2,I-b]-thiazolyl- & Arylimidazo[2,I-*b*]benzothiazolyl-acetic Acids," *Indian Journal of Chemistry*, 1982, 21B:134-138.

Stacker, et al., "Lymphangiogenesis and Cancer Metastasis," *Nature Reviews—Cancer*, 2002, 2:573-583.

Stacker, et al., "Molecular Targeting of Lymphatics for Therapy," *Current Pharmaceutical Design*, 2004, 10(1):65-74.

Stirewalt, et al., "The role of FLT3 in haematopoietic malignancies," *Nat. Rev. Cancer*, 2003, 3:650-665.

Stone, et al., "Reversible, p16-mediated Cell Cycle Arrest as Protection from Chemotherapy," *Cancer Research*, 1996, 56:3199-3202.

Strock, et al., "CEP-701 and CEP-751 Inhibit Constitutively Activated RET Tyrosine Kinase Activity and Block Medullary Thyroid Carcinoma Cell Growth," *Cancer Research*, 2003, 63:5559-5563.

Ursprung, J., "2,2'-Methylenediimidazoles," *Chemical Abstracts*, 1965, 63:18103-18104.

(56) References Cited

OTHER PUBLICATIONS

Vousden, "Interactions of human papillomavirus transforming proteins with the products of tumor suppressor genes," *FASEB J.*, 1993, 7:872-879.
Weisberg, et al., "Inhibition of mutant FLT3 receptors in leukemia cells by the small molecule tyrosine kinase inhibitor PKC412," *Cancer Cell*, 2002, 1:433-443.
Whartenby, et al., "Inhibitor of FLT3 signaling targets DCs to ameliorate autoimmune disease," *PNAS*, 2005, 102(46):16741-16746.
Yee, et al., "SU5416 and SU5614 inhibit kinase activity of wild-type and mutant FLT3 receptor tyrosine kinase," *Blood*, 2002, 100(8):2941-2949.
Zhdanov, et al., "Synthesis of Pyrylium Salts with Three-Ring Azole Substituents," *Khimiya Geterotsiklicheskikh Soedinenii*, 1987, 3: 309-313.
International Search Report dated Apr. 17, 2009 for International Application No. PCT/US2008/010884, filed Sep. 19, 2008.
International Search Report dated Oct. 29, 2007 for International Application No. PCT/US2007/006613, filed Mar. 16, 2007.
Written Opinion of the International Searching Authority for International Application No. PCT/US2007/006613, filed Mar. 16, 2007.
Chao, et al., "Identification of N-(5-tert-Butyl-isoxazol-3-yl)-N0-{4-[7-(2-morpholin-4-yl-ethoxy)imidazo-[2,1-b][1,3]benzothiazol-2-yl]phenyl}urea Dihydrochloride (AC220), a Uniquely Potent, Selective, and Efficacious FMS-Like Tyrosine Kinase-3 (FLT3) Inhibitor," *Journal of Medicinal Chemistry*, 2009, 52: 7808-7816.

* cited by examiner

SOLID FORMS COMPRISING N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL}UREA, COMPOSITIONS THEREOF, AND USES THEREWITH

This application claims priority to U.S. Provisional Patent Application No. 60/994,635, filed Sep. 19, 2007, the content of which is incorporated by reference herein in its entirety.

1. FIELD

Provided herein are solid forms comprising N-(5-tert-butyl-isoxazol-3-yl)-N' {4-[7-(2-morpholin-4-yl-ethoxy)imidazo[2,1-b][1,3]benzothiazol-2-yl]phenyl}urea, compositions comprising the solid forms, methods of making the solid forms and methods of their use for the treatment of various diseases and/or disorders.

2. BACKGROUND

There is a need for new kinase inhibitor compounds, for example, in view of drawbacks associated with existing therapies, such as Gleevec®. Kinase inhibitor compounds are currently being explored for the treatment of diseases such as cancers.

The identification and selection of a solid form of a pharmaceutical compound is complex, given that a change in solid form may affect a variety of physical and chemical properties, which may provide benefits or drawbacks in processing, formulation, stability and bioavailability, among other important pharmaceutical characteristics. Potential pharmaceutical solids include crystalline solids and amorphous solids. Amorphous solids are characterized by a lack of long-range structural order, whereas crystalline solids are characterized by structural periodicity. The desired class of pharmaceutical solid depends upon the specific application; amorphous solids are sometimes selected on the basis of, e.g., an enhanced dissolution profile, while crystalline solids may be desirable for properties such as, e.g., physical or chemical stability (see, e.g., S. R. Vippagunta et al., *Adv. Drug. Deliv. Rev.*, (2001) 48:3-26; L. Yu, *Adv. Drug. Deliv. Rev.*, (2001) 48:27-42).

Whether crystalline or amorphous, potential solid forms of a pharmaceutical compound include single-component and multiple-component solids. Single-component solids consist essentially of the pharmaceutical compound in the absence of other compounds. Variety among single-component crystalline materials may potentially arise from the phenomenon of polymorphism, wherein multiple three-dimensional arrangements exist for a particular pharmaceutical compound (see, e.g., S. R. Byrn et al., *Solid State Chemistry of Drugs*, (1999) SSCI, West Lafayette). The importance of discovering polymorphs was underscored by the case of Ritonavir, an HIV protease inhibitor that was formulated as soft gelatin capsules. About two years after the product was launched, the unanticipated precipitation of a new, less soluble polymorph in the formulation necessitated the withdrawal of the product from the market until a more consistent formulation could be developed (see S. R. Chemburkar et al., *Org. Process Res. Dev.*, (2000) 4:413-417).

Additional diversity among the potential solid forms of a pharmaceutical compound may arise from the possibility of multiple-component solids. Crystalline solids comprising two or more ionic species are termed salts (see, e.g., *Handbook of Pharmaceutical Salts: Properties. Selection and Use*, P. H. Stahl and C. G. Wermuth, Eds., (2002), Wiley, Weinheim). Additional types of multiple-component solids that may potentially offer other property improvements for a pharmaceutical compound or salt thereof include, e.g. hydrates, solvates, co-crystals and clathrates, among others (see, e.g., S. R. Byrn et al., *Solid State Chemistry of Drugs*, (1999) SSCI, West Lafayette). Moreover, multiple-component crystal forms may potentially be susceptible to polymorphism, wherein a given multiple-component composition may exist in more than one three-dimensional crystalline arrangement. The discovery of solid forms is of great importance in the development of a safe, effective, stable and marketable pharmaceutical compound.

Provided herein are embodiments addressing the need for solid forms of the compound chemically named N-(5-tert-butyl-isoxazol-3-yl)-N'-{4-[7-(2-morpholin-4-yl-ethoxy) imidazo[2,1-b][1,3]benzothiazol-2-yl]phenyl}urea ("Compound B1"). Compound B1 was disclosed in U.S. Patent Application Publication No. 2007/0232604, which published on Oct. 4, 2007. Provided herein are embodiments in which certain novel solid forms include particular advantageous physical properties making them useful, e.g., for manufacturing, processing, formulation and/or storage, while also possessing particularly advantageous biological properties, such as bioavailability and biological activity.

3. SUMMARY

Embodiments herein provide solid forms comprising the compound chemically named N-(5-tert-butyl-isoxazol-3-yl)-N'-{4-[7-(2-morpholin-4-yl-ethoxy)imidazo[2,1-b][1,3] benzothiazol-2-yl]phenyl}urea ("Compound B1"). Alternate chemical names which may be used to describe Compound B1 include, for example:

{[5-(tert-butyl)isoxazol-3-yl]amino}-N-{4-[7-(2-morpholin-4-yl-ethoxy)(4-hydroimidazolo[2,1-b]benzothiazol-2-yl)]phenyl}carboxamide;

N-(5-tert-butyl-isoxazol-3-yl)-N'-{4-[7-(2-morpholin-4-yl-ethoxy)imidazo[2,1-b][1,3]benzothiazol-2-yl]phenyl}urea;

{[5-(tert-butyl)isoxazol-3-yl]amino}-N-{4-[7-(2-morpholin-4-yl-ethoxy)(4-hydroimidazo[2,1-b]benzothiazol-2-yl)]phenyl}carboxamide; and 1-(5-tert-Butyl-isoxazol-3-yl)-3-{4-[7-(2-morpholin-4-yl-ethoxy)-benzo[d]imidazo[2,1-b]thiazol-2-yl]-phenyl}urea.

Compound B1 can be synthesized or obtained according to any method apparent to those of skill in the art based upon the teachings herein, including the methods described in the Examples below. Compound B1 can also be prepared according to the methods described in U.S. Provisional Patent App. No. 60/743,543, filed Mar. 17, 2006, U.S. patent application Ser. No. 11/724,992, filed Mar. 16, 2007, and U.S. Patent App. Publication No. 2007/0232604, published Oct. 4, 2007, the entireties of each of which is incorporated by reference herein. In its free base form, Compound B1 has the following structure (I):

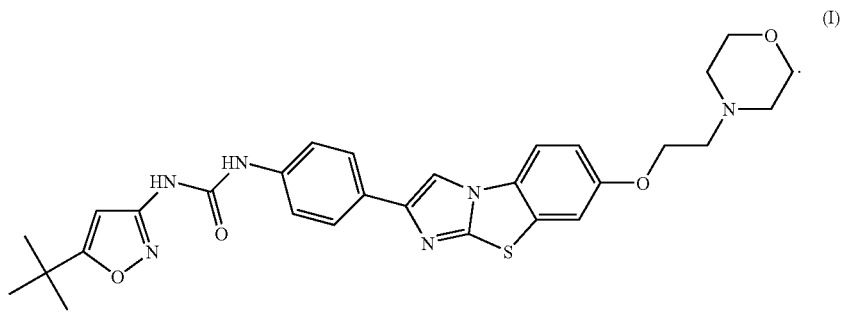 [SMILES: CC(C)(C)c1cc(NC(=O)Nc2ccc(-c3cn4c(n3)sc3cc(OCCN5CCOCC5)ccc34)cc2)no1]

In certain embodiments, the solid forms are single-component crystal forms of the free base of Compound B1. In certain embodiments, the solid forms are multiple-component crystal forms, including, but not limited to, salts, co-crystals and/or solvates, including hydrates, comprising Compound B1. In other embodiments, the solid forms are single-component amorphous forms of the free base of Compound B1. In other embodiments, the solid forms are multiple-component amorphous forms, including, but not limited to, salts of Compound B1. Without intending to be limited by any particular theory, the storage stability, compressibility, bulk density or dissolution properties of certain solid forms described herein are believed to be beneficial for manufacturing, formulation and bioavailability of Compound B1.

In particular embodiments, solid forms provided herein include solid forms comprising Compound B1, including, but not limited to, particular solid forms comprising the free base of Compound B1, as well as solid forms comprising salts of Compound B1, such as HCl salts, HBr salts, sulfate salts, mesylate salts, esylate salts, edisylate salts, besylate salts, tosylate salts, and napsylate salts. In particular embodiments, HCl salts comprising Compound B1 include mono-HCl salts and bis-HCl salts of Compound B1. In certain embodiments, solid forms provided herein include polymorphs, solvates (including hydrates) and cocrystals comprising Compound B1 and/or salts thereof. Certain embodiments herein provide methods of making, isolating and/or characterizing the solid forms provided herein.

The solid forms provided herein are useful as active pharmaceutical ingredients for the preparation of formulations for use in animals or humans. Thus, embodiments herein encompass the use of these solid forms as a final drug product. Certain embodiments provide solid forms useful in making final dosage forms with improved properties, e.g., powder flow properties, compaction properties, tableting properties, stability properties, and excipient compatibility properties, among others, that are needed for manufacturing, processing, formulation and/or storage of final drug products. Certain embodiments herein provide pharmaceutical compositions comprising a single-component crystal form, a multiple-component crystal form, a single-component amorphous form and/or a multiple-component amorphous form comprising Compound B1 and a pharmaceutically acceptable diluent, excipient or carrier. The solid forms and the final drug products provided herein are useful, for example, for the treatment, prevention or management of diseases and disorders provided herein.

Certain embodiments herein provide methods of using the solid forms provided herein or pharmaceutical compositions comprising the solid forms provided herein for the treatment, prevention or management of diseases and disorders including, but not limited to, diseases or disorders that are modulated or otherwise affected by protein kinases (PK related diseases) or one or more symptoms or causes thereof. Certain embodiments herein provide methods for the treatment, prevention or management of diseases or disorders including, but not limited to, cancers, nonmalignant proliferation diseases, atherosclerosis, restenosis following vascular angioplasty, fibroproliferative disorders, inflammatory diseases or disorders related to immune dysfunction, infectious diseases, and/or diseases or disorders that can be treated, prevented or managed by modulating the activity, binding or sub-cellular distribution of kinases, wherein such methods comprise administering to a subject, e.g., a human, in need of such treatment, prevention or management a therapeutically and prophylactically effective amount of a solid form provided herein. Such diseases or disorders are further described herein.

4. BRIEF DESCRIPTION OF THE DRAWINGS

FIG. 1 provides a representative $^1$H nuclear magnetic resonance spectroscopy (NMR) spectrum of Form A of the free base of Compound B1.

Figure 2:
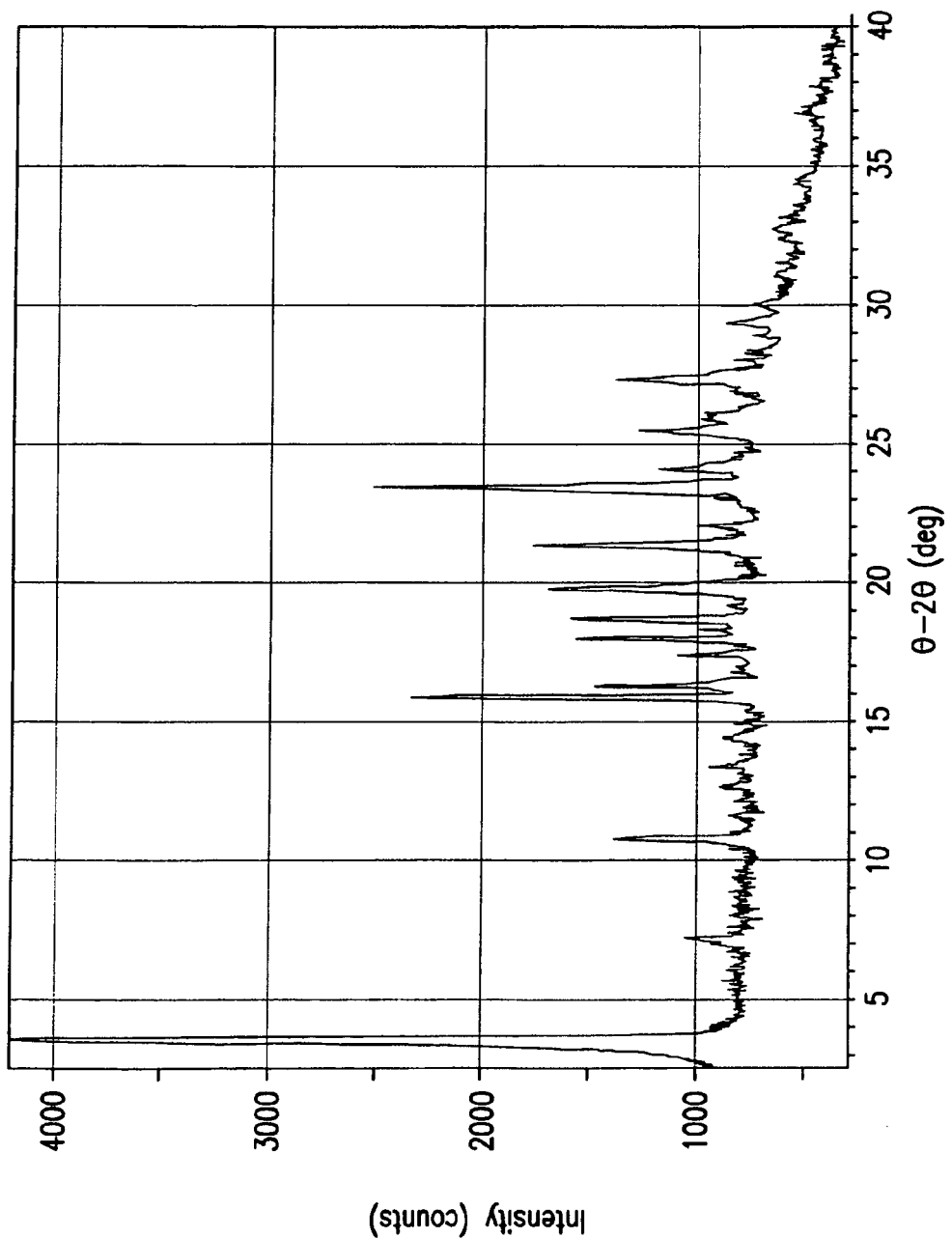

FIG. 2 provides a representative X-ray powder diffraction (XRPD) pattern of Form A of the free base of Compound B1.

Figure 3:
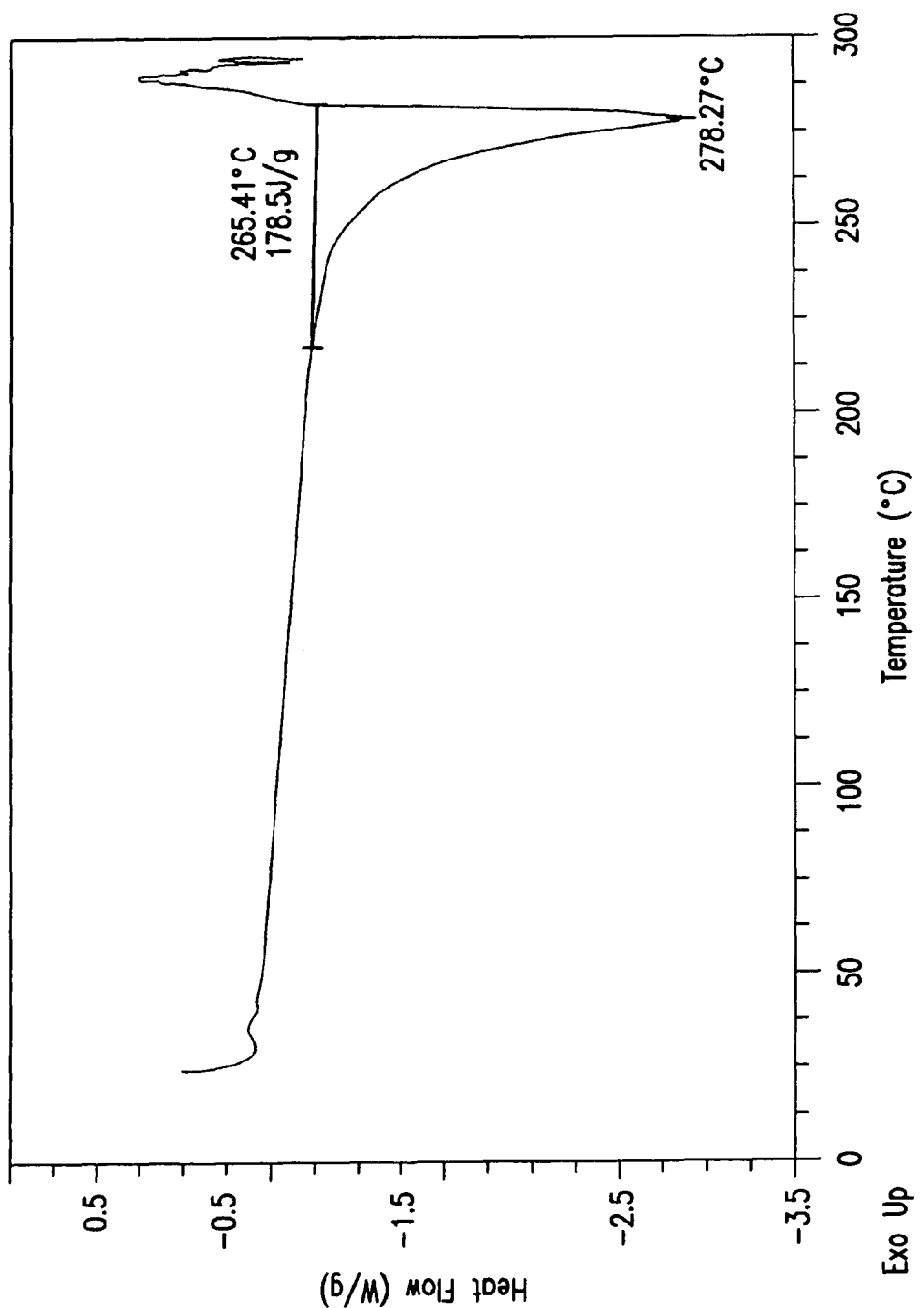

FIG. 3 provides a representative differential scanning calorimetry (DSC) thermogram of Form A of the free base of Compound B1.

Figure 4:
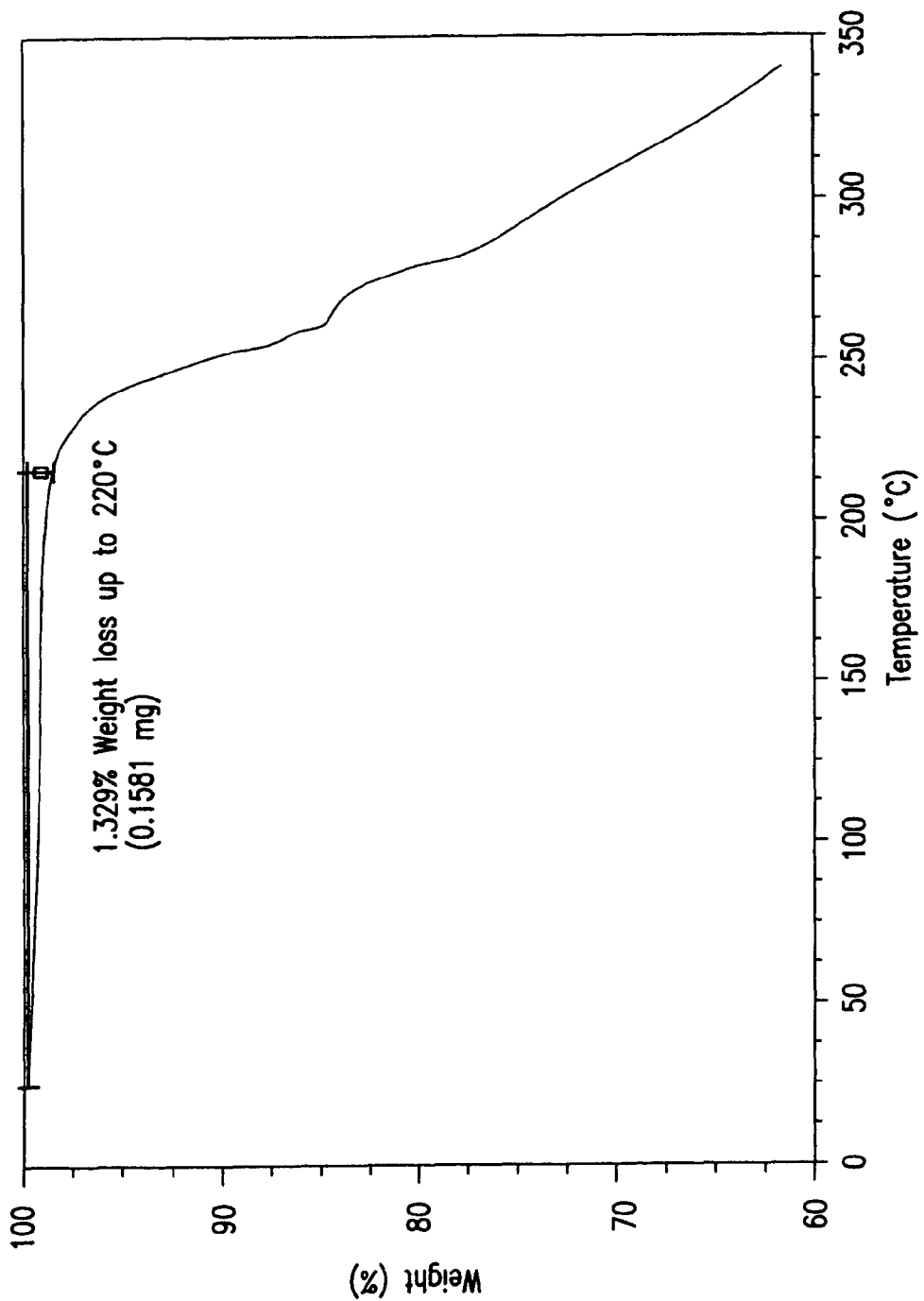

FIG. 4 provides a representative thermal gravimetric analysis (TGA) thermogram of Form A of the free base of Compound B1.

Figure 5:
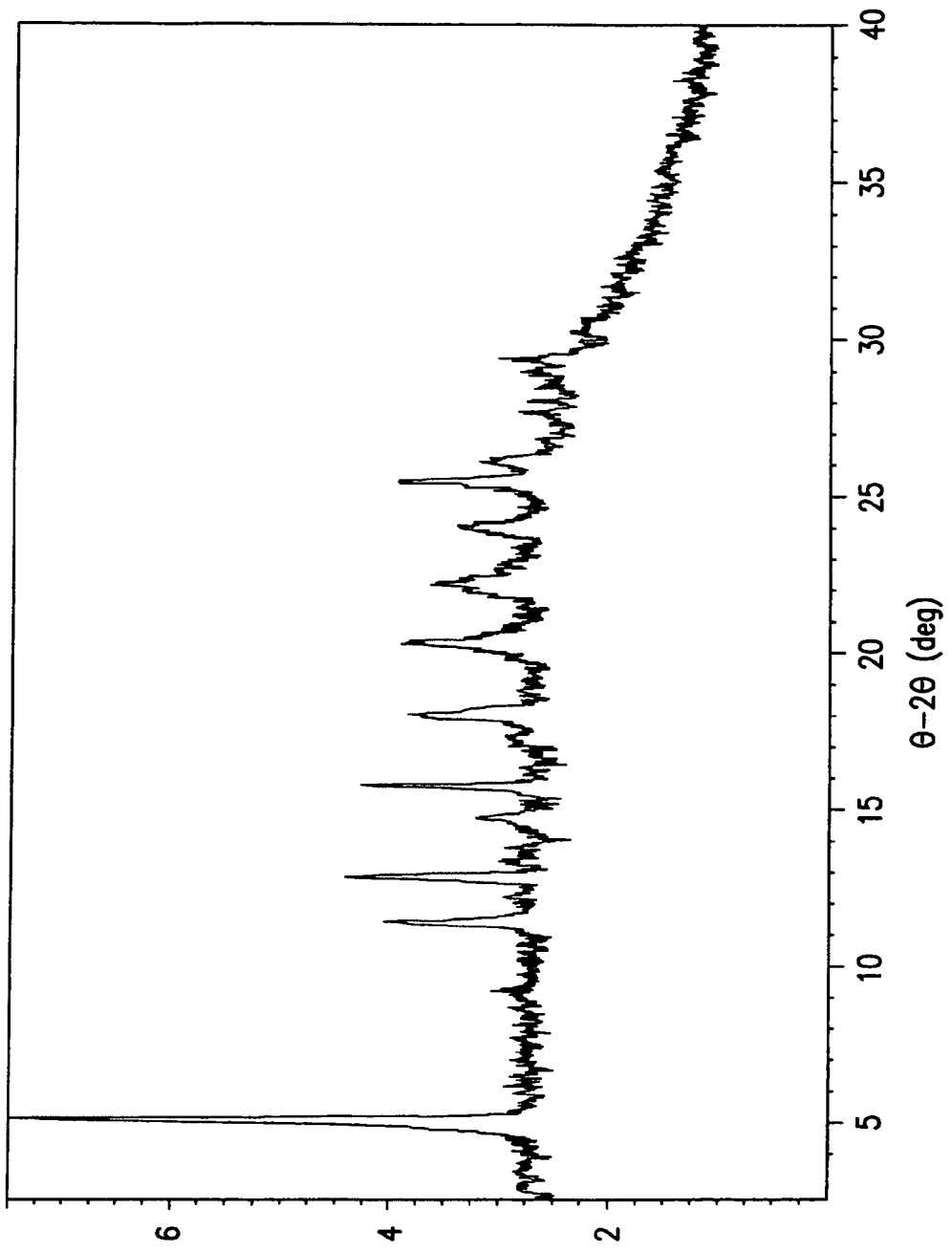

FIG. 5 provides a representative XRPD pattern of Form B of the free base of Compound B1.

Figure 6:
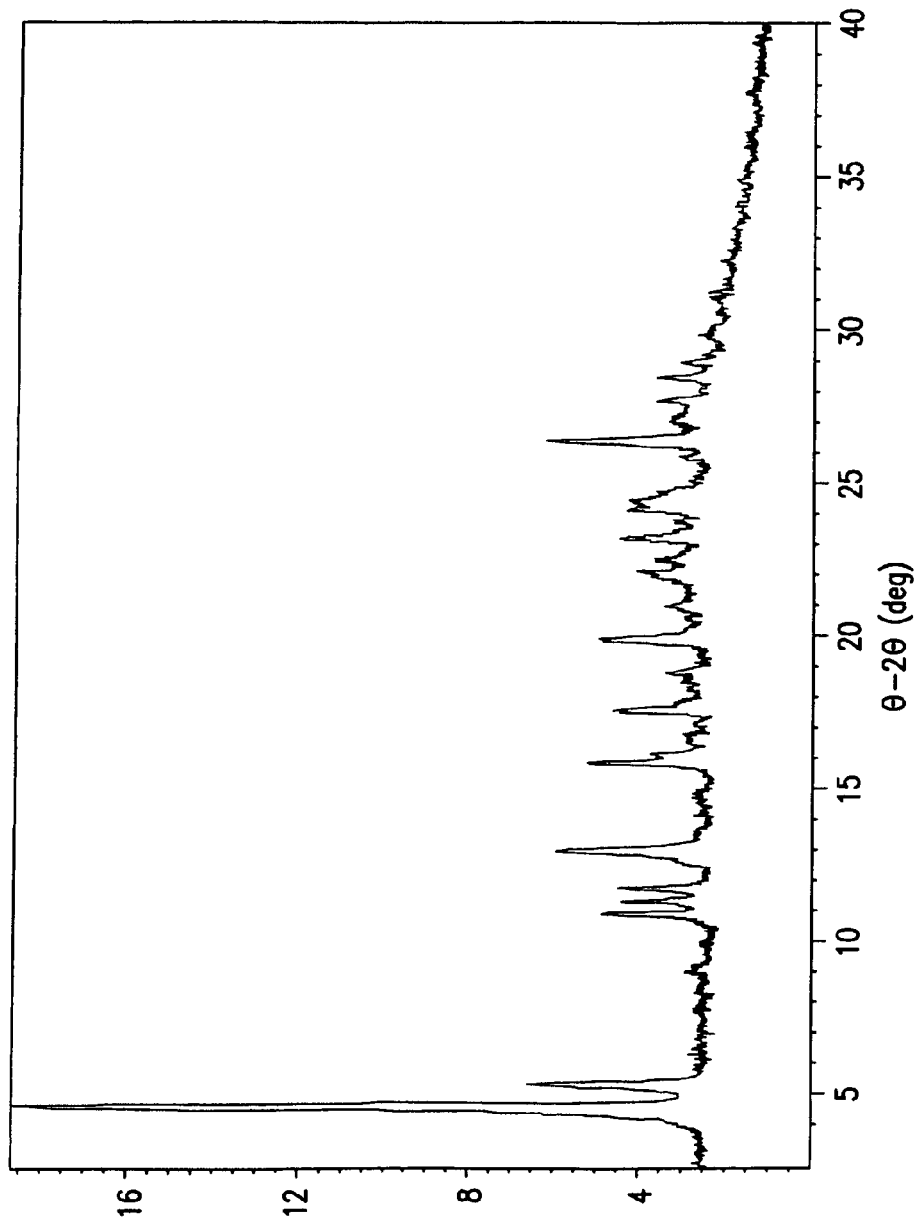

FIG. 6 provides a representative XRPD pattern of a methanol solvate of the free base of Compound B1.

Figure 7:
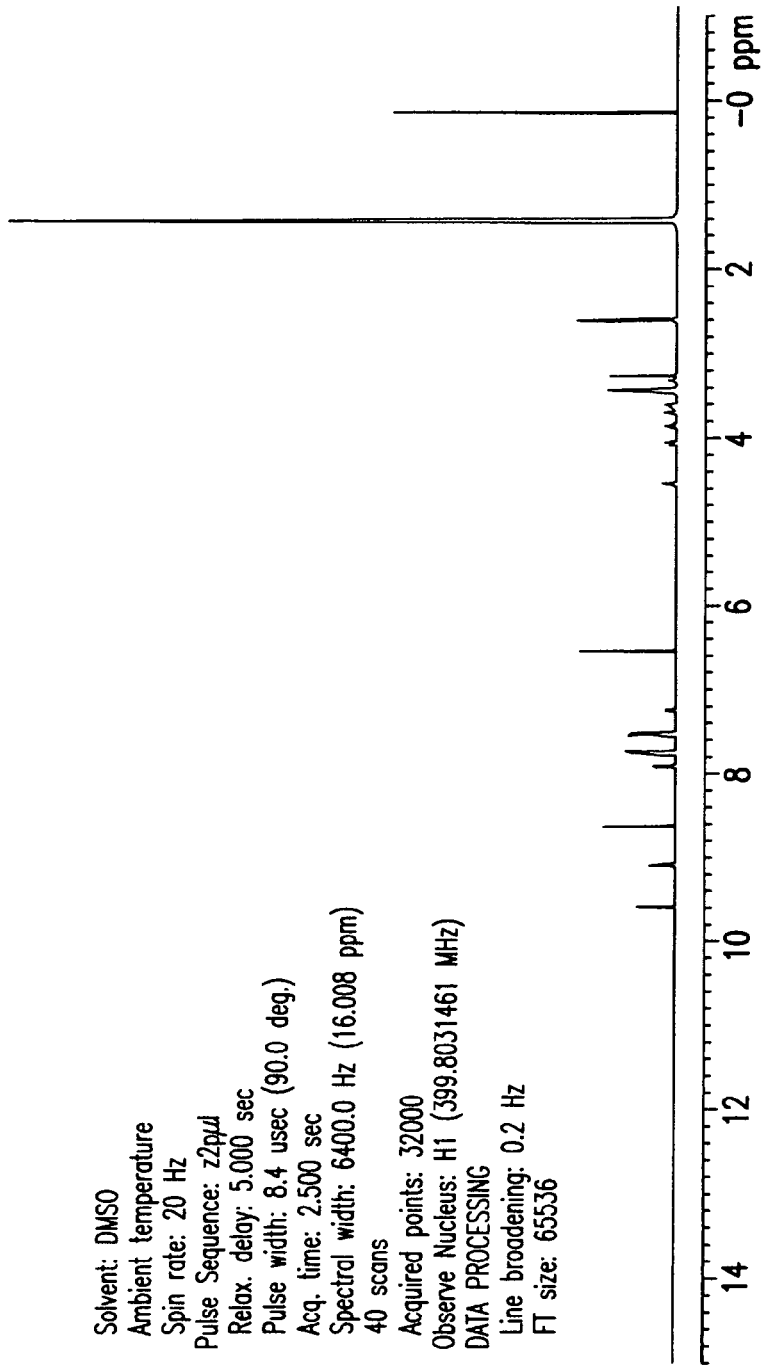

FIG. 7 provides a representative $^1$H NMR spectrum of a methanol solvate of the free base of Compound B1

Figure 8:
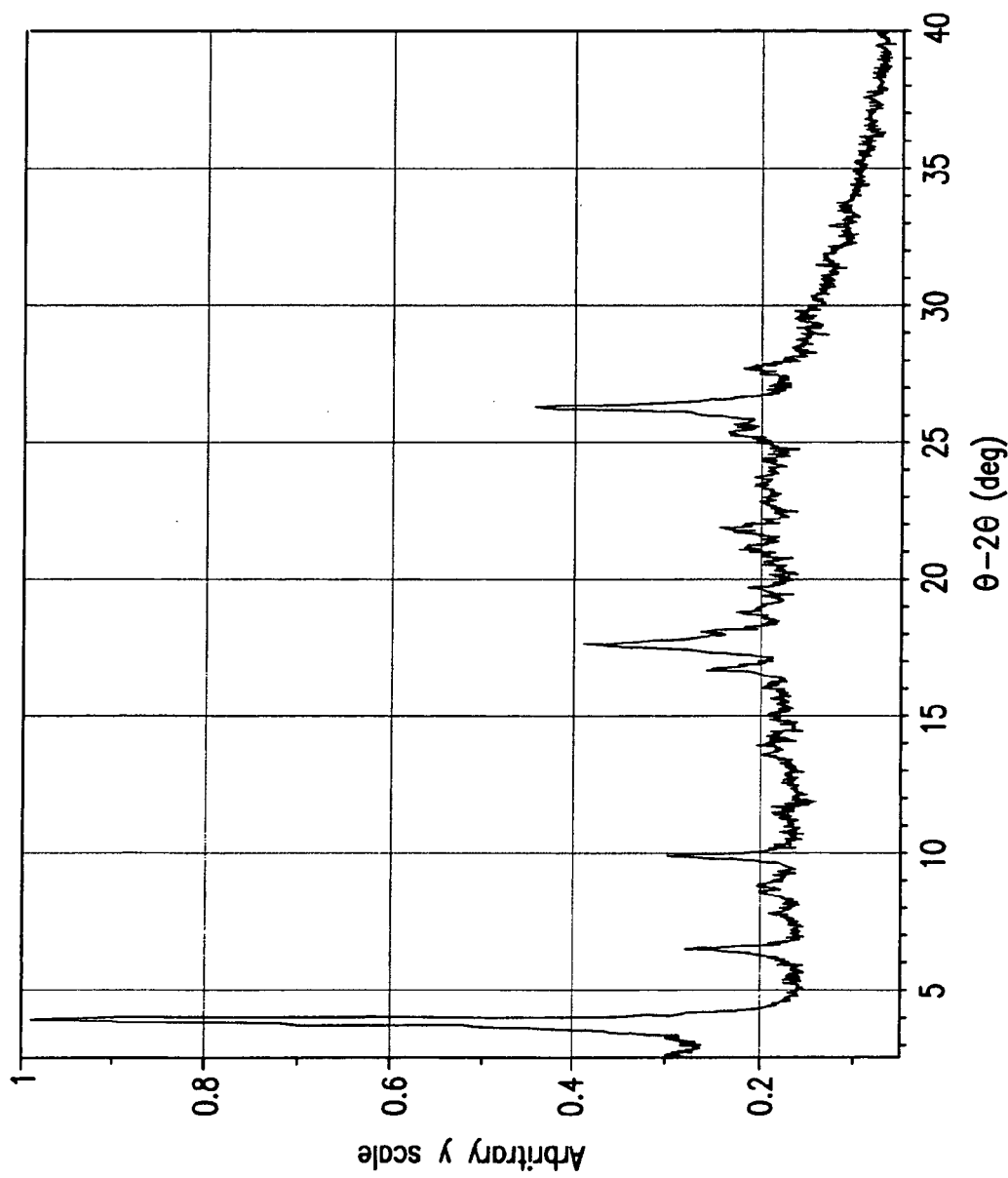

FIG. 8 provides representative XRPD patterns of Form A of the hydrochloride salt of Compound B1.

Figure 9:
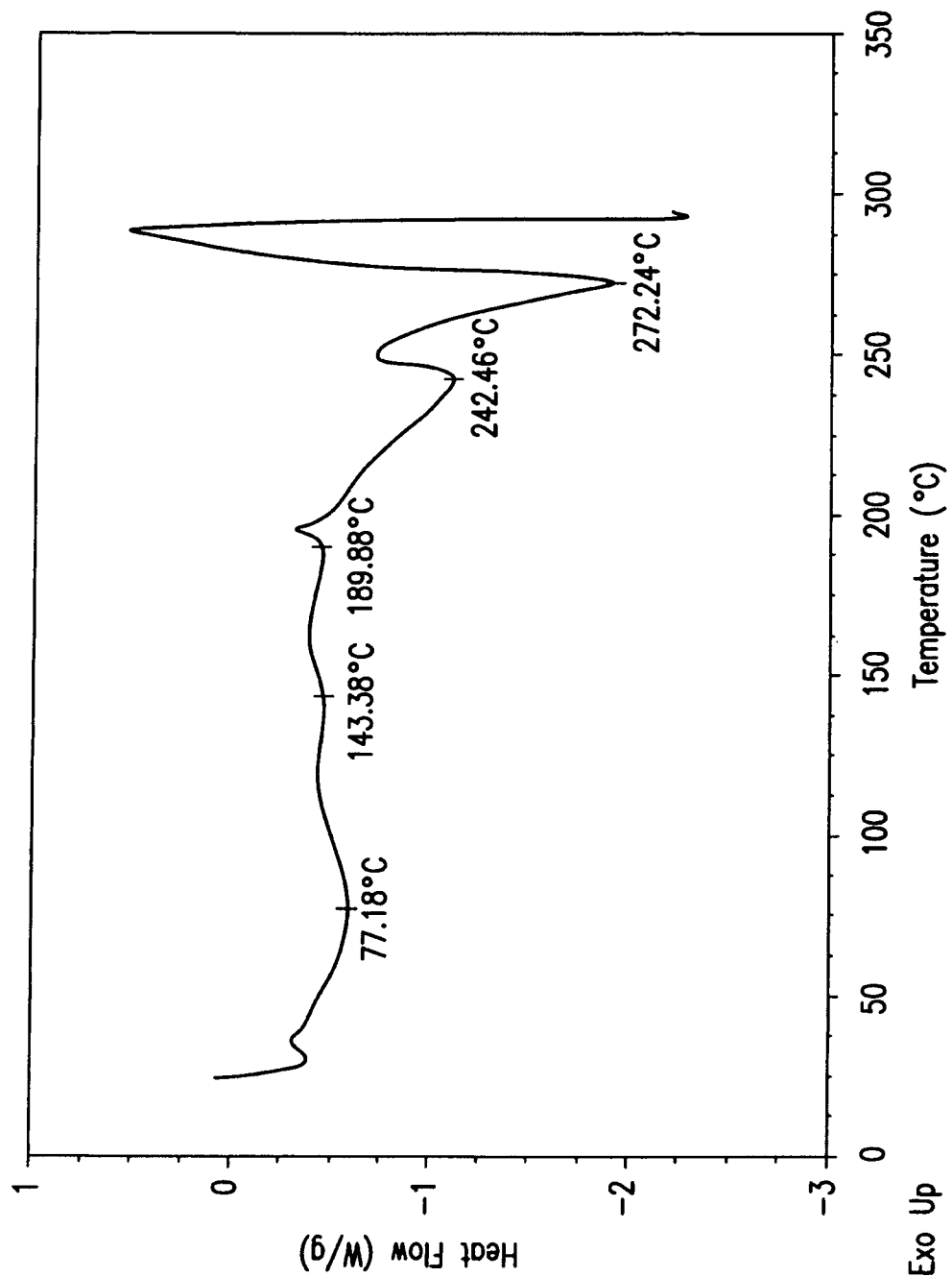

FIG. 9 provides a representative DSC thermogram of Form A of the hydrochloride salt of Compound B1.

Figure 10:
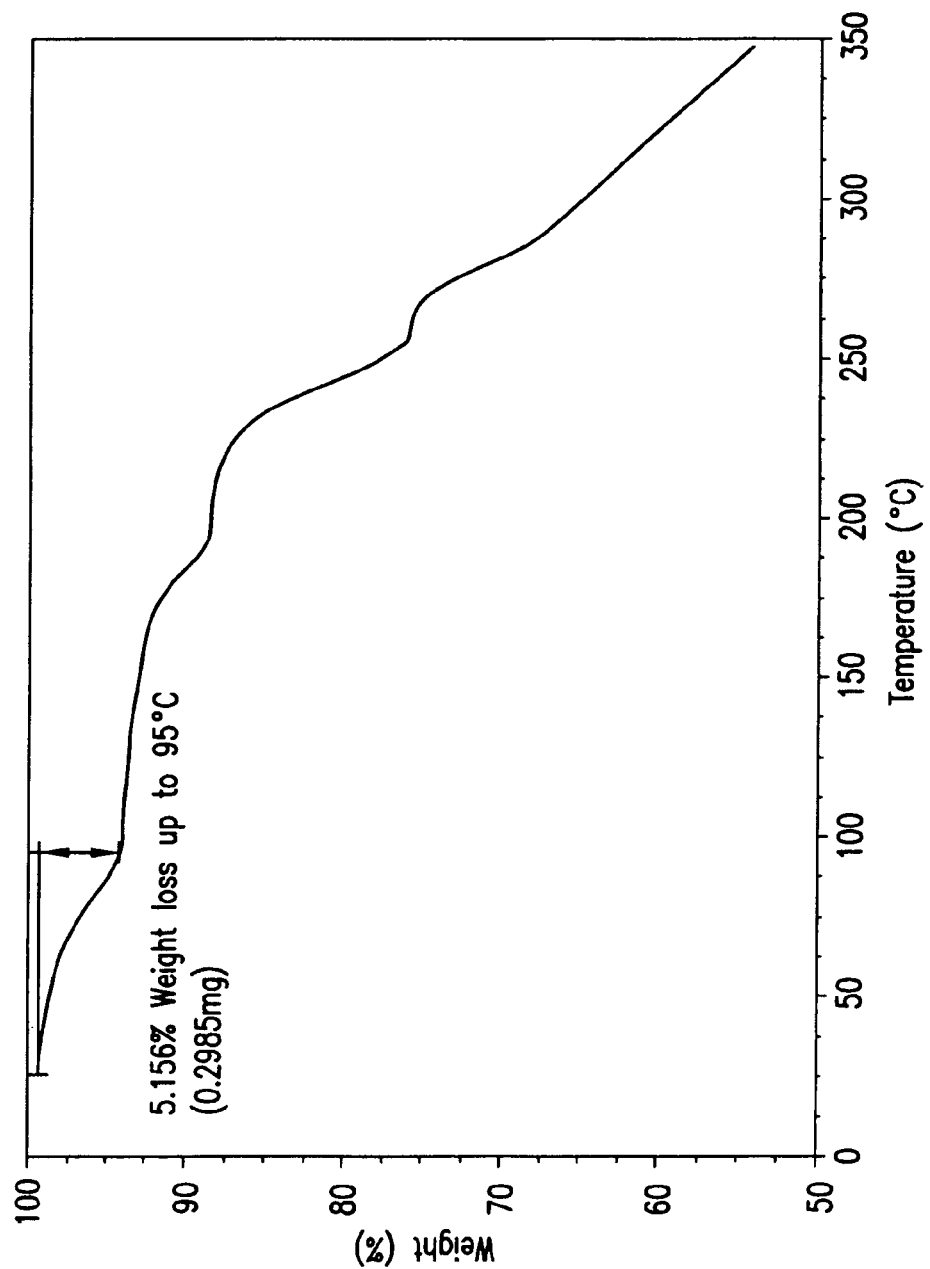

FIG. 10 provides a representative TGA thermogram of Form A of the hydrochloride salt of Compound B1.

Figure 11:
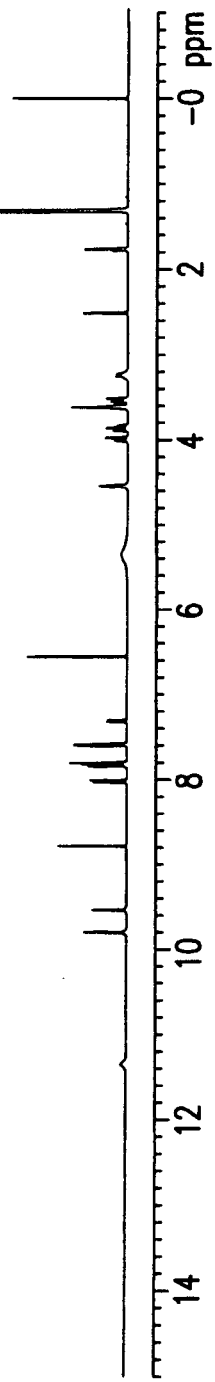

FIG. 11 provides a representative $^1$H NMR spectrum of Form A of the hydrochloride salt of Compound B1.

Figure 12:
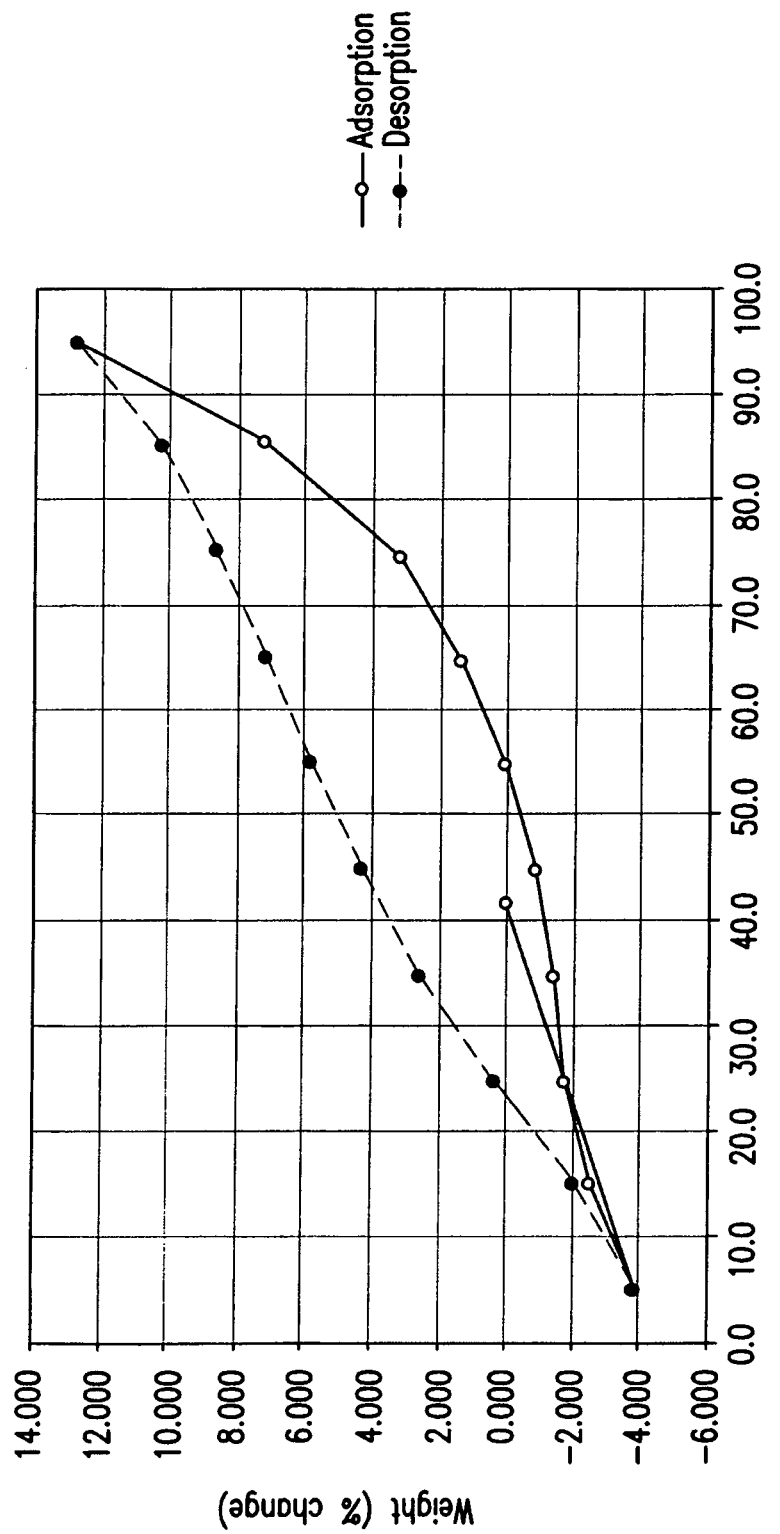

FIG. 12 provides a representative dynamic vapor sorption (DVS) profile of Form A of the hydrochloride salt of Compound B1.

Figure 13A:
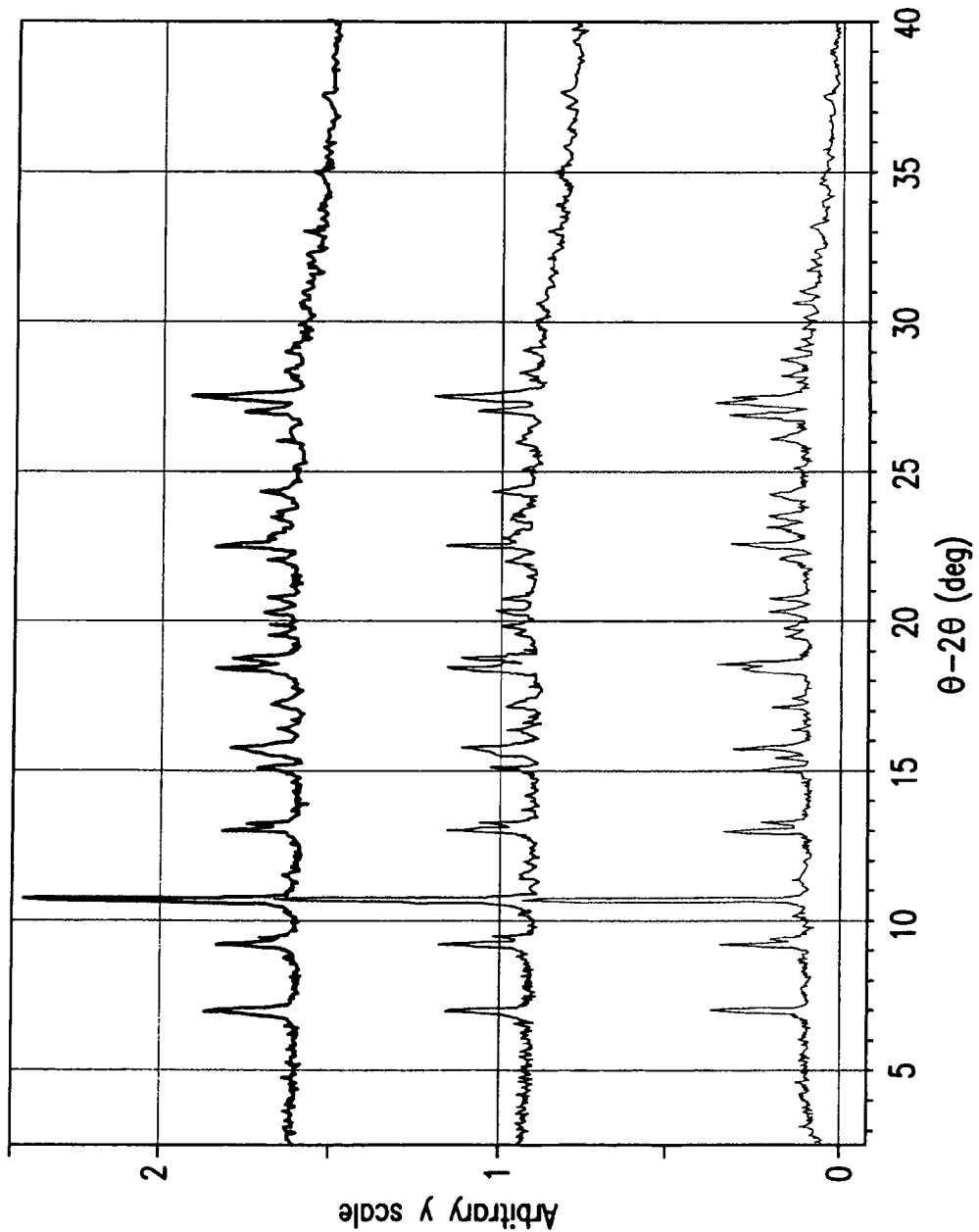
Figure 13B:
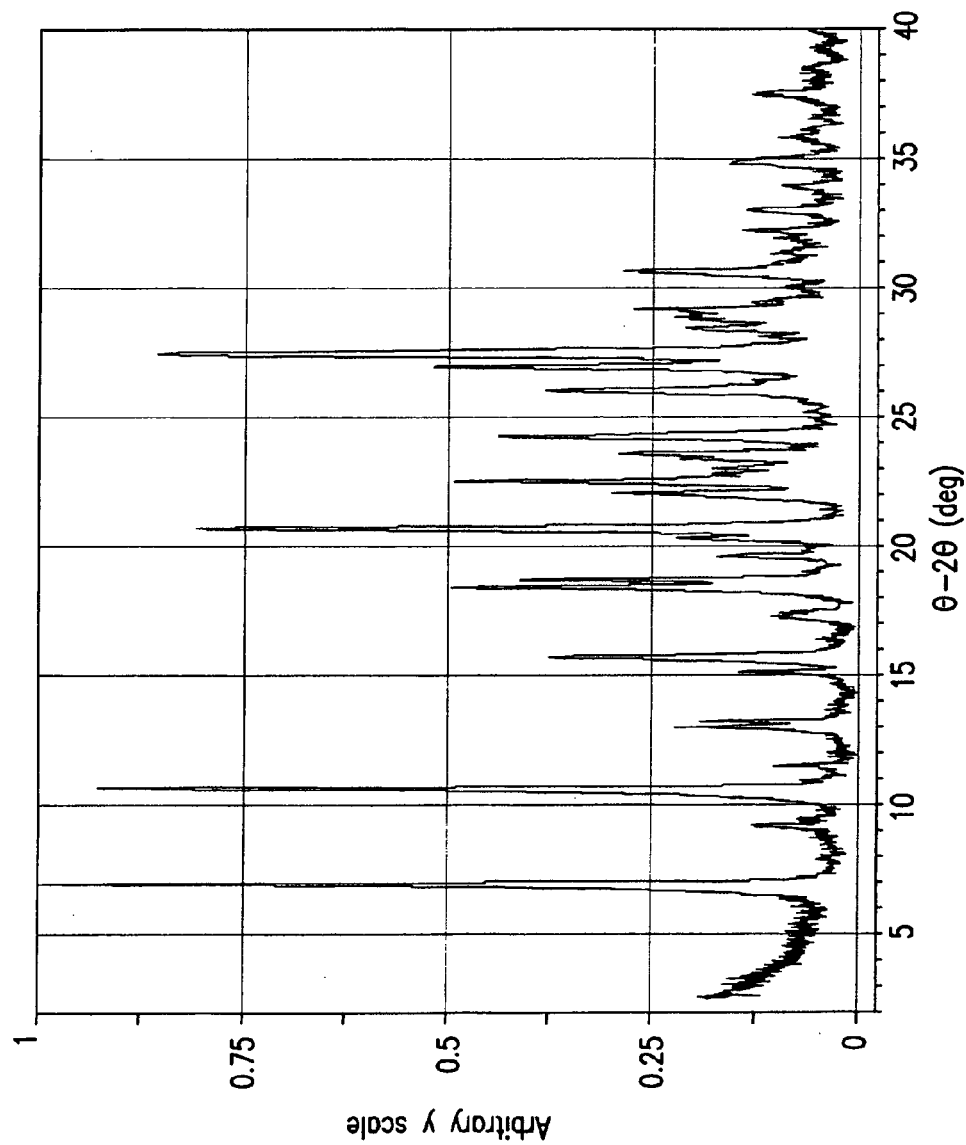

FIG. 13*a* and FIG. 13*b* provide representative XRPD patterns of Form B of the hydrochloride salt of Compound B1.

Figure 14:
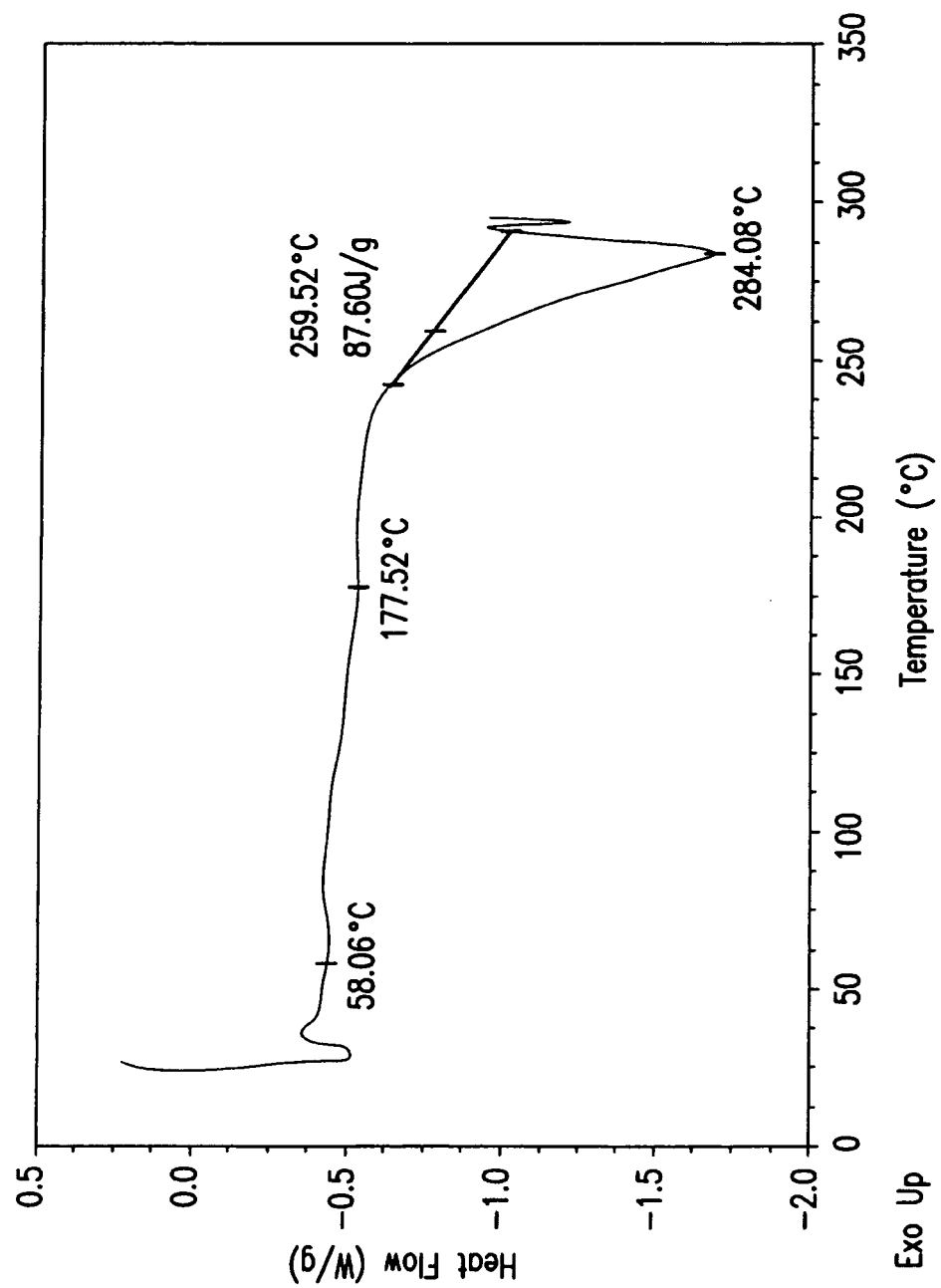

FIG. 14 provides a representative DSC thermogram of Form B of the hydrochloride salt of Compound B1.

Figure 15:
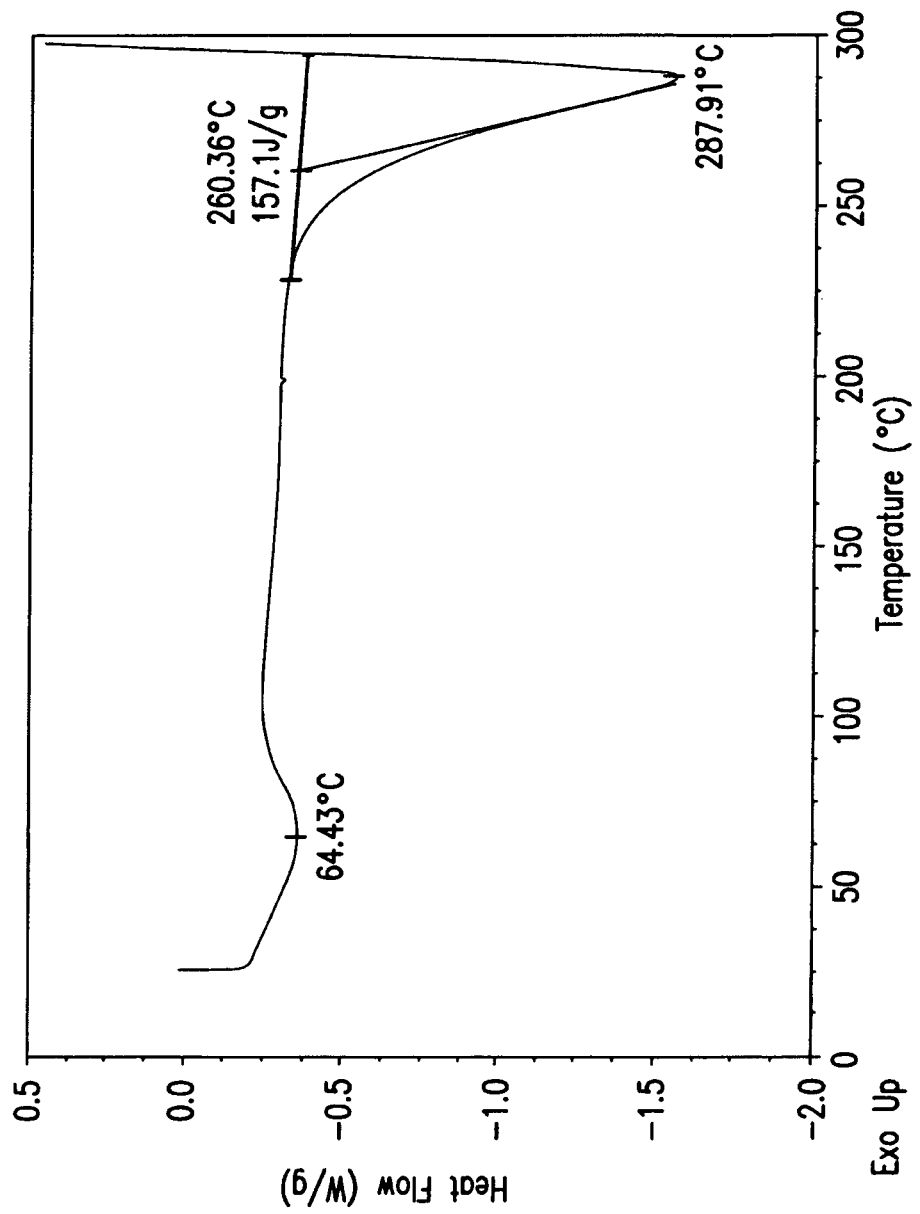

FIG. 15 provides another representative DSC thermogram of Form B of the hydrochloride salt of Compound B1.

Figure 16:
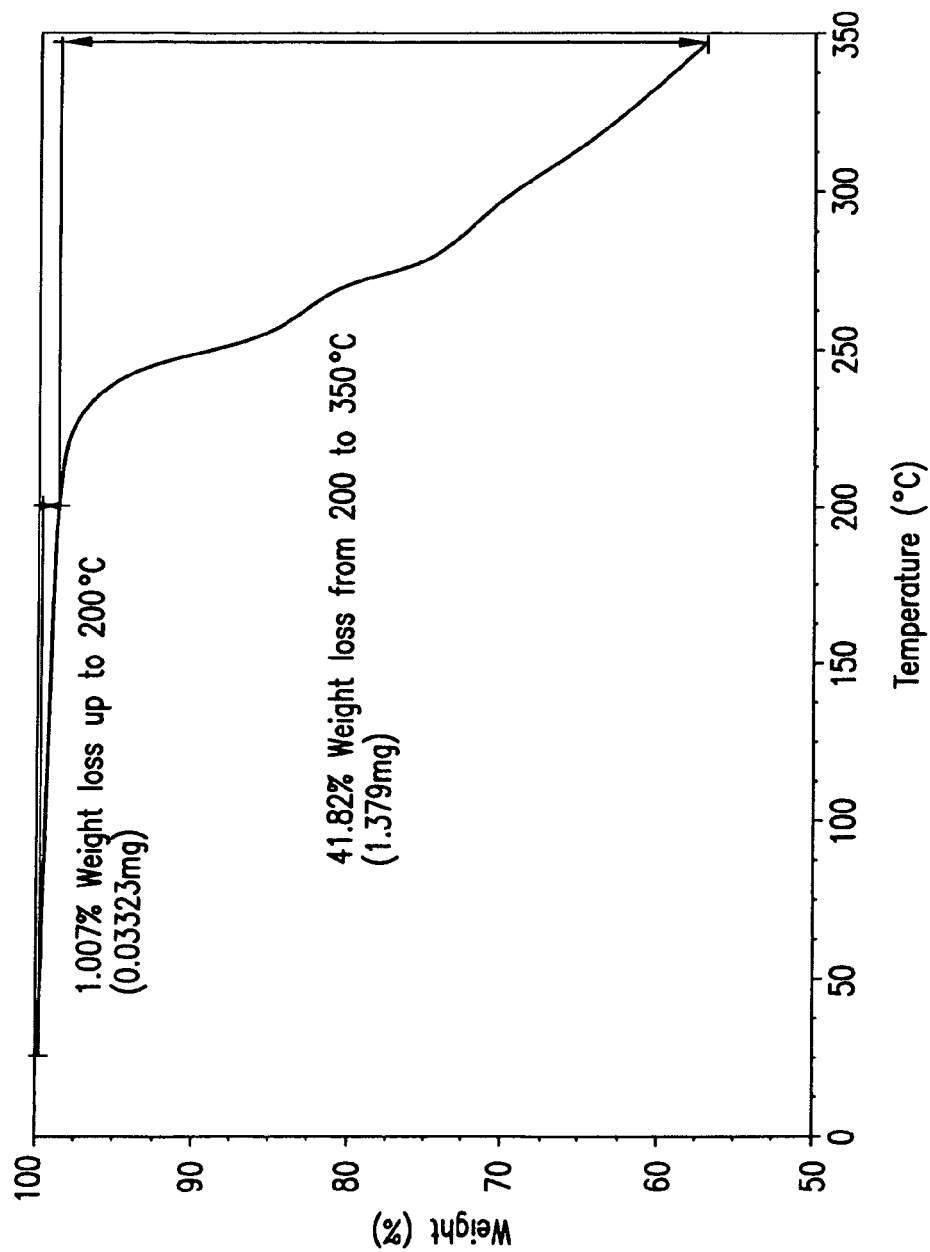

FIG. 16 provides a representative TGA thermogram of Form B of the hydrochloride salt of Compound B1.

Figure 17:
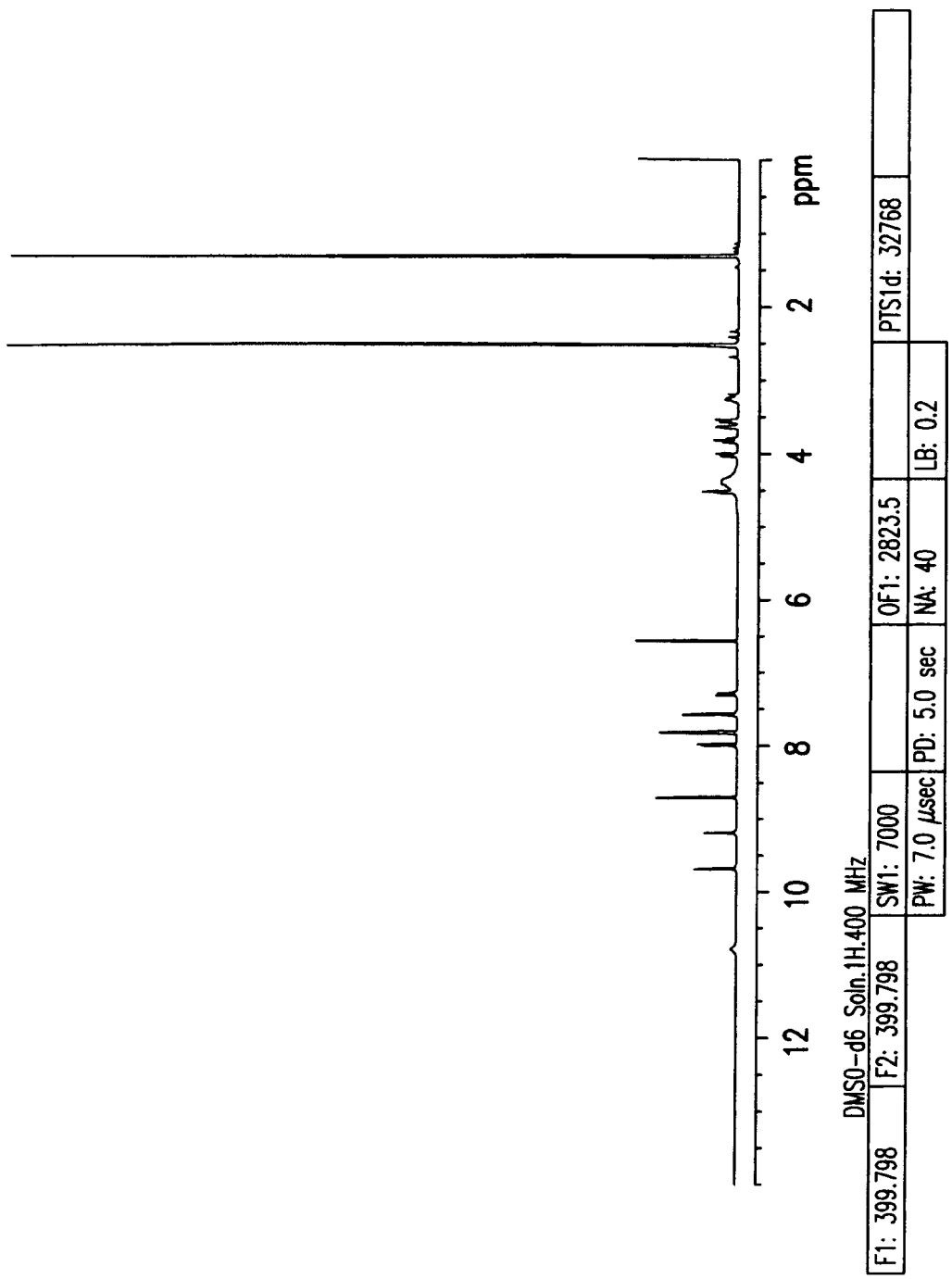

FIG. 17 provides a representative $^1$H NMR spectrum of Form B of the hydrochloride salt of Compound B1.

Figure 18:
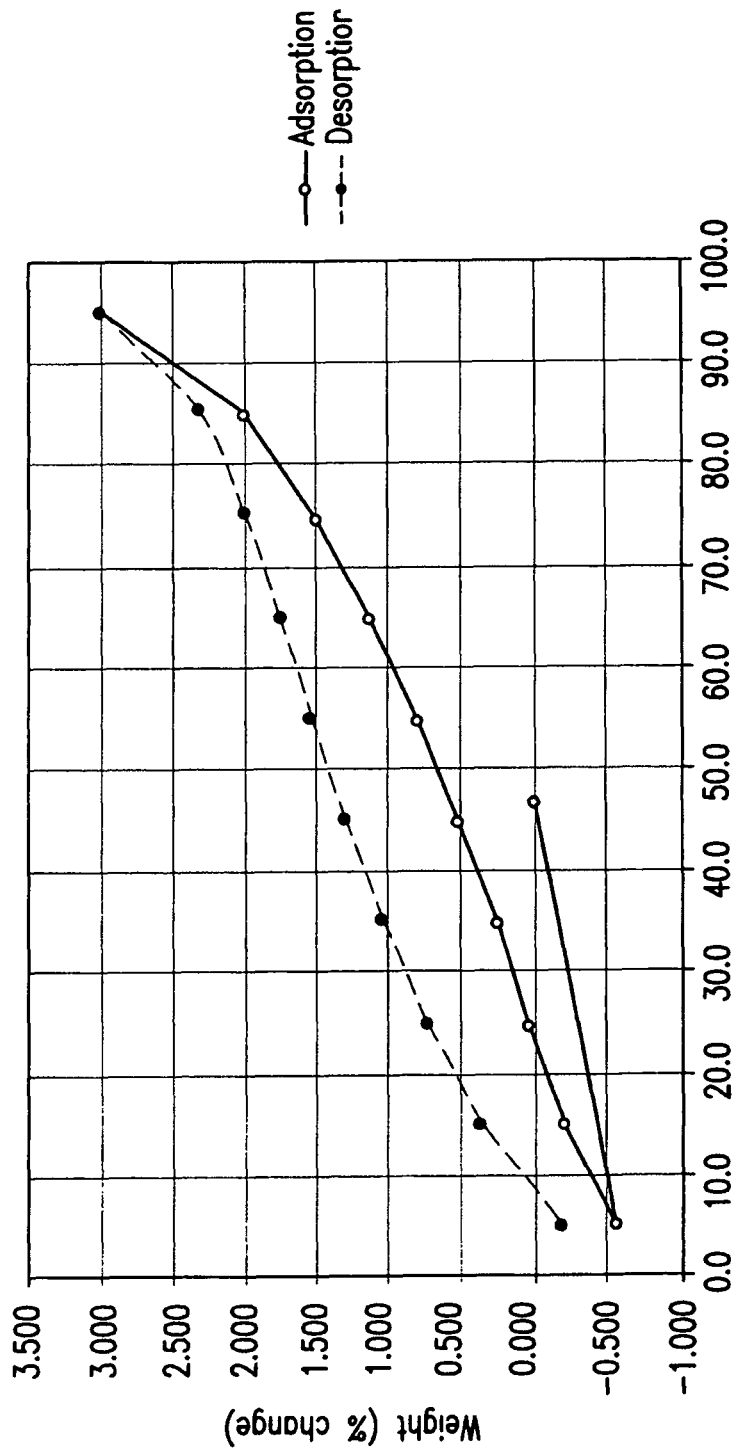

FIG. 18 provides a representative DVS profile of Form B of the hydrochloride salt of Compound B1.

Figure 19:
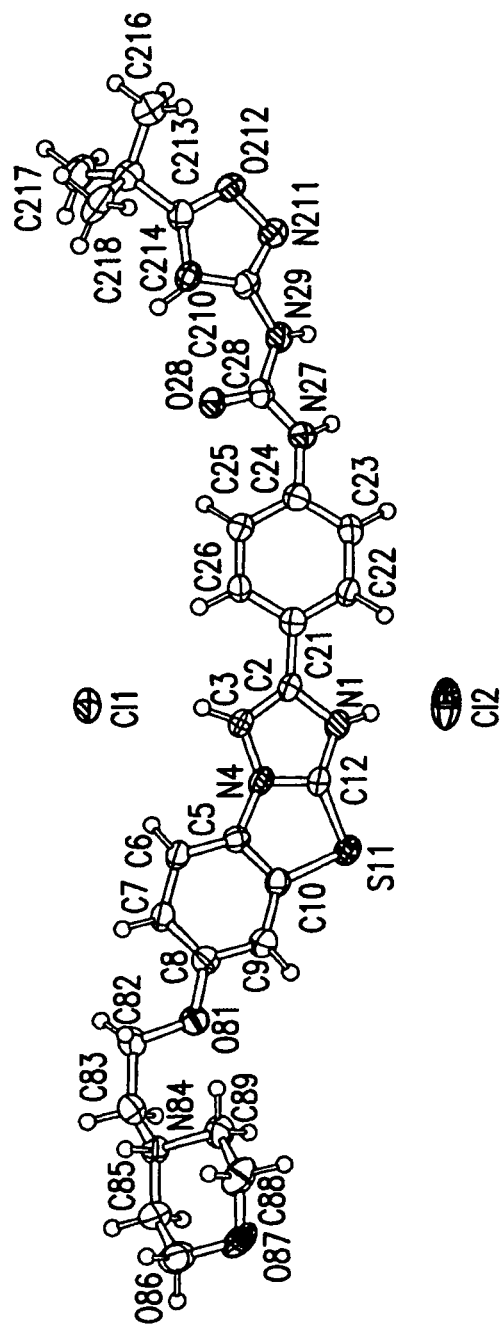

FIG. 19 provides a representative thermal ellipsoid plot derived from a single crystal XRD structure solution of Form B of the hydrochloride salt of Compound B1 obtained from data collected at 150±1 K. Atoms are represented by 50% probability anisotropic thermal ellipsoids.

Figure 20:
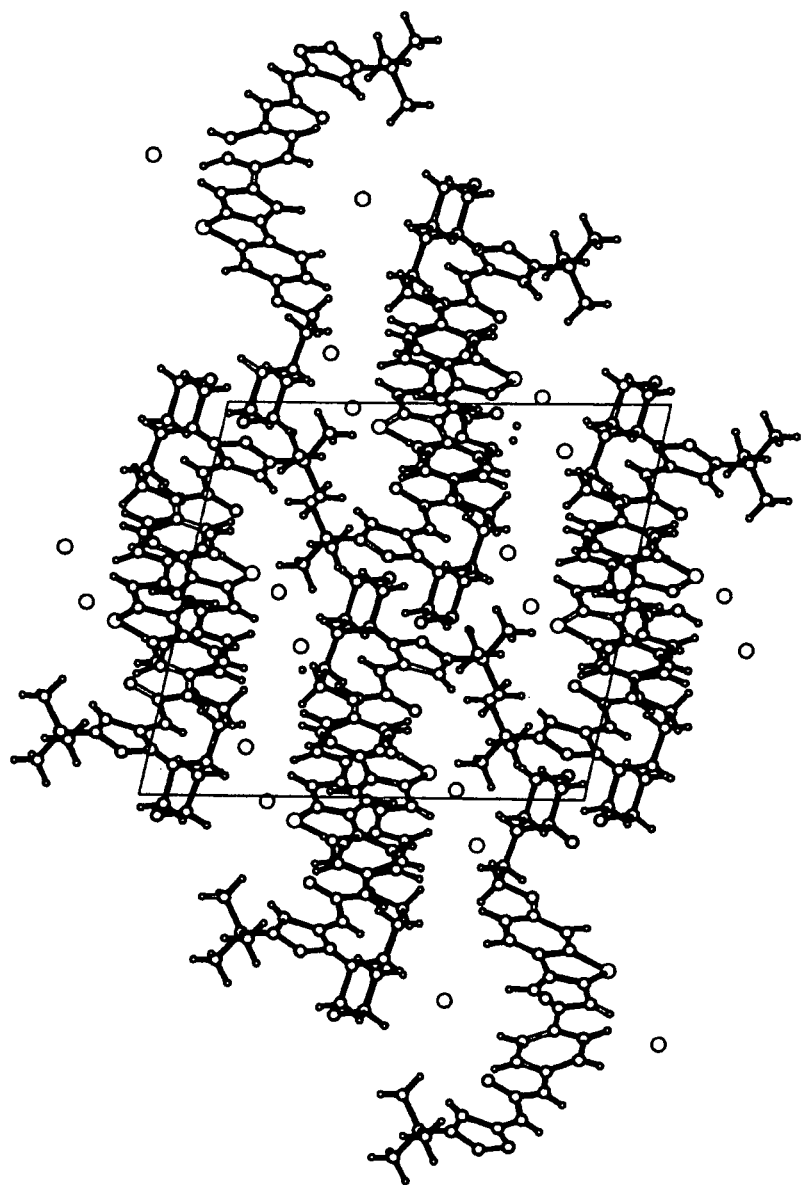

FIG. 20 provides a representative crystal packing diagram derived from a single crystal XRD structure solution of Form B of the hydrochloride salt of Compound B1 obtained from data collected at 150±1 K. Diagram comprises a view of a unit cell down the crystallographic b axis.

Figure 21:
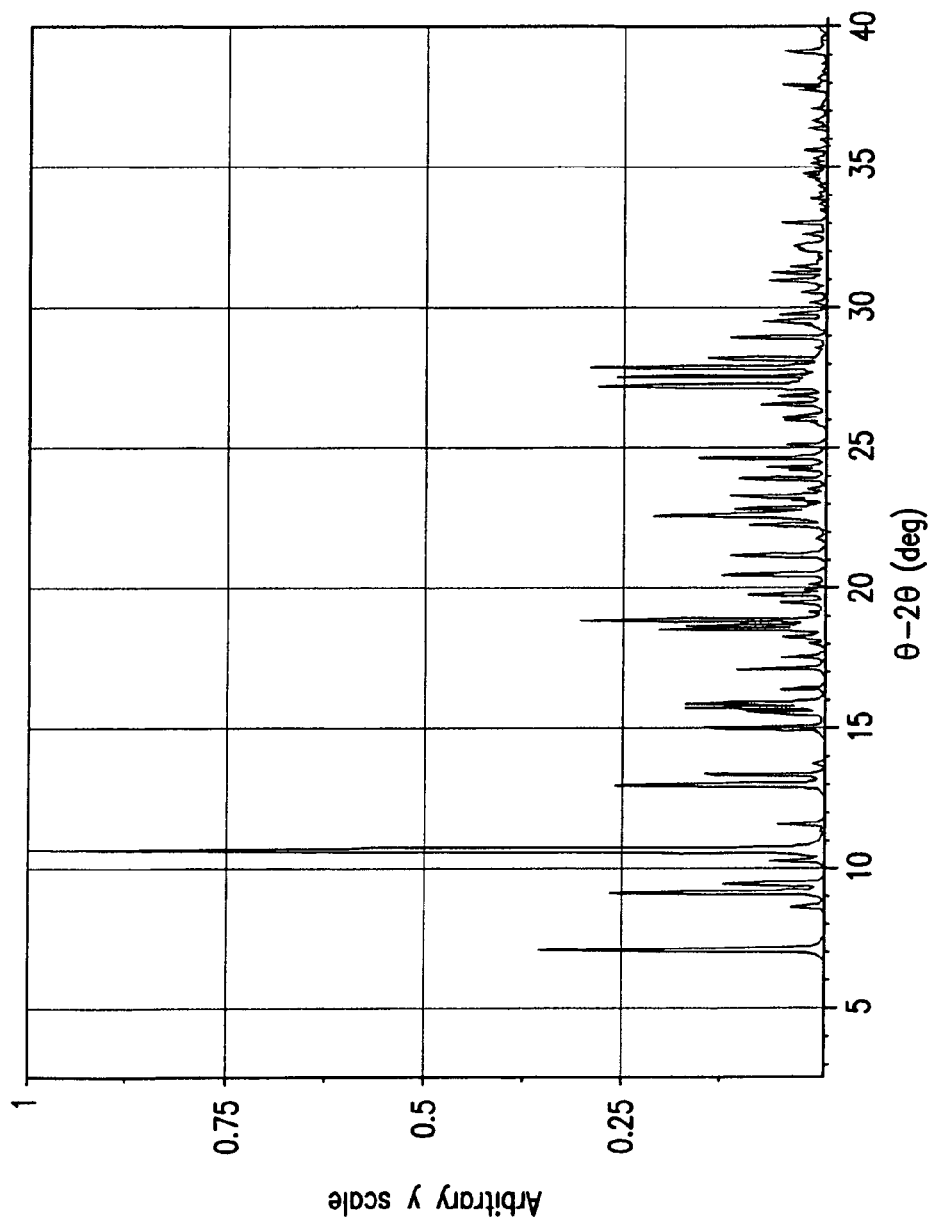

FIG. 21 provides a representative simulated XRPD pattern derived from a single crystal XRD structure solution of Form B of the hydrochloride salt of Compound B1 obtained from data collected at 150±1 K.

Figure 22:
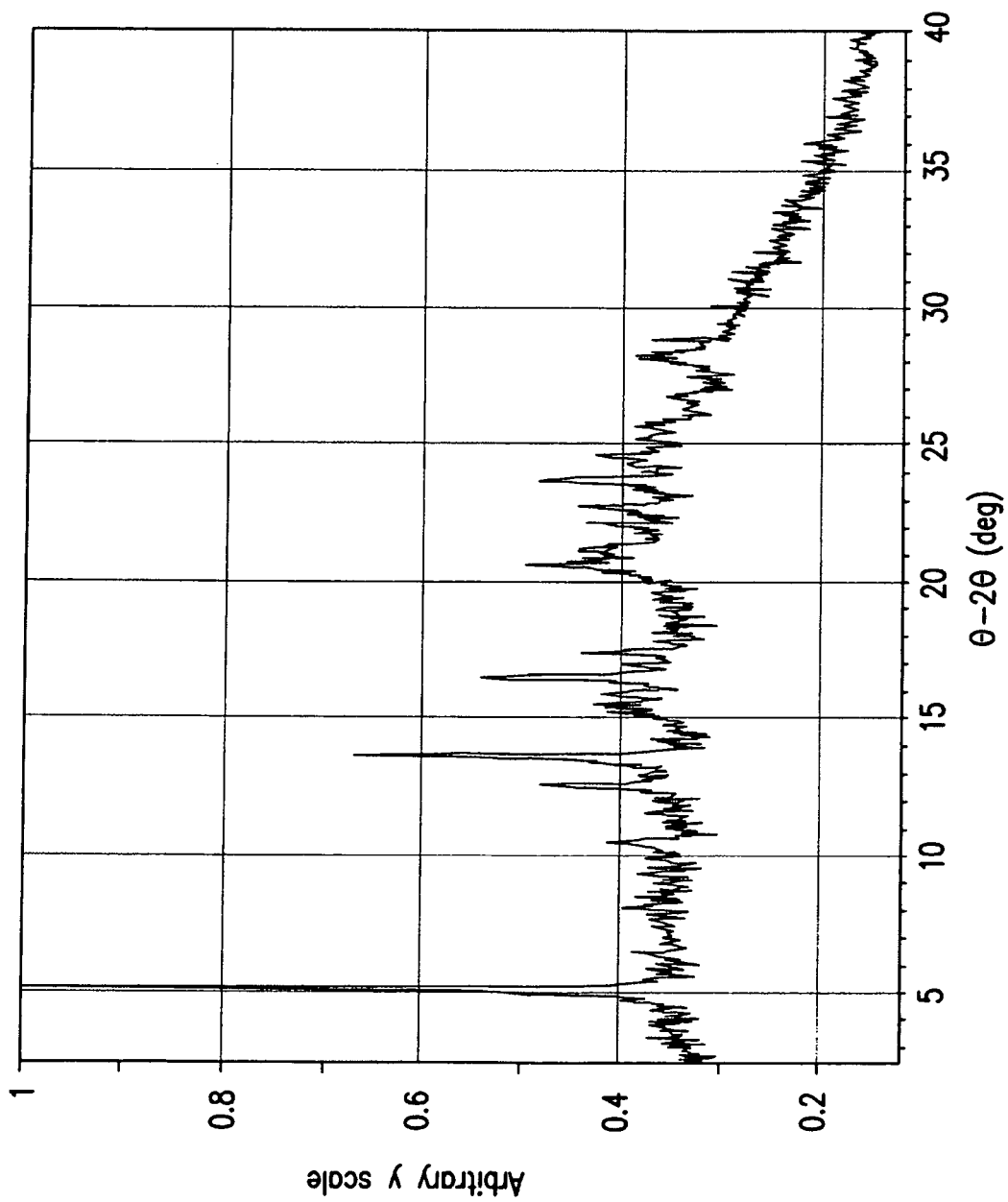

FIG. 22 provides a representative XRPD pattern of Form C of the hydrochloride salt of Compound B1.

Figure 23:
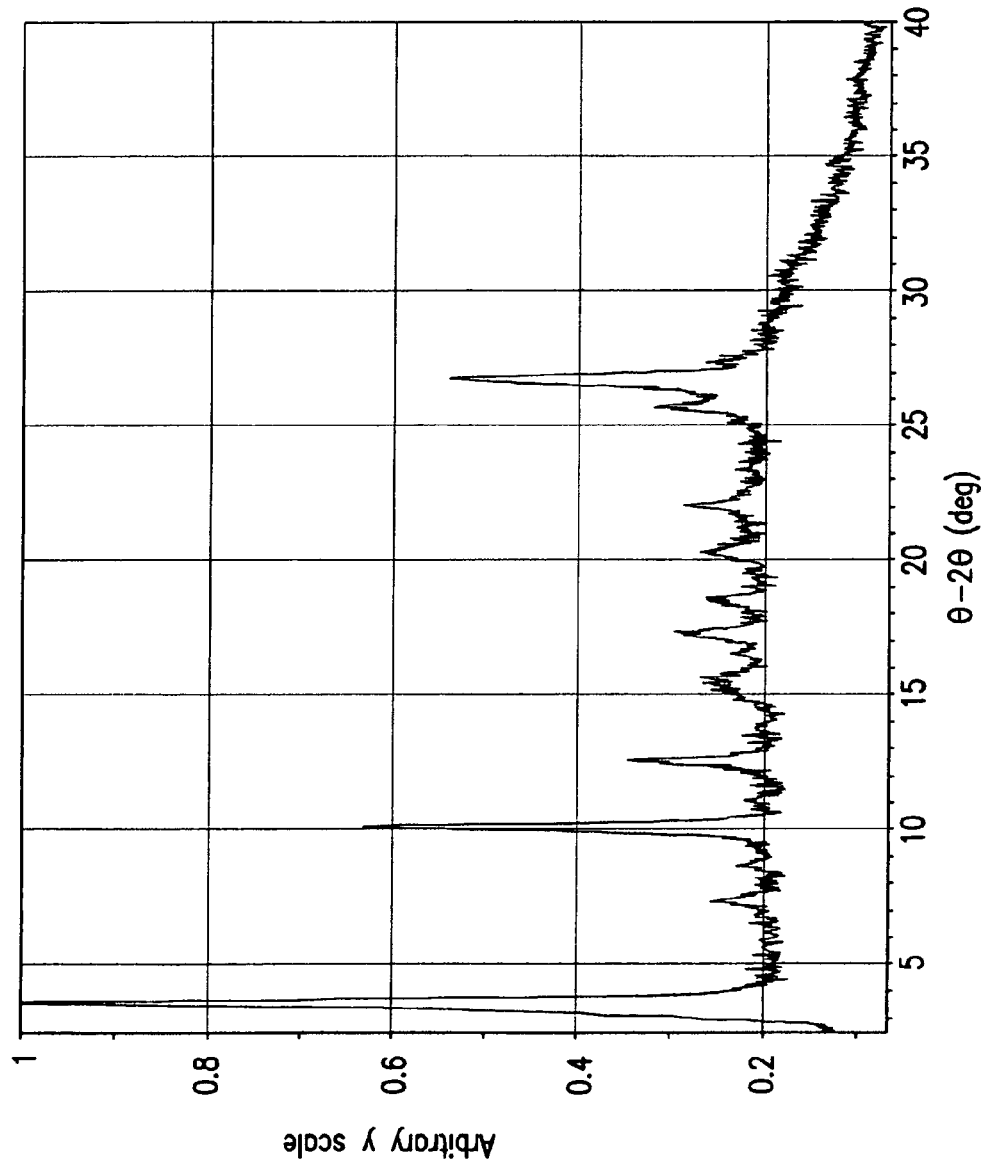

FIG. 23 provides a representative XRPD pattern of Form D of the hydrochloride salt of Compound B1.

Figure 24:
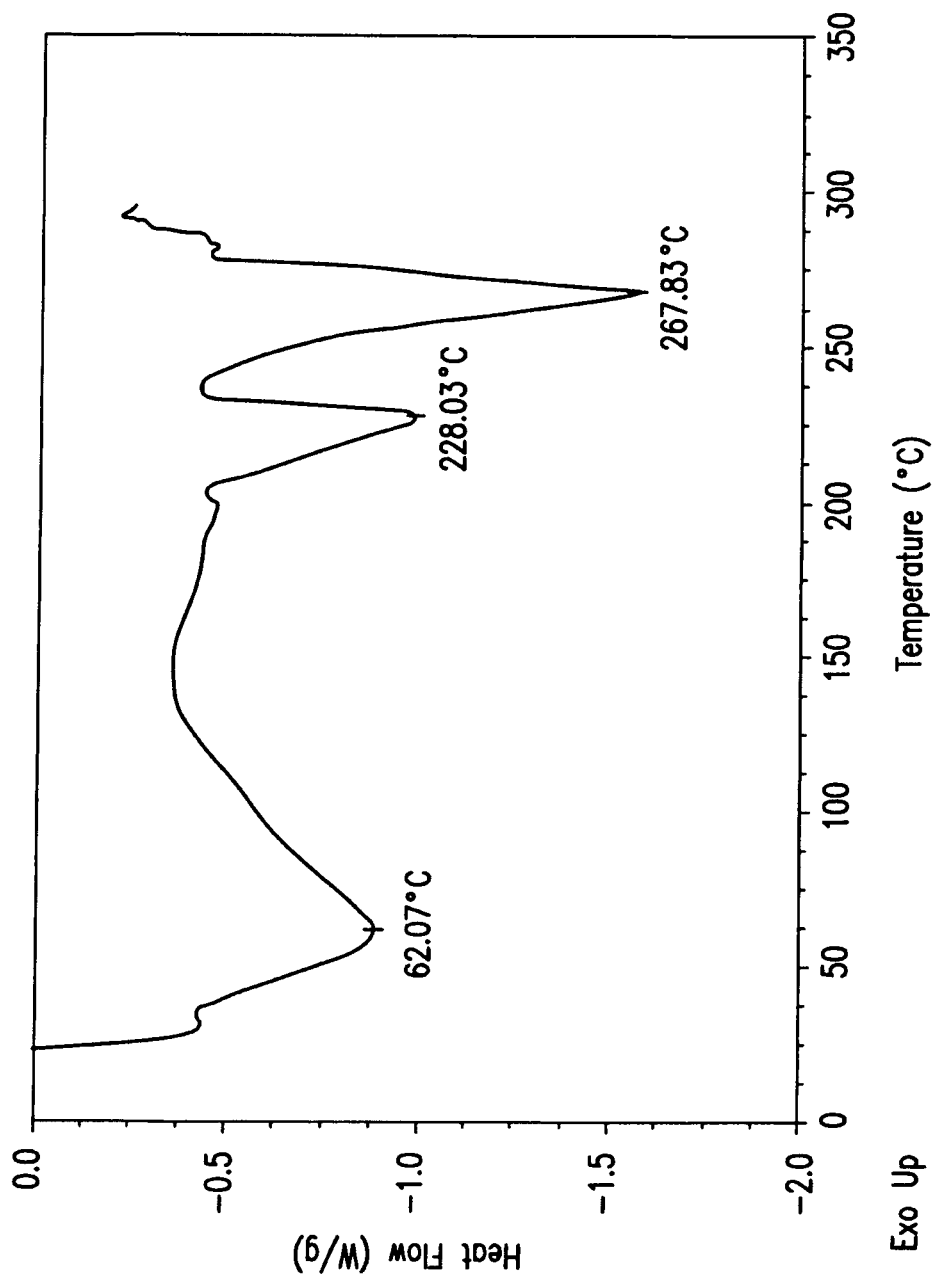

FIG. 24 provides a representative DSC thermogram of Form D of the hydrochloride salt of Compound B1.

Figure 25:
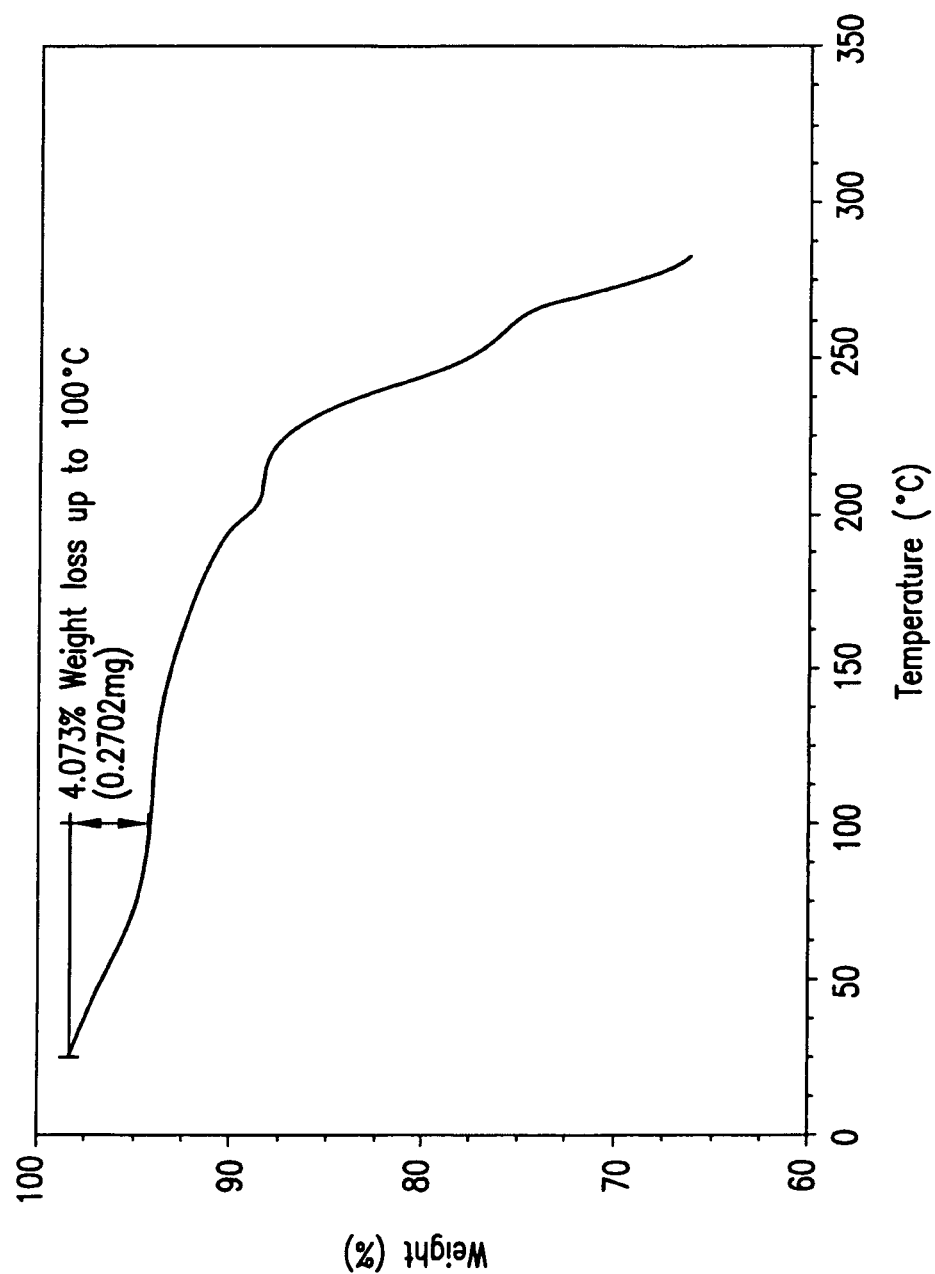

FIG. 25 provides a representative TGA thermogram of Form D of the hydrochloride salt of Compound B1.

Figure 26:
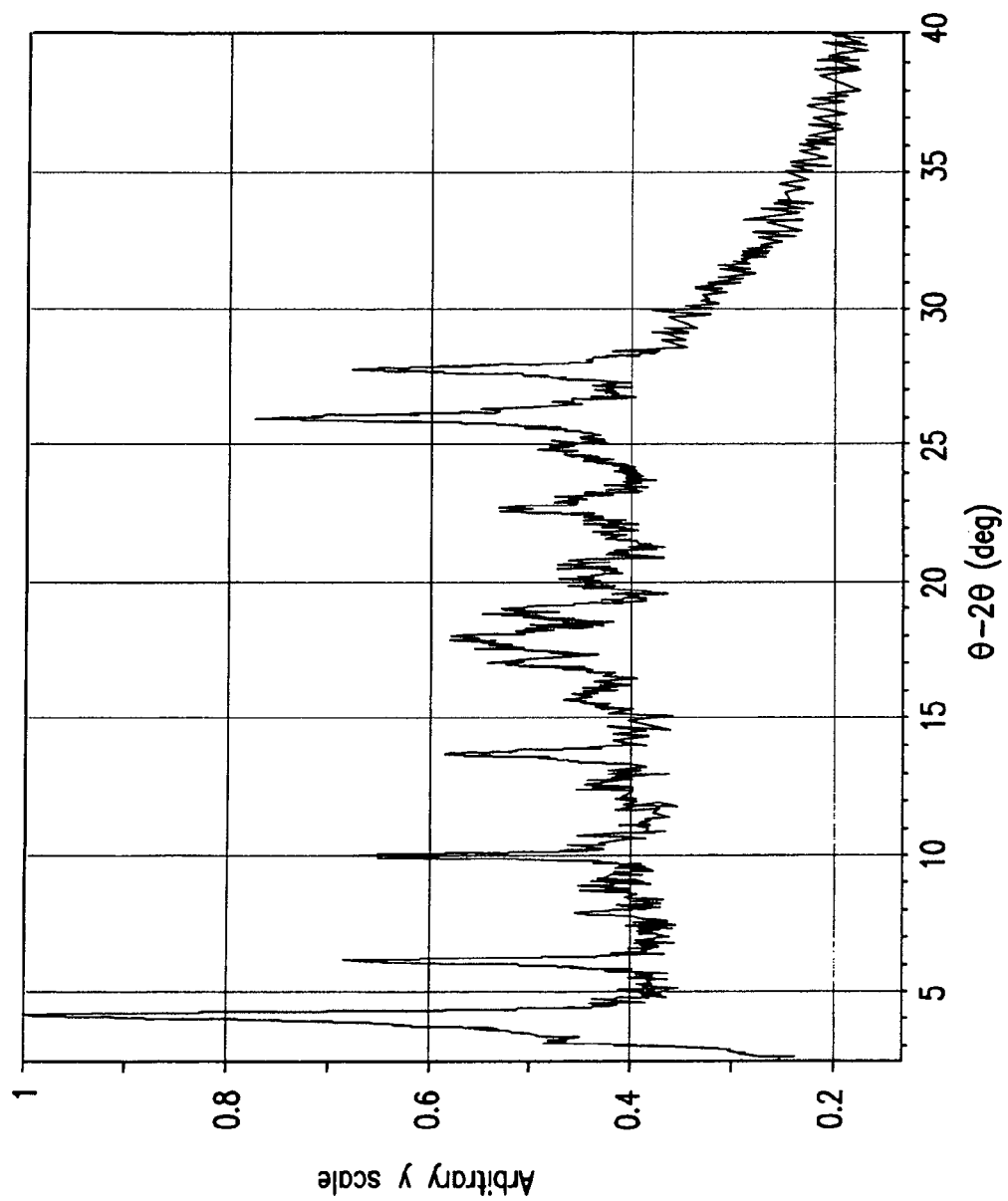

FIG. 26 provides a representative XRPD pattern of Form E of the hydrochloride salt of Compound B1.

Figure 27:
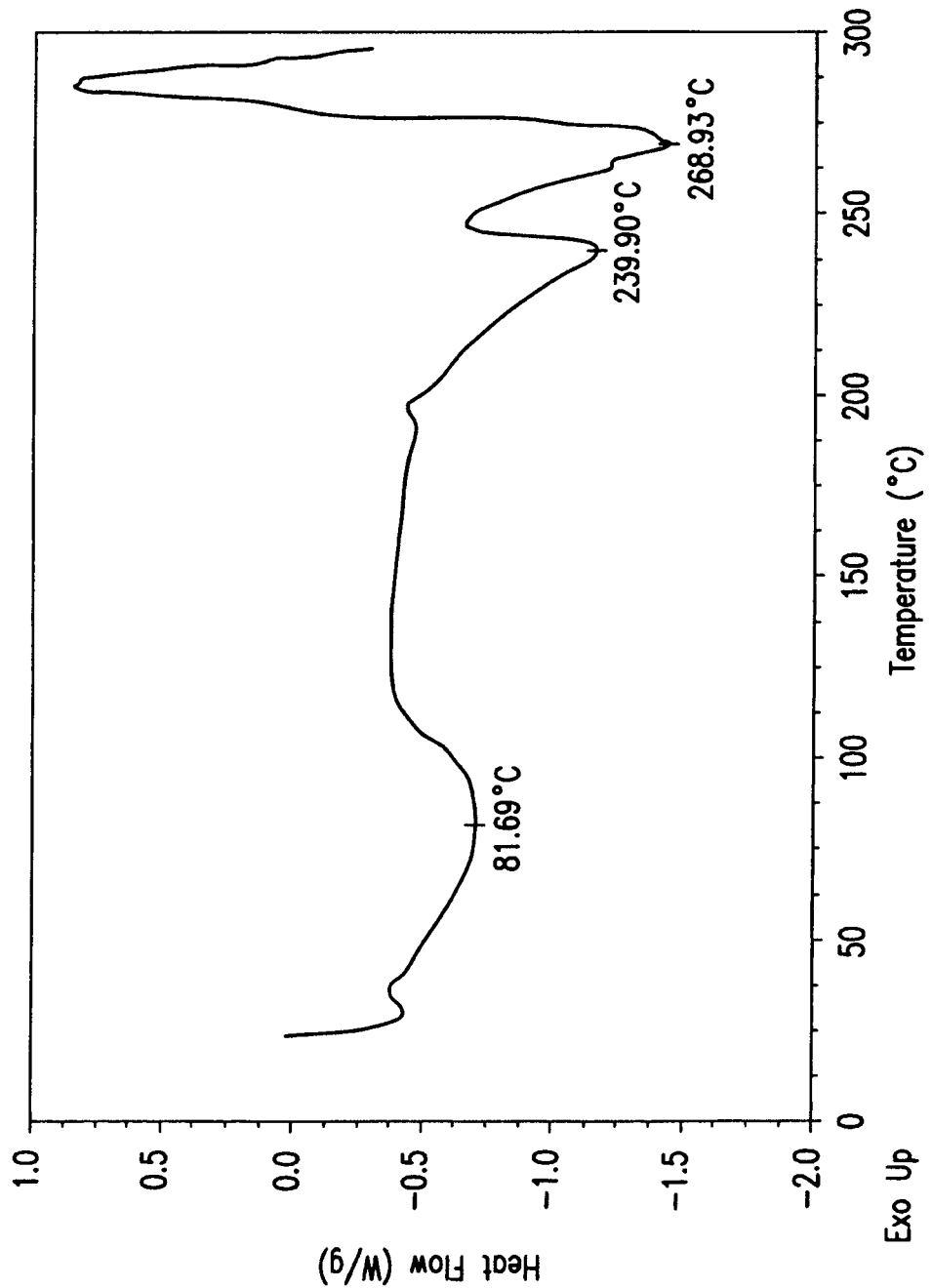

FIG. 27 provides a representative DSC thermogram of Form E of the hydrochloride salt of Compound B1.

Figure 28:
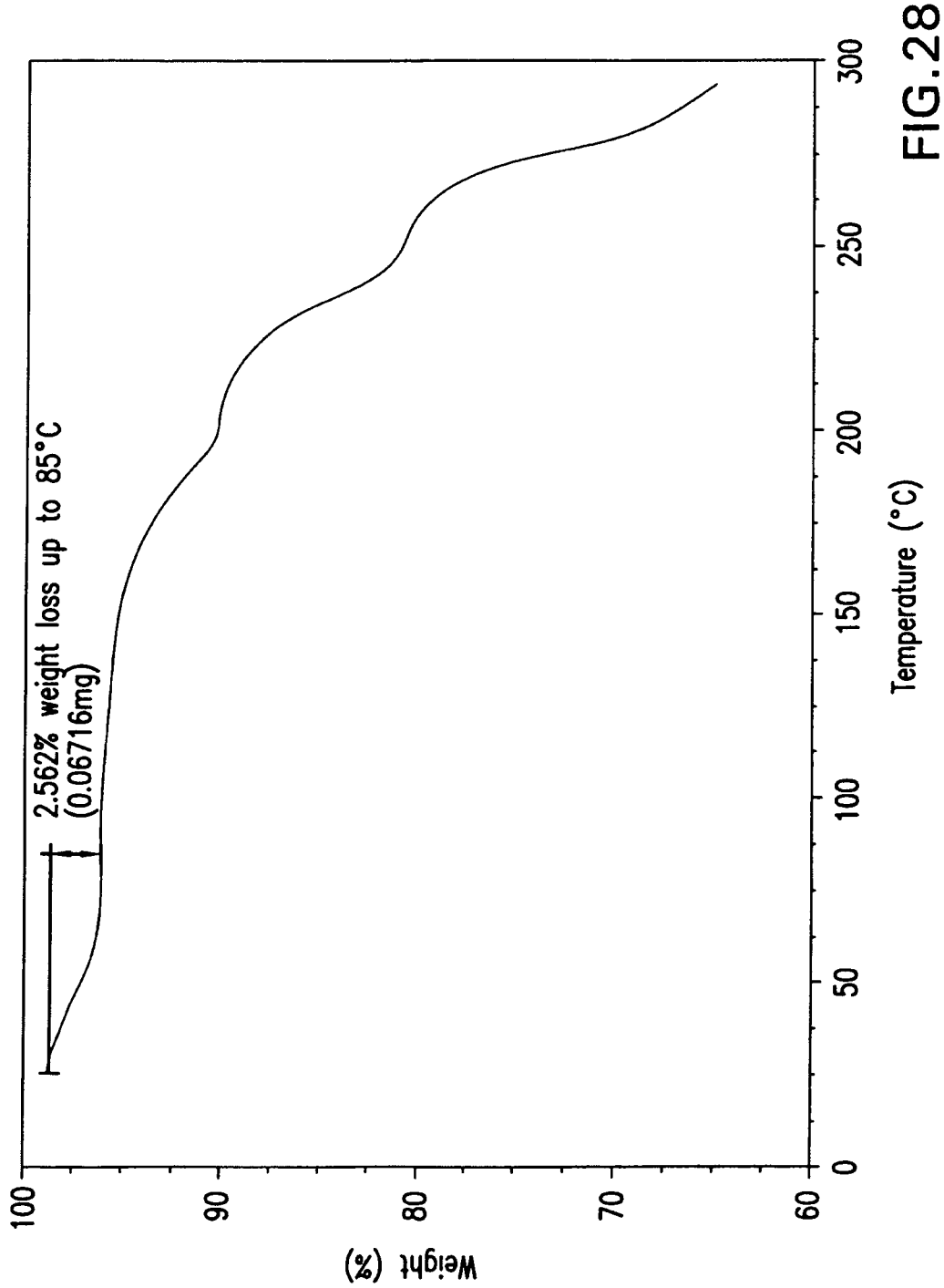

FIG. 28 provides a representative TGA thermogram of Form E of the hydrochloride salt of Compound B1.

Figure 29:
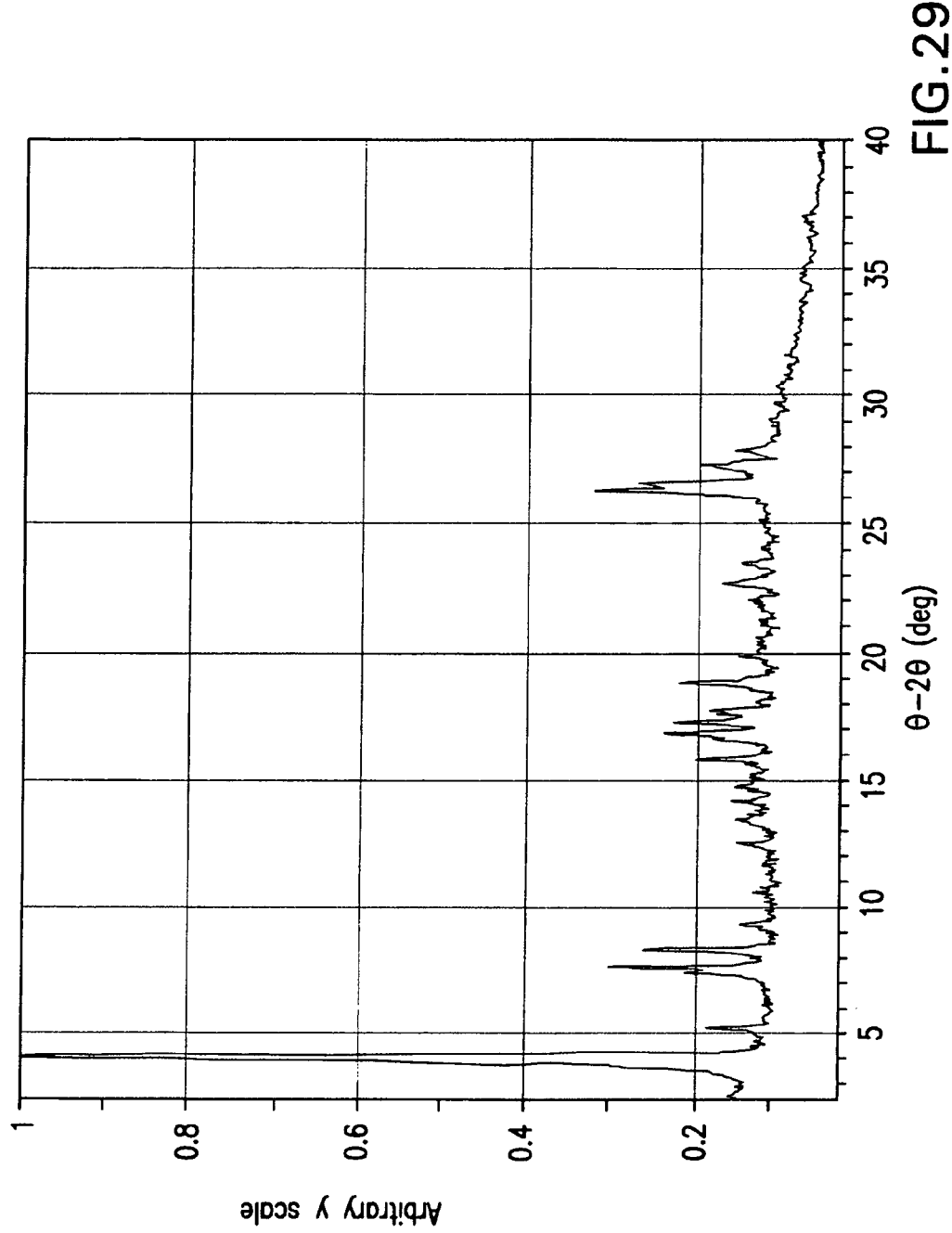

FIG. 29 provides a representative XRPD pattern of Form F of the hydrochloride salt of Compound B1.

Figure 30:
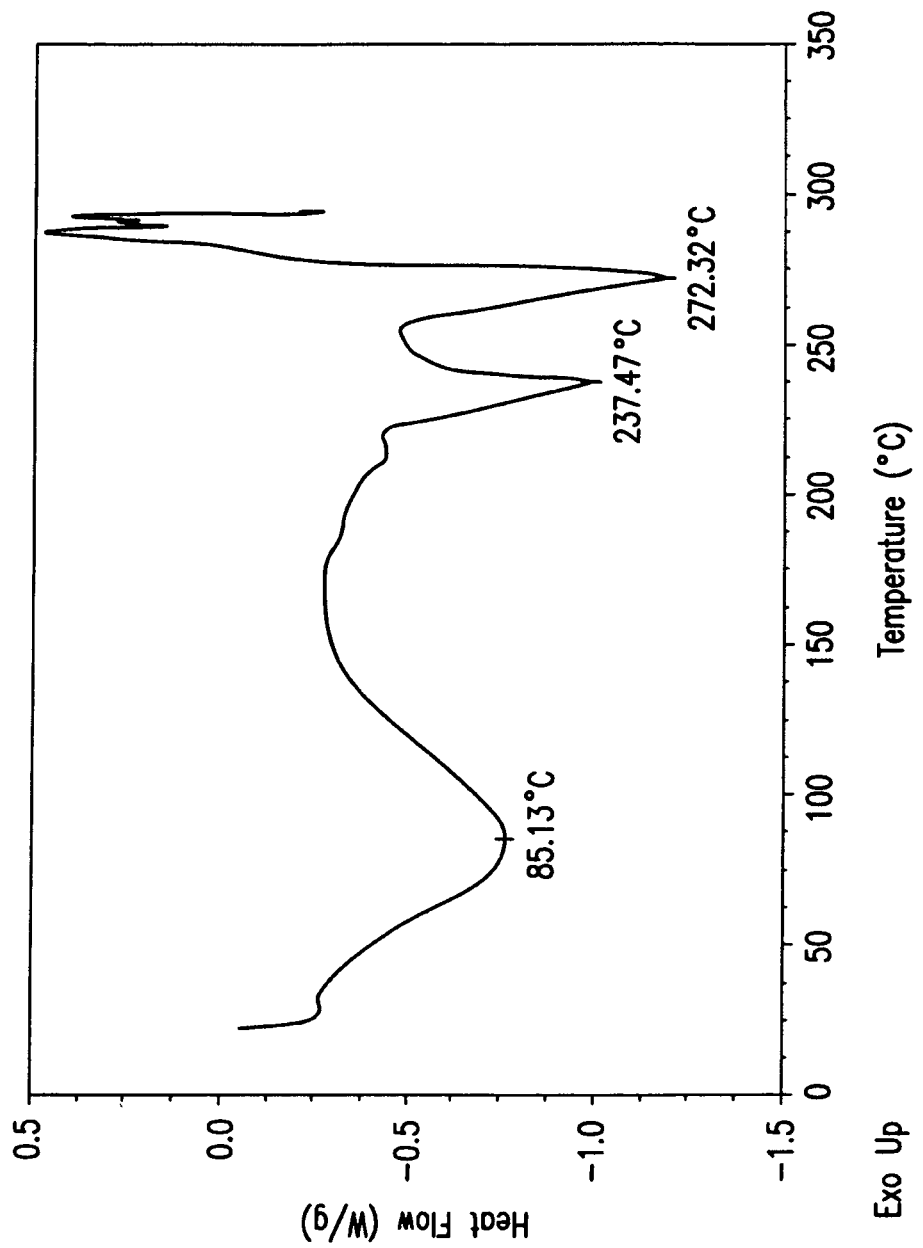

FIG. 30 provides a representative DSC thermogram of Form F of the hydrochloride salt of Compound B1.

Figure 31:
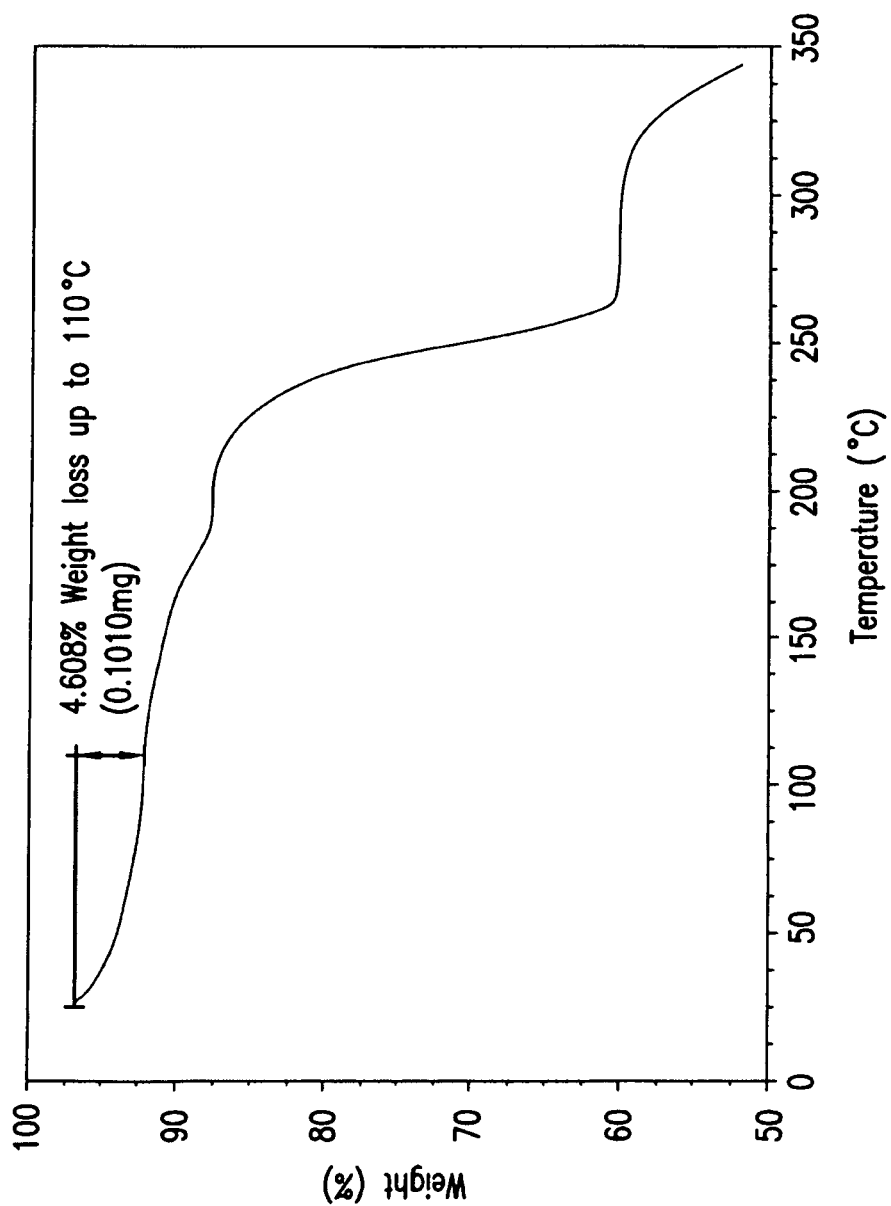

FIG. 31 provides a representative TGA thermogram of Form F of the hydrochloride salt of Compound B1.

Figure 32:
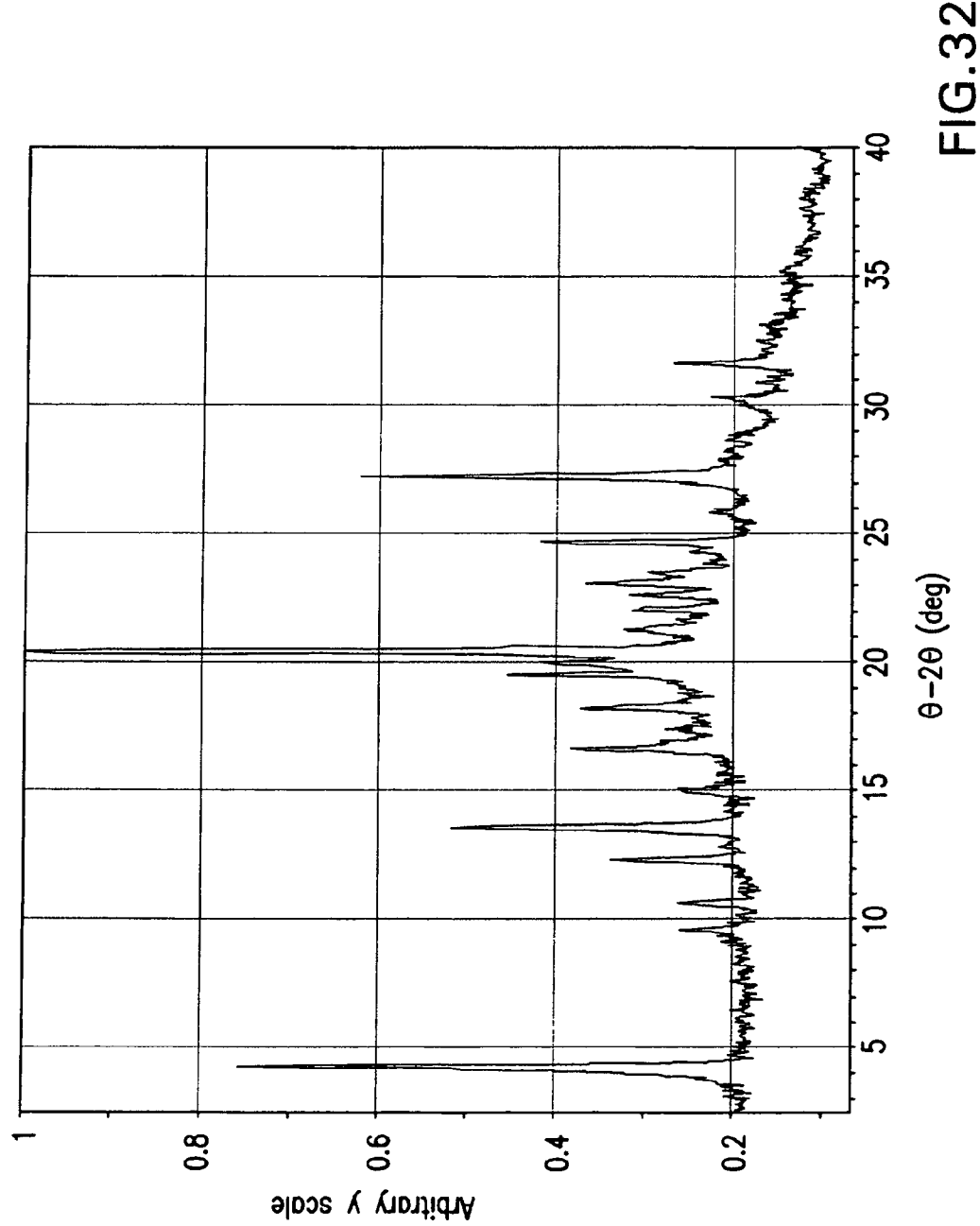

FIG. 32 provides a representative XRPD pattern of Form G of the hydrochloride salt of Compound B1.

Figure 33:
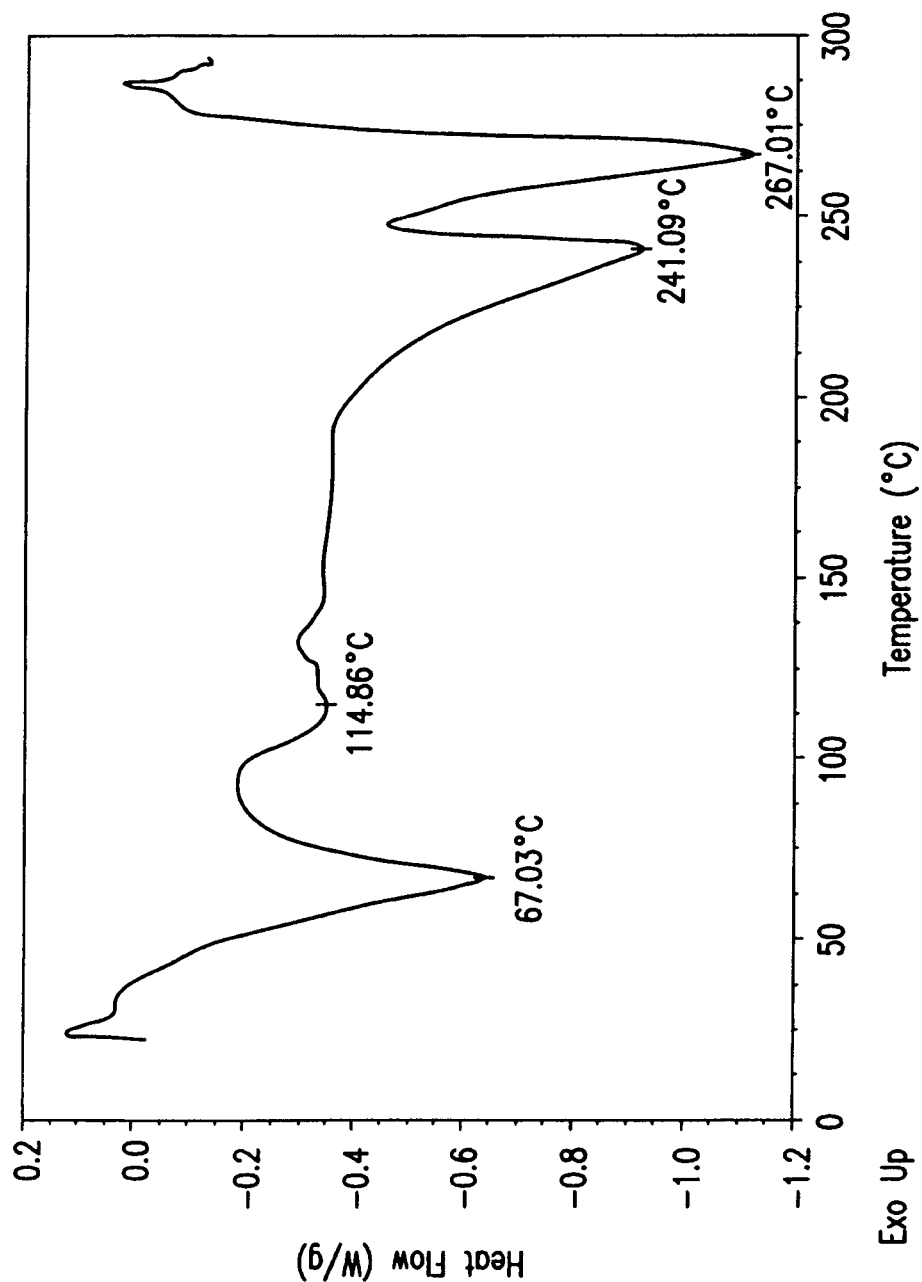

FIG. 33 provides a representative DSC thermogram of Form G of the hydrochloride salt of Compound B1.

Figure 34:
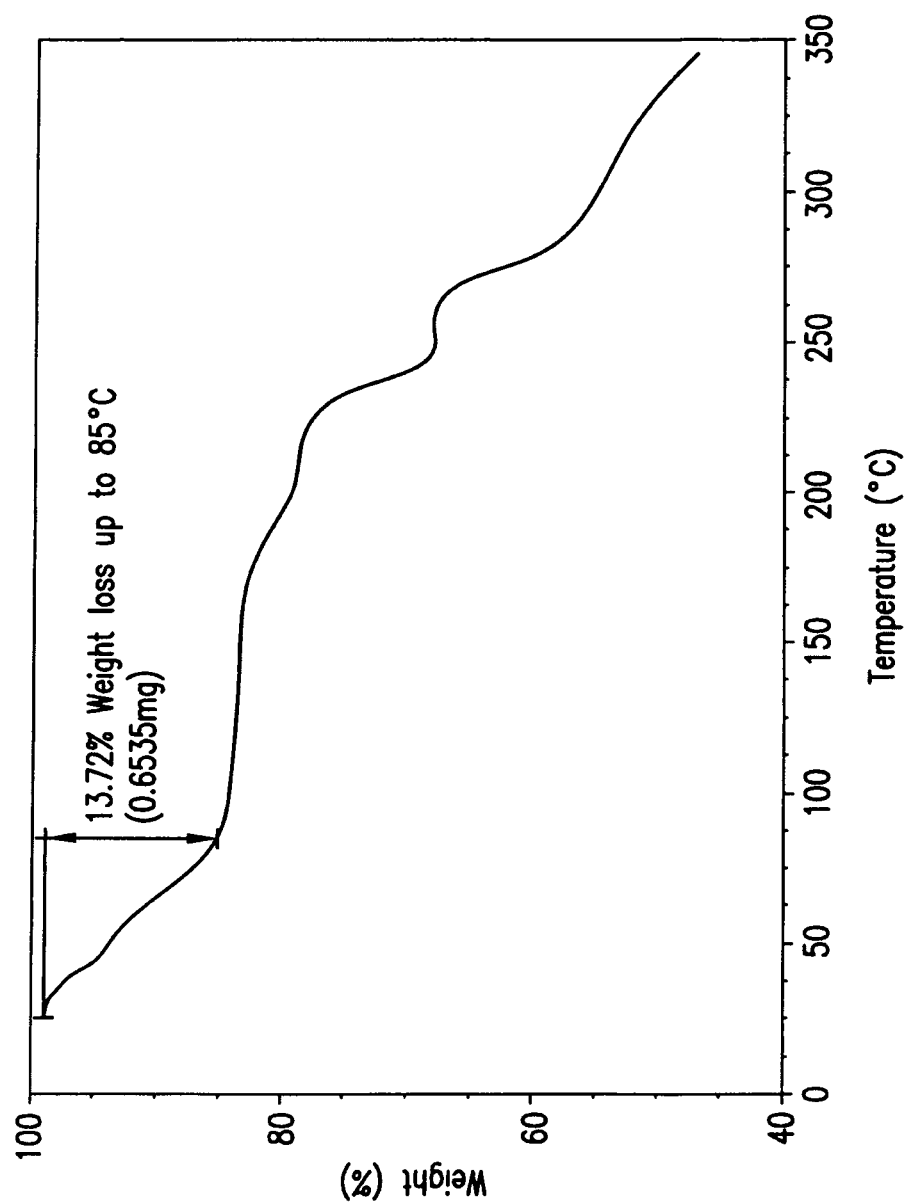

FIG. 34 provides a representative TGA thermogram of Form G of the hydrochloride salt of Compound B1.

Figure 35:
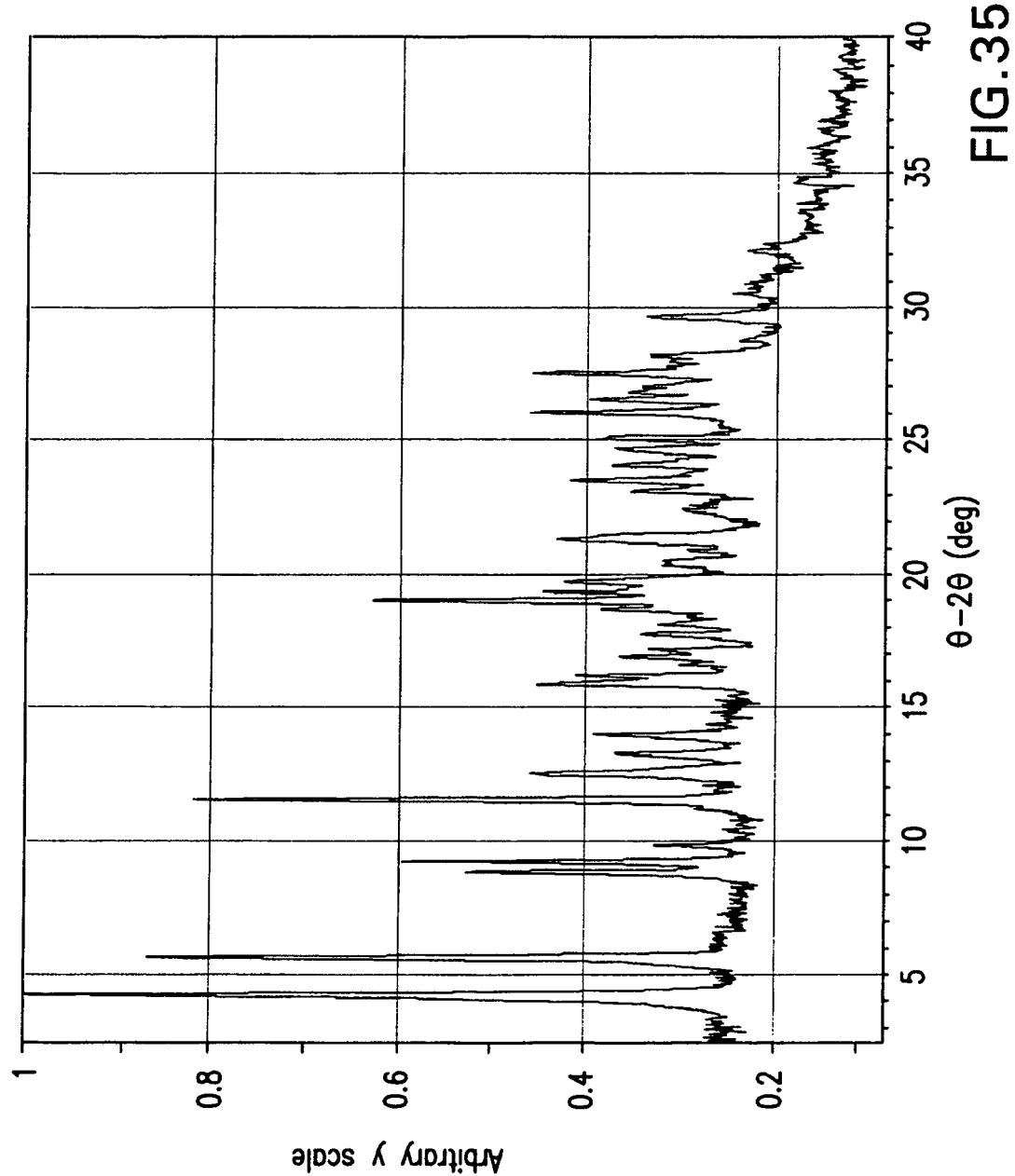

FIG. 35 provides a representative XRPD pattern of Form H of the hydrochloride salt of Compound B1.

Figure 36:
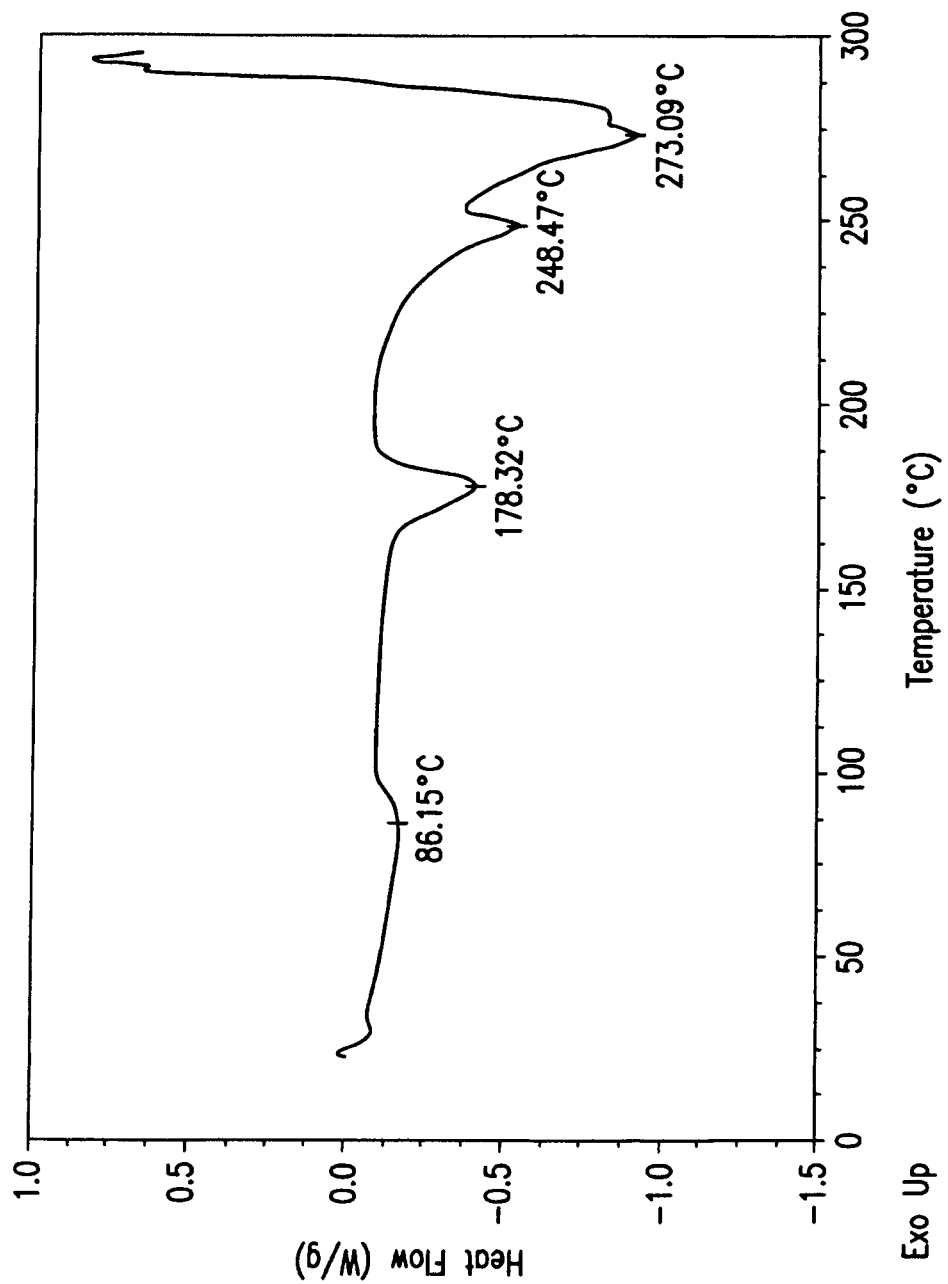

FIG. 36 provides a representative DSC thermogram of Form H of the hydrochloride salt of Compound B1.

Figure 37:
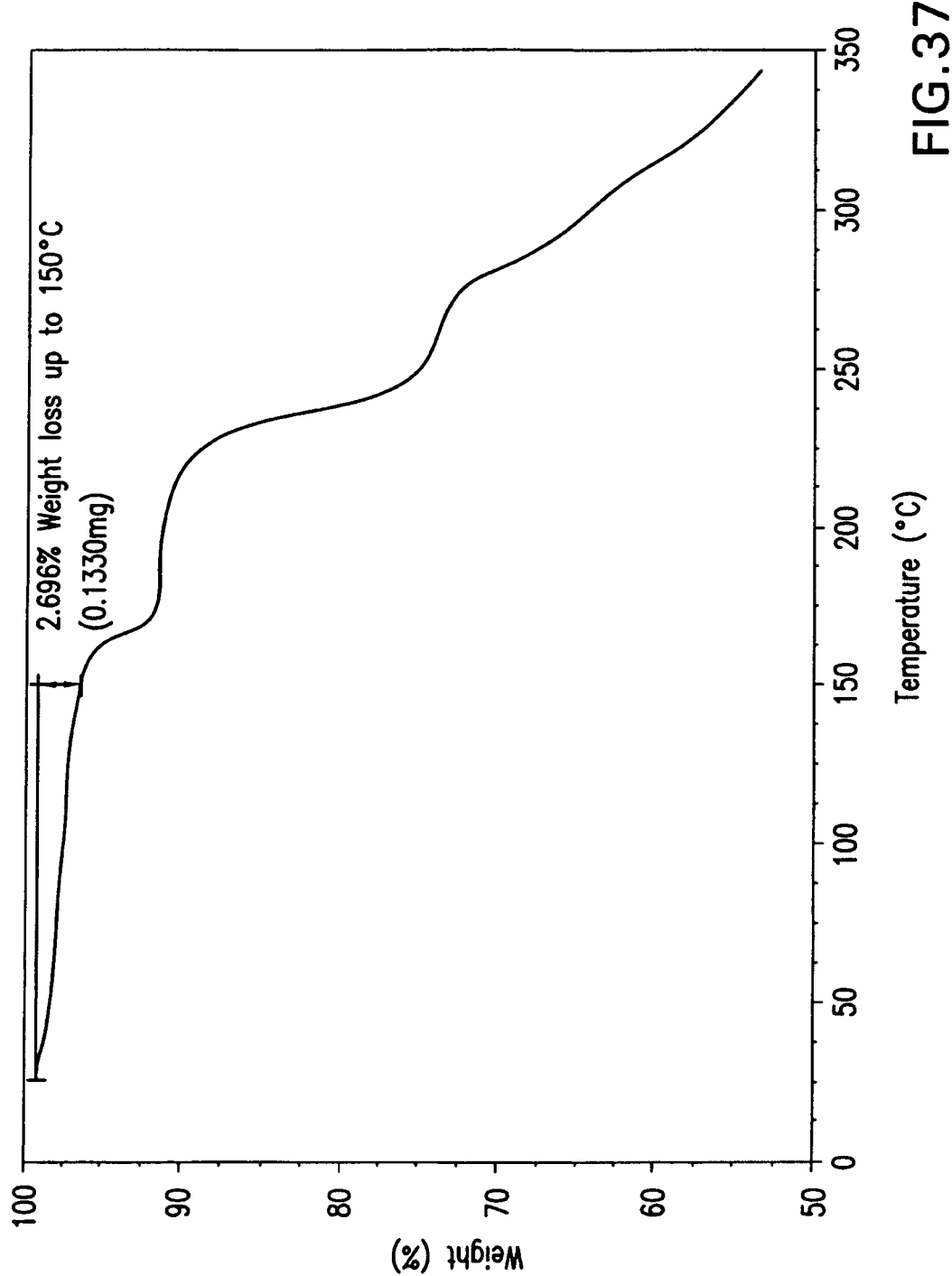

FIG. 37 provides a representative TGA thermogram of Form H of the hydrochloride salt of Compound B1.

Figure 38:
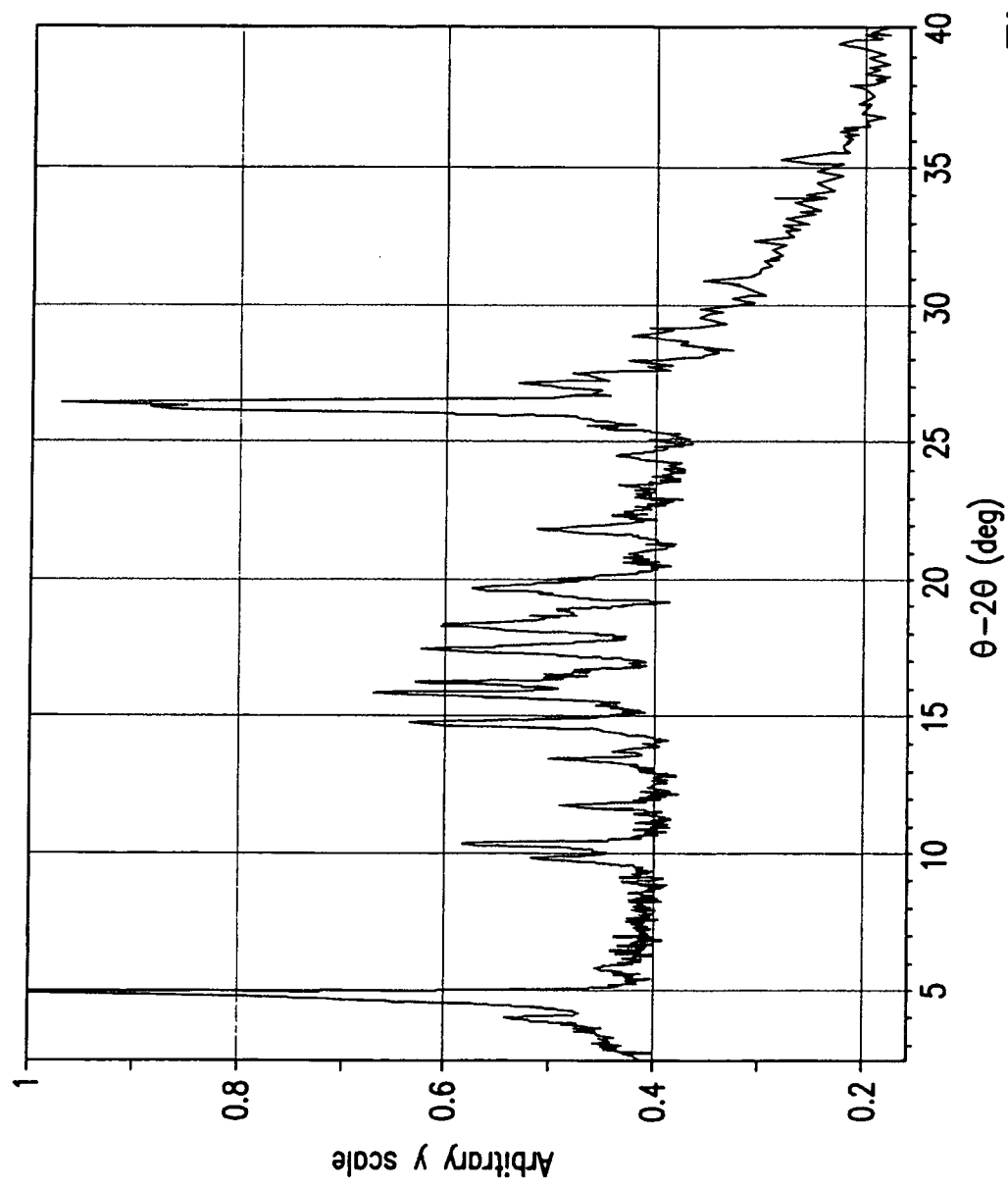

FIG. 38 provides a representative XRPD pattern of Form I of the hydrochloride salt of Compound B1.

Figure 39:
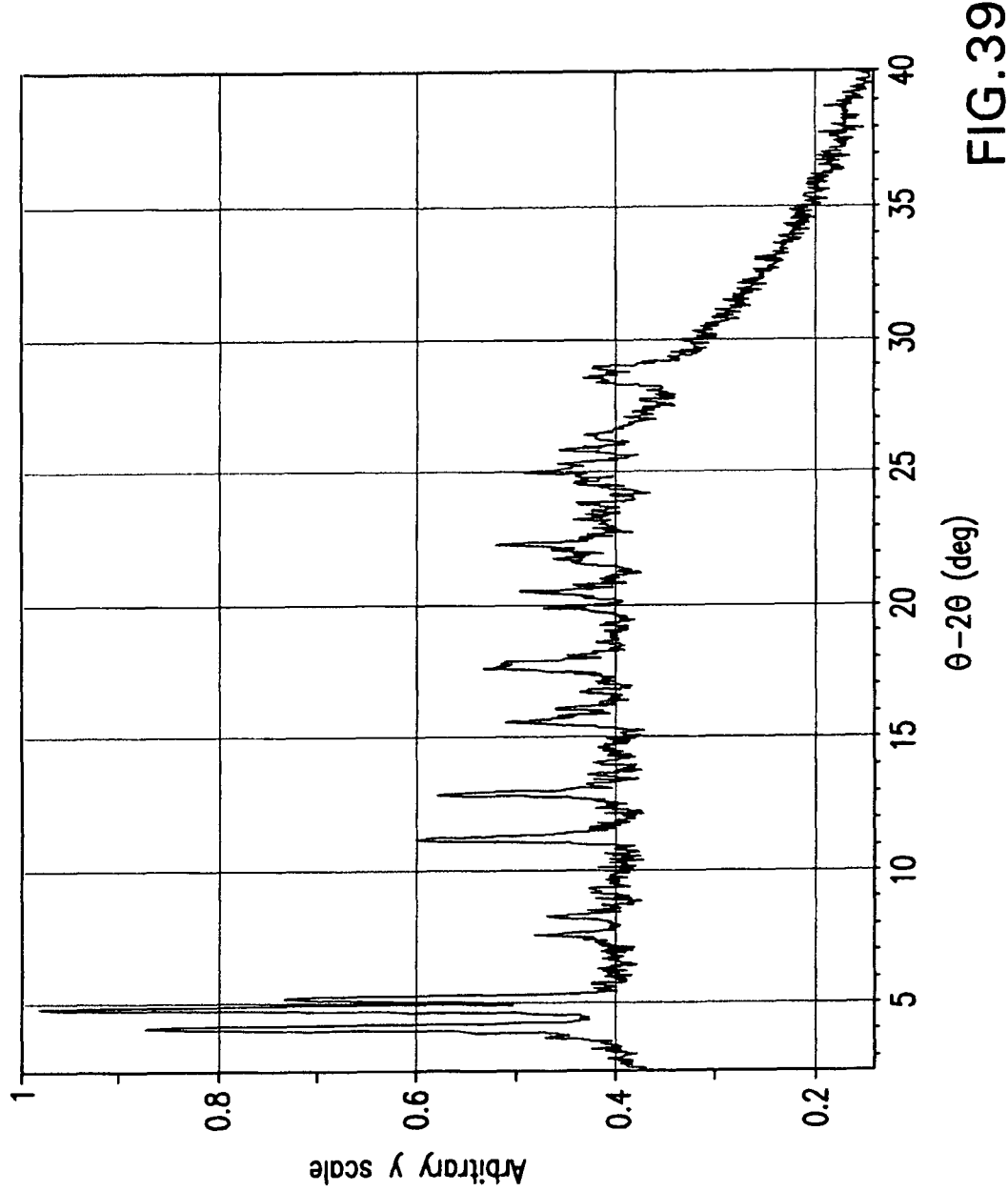

FIG. 39 provides a representative XRPD pattern of Form J of the hydrochloride salt of Compound B1.

Figure 40:
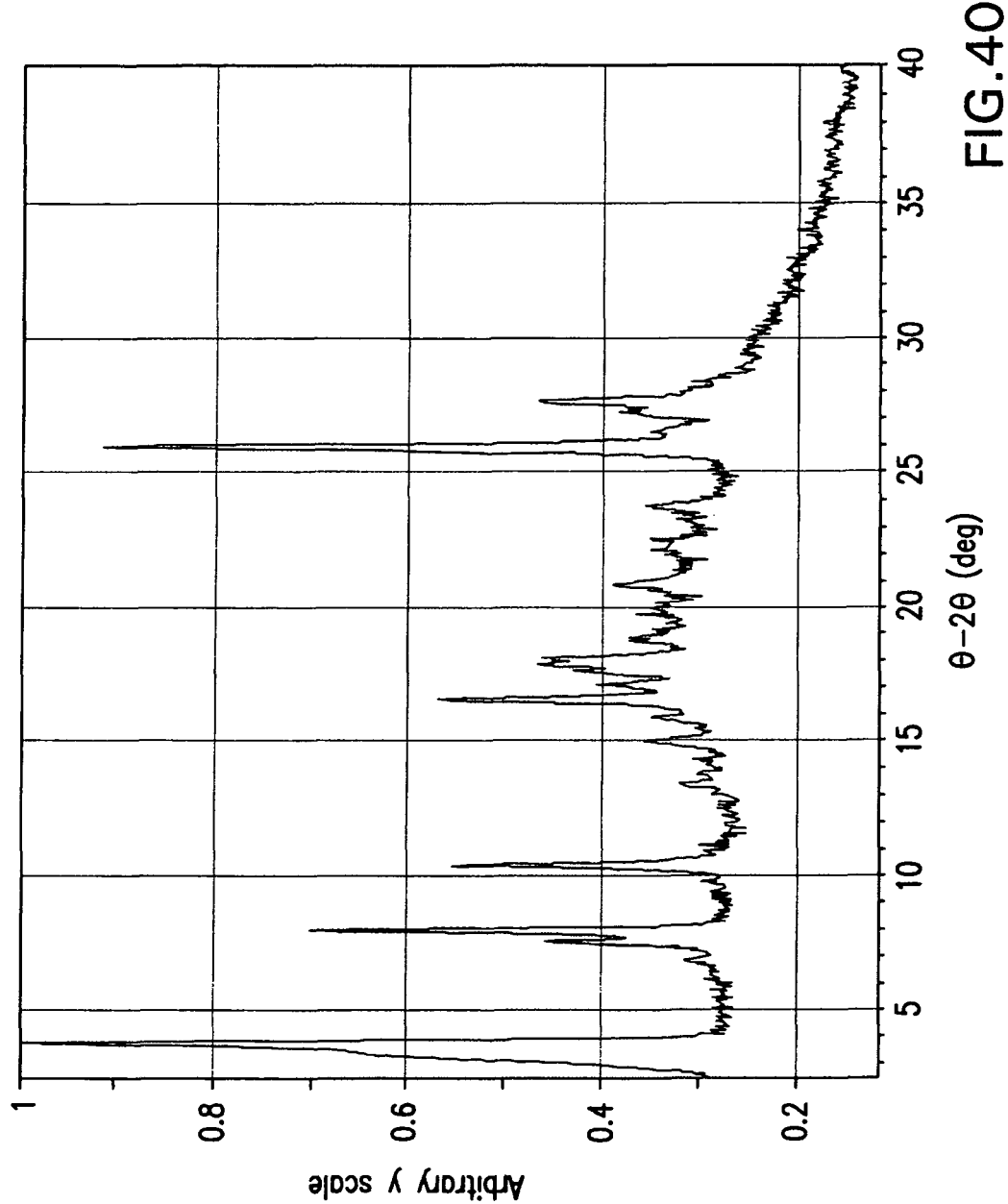

FIG. 40 provides a representative XRPD pattern of Form K of the hydrochloride salt of Compound B1.

Figure 41:
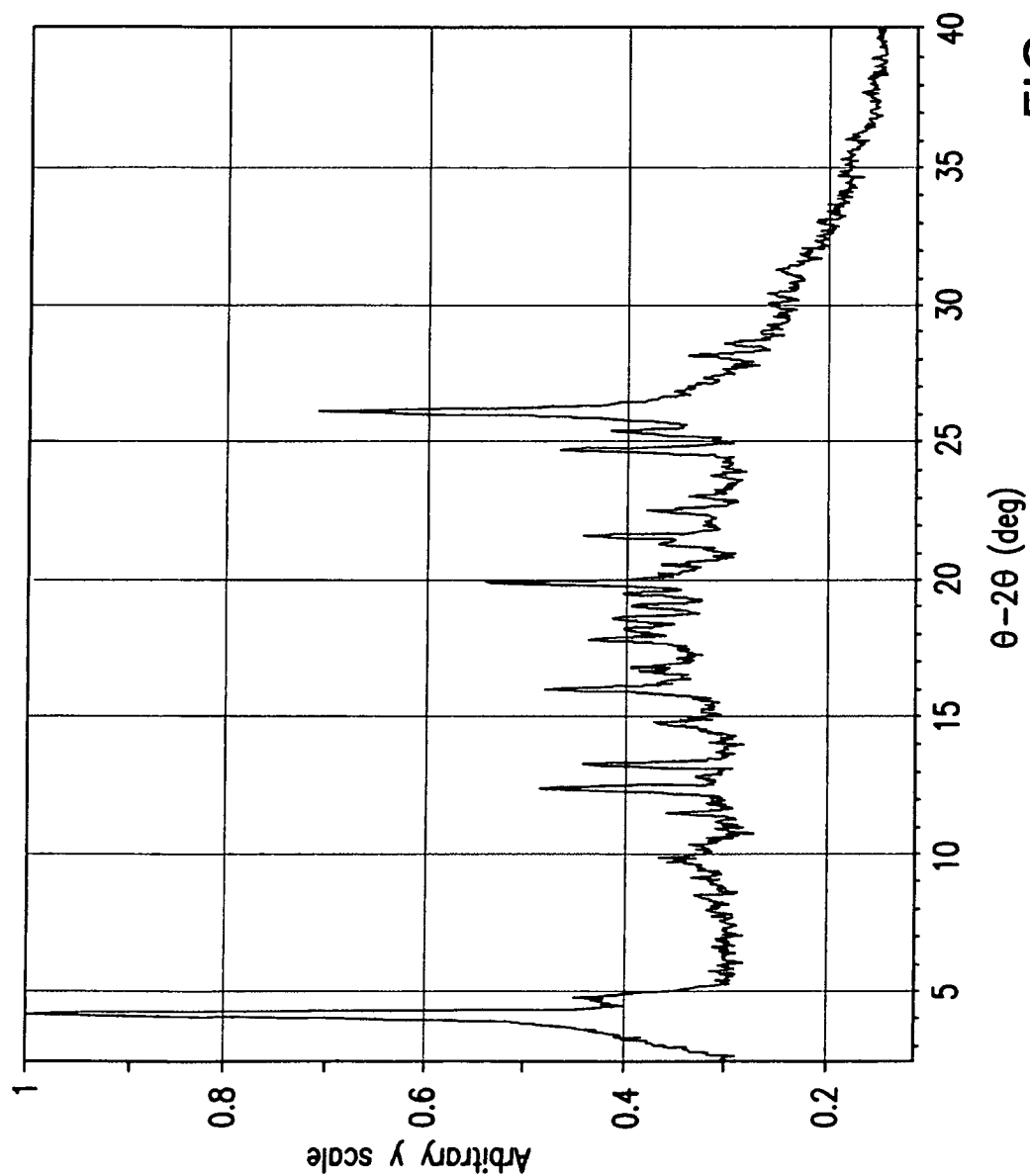

FIG. 41 provides a representative XRPD pattern of Form L of the hydrochloride salt of Compound B1.

Figure 42:
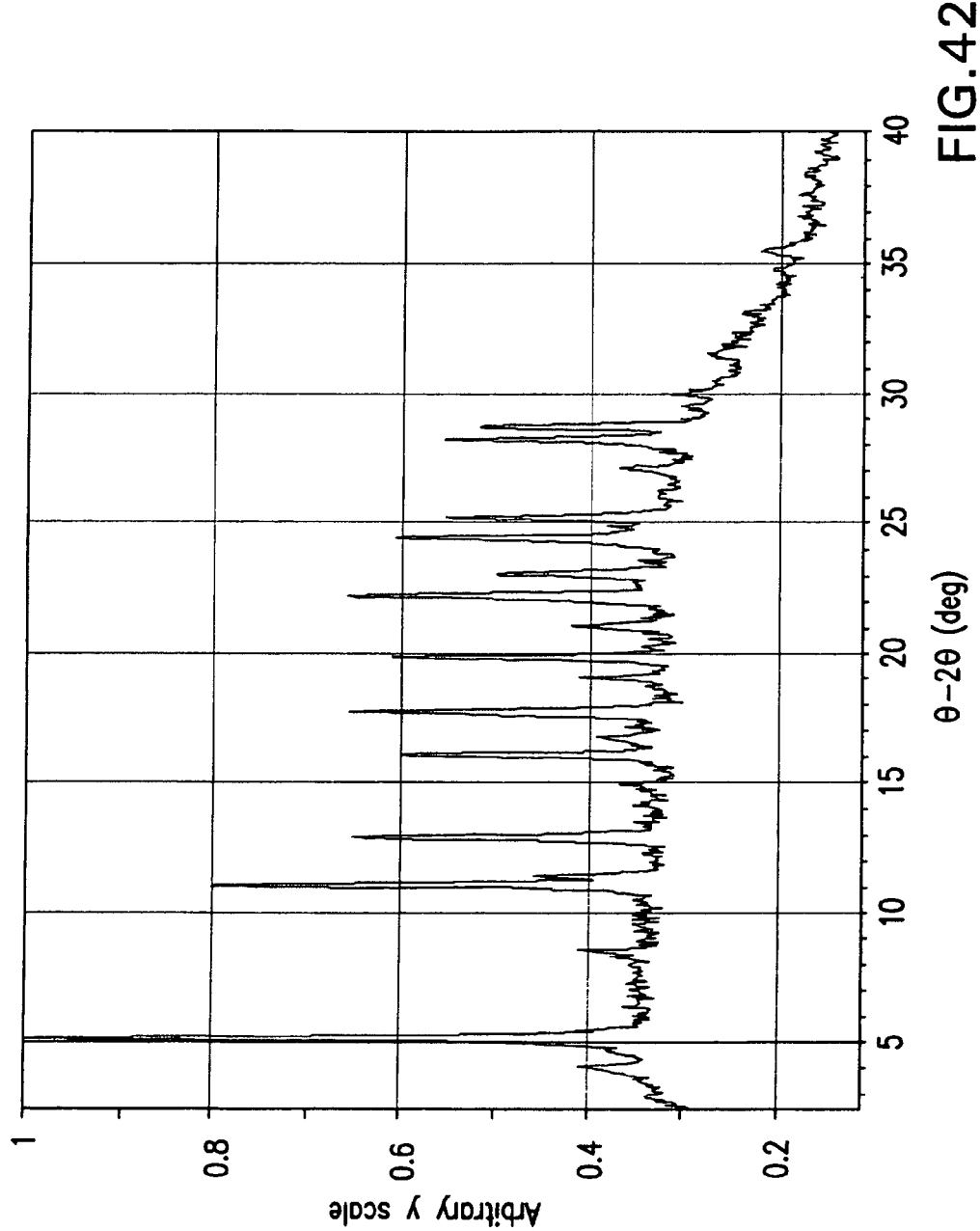

FIG. 42 provides a representative XRPD pattern of Form M of the hydrochloride salt of Compound B1.

Figure 43:
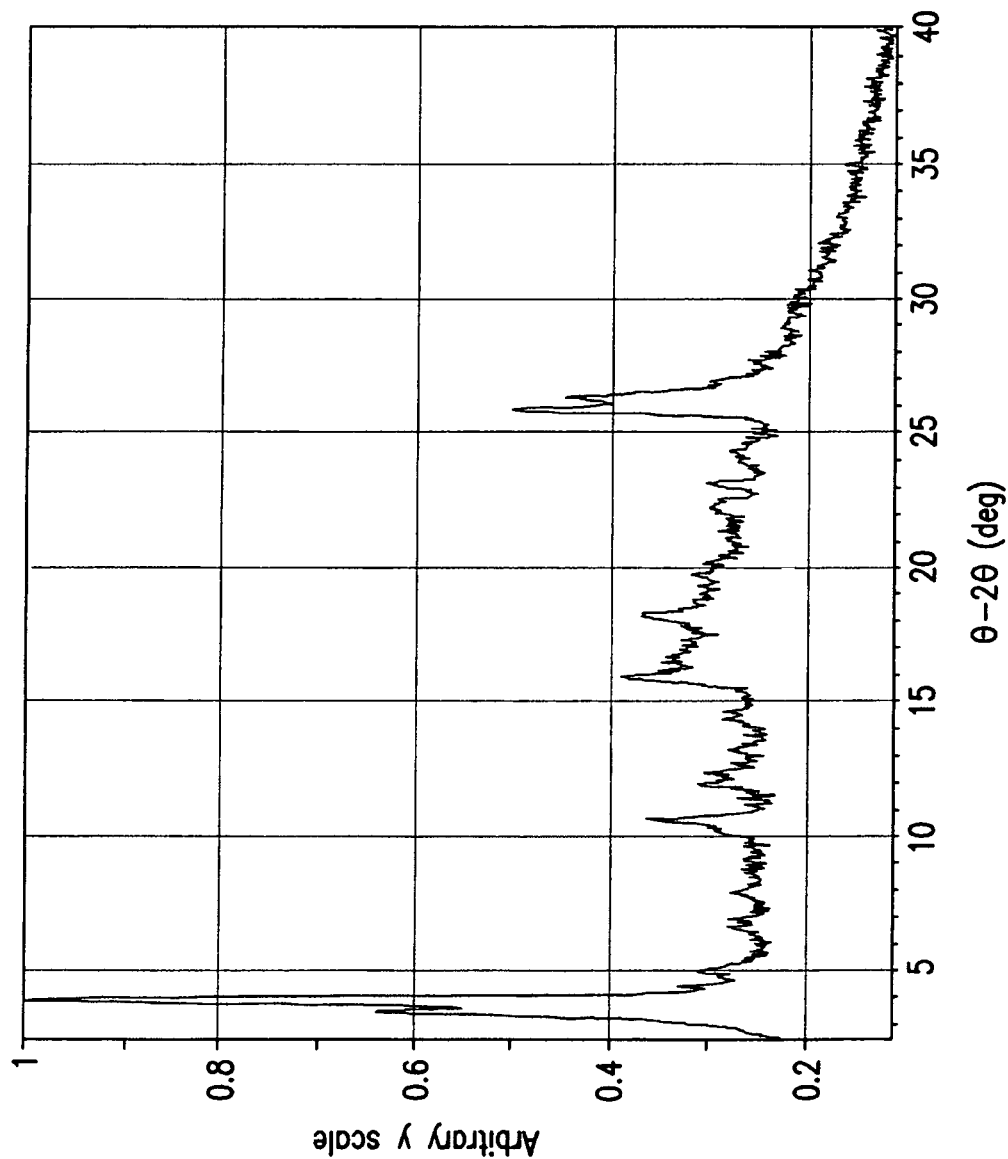

FIG. 43 provides a representative XRPD pattern of Form N of the hydrochloride salt of Compound B1.

Figure 44:
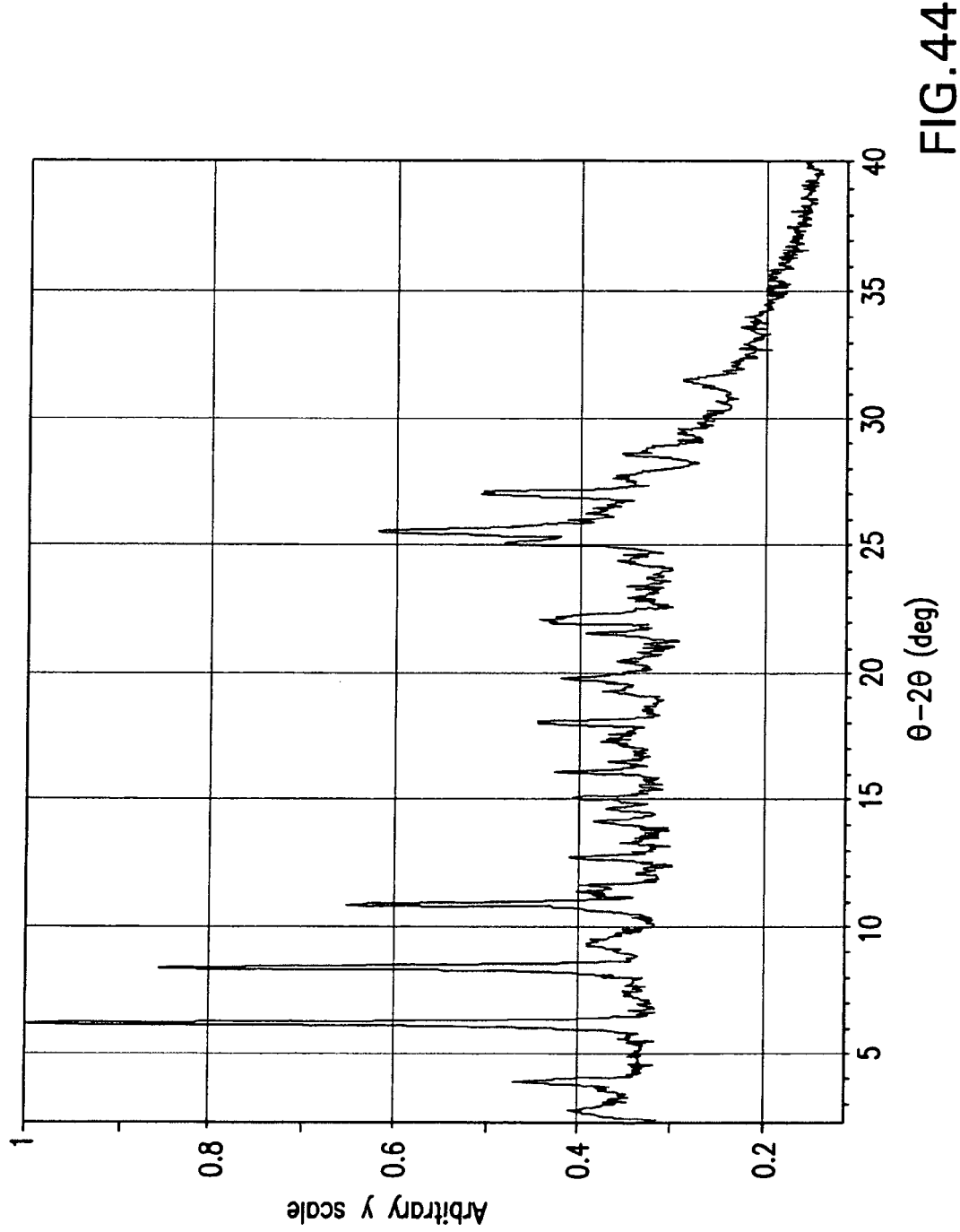

FIG. 44 provides a representative XRPD pattern of Form O of the hydrochloride salt of Compound B1.

Figure 45:
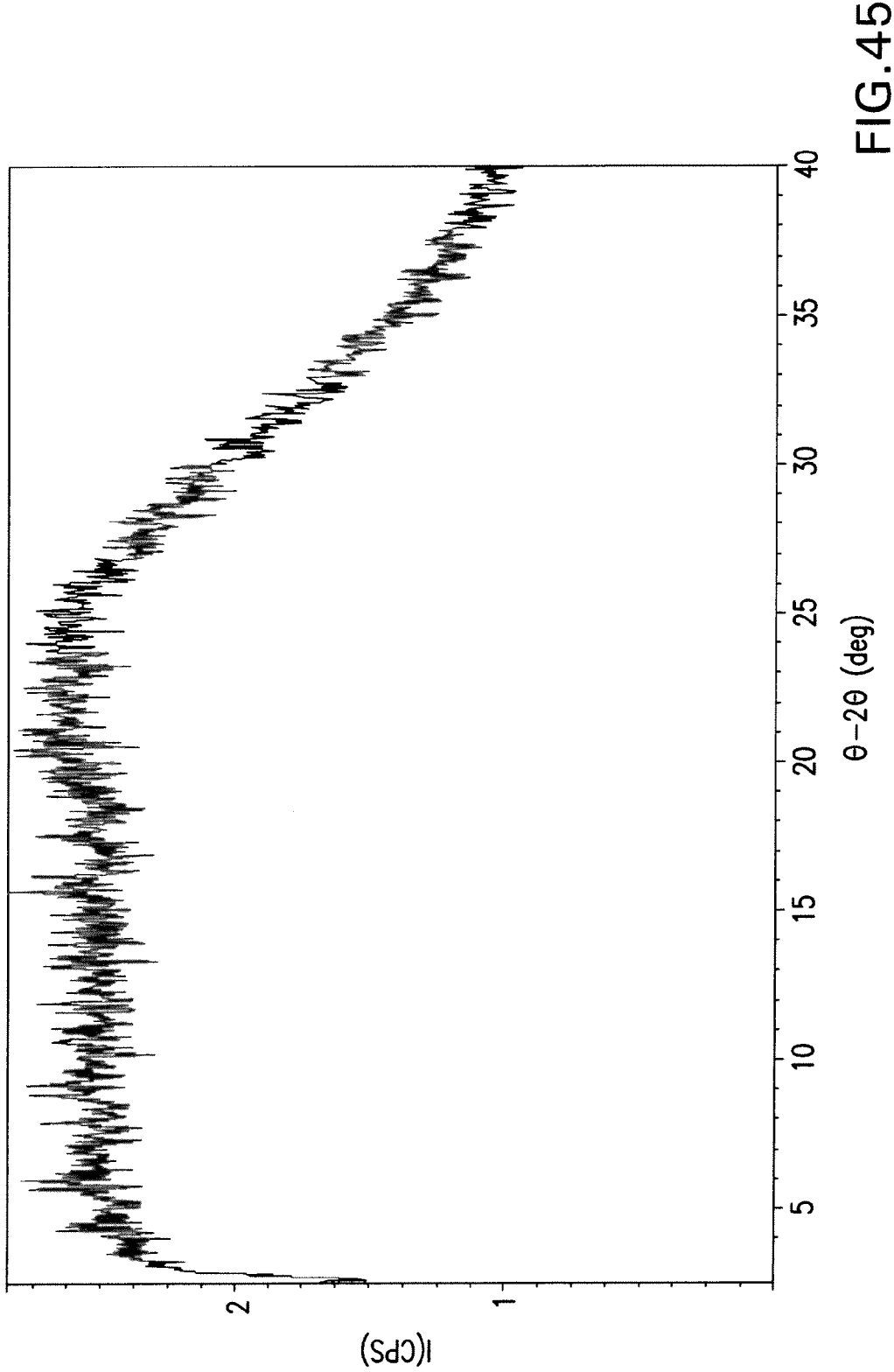

FIG. 45 provides a representative XRPD pattern of an amorphous form of the hydrochloride salt of Compound B1.

Figure 46:
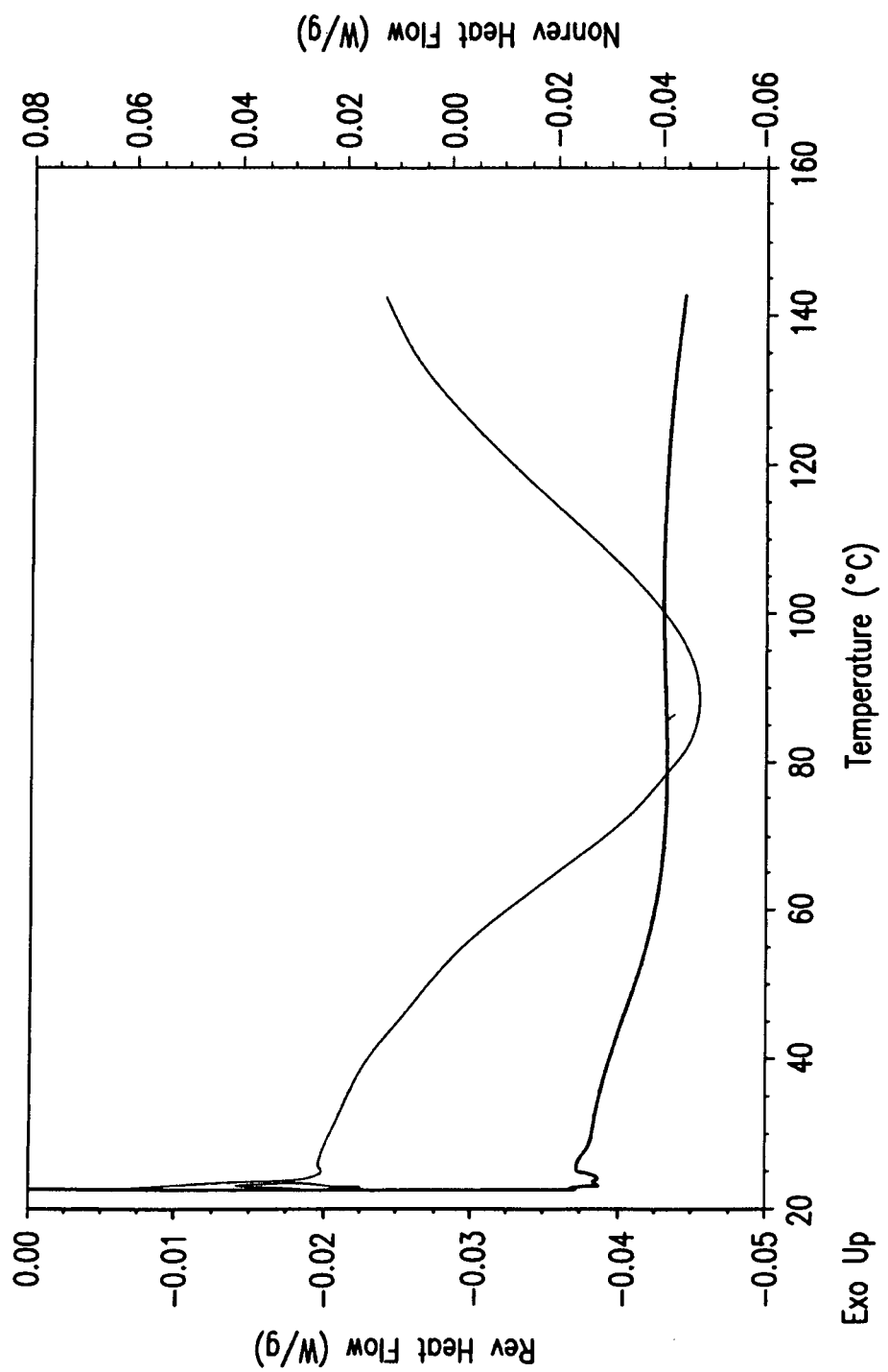

FIG. 46 provides a representative modulated DSC thermogram of an amorphous form of the hydrochloride salt of Compound B1.

Figure 47:
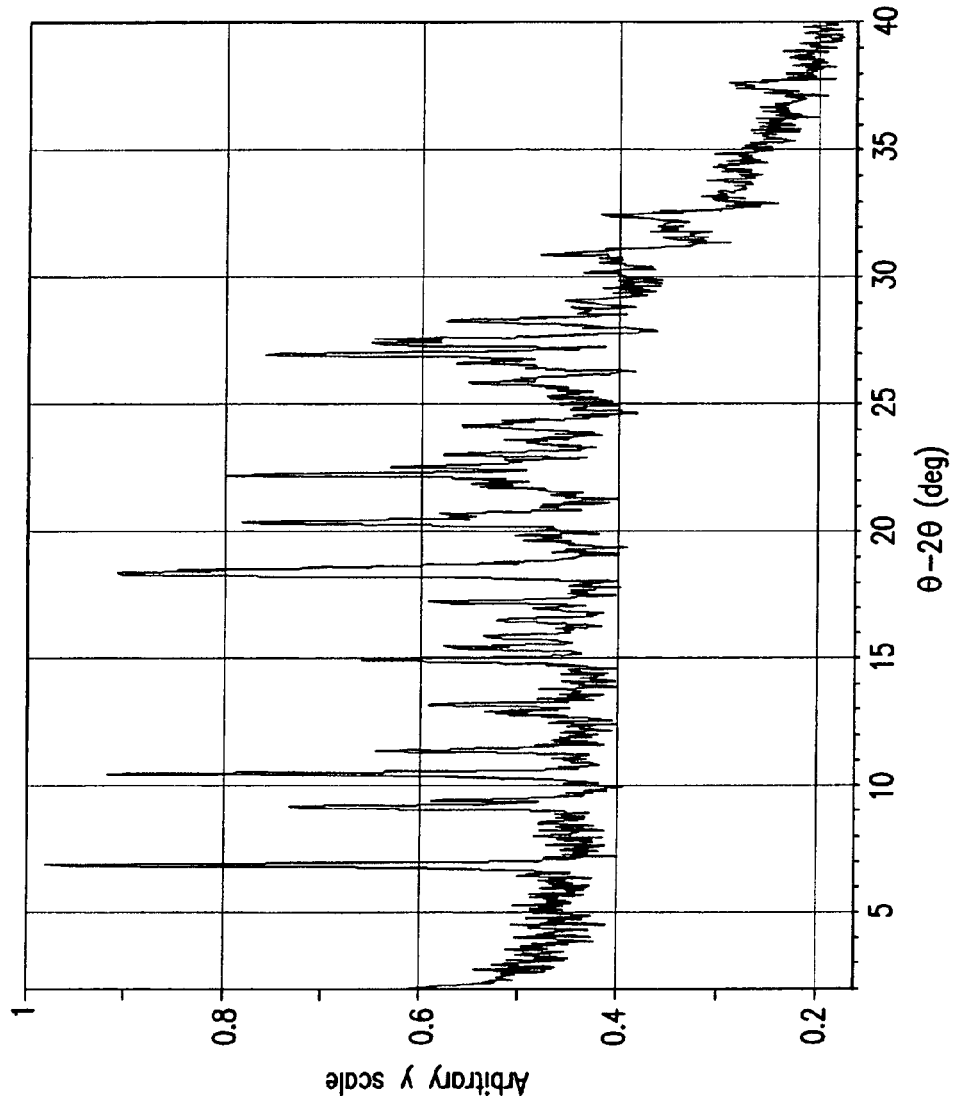

FIG. 47 provides a representative XRPD pattern of Form A of the hydrobromide salt of Compound B1.

Figure 48:
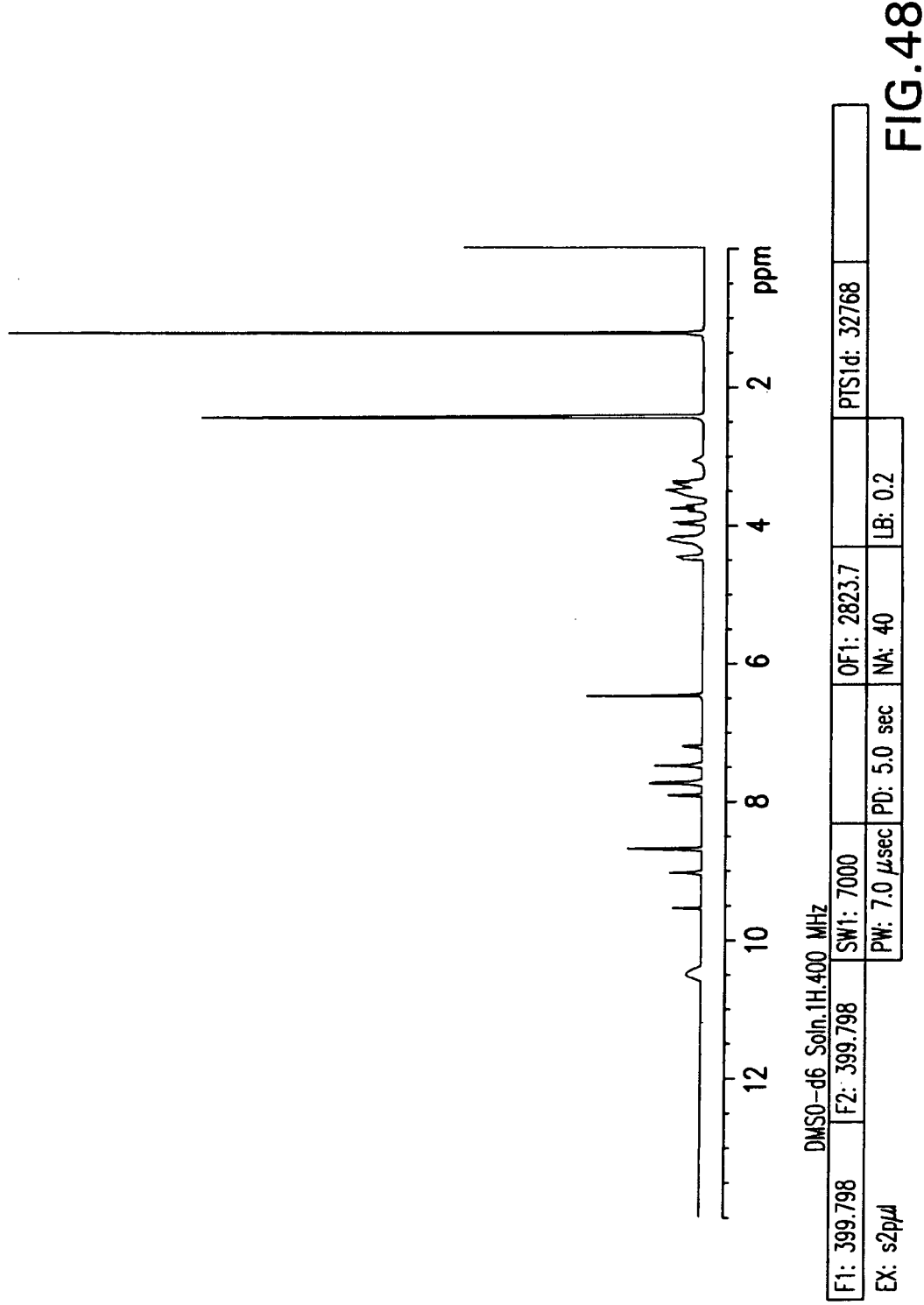

FIG. 48 provides a representative $^1$H NMR spectrum of Form A of the hydrobromide salt of Compound B1.

Figure 49:
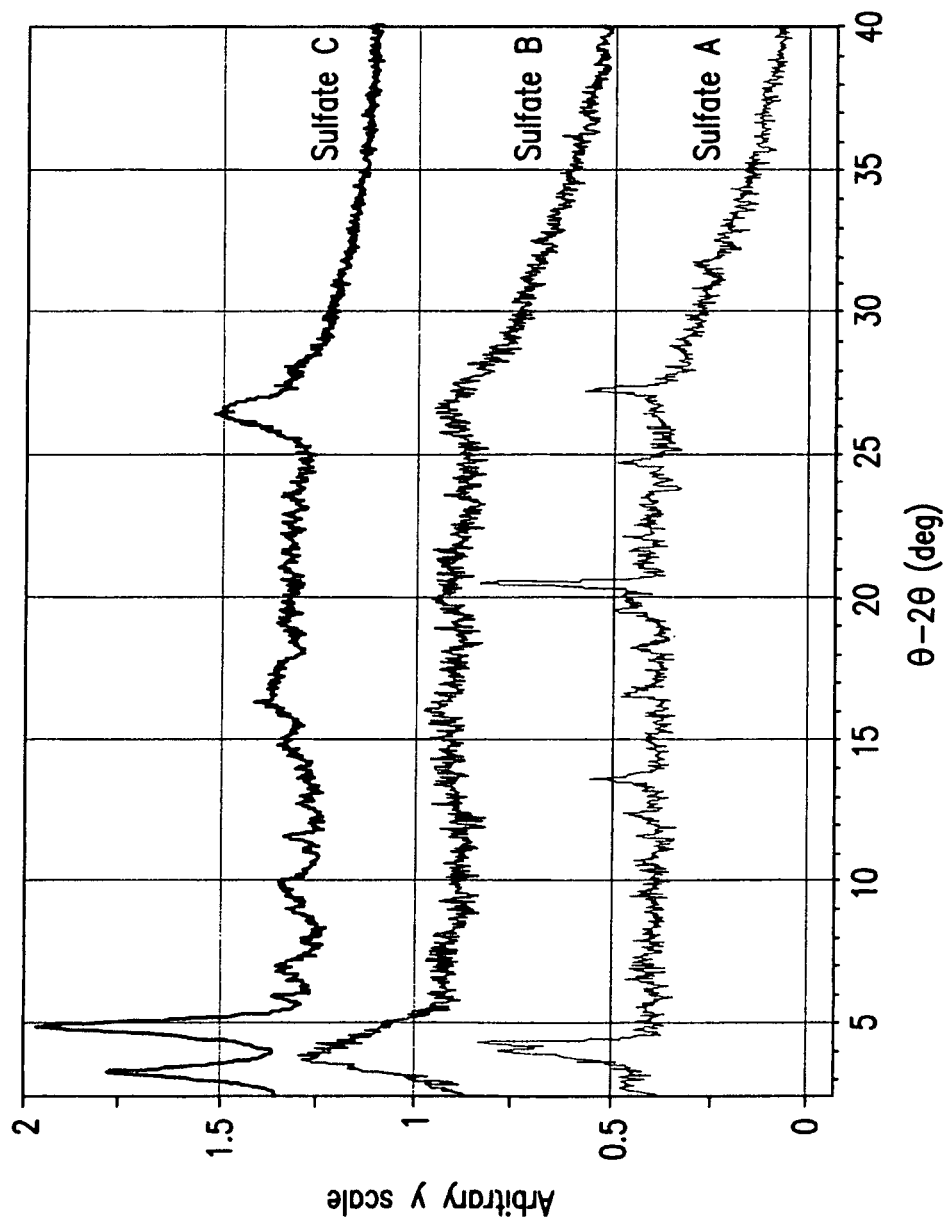

FIG. 49 provides representative XRPD patterns of Form A (bottom), Form B (middle) and Form C (top) of sulfate salts of Compound B1.

Figure 50:
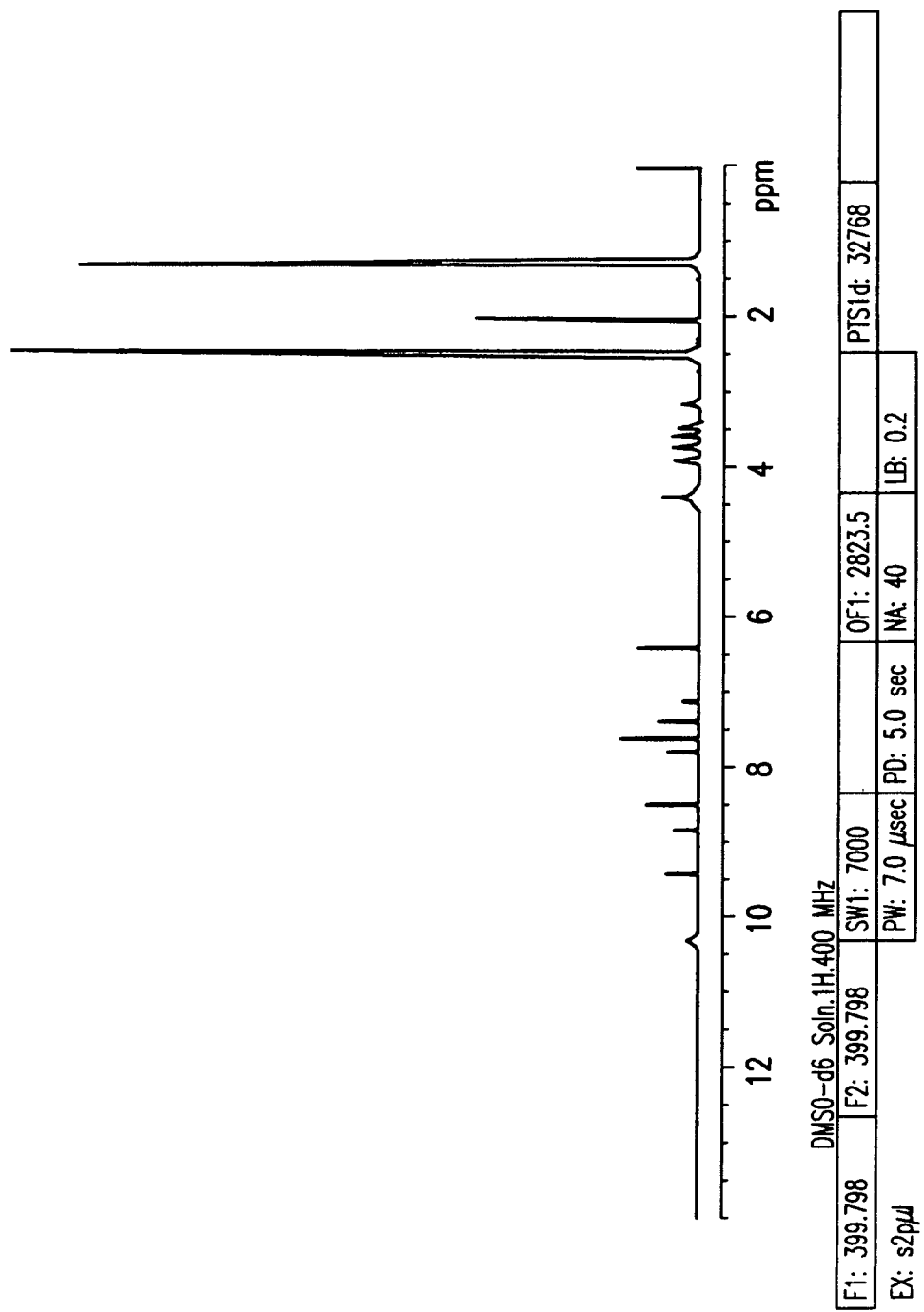

FIG. 50 provides a representative $^1$H NMR spectrum of Form C of the sulfate salt of Compound B1.

Figure 51:
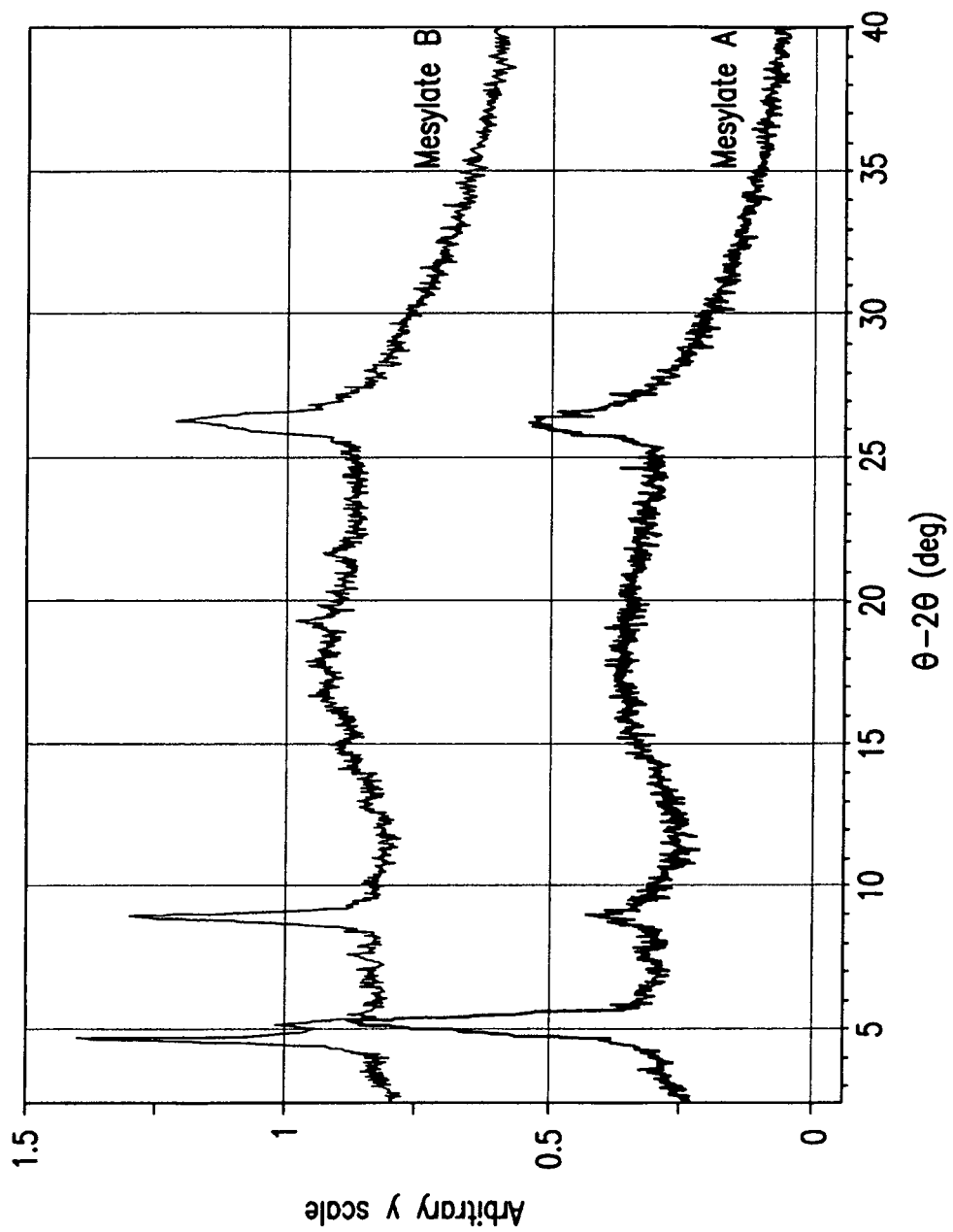

FIG. 51 provides representative XRPD patterns of Form A (bottom) and Form B (top) of mesylate salts of Compound B1.

Figure 52:
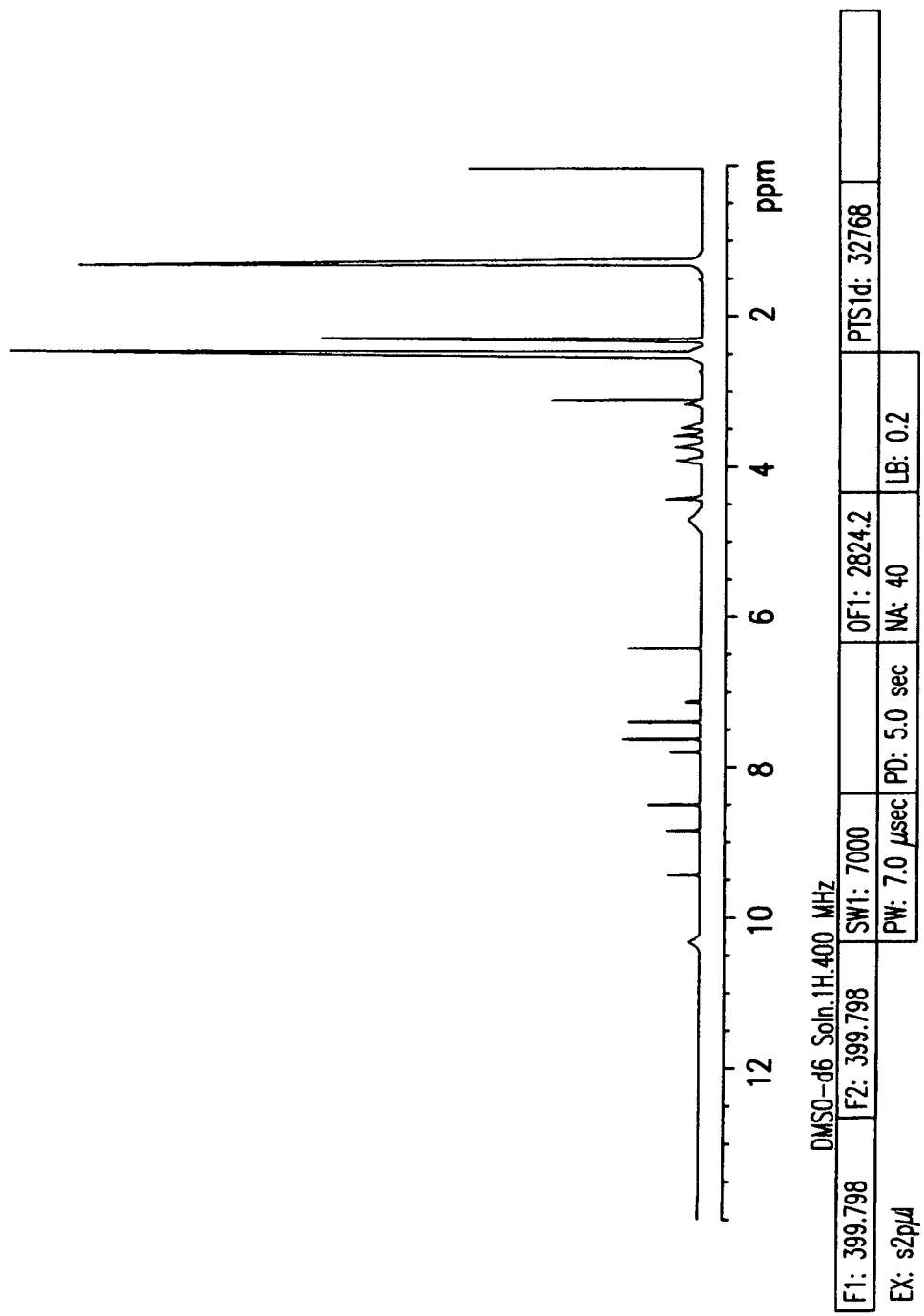

FIG. 52 provides a representative H NMR spectrum of Form A of the mesylate salt of Compound B1.

Figure 53:
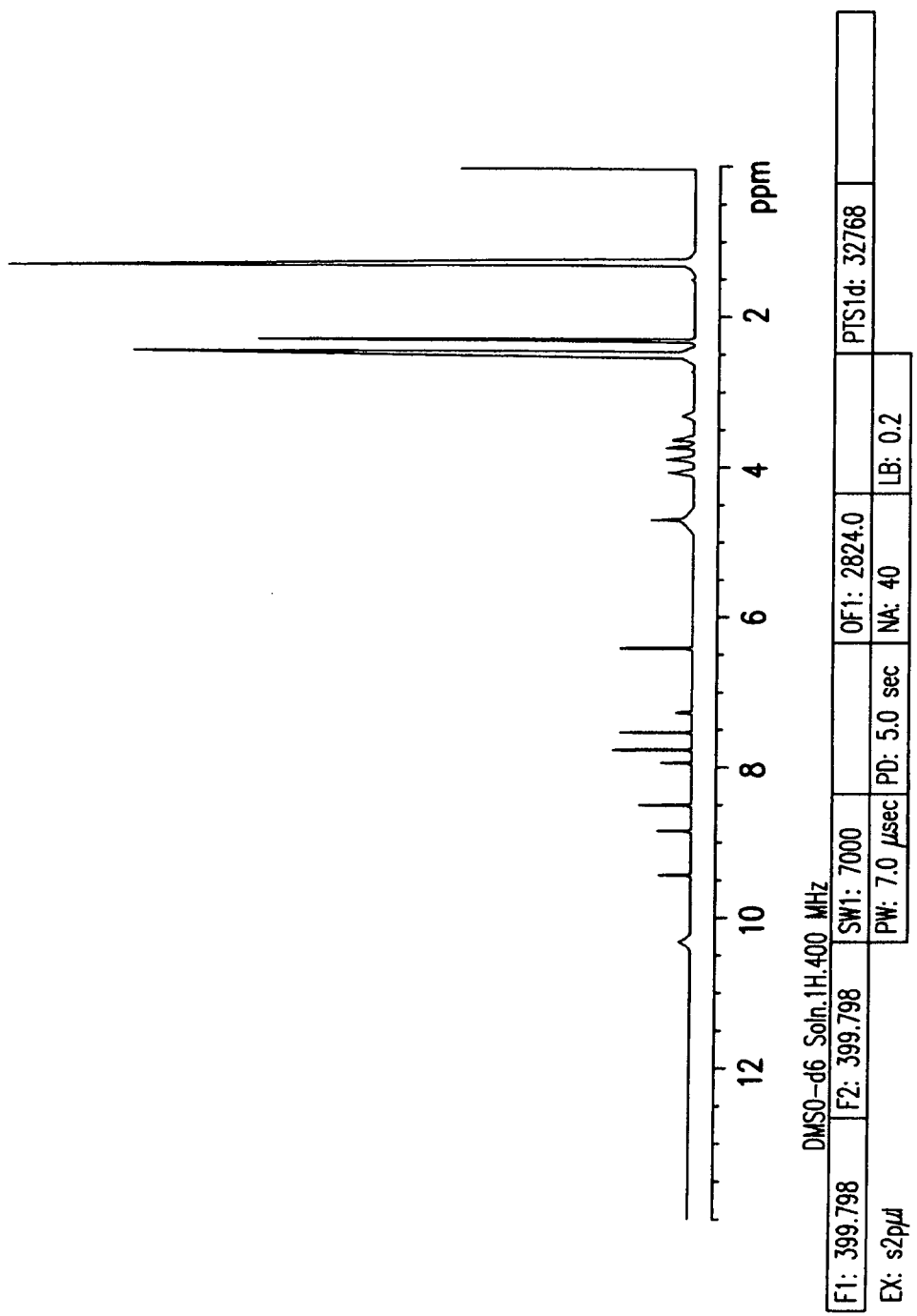

FIG. 53 provides a representative $^1$H NMR spectrum of Form B of the mesylate salt of Compound B1.

Figure 54:
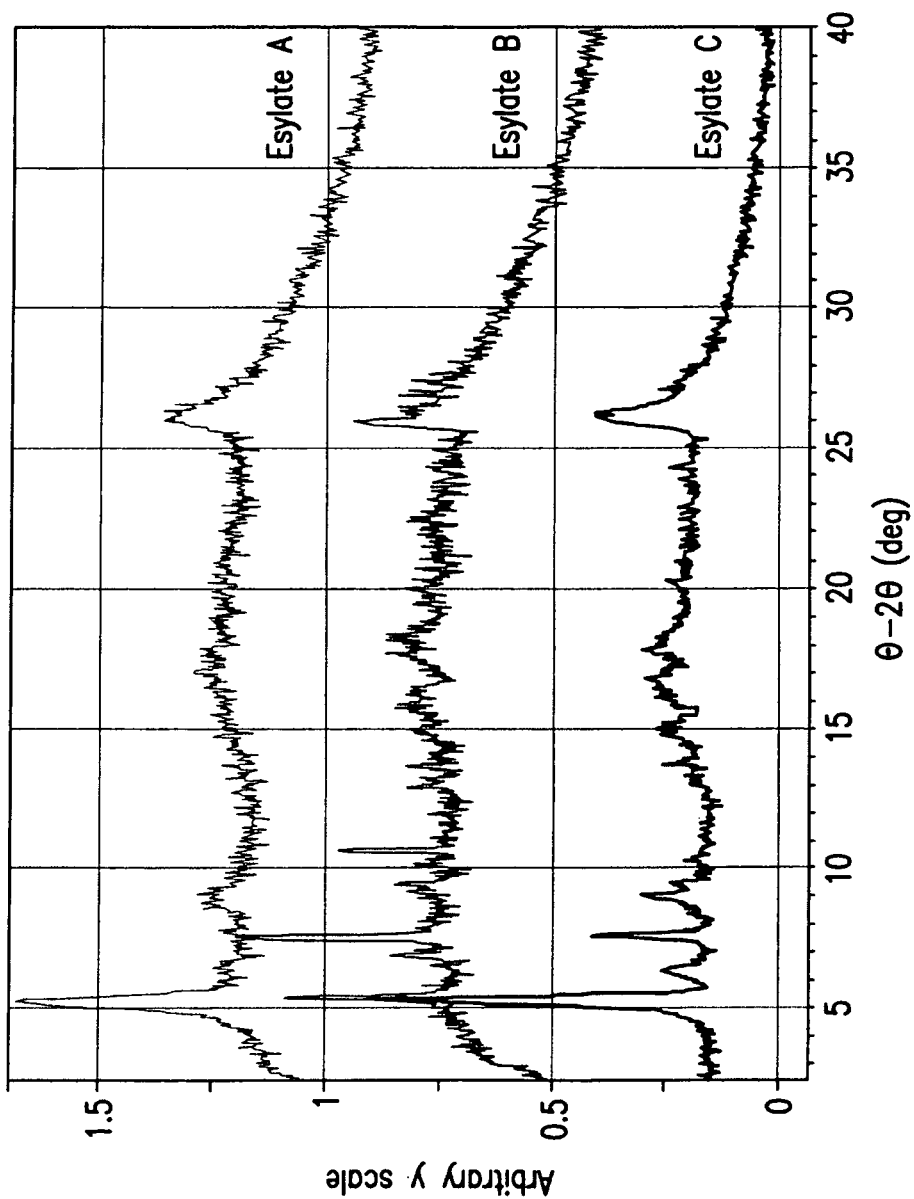

FIG. 54 provides representative XRPD patterns of Form A (top), Form B (middle) and Form C (bottom) of esylate salts of Compound B1.

Figure 55:
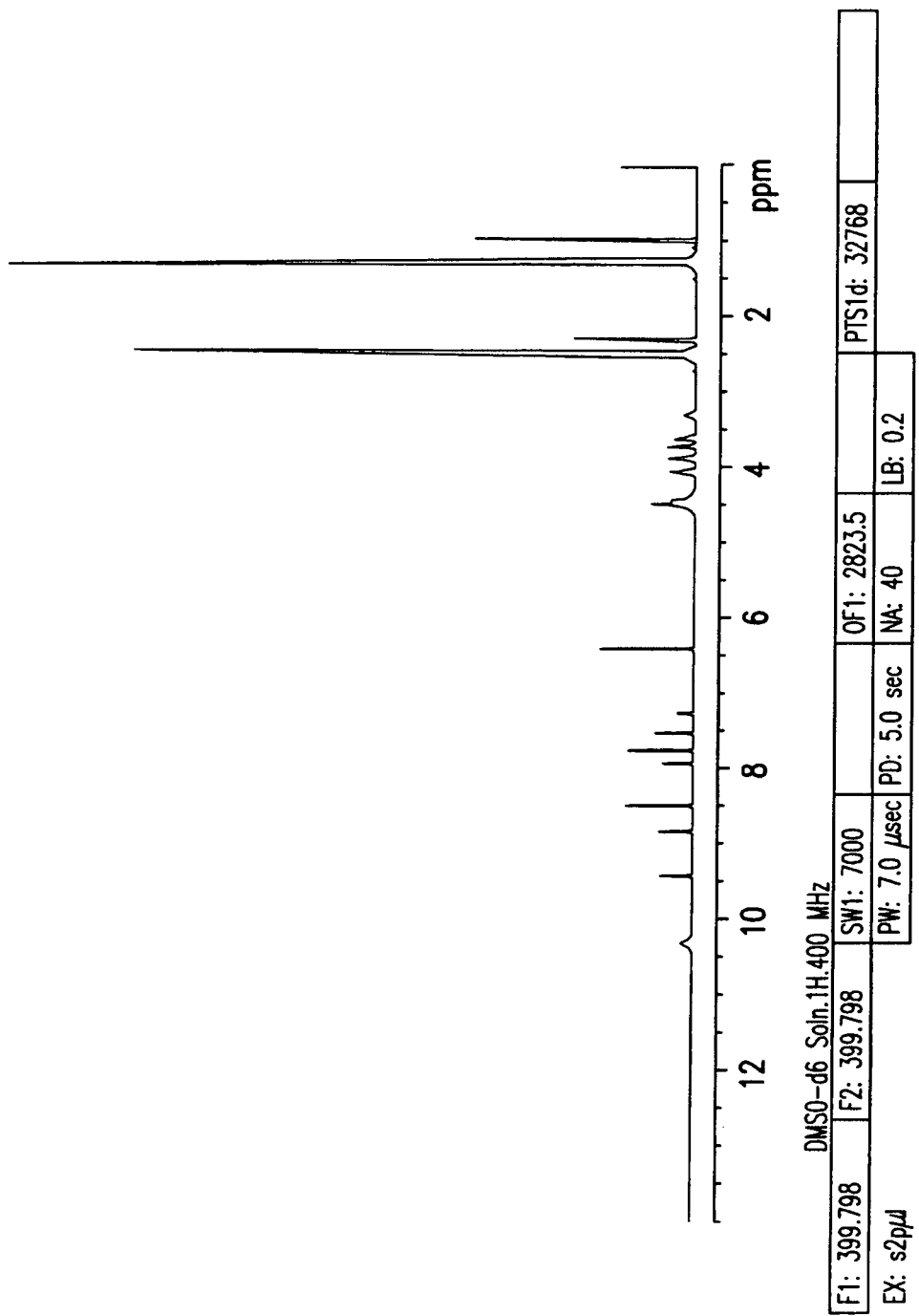

FIG. 55 provides a representative $^1$H NMR spectrum of Form B of the esylate salt of Compound B1.

Figure 56:
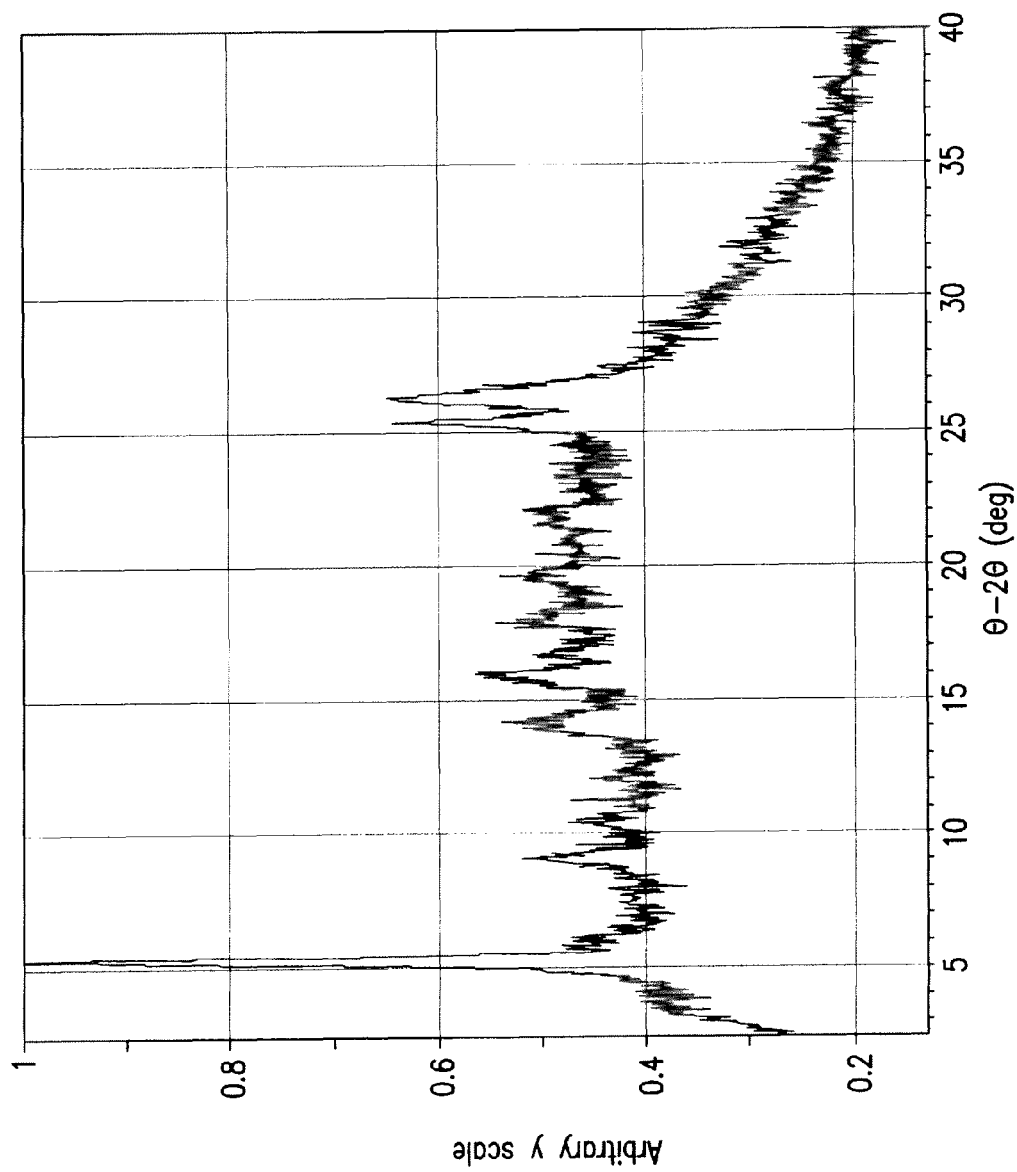

FIG. 56 provides a representative XRPD pattern of Form A of the edisylate salt of Compound B1.

Figure 57:
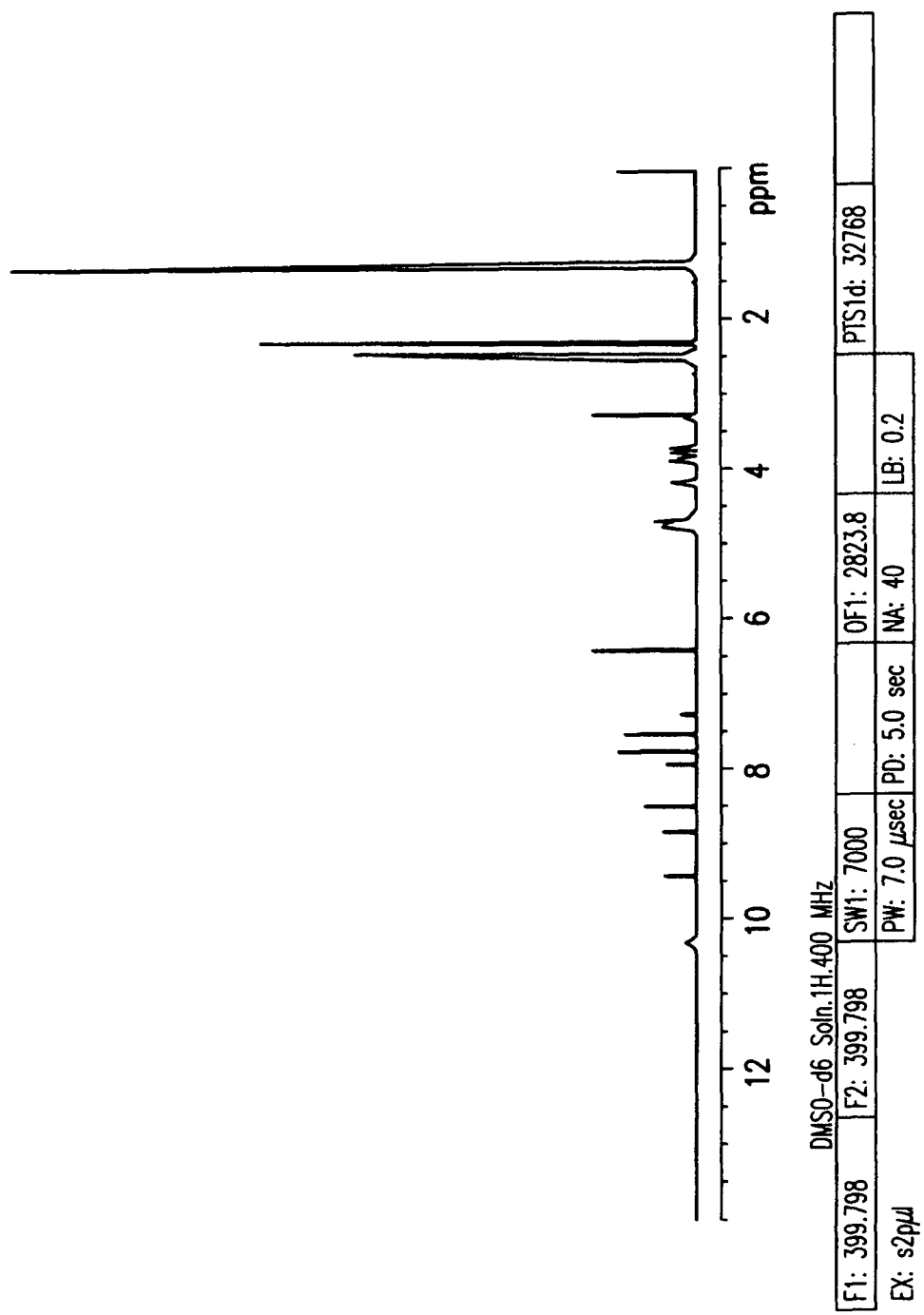

FIG. 57 provides a representative $^1$H NMR spectrum of Form A of the edisylate salt of Compound B1.

Figure 58:
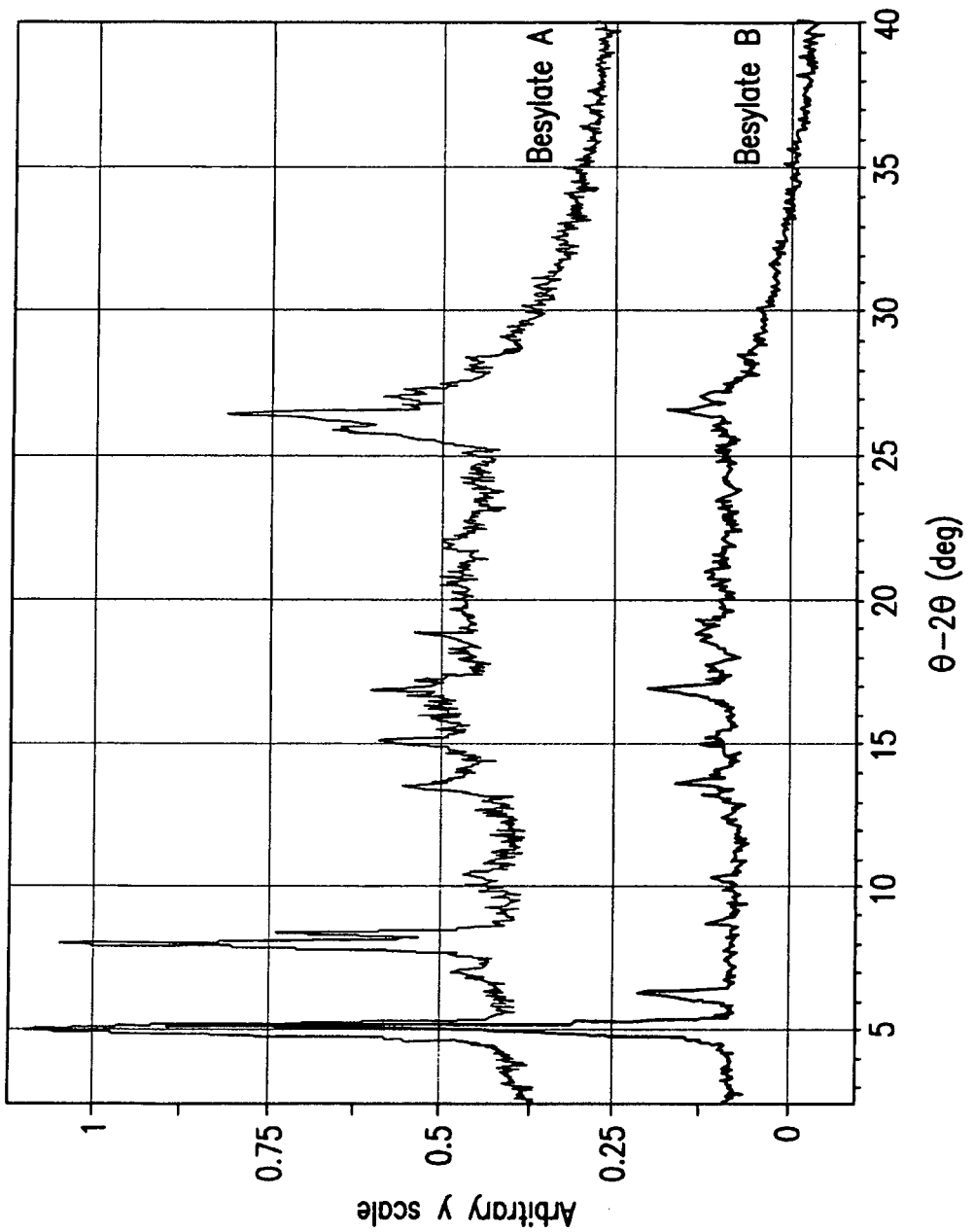

FIG. 58 provides representative XRPD patterns of Form A (top) and Form B (bottom) of besylate salts of Compound B1.

Figure 59:
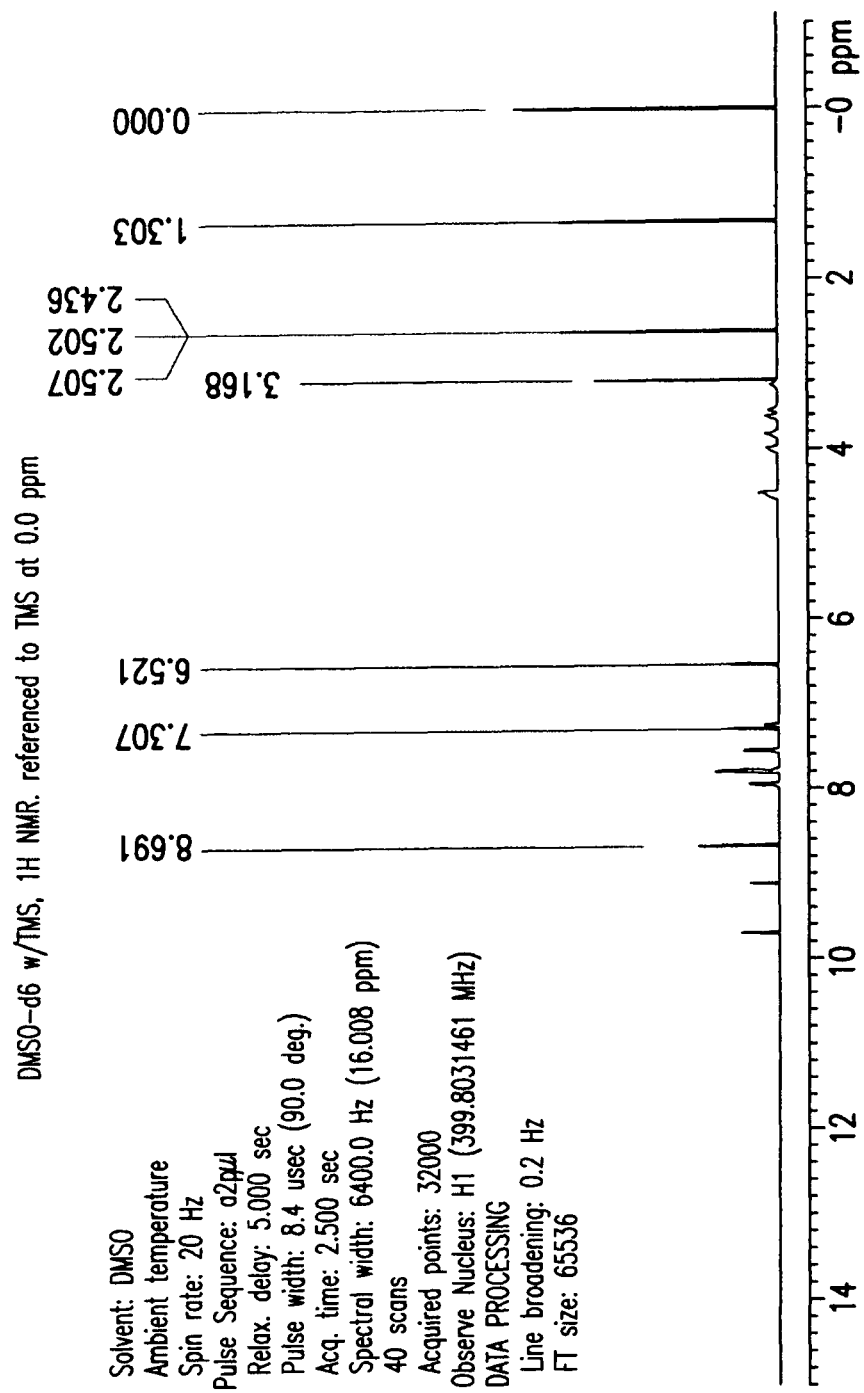

FIG. 59 provides a representative $^1$H NMR spectrum of Form A of the besylate salt of Compound B1.

Figure 60:
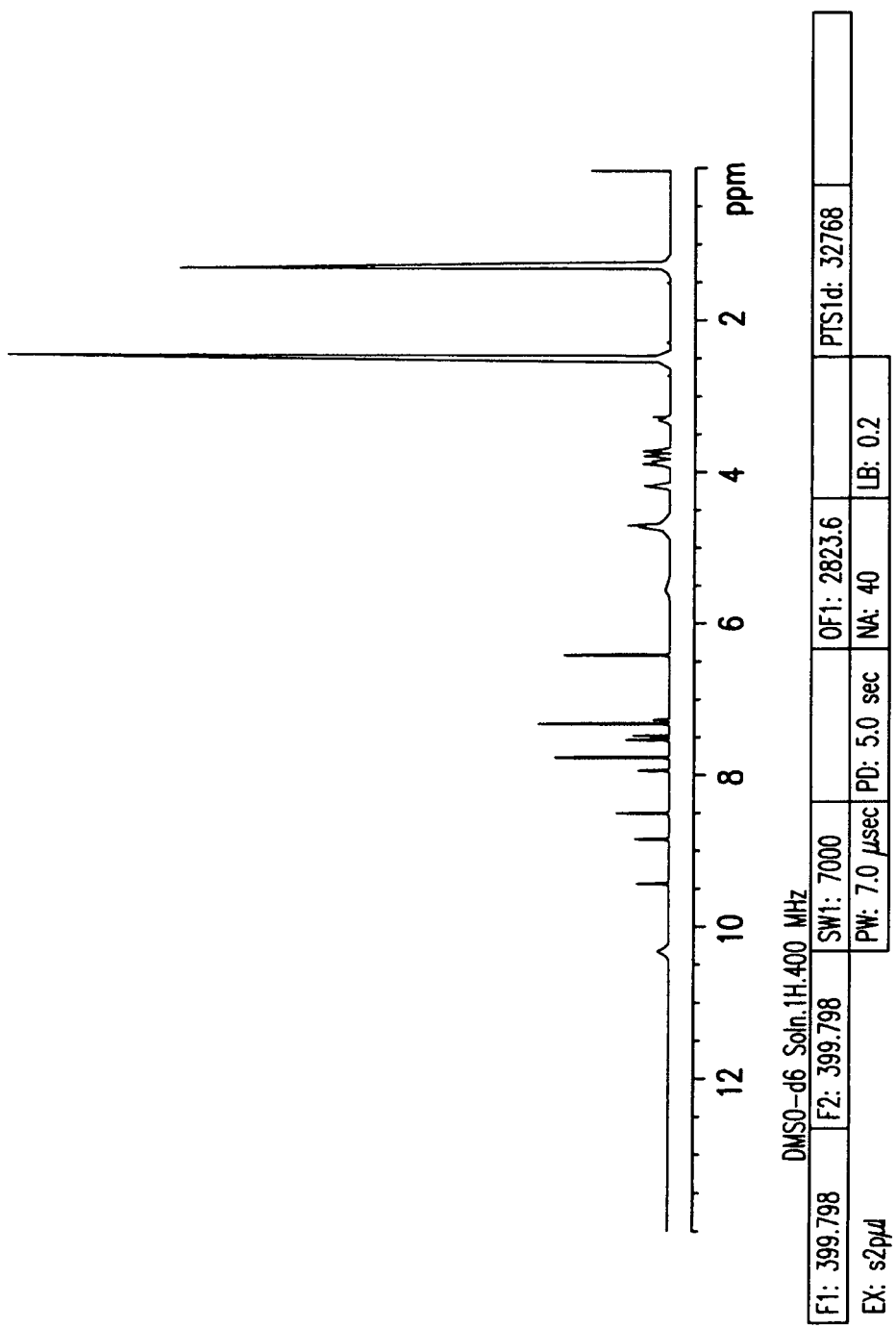

FIG. 60 provides a representative $^1$H NMR spectrum of Form B of the besylate salt of Compound B1.

Figure 61:
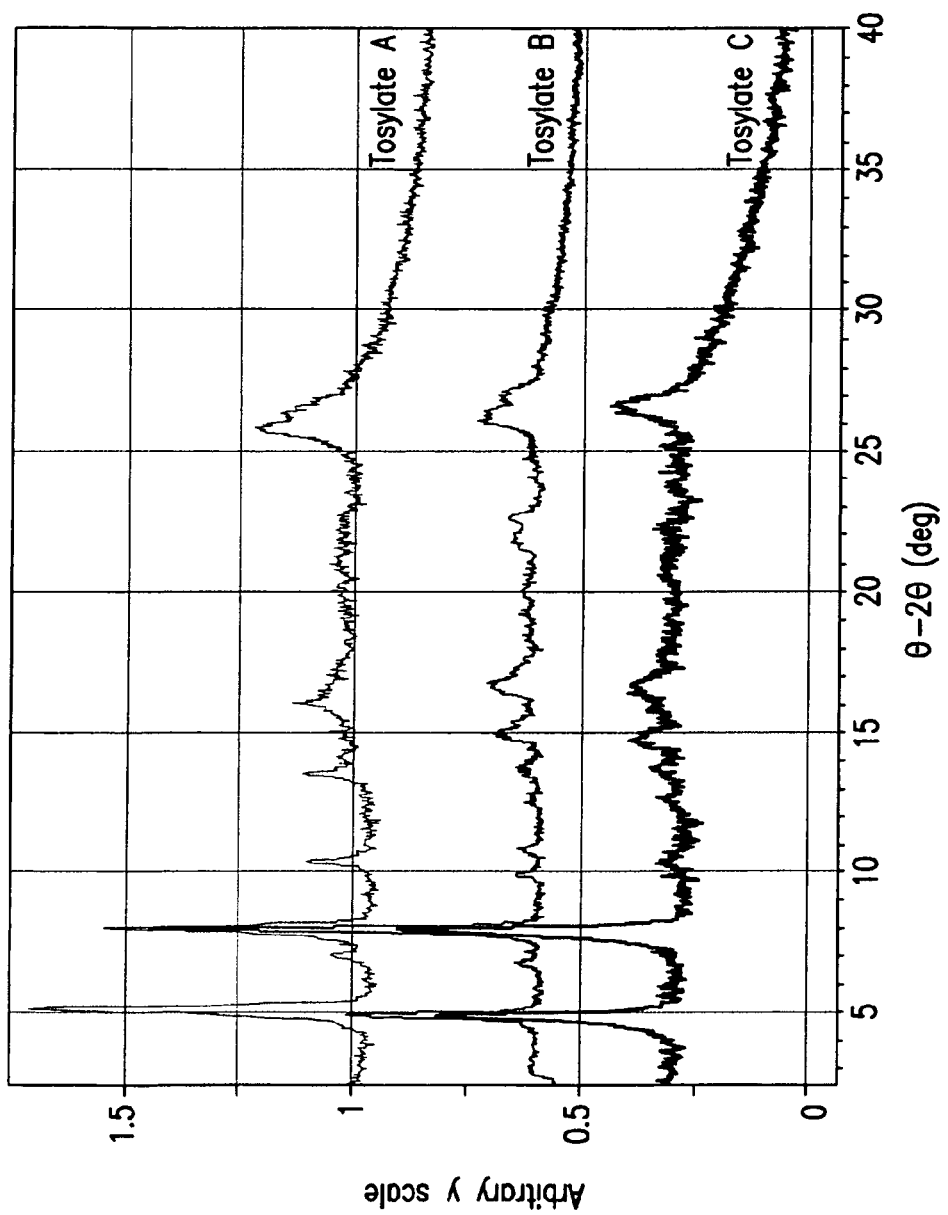

FIG. 61 provides representative XRPD patterns of Form A (top), Form B (middle) and Form C (bottom) of tosylate salts of Compound B1.

Figure 62:
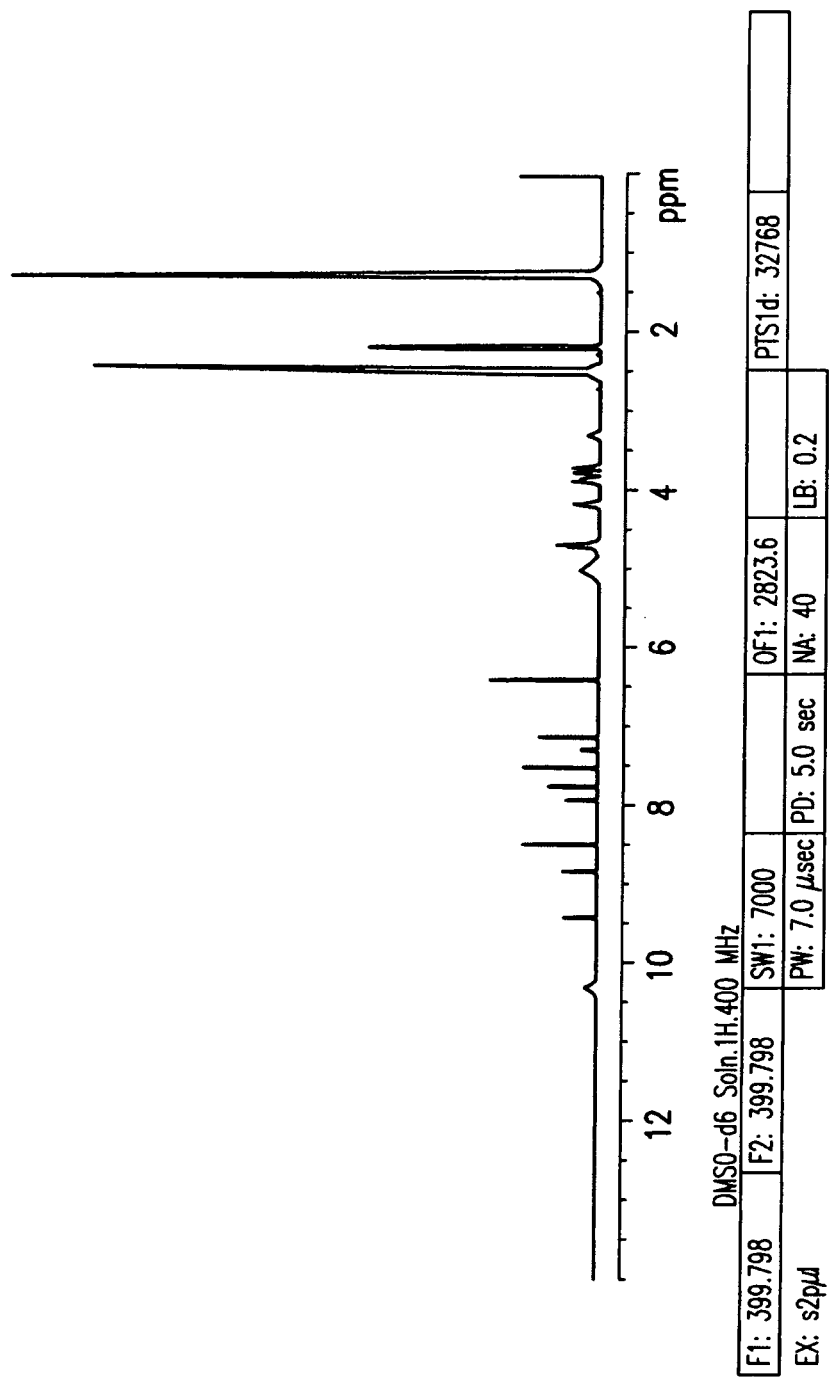

FIG. 62 provides a representative $^1$H NMR spectrum of Form B of the tosylate salt of Compound B1.

Figure 63:
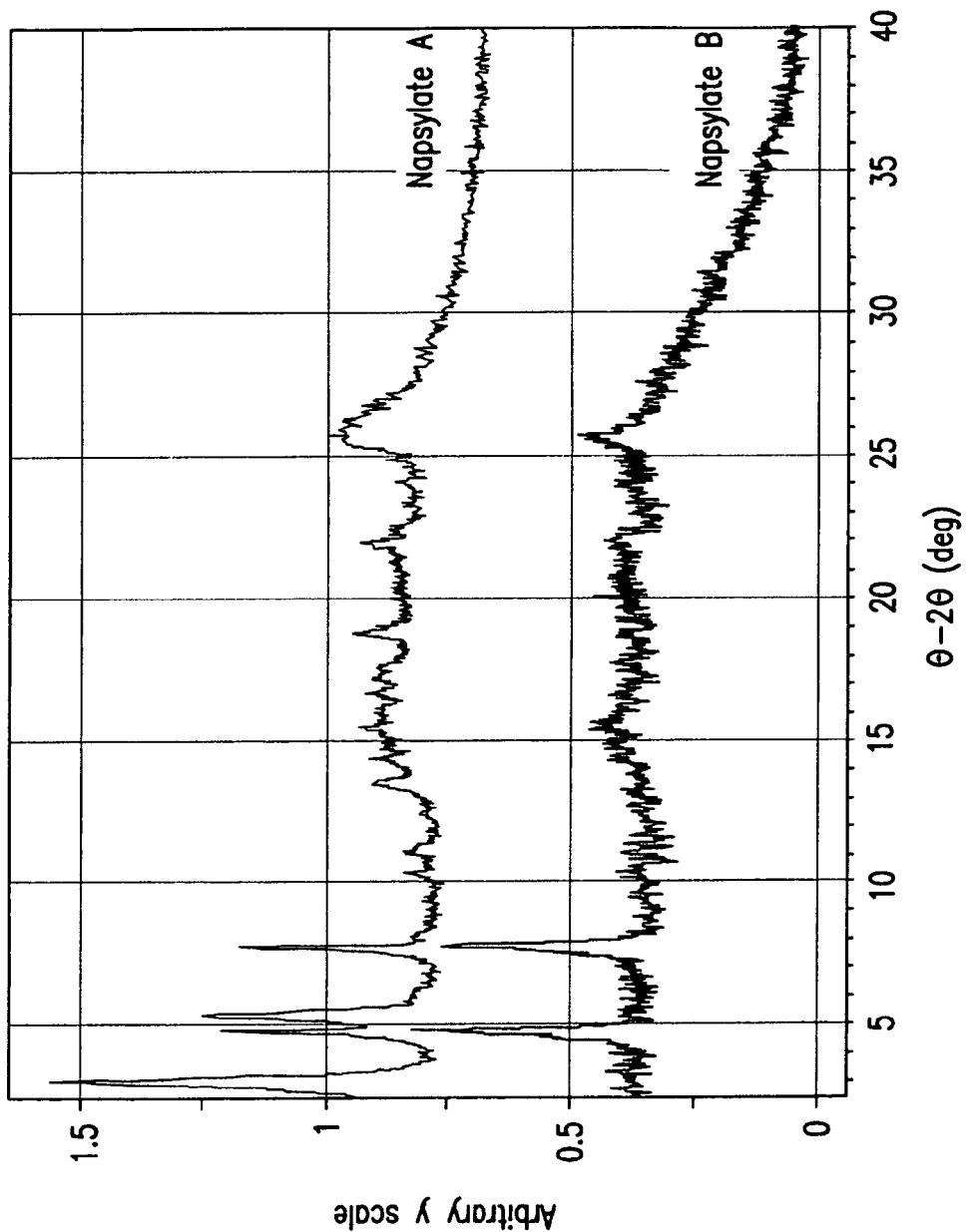

FIG. 63 provides representative XRPD patterns of Form A (top) and Form B (bottom) of napsylate salts of Compound B1.

Figure 64:
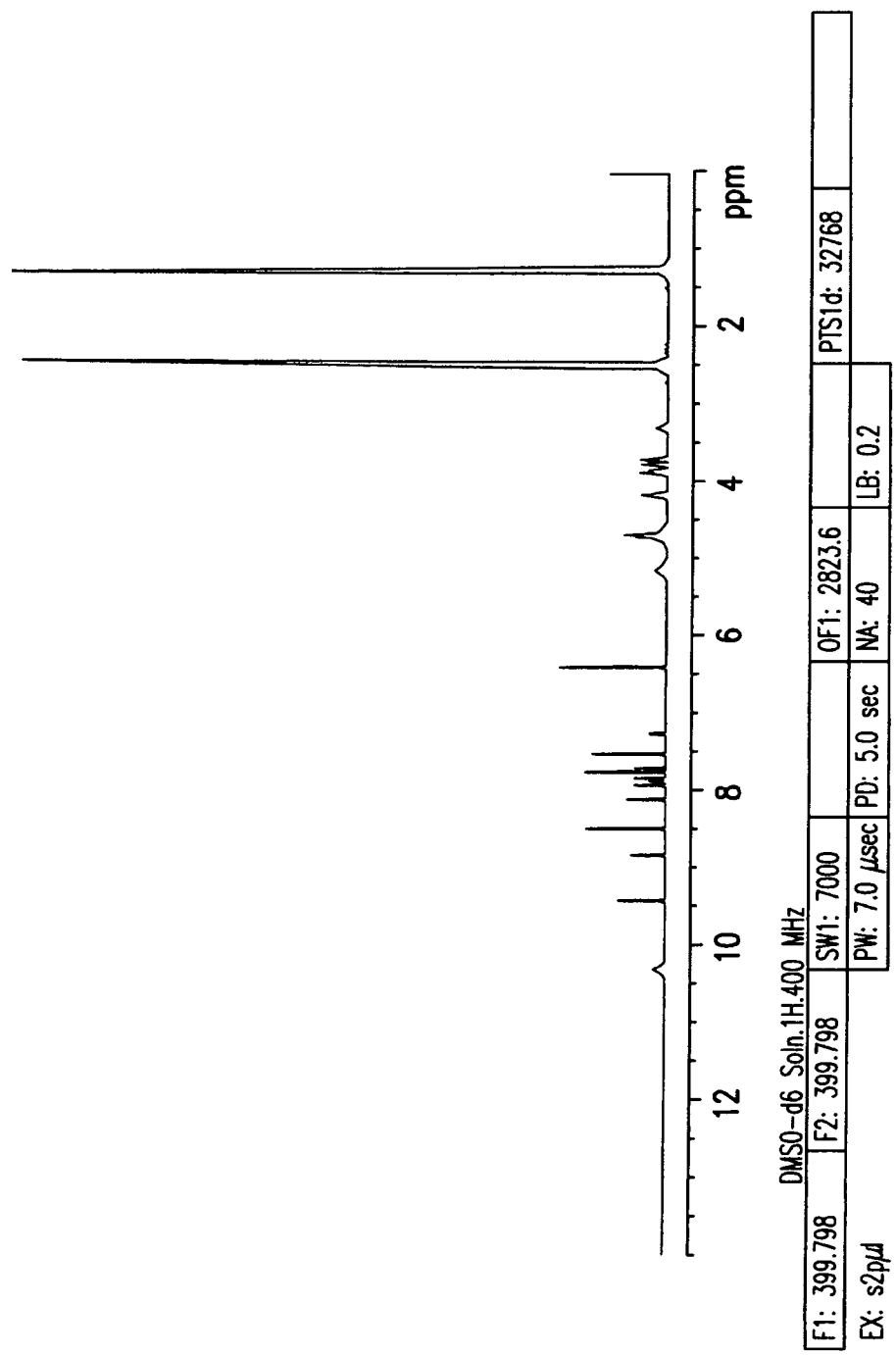

FIG. 64 provides a representative $^1$H NMR spectrum of Form A of the napsylate salt of Compound B1.

Figure 65:
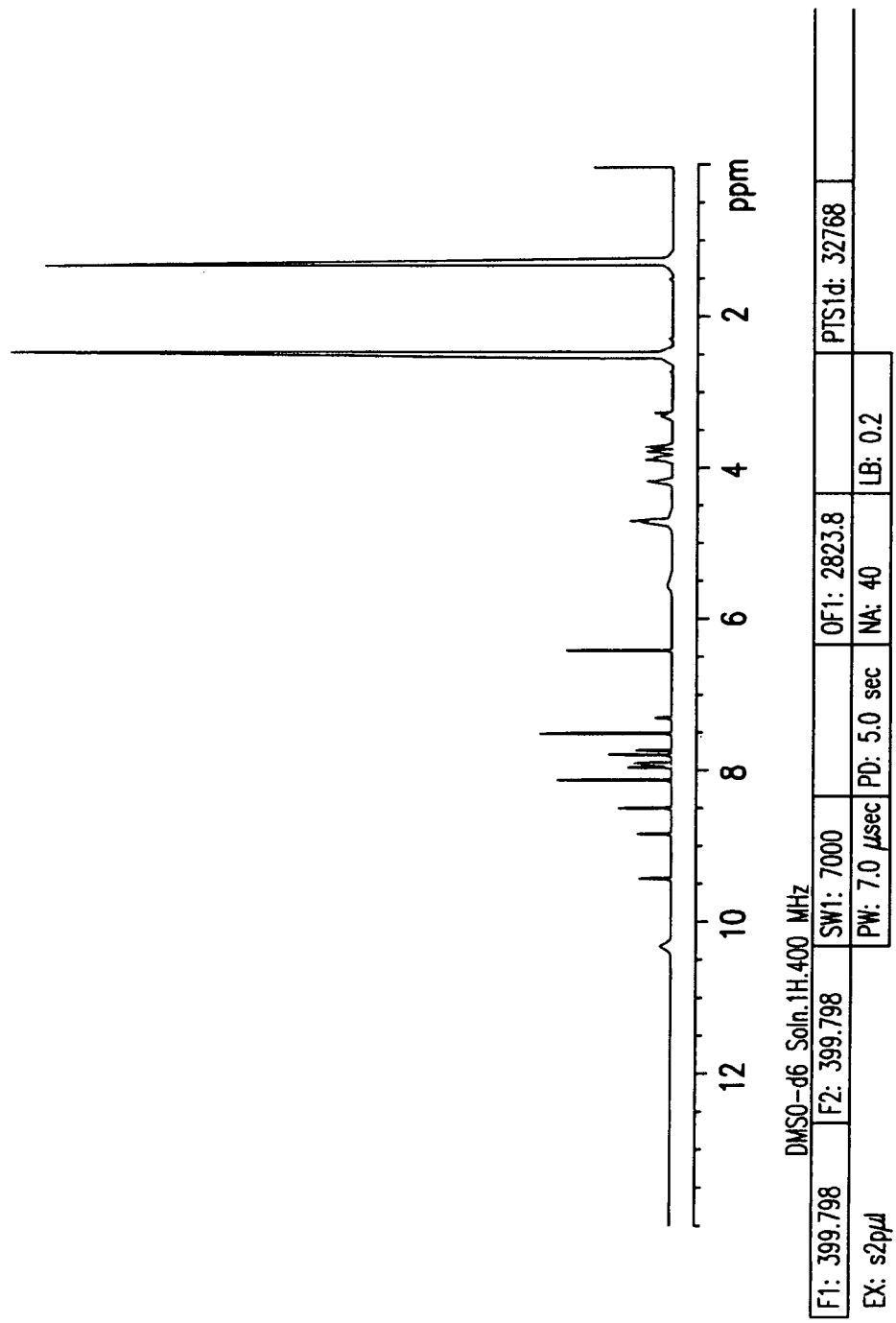

FIG. 65 provides a representative $^1$H NMR spectrum of Form B of the napsylate salt of Compound B1.

Figure 66A:
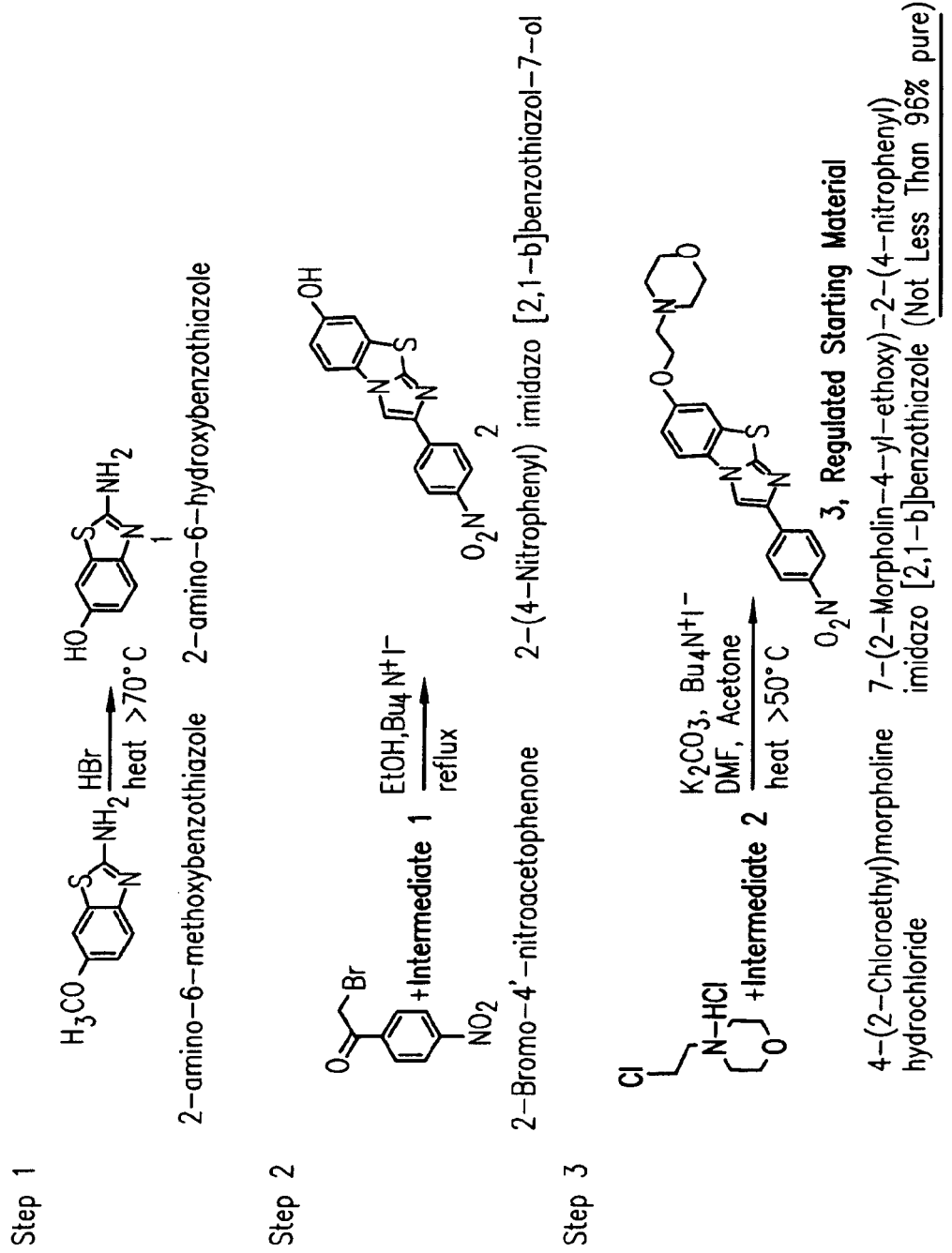
Figure 66B:
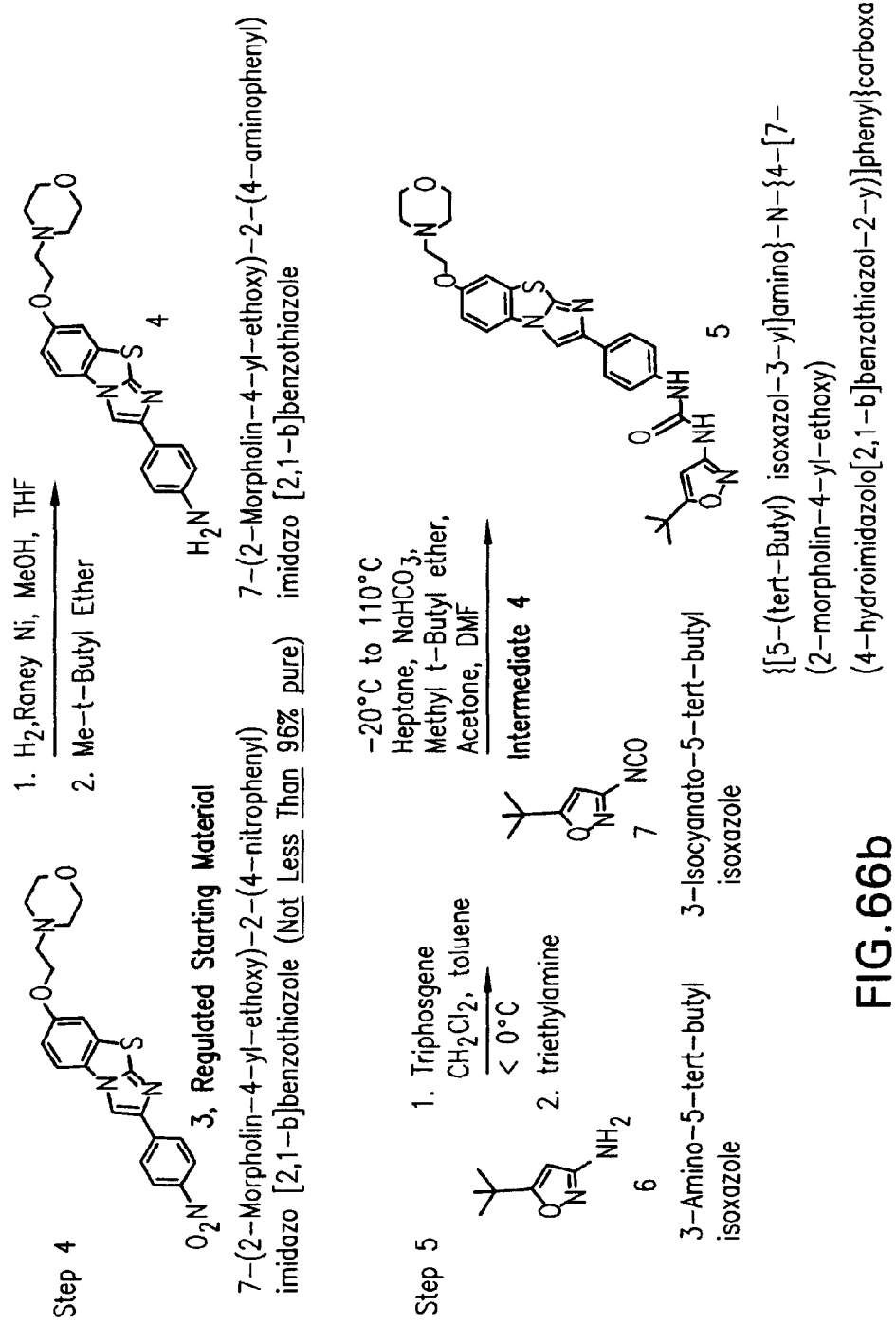

FIG. 66a and FIG. 66b provide a synthetic scheme for Compound B1.

5. DETAILED DESCRIPTION

5.1 Definitions

As used herein and unless otherwise specificed, the term "Compound B1" means the compound that is chemically named N-(5-tert-butyl-isoxazol-3-yl)-N'-{4-[7-(2-morpholin-4-yl-ethoxy)imidazo[2,1-b][1,3]benzothiazol-2-yl] phenyl}urea, depicted as structure (1) above; additionally, unless otherwise specified, the term "Compound B1" includes ionized forms of the compound depicted as structure (I) above, which have undergone salt formation such that the molecule is protonated at one or more atomic positions. To the extent that there is a discrepancy between a chemical name of a compound and a depicted chemical structure of a compound provided herein, the chemical structure shall control.

Particular salts described herein include "hydrochloride salts" or "HCl salts" of Compound B1. A hydrochloride salt or HCl salt of Compound B1 is an acid addition salt formed by reacting Compound B1 with hydrochloric acid. Particular salts described herein include "hydrobromide salts" or "HBr salts" of Compound B1. A hydrobromide salt or HBr salt of Compound B1 is an acid addition salt formed by reacting Compound B1 with hydrobromic acid. Particular salts described herein include "sulfate salts" of Compound B1. A sulfate salt of Compound B1 is an acid addition salt formed by reacting Compound B1 with sulfuric acid. Particular salts described herein include "mesylate salts" of Compound B1. A mesylate salt of Compound B1 is an acid addition salt formed by reacting Compound B1 with methanesulfonic acid. Particular salts described herein include "esylate salts" of Compound B1. An esylate salt of Compound B1 is an acid addition salt formed by reacting Compound B1 with ethanesulfonic acid. Particular salts described herein include "edisylate salts" of Compound B1. An edisylate salt of Compound B1 is an acid addition salt formed by reacting Compound B1 with 1,2-ethanedisulfonic acid. Particular salts described herein include "besylate salts" of Compound B1. A besylate salt of Compound B1 is an acid addition salt formed by reacting Compound B1 with benzensulfonic acid. Particular salts described herein include "tosylate salts" of Compound B1. A tosylate salt of Compound B1 is an acid addition salt formed by reacting Compound B1 with toluenesulfonic acid. Particular salts described herein include "napsylate salts" of Compound B1. A napsylate salt of Compound B1 is an acid addition salt formed by reacting Compound B1 with naphthalene-2-sulfonic acid.

As used herein and unless otherwise specified, the term "pharmaceutically acceptable salts" refers to salts prepared from one of the following pharmaceutically acceptable acids: hydrochloric acid; hydrobromic acid; sulfuric acid; methanesulfonic acid; ethanesulfonic acid; ethane-1,2-disulfonic acid; benzenesulfonic acid; p-toluenesulfonic acid; naphthalene-2-sulfonic acid; adipic acid; fumaric acid; glycolic acid; hippuric acid; maleic acid; phosphoric acid; and DL-tartaric acid. Acid addition salts can be obtained, e.g., by contacting the neutral form of Compound B1 with a sufficient amount of the desired acid, e.g., either neat or in a suitable solvent. As used herein and unless otherwise specified, the term "admixing" and related terms, when used in connection with salt synthesis, encompass a wide variety of methods by which one may contact an acid and a base to form a salt. As solids, salts can exist in crystalline or amorphous modifications, or mixtures thereof. Examples of methods for preparing and analyzing such salts are provided, e.g., in *Handbook of Pharmaceutical Salts: Properties Selection and Use*, P. H. Stahl and C. G. Wermuth, Eds., (2002), Wiley, Weinheim. See also A. T. M. Serajuddin, *Adv. Drug Deliv. Rev.* (2007) 59: 603-16; P. L. Gould, *Int. J. Pharm.* (1986) 33: 201-17.

As used herein and unless otherwise specified, the terms "solid form" and related terms refer to a physical form which is not predominantly in a liquid or a gaseous state. As used herein and unless otherwise specified, the term "solid form" and related terms, when used herein to refer to Compound B1, refer to a physical form comprising Compound B1 which is not predominantly in a liquid or a gaseous state. Solid forms may be crystalline, amorphous or mixtures thereof. In particular embodiments, solid forms may be liquid crystals. A "single-component" solid form comprising Compound B1 consists essentially of Compound B1. A "multiple-component" solid form comprising Compound B1 comprises a significant quantity of one or more additional species, such as ions and/or molecules, within the solid form. For example, in particular embodiments, a crystalline multiple-component solid form comprising Compound B1 further comprises one or more species non-covalently bonded at regular positions in the crystal lattice.

As used herein and unless otherwise specified, the term "crystalline" and related terms used herein, when used to describe a substance, modification, material, component or product, unless otherwise specified, mean that the substance, modification, material, component or product is substantially crystalline as determined by X-ray diffraction. See, e.g., *Remington: The Science and Practice of Pharmacy*, $21^{st}$ edition, Lippincott, Williams and Wilkins, Baltimore, Md. (2005); *The United States Pharmacopeia*, $23^{rd}$ ed., 1843-1844 (1995).

As used herein and unless otherwise specified, the term "crystal forms" and related terms herein refer to solid forms that are crystalline. Crystal forms include single-component crystal forms and multiple-component crystal forms, and include, but are not limited to, polymorphs, solvates, hydrates, and other molecular complexes, as well as salts, solvates of salts, hydrates of salts, other molecular complexes of salts, and polymorphs thereof. In certain embodiments, a crystal form of a substance may be substantially free of amorphous forms and/or other crystal forms. In certain embodiments, a crystal form of a substance may contain less than about 1%, 2%, 3%, 4%, 5%, 6%, 7%, 8%, 9%, 10%, 15%, 20%, 25%, 30%, 35%, 40%, 45% or 50% of one or more amorphous forms and/or other crystal forms on a weight basis. In certain embodiments, a crystal form of a substance may be physically and/or chemically pure. In certain embodiments, a crystal form of a substance may be about 99%, 98%, 97%, 96%, 95%, 94%, 93%, 92%, 91% or 90% physically and/or chemically pure. Crystal forms of a substance may be obtained by a number of methods, as known in the art.

As used herein and unless otherwise specified, the terms "polymorphs," "polymorphic forms" and related terms herein, refer to two or more crystal forms that consist essentially of the same molecule, molecules or ions. Like different crystal forms, different polymorphs may have different physical properties such as, for example, melting temperatures, heats of fusion, solubilities, dissolution rates and/or vibrational spectra, as a result of the arrangement or conformation of the molecules and/or ions in the crystal lattice. The differences in physical properties may affect pharmaceutical parameters such as storage stability, compressibility and density (important in formulation and product manufacturing), and dissolution rate (an important factor in bioavailability). Differences in stability can result from changes in chemical reactivity (e.g., differential oxidation, such that a dosage form discolors more rapidly when comprised of one polymorph than when comprised of another polymorph) or mechanical changes (e.g., tablets crumble on storage as a kinetically favored polymorph converts to a thermodynamically more stable polymorph) or both (e.g., tablets of one polymorph are more susceptible to breakdown at high humidity). As a result of solubility/dissolution differences, in the extreme case, some solid-state transitions may result in lack of potency or, at the other extreme, toxicity. In addition, the physical properties may be important in processing (for example, one polymorph might be more likely to form solvates or might be difficult to filter and wash free of impurities, and particle shape and size distribution might be different between polymorphs).

As used herein and unless otherwise specified, the term "solvate" and "solvated," refer to a crystal form of a substance which contains solvent. The term "hydrate" and "hydrated" refer to a solvate wherein the solvent comprises water. "Polymorphs of solvates" refers to the existence of more than one crystal form for a particular solvate composition. Similarly, "polymorphs of hydrates" refers to the existence of more than one crystal form for a particular hydrate composition. The term "desolvated solvate," as used herein, refers to a crystal form of a substance which may be prepared by removing the solvent from a solvate.

As used herein and unless otherwise specified, the term "amorphous," "amorphous form," and related terms used herein, mean that the substance, component or product in question is not substantially crystalline as determined by X-ray diffraction. In particular, the term "amorphous form" describes a disordered solid form, i.e., a solid form lacking long range crystalline order. In certain embodiments, an amorphous form of a substance may be substantially free of other amorphous forms and/or crystal forms. In other embodiments, an amorphous form of a substance may contain less than about 1%, 2%, 3%, 4%, 5%, 10%, 15%, 20%, 25%, 30%, 35%, 40%, 45% or 50% of one or more other amorphous forms and/or crystal forms on a weight basis. In certain embodiments, an amorphous form of a substance may be physically and/or chemically pure. In certain embodiments, an amorphous form of a substance may be about 99%, 98%, 97%, 96%, 95%, 94%, 93%, 92%, 91% or 90% physically and/or chemically pure. Amorphous forms of a substance may be obtained by a number of methods, as known in the art.

Techniques for characterizing crystal forms and amorphous forms include, but are not limited to, thermal gravimetric analysis (TGA), differential scanning calorimetry (DSC), X-ray powder diffractometry (XRPD), single-crystal X-ray diffractometry, vibrational spectroscopy, e.g., infrared (IR) and Raman spectroscopy, solid-state and solution nuclear magnetic resonance (NMR) spectroscopy, optical microscopy, hot stage optical microscopy, scanning electron microscopy (SEM), electron crystallography and quantitative analysis, particle size analysis (PSA), surface area analysis, solubility measurements, dissolution measurements, elemental analysis and Karl Fischer analysis. Characteristic unit cell parameters may be determined using one or more techniques such as, but not limited to, X-ray diffraction and neutron diffraction, including single-crystal diffraction and powder diffraction. Techniques useful for analyzing powder diffraction data include profile refinement, such as Rietveld refinement, which may be used, e.g., to analyze diffraction peaks associated with a single phase in a sample comprising more than one solid phase. Other methods useful for analyzing powder diffraction data include unit cell indexing, which allows one of skill in the art to determine unit cell parameters from a sample comprising crystalline powder.

As used herein and unless otherwise specified, the terms "about" and "approximately," when used in connection with a numeric value or a range of values which is provided to characterize a particular solid form, e.g., a specific temperature or temperature range, such as, for example, that describing a melting, dehydration, desolvation or glass transition temperature; a mass change, such as, for example, a mass change as a function of temperature or humidity; a solvent or water content, in terms of, for example, mass or a percentage; or a peak position, such as, for example, in analysis by IR or Raman spectroscopy or XRPD; indicate that the value or range of values may deviate to an extent deemed reasonable to one of ordinary skill in the art while still describing the particular solid form. For example, in particular embodiments, the terms "about" and "approximately," when used in this context, indicate that the numeric value or range of values may vary within 25%, 20%, 15%, 10%, 9%, 8%, 7%, 6%, 5%, 4%, 3%, 2%, 1.5%, 1%, 0.5%, or 0.25% of the recited value or range of values. As used herein, a tilde (i.e., "~") preceding a numerical value or range of values indicates "about" or "approximately."

As used herein and unless otherwise specified, a sample comprising a particular crystal form or amorphous form that is "substantially pure," e.g., substantially free of other solid forms and/or of other chemical compounds, contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or of other chemical compounds.

As used herein and unless otherwise specified, a sample or composition that is "substantially free" of one or more other solid forms and/or other chemical compounds means that the composition contains, in particular embodiments, less than about 25%, 20%, 15%, 10%, 9%, 8%, 7%, 6%, 5%, 4%, 3%, 2%, 1%, 0.75%, 0.5%, 0.25% or 0.1% percent by weight of one or more other solid forms and/or other chemical compounds.

As used herein, and unless otherwise specified, the terms "treat," "treating" and "treatment" refer to the eradication or amelioration of a disease or disorder, or of one or more symptoms associated with the disease or disorder. In certain embodiments, the terms refer to minimizing the spread or worsening of the disease or disorder resulting from the administration of one or more prophylactic or therapeutic agents to a subject with such a disease or disorder. In some embodiments, the terms refer to the administration of a compound provided herein, with or without other additional active agent, after the onset of symptoms of the particular disease.

As used herein, and unless otherwise specified, the terms "prevent," "preventing" and "prevention" refer to the prevention of the onset, recurrence or spread of a disease or disorder, or of one or more symptoms thereof. In certain embodiments, the terms refer to the treatment with or administration of a compound provided herein, with or without other additional active compound, prior to the onset of symptoms, particularly to patients at risk of disease or disorders provided herein. The terms encompass the inhibition or reduction of a symptom of the particular disease. Patients with familial history of a disease in particular are candidates for preventive regimens in certain embodiments. In addition, patients who have a history of recurring symptoms are also potential candidates for the prevention. In this regard, the term "prevention" may be interchangeably used with the term "prophylactic treatment."

As used herein, and unless otherwise specified, the terms "manage," "managing" and "management" refer to preventing or slowing the progression, spread or worsening of a disease or disorder, or of one or more symptoms thereof. Often, the beneficial effects that a subject derives from a prophylactic and/or therapeutic agent do not result in a cure of the disease or disorder. In this regard, the term "managing" encompasses treating a patient who had suffered from the particular disease in an attempt to prevent or minimize the recurrence of the disease.

As used herein, and unless otherwise specified, a "therapeutically effective amount" of a compound is an amount sufficient to provide a therapeutic benefit in the treatment or management of a disease or disorder, or to delay or minimize one or more symptoms associated with the disease or disorder. A therapeutically effective amount of a compound means an amount of therapeutic agent, alone or in combination with other therapies, which provides a therapeutic benefit in the treatment or management of the disease or disorder. The term "therapeutically effective amount" can encompass an amount that improves overall therapy, reduces or avoids symptoms or causes of disease or disorder, or enhances the therapeutic efficacy of another therapeutic agent.

As used herein, and unless otherwise specified, a "prophylactically effective amount" of a compound is an amount sufficient to prevent a disease or disorder, or prevent its recurrence. A prophylactically effective amount of a compound means an amount of therapeutic agent, alone or in combination with other agents, which provides a prophylactic benefit in the prevention of the disease. The term "prophylactically effective amount" can encompass an amount that improves overall prophylaxis or enhances the prophylactic efficacy of another prophylactic agent.

The term "composition" as used herein is intended to encompass a product comprising the specified ingredients (and in the specified amounts, if indicated), as well as any product which results, directly or indirectly, from combination of the specified ingredients in the specified amounts. By "pharmaceutically acceptable" it is meant the diluent, excipient or carrier must be compatible with the other ingredients of the formulation and not deleterious to the recipient thereof.

The term "subject" is defined herein to include animals such as mammals, including, but not limited to, primates (e.g., humans), cows, sheep, goats, horses, dogs, cats, rabbits, rats, mice and the like. In specific embodiments, the subject is a human.

In addition to solid forms comprising Compound B1, provided herein are solid forms comprising prodrugs of Compound B1.

Solid forms provided herein may also comprise unnatural proportions of atomic isotopes at one or more of the atoms in Compound B1. For example, the compound may be radiolabeled with radioactive isotopes, such as for example tritium ($^3$H), iodine-125 ($^{125}$I) sulfur-35 ($^{35}$S), or carbon-14 ($^{14}$C). Radiolabeled compounds are useful as therapeutic agents, e.g., cancer therapeutic agents, research reagents, e.g., binding assay reagents, and diagnostic agents, e.g., in vivo imaging agents. All isotopic variations of Compound B1, whether radioactive or not, are intended to be encompassed within the scope of the embodiments provided herein.

5.2 Solid Forms Comprising Compound B1

Certain embodiments herein provide single-component and multiple-component solid forms comprising Compound B1, which has the chemical structure shown above as structure (I).

Compound B1 can be synthesized or obtained according to any method apparent to those of skill in the art based upon the teachings herein, including the methods described in the Examples below. Compound B1 can also be prepared according to the methods described in U.S. Provisional Patent App. No. 60/743,543, filed Mar. 17, 2006, U.S. patent application Ser. No. 11/724,992, filed Mar. 16, 2007, and U.S. Patent App. Publication No. 2007/0232604, published Oct. 4, 2007, the entireties of each of which are incorporated by reference herein. In its free base form, Compound B1 has the chemical structure shown above as structure (I).

Solid forms comprising Compound B1 include single-component and multiple-component forms, including crystal forms and amorphous forms, and including, but not limited to, polymorphs, salts, solvates, hydrates, co-crystals and clathrates. Particular embodiments herein provide single-component amorphous solid forms of the free base of Compound B1. Particular embodiments herein provide single-component crystalline solid forms of the free base of Compound B1. Particular embodiments herein provide multiple-component amorphous forms comprising Compound B1. Particular embodiments herein provide multiple-component crystalline solid forms comprising Compound B1. The multiple-component solid forms comprising Compound B1 may be neutral or ionic complexes, or may comprise both neutral and ionic components together in the solid form. Multiple-component solid forms provided herein include solid forms which may be described by the terms salt, co-crystal, hydrate, solvate, clathrate and/or polymorph, and include solid forms which may be described by one or more of these terms.

Solid forms comprising Compound B1 can be prepared by the methods described herein, including the methods described in the Examples below, or by techniques known in the art, including heating, cooling, freeze drying, lyophilization, quench cooling the melt, rapid solvent evaporation, slow solvent evaporation, solvent recrystallization, antisolvent addition, slurry recrystallization, crystallization from the melt, desolvation, recrystallization in confined spaces such as, e.g., in nanopores or capillaries, recrystallization on surfaces or templates such as, e.g., on polymers, recrystallization in the presence of additives, such as, e.g., co-crystal counter-molecules, desolvation, dehydration, rapid cooling, slow cooling, exposure to solvent and/or water, drying, including, e.g., vacuum drying, vapor diffusion, sublimation, grinding (including, e.g., cryo-grinding and solvent-drop grinding), microwave-induced precipitation, sonication-induced precipitation, laser-induced precipitation and precipitation from a supercritical fluid. The particle size of the resulting solid forms, which can vary, (e.g., from nanometer dimensions to millimeter dimensions), can be controlled, e.g., by varying crystallization conditions, such as, e.g., the rate of crystallization and/or the crystallization solvent system, or by particle-size reduction techniques, e.g., grinding, milling, micronizing or sonication.

While not intending to be bound by any particular theory, certain solid forms are characterized by physical properties, e.g., stability, solubility and dissolution rate, appropriate for clinical and therapeutic dosage forms. Moreover, while not wishing to be bound by any particular theory, certain solid forms are characterized by physical properties (e.g., density, compressibility, hardness, morphology, cleavage, stickiness, solubility, water uptake, electrical properties, thermal behavior, solid-state reactivity, physical stability, and chemical stability) affecting particular processes (e.g., yield, filtration, washing, drying, milling, mixing, tableting, flowability, dissolution, formulation, and lyophilization) which make certain solid forms suitable for the manufacture of a solid dosage form. Such properties can be determined using particular analytical chemical techniques, including solid-state analytical techniques (e.g., X-ray diffraction, microscopy, spectroscopy and thermal analysis), as described herein and known in the art.

Certain embodiments herein provide compositions comprising one or more of the solid forms. Certain embodiments provide compositions of one or more solid forms in combination with other active ingredients. Certain embodiments provide methods of using these compositions in the treatment, prevention or management of diseases and disorders including, but not limited to, the diseases and disorders provided herein.

With regard to the solid forms herein which comprise an HCl salt of Compound B1, the following terminology applies unless otherwise specified. A "mono-hydrochloride salt" or "mono-HCl salt" of Compound B1 is a hydrochloride salt which contains about one molar equivalent of chloride ion per mole of Compound B1. A "bis-hydrochloride salt," "bis-HCl salt," "di-hydrochloride salt," or "di-HCl salt" of Compound B1 is a hydrochloride salt which contains about two molar equivalents of chloride ion per mole of Compound B1. In particular embodiments, "about 2 molar equivalents of HCl" and "approximately 2 molar equivalents of HCl" indicate approximately 1.5, 1.6, 1.7, 1.8, 1.9, 2.0, 2.1, 2.2, 2.3, 2.4 or 2.5 molar equivalents of HCl per mole of Compound B1.

5.2.1 Form A of the Free Base of Compound B1

Certain embodiments herein provide the Form A crystal form of the free base of Compound B1. In certain embodiments, Form A of the free base of Compound B1 can be obtained from various solvents, including, but not limited to, solvent systems comprising dimethylformamide (DMF), diethyl ether, water, and mixtures of two or more thereof. A representative solution $^1$H NMR spectrum of the Form A crystal form of the free base of Compound B1 is provided in FIG. 1. A representative XRPD pattern of Form A of the free base of Compound B1 is provided in FIG. 2. Form A of the free base of Compound B1 is characterized by XRPD peaks located, in particular embodiments, at one, two, three, four, five, six, seven, eight, nine, ten, eleven or twelve of the following approximate positions: 3.58, 10.79, 15.95, 16.33, 18.06, 18.79, 19.9, 21.45, 23.53, 24.19, 25.61, 27.44 degrees 2θ. In certain embodiments, Form A of the free base of Compound B1 is characterized by an XRPD pattern which matches the pattern exhibited in FIG. 2.

Representative thermal characteristics of Form A of the free base of Compound B1 are shown in FIG. 3 and FIG. 4. A representative DSC thermogram, presented in FIG. 3, comprises an endothermic event with an onset temperature at about 265° C. A representative TGA thermogram, presented in FIG. 4, comprises a mass loss of about 1% of the total mass of the sample upon heating from ambient temperature to about 220° C. The thermal data indicate that Form A of the free base of Compound B1 does not contain substantial amounts of either water or other solvent in the crystal lattice.

5.2.2 Form B of the Free Base of Compound B1

Certain embodiments herein provide the Form B crystal form of the free base of Compound B1. In certain embodiments, Form B of the free base of Compound B1 can be obtained from various solvents, including, but not limited to, solvent systems comprising methanol, hexanes, tetrahydrofuran, water, and mixtures of two or more thereof. In certain embodiments, Form B can be obtained by crystallization from solvent, water or solvent/water mixtures including, but not limited to, common laboratory organic solvents. In certain embodiments, Form B contains water and/or solvent of crystallization in the crystal lattice. In certain embodiments, Form B is crystallized from solution in the presence of additives, including, but not limited to, hippuric acid and maleic acid. A representative XRPD pattern of Form B of the free base of Compound B1 is provided in FIG. 5. Form B of the free base of Compound B1 is characterized by XRPD peaks located, in particular embodiments, at one, two, three, four, five, six, seven, eight, nine, ten or eleven of the following approximate positions: 5.0, 11.34, 12.8, 14.7, 15.71, 17.99, 20.31, 22.18, 24.02, 25.47, 26.09 degrees 2θ. In certain embodiments, Form B of the free base of Compound B1 is characterized by an XRPD pattern which matches the pattern exhibited in FIG. 5.

5.2.3 Methanol Solvate Comprising Compound B1

Certain embodiments herein provide a crystalline methanol solvate comprising the free base of Compound B1. In certain embodiments, this methanol solvate of the free base of Compound B1 can be obtained from various solvents, including, but not limited to, solvent systems comprising methanol, ether, or combinations thereof. In certain embodiments, this methanol solvate comprising the free base of Compound B1 can be obtained by crystallization from solvent, water or solvent/water mixtures including, but not limited to, common laboratory organic solvents. In certain embodiments, this methanol solvate of the free base of Compound B1 is crystallized from solution in the presence of an additive, including, but not limited to, fumaric acid. A representative XRPD pattern of this methanol solvate of the free base of Compound B1 is provided in FIG. 6. A representative solution $^1$H NMR spectrum of this methanol solvate of the free base of Compound B1 is provided in FIG. 7. This methanol solvate of the free base of Compound B1 is characterized by XRPD peaks located, in particular embodiments, at one, two, three, four, five, six, seven, eight, nine, ten, eleven, twelve, thirteen or fourteen of the following approximate positions: 4.52, 5.28, 10.89, 11.31, 11.72, 12.97, 15.91, 16.12, 17.61, 19.9, 22.15, 23.22, 24.22, 26.44 degrees 2θ. In certain embodiments, this methanol solvate of the free base of Compound B1 is characterized by an XRPD pattern which matches the pattern exhibited in FIG. 6.

5.2.4 Form A of the HCl Salt of Compound B1

Certain embodiments herein provide the Form A crystal form of the HCl salt of Compound B1. In certain embodiments, Form A of the HCl salt of Compound B1 can be obtained by reacting Compound B1 with HCl in a variety of solvent systems, including, but not limited to, solvent systems comprising tetrahydrofuran. In certain embodiments, the HCl may be charged to the reaction as a gas or as a solution, e.g., a concentrated aqueous solution, an ether solution, or a dioxane solution. In certain embodiments, the Form A crystal form of the HCl salt of Compound B1 can be prepared by crystallization from a variety of solvent systems, including, but not limited to, solvent systems comprising tetrahydrofuran, trifluoroethanol, 2-butanone, 1,4-dioxane, nitromethane, and mixtures of two or more thereof. In certain embodiments, Form A of the HCl salt of Compound B1 can be obtained by crystallization from solvent, water or solvent/water mixtures including, but not limited to, common laboratory organic solvents.

In certain embodiments, the chloride content of the salt is determined by analyzing a sample of Form A for chloride content, e.g., by performing elemental analysis, chloride titration, and/or ion chromatography. In certain embodiments, Form A has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form A has a chloride content corresponding to about 2 molar equivalents of HCl per mole of Compound B1. In certain embodiments, Form A is a bis-HCl salt of Compound B1.

A representative XRPD pattern of Form A of the HCl salt of Compound B1 is provided in FIG. 8. In certain embodiments, Form A of the HCl salt of Compound B1 is characterized by XRPD peaks located at one, two, three, four, five, six, seven, eight, nine, ten or more of the following approximate positions: 2.34, 3.86, 6.46, 7.77, 8.5, 8.74, 9.85, 11.41, 13.56, 14.98, 16.02, 16.68, 17.54, 18.03, 18.75, 19.62, 21.14, 21.77, 22.77, 23.32, 24.33, 25.3, 26.2, 27.68 degrees 2θ. In certain embodiments, Form A of the HCl salt of Compound B1 is characterized by XRPD peaks located at one, two, three, four, five, six or seven of the following approximate positions: 2.34, 3.86, 6.46, 9.85, 16.68, 17.54, 26.2 degrees 2θ. In certain embodiments, Form A of the HCl salt of Compound B1 is characterized by an XRPD pattern which matches the pattern exhibited in FIG. 8.

Representative thermal characteristics of Form A of the HCl salt of Compound B1 are shown in FIG. 9 and FIG. 10. A representative DSC thermogram, presented in FIG. 9, comprises multiple broad thermal events with maxima at approximately 77, 143 and 190° C., followed by thermal events with maxima at about 242 and 272° C. In certain embodiments, Form A is characterized by a DSC thermogram comprising one or more thermal events with the following approximate temperature maxima: 77, 143, 190, 242 and 272° C. A representative TGA thermogram, presented in FIG. 10, comprises a mass loss of between about 5% and about 6% of the total mass of the sample upon heating from ambient temperature to about 95° C. In certain embodiments, this observed mass loss comprises the loss of THF solvent, as indicated, e.g., by analysis involving thermal gravimetry equipped with infrared spectroscopy off-gas analysis (TG-IR). In certain embodiments, Form A of the HCl salt of Compound B1 contains THF in the crystal lattice. In certain embodiments, the amount of THF in Form A is between about 0.1 and 2.0 molar equivalents of THF per mole of the HCl salt of Compound B1. In one embodiment, Form A contains about 0.6 molar equivalents of THF per mole of the HCl salt of Compound B1.

In certain embodiments, the chemical profile of a sample of Form A of the HCl salt of Compound B1 can be characterized by solution NMR analysis. A representative $^1$H NMR spectrum of a sample of Form A dissolved in DMSO-d6 is provided as FIG. 11.

In certain embodiments, Form A of the HCl salt of Compound B1 may be characterized by isothermic moisture sorption and/or desorption analysis. For example, in one embodiment, a mass loss of about 3.9% accompanied an initial equilibration at about 5% RH; this was followed by a total mass gain of about 16.7% when humidity was increased from 5% to 95% RH; and this was followed by a total mass loss of about 16.7% when humidity was decreased from about 95% to about 5% RH. In certain embodiments, the resulting material is characterized as Form D of the HCl salt of Compound B1, as described herein. A representative dynamic vapor sorption/desorption curve for Form A of the HCl salt of Compound B1 is presented in FIG. 12.

In certain embodiments, Form A of the HCl salt of Compound B1 may be characterized by its behavior upon storage at stress conditions. For example, in one embodiment, when stressed at 75% RH at ambient temperature for 4 days, a sample of Form A exhibits a weight gain of between about 3% and 4%, and the resulting material exhibits an XRPD pattern corresponding to Form D of the HCl salt of Compound B1, described herein. In another embodiment, when stored at 40° C. for 4 days, a sample of Form A exhibits a weight loss of between about 2% and 4%, and the resulting material exhibits an XRPD pattern corresponding to a mixture of Form A and Form E of the HCl salt of Compound B1, as described herein.

5.2.5 Form B of the HCl Salt of Compound B1

Certain embodiments herein provide the Form B crystal form of the HCl salt of Compound B1. In certain embodiments, Form B of the HCl salt of Compound B1 can be obtained by reacting Compound B1 with HCl. In certain embodiments, Form B can be obtained by reacting Compound B1 with HCl in various solvent systems, including, but not limited to, solvent systems comprising an alcohol (e.g., methanol) a hydrocarbon (e.g., benzene) and/or one or more other solvents (e.g., ether and/or dioxane). In certain embodiments, in preparing Form B of the HCl salt of Compound B1, HCl can be reacted as a solution, e.g., a concentrated aqueous solution, or as a gas. In certain embodiments, the Form B crystal form of the HCl salt of Compound B1 can be prepared by crystallization from solvent, water or solvent/water mixtures including, but not limited to, methanol, ethanol, water, acetone, acetonitrile, 2-butanone, dichloromethane, p-dioxane, ethyl acetate, isopropanol, methylene chloride, nitromethane, tetrahydrofuran, trifluorotoluene, and mixtures of two or more solvents thereof. For example, in one embodiment, Form B is obtained by precipitation from a solution comprising methanol. In another embodiment, Form B is prepared by precipitation via evaporation and/or cooling from a solution comprising methanol. In another embodiment, Form B is obtained by slurry in a solvent system comprising ethanol. In another embodiment, Form B is obtained by slurry in a solvent system comprising a 1:24 ethanol:water mixture at 60° C. In certain embodiments, Form B of the HCl salt of Compound B1 can be obtained by crystallization from solvent, water or solvent/water mixtures including, but not limited to, common laboratory organic solvents. In certain embodiments, Form B is obtained by crystallization methods including, but not limited to, precipitation, slurry at ambient temperature, slurry at elevated temperature, slurry at subambient temperature, evaporation, slow evaporation, fast evaporation and/or concentration.

In certain embodiments, the chloride content of the Form B HCl salt is determined by analyzing a sample of Form B for chloride content, e.g., by performing elemental analysis, chloride titration, and/or ion chromatography. In certain embodiments, Form B has chloride content corresponding to about 1.5 to about 2.0 or about 2.0 to about 2.5 molar equivalents of HCl per mole of Compound B1. In certain embodiments, Form B has a chloride content corresponding to about 2 molar equivalents of HCl per mole of Compound B1. In certain embodiments, Form B is a bis-HCl salt of Compound B1. In certain embodiments, Form B has a chloride content of 11.22% 11% chloride ion on a mass basis.

In certain embodiments, a single crystal of Form B of the HCl salt of Compound B1 is obtained by a process comprising one or more of the following steps: dissolving a sample of the HCl salt of Compound B1 in methanol; filtering through a 0.2 mm nylon filter into a glass vial; covering the vial with aluminum foil with pin-holes; and leaving at ambient to evaporate; and removing a single crystal for analysis.

In certain embodiments, Form B of the HCl salt of Compound B1 is obtained by a process comprising the steps of: (1) admixing the free base of Compound B1 with approximately 2 molar equivalents of HCl; and (2) obtaining Form B of the HCl salt of Compound B1. In certain embodiments, Form B of the HCl salt of Compound B1 is obtained by a process comprising the steps of: (1) admixing the free base of Compound B1 with approximately 2.5 molar equivalents of HCl; and (2) obtaining Form B of the HCl salt of Compound B1. In certain embodiments, Form B of the HCl salt of Compound B1 is obtained by a process comprising the steps of: (1) admixing the free base of Compound B1 with approximately 2 molar equivalents of HCl; and (2) obtaining Form B of the HCl salt of Compound B1 in a yield equal to or greater than about 70% of the theoretical maximum yield of Form B of the HCl salt of Compound B1, based on the quantities of starting materials. In certain embodiments, Form B of the HCl salt of Compound B1 is obtained by a process comprising the steps of: (1) admixing the free base of Compound B1 with approximately 2.5 molar equivalents of HCl; and (2) obtaining Form B of the HCl salt of Compound B1 in a yield equal to or greater than about 70% of the theoretical maximum yield of Form B of the HCl salt of Compound B1, based on the quantities of starting materials. In certain embodiments, such yield is about 75%, about 80%, about 85%, about 90%, about 95%, about 96%, about 97%, about 98%, about 99% or about 100% of the theoretical maximum yield of Form B of the HCl salt of Compound B1 based on the quantities of starting materials.

In certain embodiments, Form B of the HCl salt of Compound B1 is obtained by a process comprising the steps of: (1) contacting Form B of the HCl salt of Compound B1 with a solvent; and (2) isolating Form B of the HCl salt of Compound B1. In certain embodiments, Form B of the HCl salt of Compound B1 is purified via solvent-based purification methods, including solvent slurry. In particular embodiments, purification via solvent slurry reduces or removes one or more chemical impurities and/or physical impurities (e.g., one or more other crystal forms and/or amorphous forms).

In certain embodiments, Form B of the HCl salt of Compound B1 is obtained by a process comprising the steps of: (1) dissolving Form B of the HCl salt of Compound B1; and (2) recrystallizing Form B of the HCl salt of Compound B1. In certain embodiments, Form B of the HCl salt of Compound B1 is purified via recrystallization. In particular embodiments, such purification via recrystallization reduces or removes one or more chemical impurities and/or physical impurities (e.g., one or more other crystal forms and/or amorphous forms).

In certain embodiments, Form B of the HCl salt of Compound B1 is substantially pure. In certain embodiments, Form B of the HCl salt of Compound B1 is substantially free of chemical impurities. In certain embodiments, Form B of the HCl salt of Compound B1 is substantially free of physical impurities, e.g., one or more other crystal forms and/or amorphous forms. In certain embodiments, Form B of the HCl salt of Compound B1 is substantially free of the free base of Compound B1. In certain embodiments, Form B of the HCl salt of Compound B1 is substantially free of other crystal forms comprising Compound B1.

Representative XRPD patterns of Form B of the HCl salt of Compound B1 are provided in FIG. 13a and FIG. 13b. In certain embodiments, Form B of the HCl salt of Compound B1 is characterized by XRPD peaks located at one, two, three, four, five, six, seven, eight, nine, ten or more of the following approximate positions: 6.98, 9.18, 10.7, 11.48, 13.04, 13.26, 15.14, 15.78, 17.32, 18.48, 18.8, 19.64, 20.42, 20.82, 22.16, 22.62, 23.1, 23.72, 24.38, 26.16, 27.08, 27.6, 28.52, 28.96, 29.24, 30.78, 32.34, 33.14, 34.04, 35.02, 35.92, 37.64, 38.62 degrees 2θ. In certain embodiments, Form B of the HCl salt of Compound B1 is characterized by XRPD peaks located at one, two, three, four, five, six, seven, eight, nine, ten or more of the following approximate positions: 6.98, 10.7, 13.04, 13.26, 15.78, 18.48, 18.8, 20.42, 20.82, 22.16, 22.62, 23.72, 24.38, 26.16, 27.08, 27.6 degrees 2θ. In certain embodiments, Form B of the HCl salt of Compound B1 is characterized by XRPD peaks located at one or both of the following approximate positions: 6.98, 20.82 degrees 2θ. In certain embodiments, Form B of the HCl salt of Compound B1 is characterized by an XRPD pattern which matches a pattern exhibited in FIG. 13a or FIG. 13b.

Representative thermal characteristics of Form B of the HCl salt of Compound B1 are shown in FIG. 14, FIG. 15 and FIG. 16. A representative DSC thermogram, presented in FIG. 14, comprises broad, shallow thermal events with maxima at approximately 58 and 178° C., followed by an endothermic event with an onset of approximately 260° C. Another representative thermogram, presented in FIG. 15, comprises an endotherm with a maximum at about 64° C. and an endotherm with an onset at about 260° C. In certain embodiments, Form B is characterized by a DSC thermogram comprising one or more thermal events between about ambient temperature and about 200° C., followed by an endothermic event with an onset of approximately 260° C. In certain embodiments, Form B is characterized by a DSC thermogram comprising an endotherm with an onset temperature of about 260° C. A representative TGA thermogram, presented in FIG. 16, comprises a mass loss of about 1% of the total mass of the sample upon heating from ambient temperature to about 200° C. In certain embodiments, the mass loss upon heating Form B from ambient temperature to about 200° C. is about 3% or less, about 2% or less, about 1% or less, or about 0.5% or less of the total mass of the sample. In certain embodiments, the aforementioned mass loss comprises a loss of solvent, such as, e.g., a loss of water. In certain embodiments, the Form B material decomposes above about 200° C. In certain embodiments, samples of Form B comprise solvent, e.g. water and/or alcohol. In certain embodiments, samples of Form B are substantially free solvent, e.g., water and/or alcohol. Thus, in certain embodiments Form B is unsolvated, and in certain embodiments Form B is anhydrous.

In certain embodiments, the chemical profile of a sample of Form B of the HCl salt of Compound B1 can be characterized by solution NMR analysis. A representative $^1$H NMR spectrum of a sample of Form B dissolved in DMSO-d6 is provided as FIG. 17.

In certain embodiments, Form B of the HCl salt of Compound B1 may be characterized by isothermic moisture sorption and/or desorption analysis. For example, in one embodiment, a mass loss of about 0.6% accompanied an initial equilibration at about 5% RH; this was followed by a total mass gain of about 3.6%, corresponding to about 1.2 molar equivalents of water, when humidity was increased from 5% to 95% RH; and this was followed by a total mass loss of about 3.6% when humidity was decreased from about 95% to about 5% RH. In certain embodiments, the resulting material is characterized as Form B of the HCl salt of Compound B1, indicating the stability of Form B in the presence of humidity. A representative dynamic vapor sorption/desorption curve for Form B of the HCl salt of Compound B1 is presented in FIG. 18.

In certain embodiments, Form B of the HCl salt of Compound B1 may be characterized by its behavior upon storage at stress conditions. For example, in certain embodiments, when stressed at about 75% RH at about ambient temperature for periods of about 2 and 4 days, samples of Form B exhibited no substantial weight change, and the resulting samples exhibited an XRPD pattern corresponding to Form B. Thus, in certain embodiments, Form B is physically stable at about 75% RH at about ambient temperature.

In certain embodiments, Form B of the HCl salt of Compound B1 may be characterized by certain crystallographic parameters that may be obtained, e.g., from single-crystal X-ray diffraction parameters, among other techniques. For example, in certain embodiments, Form B of the HCl salt of Compound B1 crystallizes in a primitive monoclinic space group. In certain embodiments, the space group is P2$_1$/n. In certain embodiments, Form B of the HCl salt of Compound B1, having a chemical formula of $C_{29}H_{34}Cl_2N_6O_4S$ and having a formula weight of 633.60, has unit cell parameters consistent with the following approximate values, when measured at about 150 K: a=15.6089 Å; b=11.9443 Å; c=16.9448 Å; α=γ=90°; β=101.249°; V=3098.5 Å$^3$; Z=4. In certain embodiments, the calculated density of Form B is approximately d$_{calc}$=1.358 g cm$^{-3}$ at about 150 K.

In certain embodiments, Form B of the HCl salt of Compound B1 may be represented by the thermal ellipsoid plot depicted in FIG. 19. In certain embodiments, the crystal packing of Form B may be represented by the crystal packing depicted in FIG. 20. In certain embodiments, Form B of the HCl salt of Compound B1 has an XRPD pattern matching the simulated XRPD pattern presented in FIG. 21, which was simulated using single-crystal XRD data collected at about 150 K. One skilled in the art will recognize that the precise peak locations of an XRPD pattern, including a simulated XRPD pattern, may shift to a certain extent depending upon, e.g., the temperature at which the X-ray diffraction data was obtained. In particular embodiments, a simulated XRPD pattern for Form B of the HCl salt of Compound B1, based on single-crystal XRD data collected at about 150 K, comprises XRPD peaks located at one, two, three, four, five, six, seven, eight, nine, ten or more of the following approximate positions: 7.05, 9.1, 9.4, 10.65, 12.95, 13.35, 15.05, 15.55, 15.75, 15.9, 17.15, 18.55, 18.7, 18.9, 20.5, 21.25, 22.3, 22.65, 22.75, 22.9, 23.35, 24.0, 24.4, 24.75, 26.65, 27.3, 27.65, 28.0, 28.3, 29.05, 29.65 degrees 2θ.

5.2.6 Form C of the HCl Salt of Compound B1

Certain embodiments herein provide the Form C crystal form of the HCl salt of Compound B1. In certain embodiments, Form C of the HCl salt of Compound B1 can be obtained by slow evaporation of an aqueous solution comprising the HCl salt of Compound B1. In certain embodiments, Form C can be obtained by crystallization from solvent, water or solvent/water mixtures including, but not limited to, common laboratory organic solvents.

In certain embodiments, the chloride content of the Form C HCl salt is determined by analyzing a sample of Form C for chloride content, e.g., by performing elemental analysis, chloride titration, and/or ion chromatography. In certain embodiments, Form C has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form C has a chloride content corresponding to about 2 molar equivalents of HCl per mole of Compound B1. In certain embodiments, Form C is a bis-HCl salt of Compound B1.

A representative XRPD pattern of Form C of the HCl salt of Compound B1 is provided in FIG. 22. In certain embodiments, Form C of the HCl salt of Compound B1 is characterized by XRPD peaks located at one, two, three, four, five, six, seven, eight, nine, ten or more of the following approximate positions: 4.69, 5.14, 6.46, 8.05, 10.44, 12.52, 13.59, 15.22, 15.53, 15.91, 16.54, 16.99, 17.37, 17.78, 20.59, 21.07, 22.11, 22.7, 23.63, 24.33, 24.6, 26.68, 28.24, 28.79 degrees 2θ. In certain embodiments, Form C of the HCl salt of Compound B1 is characterized by XRPD peaks located at one, two, three, four, five or six of the following approximate positions: 4.69, 12.52, 13.59, 16.54, 20.59, 23.63 degrees 2θ. In certain embodiments, Form C of the HCl salt of Compound B1 is characterized by an XRPD pattern which matches the pattern exhibited in FIG. 22.

5.2.7 Form D of the HCl Salt of Compound B1

Certain embodiments herein provide the Form D crystal form of the HCl salt of Compound B1. In certain embodiments, Form D of the HCl salt of Compound B1 can be obtained by slurrying the HCl salt of Compound B1 in one or more solvents, including, but not limited to, acetone, acetonitrile, ethyl acetate and trifluorotoluene. In certain embodiments, Form D can be prepared by exposing Form A of the HCl salt of Compound B1 to high humidity, e.g., as described herein. In certain embodiments, Form D can be obtained by crystallization from solvent, water or solvent/water mixtures including, but not limited to, common laboratory organic solvents.

In certain embodiments, the chloride content of the Form D HCl salt is determined by analyzing a sample of Form D for chloride content, e.g., by performing elemental analysis, chloride titration, and/or ion chromatography. In certain embodiments, Form D has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form D has a chloride content corresponding to about 2 molar equivalents of HCl per mole of Compound B1. In certain embodiments, Form D is a bis-HCl salt of Compound B1.

A representative XRPD pattern of Form D of the HCl salt of Compound B1 is provided in FIG. 23. In certain embodiments, Form D of the HCl salt of Compound B1 is characterized by XRPD peaks located at one, two, three, four, five, six, seven, eight, nine, ten or more of the following approximate positions: 3.65, 7.36, 8.67, 10.13, 11.1, 12.55, 15.64, 16.5, 17.33, 18.62, 20.31, 22.08, 23.39, 25.16, 25.71, 26.78 degrees 2θ. In certain embodiments, Form D of the HCl salt of Compound B1 is characterized by XRPD peaks located at one, two, three, four, five, six, seven, eight, nine, ten or more of the following approximate positions: 3.65, 7.36, 10.13, 12.55, 15.64, 17.33, 18.62, 20.31, 22.08, 25.71, 26.78 degrees 2θ. In certain embodiments, Form D of the HCl salt of Compound B1 is characterized by an XRPD pattern which matches the pattern exhibited in FIG. 23.

Representative thermal characteristics of Form D of the HCl salt of Compound B1 are shown in FIG. 24 and FIG. 25. A representative DSC thermogram, presented in FIG. 24, comprises thermal events with maxima at approximately 62, 228 and 268° C. In certain embodiments, Form D is characterized by a DSC thermogram comprising one or more thermal events with the following approximate temperature maxima: 62, 228 and 268° C. A representative TGA thermogram, presented in FIG. 25, comprises a mass loss of about 4.1% % of the total mass of the sample upon heating from ambient temperature to about 100° C. In certain embodiments, the aforementioned mass loss comprises a loss of solvent, such as, e.g., a loss of water. In certain embodiments, Form D is a solvate, such as, e.g., a hydrate. In certain embodiments, Form D comprises approximately 0.1, 0.2, 0.3, 0.4, 0.5, 1.0, 1.5, 2.0, 2.5 or 3.0 molar equivalents of solvent, such as, e.g., water, per mole of HCl salt of Compound B1.

In certain embodiments, Form D of the HCl salt of Compound B1 may be characterized by its behavior upon storage at stress conditions. For example, in certain embodiments, when a sample of Form D is stressed at 80° C. for 3 days, the resulting material exhibits an XRPD pattern corresponding to Form D. Thus, in certain embodiments, Form D is physically stable at 80° C.

5.2.8 Form E of the HCl Salt of Compound B1

Certain embodiments herein provide the Form E crystal form of the HCl salt of Compound B1. In certain embodiments, Form E of the HCl salt of Compound B1 can be obtained by slurrying the HCl salt of Compound B1 in one or more solvents, including, but not limited to, dichloromethane. In certain embodiments, Form E can be obtained by crystallization from solvent, water or solvent/water mixtures including, but not limited to, common laboratory organic solvents.

In certain embodiments, the chloride content of the Form E HCl salt is determined by analyzing a sample of Form E for chloride content, e.g., by performing elemental analysis, chloride titration, and/or ion chromatography. In certain embodiments, Form E has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form E has a chloride content corresponding to about 2 molar equivalents of HCl per mole of Compound B1. In certain embodiments, Form E is a bis-HCl salt of Compound B1.

A representative XRPD pattern of Form E of the HCl salt of Compound B1 is provided in FIG. 26. In certain embodiments, Form E of the HCl salt of Compound B1 is characterized by XRPD peaks located at one, two, three, four, five, six, seven, eight, nine, ten or more of the following approximate positions: 3.1, 4.1, 6.08, 7.84, 8.81, 9.96, 12.55, 13.63, 15.67, 16.99, 17.85, 19.0, 20.14, 20.62, 22.56, 24.78, 25.95, 27.75 degrees 2θ. In certain embodiments, Form E of the HCl salt of Compound B1 is characterized by XRPD peaks located at one, two, three, four, five, six, seven, eight, nine, ten or more of the following approximate positions: 4.1, 6.08, 9.96, 13.63, 16.99, 17.85, 19.0, 22.56, 24.78, 25.95, 27.75 degrees 2θ. In certain embodiments, Form E of the HCl salt of Compound B1 is characterized by an XRPD peak located at approximately 6.08 degrees 2θ. In certain embodiments, Form E of the HCl salt of Compound B1 is characterized by an XRPD pattern which matches the pattern exhibited in FIG. 26.

Representative thermal characteristics of Form E of the HCl salt of Compound B1 are shown in FIG. 27 and FIG. 28. A representative DSC thermogram, presented in FIG. 27, comprises thermal events with maxima at approximately 82, 240 and 269° C. In certain embodiments, Form E is characterized by a DSC thermogram comprising one or more thermal events with the following approximate temperature maxima: 82, 240 and 269° C. A representative TGA thermogram, presented in FIG. 28, comprises a mass loss of about 2.6% of the total mass of the sample upon heating from ambient temperature to about 85° C. In certain embodiments, the aforementioned mass loss comprises a loss of solvent, such as, e.g., a loss of water. In certain embodiments, Form E is a solvate, such as, e.g., a hydrate. In certain embodiments, Form E comprises approximately 0.1, 0.2, 0.3, 0.4, 0.5, 1.0, 1.5, 2.0, 2.5 or 3.0 molar equivalents of solvent, such as, e.g., water and/or dichloromethane, per mole of the HCl salt of Compound B1.

5.2.9 Form F of the HCl Salt of Compound B1

Certain embodiments herein provide the Form F crystal form of the HCl salt of Compound B1. In certain embodiments, Form F of the HCl salt of Compound B1 can be obtained by crystallization of the HCl salt of Compound B1 in one or more solvents, including, but not limited to, ethanol and water. In certain embodiments, Form F is obtained by fast evaporation of a solution comprising the HCl salt of Compound B1 in ethanol. In certain embodiments, Form F is obtained by slowly cooling a solution of the HCl salt of compound B1 in a solution of 1:4 water:ethanol. In certain embodiments, Form F can be obtained by crystallization from solvent, water or solvent/water mixtures including, but not limited to, common laboratory organic solvents.

In certain embodiments, the chloride content of the Form F HCl salt is determined by analyzing a sample of Form F for chloride content, e.g., by performing elemental analysis, chloride titration, and/or ion chromatography. In certain embodiments, Form F has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form F has a chloride content corresponding to about 2 molar equivalents of HCl per mole of Compound B1. In certain embodiments, Form F is a bis-HCl salt of Compound B1.

A representative XRPD pattern of Form F of the HCl salt of Compound B1 is provided in FIG. 29. In certain embodiments, Form F of the HCl salt of Compound B1 is characterized by XRPD peaks located at one, two, three, four, five, six, seven, eight, nine, ten or more of the following approximate positions: 2.26, 4.1, 5.24, 7.39, 7.67, 8.29, 9.3, 10.55, 12.45, 13.39, 14.11, 14.7, 15.78, 16.78, 17.23, 17.71, 18.79, 19.83, 21.97, 22.67, 23.39, 23.95, 26.3, 26.58, 27.34, 27.93 degrees 2θ. In certain embodiments, Form F of the HCl salt of Compound B1 is characterized by XRPD peaks located at one, two, three, four, five, six, seven, eight, nine, ten or more of the following approximate positions: 2.26, 4.1, 5.24, 7.39, 7.67, 8.29, 15.78, 16.78, 17.23, 17.71, 18.79, 26.3, 26.58, 27.34 degrees 2θ. In certain embodiments, Form F of the HCl salt of Compound B1 is characterized by an XRPD peak located at approximately 8.29 degrees 2θ. In certain embodiments, Form F of the HCl salt of Compound B1 is characterized by an XRPD pattern which matches the pattern exhibited in FIG. 29.

Representative thermal characteristics of Form F of the HCl salt of Compound B1 are shown in FIG. 30 and FIG. 31. A representative DSC thermogram, presented in FIG. 30, comprises thermal events with maxima at approximately 85, 237 and 272° C. In certain embodiments, Form F is characterized by a DSC thermogram comprising one or more thermal events with the following approximate temperature maxima: 85, 237 and 272° C. A representative TGA thermogram, presented in FIG. 31, comprises a mass loss of about 4.6% of the total mass of the sample upon heating from ambient temperature to about 110° C. In certain embodiments, the aforementioned mass loss comprises a loss of solvent, such as, e.g., a loss of water, ethanol or water and ethanol. In certain embodiments, Form F is a solvate, such as, e.g., a hydrate or ethanol solvate or mixed hydrate/ethanol solvate. In certain embodiments, Form F comprises approximately 0.1, 0.2, 0.3, 0.4, 0.5, 1.0, 1.5, 2.0, 2.5 or 3.0 molar equivalents of solvent, such as, e.g., ethanol and/or water, per mole of HCl salt of Compound B1.

In certain embodiments, Form F of the HCl salt of Compound B1 may be characterized by its behavior upon storage at stress conditions. For example, in certain embodiments, when a sample of Form F is stressed at 80° C. for 3 days, the resulting material exhibits an XRPD pattern is indicative of a solid which is substantially disordered, but which retains some Form F content, as indicated by minor peaks corresponding to those characteristic of Form F.

5.2.10 Form G of the HCl Salt of Compound B1

Certain embodiments herein provide the Form G crystal form of the HCl salt of Compound B1. In certain embodiments, Form G of the HCl salt of Compound B1 can be obtained by crystallization of the HCl salt of Compound B1 in one or more solvents, including, but not limited to, water, 1,4-dioxane, and water/dioxane mixtures. In certain embodiments, Form G is obtained by slurrying the HCl salt of Compound B1 in a solvent system comprising 1:9 water: 1,4-dioxane. In certain embodiments, Form F can be obtained by crystallization from solvent, water or solvent/water mixtures including, but not limited to, common laboratory organic solvents.

In certain embodiments, the chloride content of the Form G HCl salt is determined by analyzing a sample of Form G for chloride content, e.g., by performing elemental analysis, chloride titration, and/or ion chromatography. In certain embodiments, Form G has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form G has a chloride content corresponding to about 2 molar equivalents of HCl per mole of Compound B1. In certain embodiments, Form G is a bis-HCl salt of Compound B1.

A representative XRPD pattern of Form G of the HCl salt of Compound B1 is provided in FIG. 32. In certain embodiments, Form G of the HCl salt of Compound B1 is characterized by XRPD peaks located at one, two, three, four, five, six, seven, eight, nine, ten or more of the following approximate positions: 4.27, 9.58, 10.61, 12.31, 13.56, 15.01, 16.61, 17.4, 18.23, 19.52, 20.0, 20.42, 21.28, 22.01, 22.63, 23.08, 23.53, 24.33, 24.67, 25.85, 27.27, 30.24, 31.63 degrees 2θ. In certain embodiments, Form G of the HCl salt of Compound B1 is characterized by XRPD peaks located at one, two, three, four, five, six, seven, eight, nine, ten or more of the following approximate positions: 4.27, 12.31, 13.56, 16.61, 18.23, 19.52, 20.0, 20.42, 21.28, 22.01, 22.63, 23.08, 23.53, 24.67, 27.27 degrees 2θ. In certain embodiments, Form G of the HCl salt of Compound B1 is characterized by an XRPD peak located at approximately 21.28 degrees 2θ. In certain embodiments, Form G of the HCl salt of Compound B1 is characterized by an XRPD pattern which matches the pattern exhibited in FIG. 32.

Representative thermal characteristics of Form G of the HCl salt of Compound B1 are shown in FIG. 33 and FIG. 34. A representative DSC thermogram, presented in FIG. 33, comprises thermal events with maxima at approximately 67, 115, 241 and 267° C. In certain embodiments, Form G is characterized by a DSC thermogram comprising one or more thermal events with the following approximate temperature maxima: 67, 115, 241 and 267° C. A representative TGA thermogram, presented in FIG. 34, comprises a mass loss of about 13.7% of the total mass of the sample upon heating from ambient temperature to about 85° C. In certain embodiments, the aforementioned mass loss comprises a loss of solvent, such as, e.g., a loss of water, 1,4-dioxane or water and 1,4-dioxane. In certain embodiments, Form G is a solvate, such as, e.g., a hydrate or 1,4-dioxane solvate or mixed hydrate/1,4-dioxane solvate. In certain embodiments, Form G comprises approximately 0.1, 0.2, 0.3, 0.4, 0.5, 1.0, 1.5, 2.0, 2.5 or 3.0 molar equivalents of solvent, such as, e.g., water and/or 1,4-dioxane, per mole of HCl salt of Compound B1.

5.2.11 Form H of the HCl Salt of Compound B1

Certain embodiments herein provide the Form H crystal form of the HCl salt of Compound B1. In certain embodiments, Form H of the HCl salt of Compound B1 can be obtained by crystallization of the HCl salt of Compound B1 in one or more solvents, including, but not limited to, isopropanol, water, methanol, acetone and mixtures of two or more thereof. In certain embodiments, Form H is obtained by slurrying the HCl salt of Compound B1 in a solvent system comprising isopropanol and water. In certain embodiments, Form H is obtained by slurrying the HCl salt of Compound B1 in a solvent system comprising methanol and acetone. In certain embodiments, Form H can be obtained by crystallization from solvent, water or solvent/water mixtures including, but not limited to, common laboratory organic solvents.

In certain embodiments, the chloride content of the Form H HCl salt is determined by analyzing a sample of Form H for chloride content, e.g., by performing elemental analysis, chloride titration, and/or ion chromatography. In certain embodiments, Form H has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form H has a chloride content corresponding to about 2 molar equivalents of HCl per mole of Compound B1. In certain embodiments, Form H is a bis-HCl salt of Compound B1.

A representative XRPD pattern of Form H of the HCl salt of Compound B1 is provided in FIG. 35. In certain embodiments, Form H of the HCl salt of Compound B1 is characterized by XRPD peaks located at one, two, three, four, five, six, seven, eight, nine, ten or more of the following approximate positions: 4.24, 5.66, 8.81, 9.23, 9.85, 11.55, 12.49, 13.28, 14.01, 15.88, 16.23, 16.64, 16.95, 17.2, 17.78, 18.13, 18.72, 19.03, 19.34, 19.76, 20.38, 21.32, 22.39, 23.15, 23.53, 24.12, 24.71, 25.12, 26.06, 26.58, 26.85, 27.58, 28.17, 29.66, 30.55, 32.18, 34.7 degrees 2θ. In certain embodiments, Form H of the HCl salt of Compound B1 is characterized by XRPD peaks located at one, two, three, four, five, six, seven, eight, nine, ten or more of the following approximate positions: 4.24, 5.66, 8.81, 9.23, 11.55, 12.49, 13.28, 14.01, 15.88, 16.23, 16.95, 17.78, 18.72, 19.03, 19.34, 19.76, 21.32, 23.53, 24.12, 24.71, 25.12, 26.06, 26.58, 26.85, 27.58, 29.66 degrees 2θ. In certain embodiments, Form H of the HCl salt of Compound B1 is characterized by XRPD peaks located at one, two, three, four, five or six of the following approximate positions: 5.66, 8.81, 9.23, 14.01, 24.12, 29.66 degrees 2θ. In certain embodiments, Form H of the HCl salt of Compound B1 is characterized by an XRPD pattern which matches the pattern exhibited in FIG. 35.

Representative thermal characteristics of Form H of the HCl salt of Compound B1 are shown in FIG. 36 and FIG. 37. A representative DSC thermogram, presented in FIG. 36, comprises thermal events with maxima at approximately 86, 178, 248 and 273° C. In certain embodiments, Form H is characterized by a DSC thermogram comprising one or more thermal events with the following approximate temperature maxima: 86, 178, 248 and 273° C. A representative TGA thermogram, presented in FIG. 37, comprises a mass loss of about 2.7% of the total mass of the sample upon heating from ambient temperature to about 150° C. In certain embodiments, the aforementioned mass loss comprises a loss of solvent, such as, e.g., a loss of isopropanol, water, methanol, acetone or mixtures of two or more thereof. In certain embodiments, Form H is a solvate, such as, e.g., a hydrate or solvate or mixed hydrate/solvate. In certain embodiments, Form H comprises approximately 0.1, 0.2, 0.3, 0.4, 0.5, 1.0, 1.5, 2.0, 2.5 or 3.0 molar equivalents of solvent, such as, e.g., isopropanol, water, methanol, acetone, per mole of HCl salt of Compound B1.

5.2.12 Form I of the HCl Salt of Compound B1

Certain embodiments herein provide the Form I crystal form of the HCl salt of Compound B1. In certain embodiments, Form I of the HCl salt of Compound B1 can be obtained by precipitation from a solution comprising the HCl salt of Compound B1 in methanol, ethyl acetate or a mixture thereof. In certain embodiments, Form I can be obtained by crystallization from solvent, water or solvent/water mixtures including, but not limited to, common laboratory organic solvents.

In certain embodiments, the chloride content of the Form I HCl salt is determined by analyzing a sample of Form I for chloride content, e.g., by performing elemental analysis, chloride titration, and/or ion chromatography. In certain embodiments, Form I has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form I has a chloride content corresponding to about 2 molar equivalents of HCl per mole of Compound B1. In certain embodiments, Form I is a bis-HCl salt of Compound B1.

A representative XRPD pattern of Form I of the HCl salt of Compound B1 is provided in FIG. 38. In certain embodiments, Form I of the HCl salt of Compound B1 is characterized by XRPD peaks located at one, two, three, four, five, six, seven, eight, nine, ten or more of the following approximate positions: 3.96, 4.82, 5.79, 9.81, 10.29, 11.74, 13.41, 13.72, 14.72, 15.8, 16.21, 17.39, 18.25, 18.88, 19.64, 19.99, 20.92, 21.79, 23.42, 24.53, 25.53, 26.36, 27.06, 27.47, 27.96, 28.89, 29.83, 30.94, 32.43, 35.31, 37.87, 39.4 degrees 2θ. In certain embodiments, Form I of the HCl salt of Compound B1 is characterized by XRPD peaks located at one, two, three, four, five, six, seven, eight, nine, ten or more of the following approximate positions: 3.96, 4.82, 9.81, 10.29, 14.72, 15.8, 16.21, 17.39, 18.25, 19.64, 21.79, 26.36, 27.06 degrees 2θ. In certain embodiments, Form I of the HCl salt of Compound B1 is characterized by XRPD peaks located at one or both of the following approximate positions: 9.81, 14.72 degrees 2θ. In certain embodiments, Form I of the HCl salt of Compound B1 is characterized by an XRPD pattern which matches the pattern exhibited in FIG. 38.

5.2.13 Form J of the HCl Salt of Compound B1

Certain embodiments herein provide the Form J crystal form of the HCl salt of Compound B1. In certain embodiments, Form J of the HCl salt of Compound B1 can be obtained by precipitation from a solution comprising the HCl salt of Compound B1 in methanol, water or a mixture thereof. In certain embodiments, Form J can be obtained by crystallization from solvent, water or solvent/water mixtures including, but not limited to, common laboratory organic solvents. In particular embodiments, Form J can be obtained by fast evaporation or crash cooling of a solution comprising methanol and the HCl salt of Compound B1.

In certain embodiments, the chloride content of the Form J HCl salt is determined by analyzing a sample of Form J for chloride content, e.g., by performing elemental analysis, chloride titration, and/or ion chromatography. In certain embodiments, Form J has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form J has a chloride content corresponding to about 2 molar equivalents of HCl per mole of Compound B1. In certain embodiments, Form J is a bis-HCl salt of Compound B1.

A representative XRPD pattern of Form J of the HCl salt of Compound B1 is provided in FIG. 39. In certain embodiments, Form J of the HCl salt of Compound B1 is characterized by XRPD peaks located at one, two, three, four, five, six, seven, eight, nine, ten or more of the following approximate positions: 3.71, 4.82, 5.24, 9.36, 11.19, 12.89, 15.55, 16.07, 16.7, 17.6, 19.88, 20.47, 21.68, 22.24, 23.21, 23.83, 24.66, 25.01, 25.81, 26.4, 28.58, 28.89 degrees 2θ. In certain embodiments, Form J of the HCl salt of Compound B1 is characterized by XRPD peaks located at one, two, three, four, five, six, seven or eight of the following approximate positions: 4.82, 5.24, 11.19, 12.89, 15.55, 17.6, 20.47, 22.24 degrees 2θ. In certain embodiments, Form J of the HCl salt of Compound B1 is characterized by an XRPD pattern which matches the pattern exhibited in FIG. 39.

5.2.14 Form K of the HCl Salt of Compound B1

Certain embodiments herein provide the Form K crystal form of the HCl salt of Compound B1. In certain embodiments, Form K of the HCl salt of Compound B1 can be obtained by precipitation from a solution comprising the HCl salt of Compound B1 in 2,2,2,-trifluoroethanol (TFE), p-dioxane, water or a mixture of two or more thereof. In certain embodiments, Form K can be obtained by crystallization from solvent, water or solvent/water mixtures including, but not limited to, common laboratory organic solvents. In particular embodiments, Form K can be obtained by crash precipitation from a solution comprising TFE, p-dioxane and the HCl salt of Compound B1.

In certain embodiments, the chloride content of the Form K HCl salt is determined by analyzing a sample of Form K for chloride content, e.g., by performing elemental analysis, chloride titration, and/or ion chromatography. In certain embodiments, Form K has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form K has a chloride content corresponding to about 2 molar equivalents of HCl per mole of Compound B1. In certain embodiments, Form K is a bis-HCl salt of Compound B1.

A representative XRPD pattern of Form K of the HCl salt of Compound B1 is provided in FIG. 40. In certain embodiments, Form K of the HCl salt of Compound B1 is characterized by XRPD peaks located at one, two, three, four, five, six, seven, eight, nine, ten or more of the following approximate positions: 3.71, 6.86, 7.52, 7.94, 10.36, 15.0, 15.9, 16.52, 17.11, 17.63, 17.84, 18.95, 20.06, 20.89, 22.58, 23.83, 25.95, 26.5, 27.3, 27.71 degrees 2θ. In certain embodiments, Form K of the HCl salt of Compound B1 is characterized by XRPD peaks located at one, two, three, four, five, six, seven, eight, nine, ten or more of the following approximate positions: 3.71, 7.52, 7.94, 10.36, 16.52, 17.11, 17.63, 17.84, 25.95, 27.3, 27.71 degrees 2θ. In certain embodiments, Form K of the HCl salt of Compound B1 is characterized by an XRPD peak at approximately 7.94 degrees 2θ. In certain embodiments, Form K of the HCl salt of Compound B1 is characterized by an XRPD pattern which matches the pattern exhibited in FIG. 40.

5.2.15 Form L of the HCl Salt of Compound B1

Certain embodiments herein provide the Form L crystal form of the HCl salt of Compound B1. In certain embodiments, Form L of the HCl salt of Compound B1 can be obtained by precipitation from a solution comprising the HCl salt of Compound B1 in ethanol, 2,2,2,-trifluoroethanol (TFE), water or a mixture of two or more thereof. In certain embodiments, Form L can be obtained by crystallization from solvent, water or solvent/water mixtures including, but not limited to, common laboratory organic solvents. In particular embodiments, Form L can be obtained by slow evaporation of a solution comprising ethanol, TFE and the HCl salt of Compound B1.

In certain embodiments, the chloride content of the Form L HCl salt is determined by analyzing a sample of Form L for chloride content, e.g., by performing elemental analysis, chloride titration, and/or ion chromatography. In certain embodiments, Form L has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form L has a chloride content corresponding to about 2 molar equivalents of HCl per mole of Compound B1. In certain embodiments, Form L is a bis-HCl salt of Compound B1.

A representative XRPD pattern of Form L of the HCl salt of Compound B1 is provided in FIG. 41. In certain embodiments, Form L of the HCl salt of Compound B1 is characterized by XRPD peaks located at one, two, three, four, five, six, seven, eight, nine, ten or more of the following approximate positions: 4.2, 4.82, 8.46, 9.88, 11.5, 12.37, 13.23, 14.76, 15.97, 16.8, 17.77, 18.15, 18.53, 19.05, 19.43, 19.85, 20.47, 21.23, 21.51, 22.45, 23.0, 24.66, 25.32, 26.05, 28.1, 28.51 degrees 2θ. In certain embodiments, Form L of the HCl salt of Compound B1 is characterized by XRPD peaks located at one, two, three, four, five, six, seven, eight, nine, ten or more of the following approximate positions: 4.2, 4.82, 12.37, 13.23, 15.97, 17.77, 18.15, 18.53, 19.05, 19.43, 19.85, 21.51, 24.66, 25.32, 26.05 degrees 2θ. In certain embodiments, Form L of the HCl salt of Compound B1 is characterized by an XRPD pattern which matches the pattern exhibited in FIG. 41.

5.2.16 Form M of the HCl Salt of Compound B1

Certain embodiments herein provide the Form M crystal form of the HCl salt of Compound B1. In certain embodiments, Form M of the HCl salt of Compound B1 can be obtained by precipitation from a solution comprising the HCl salt of Compound B1 in methanol, water or a mixture of two or more thereof. In certain embodiments, Form M can be obtained by crystallization from solvent, water or solvent/water mixtures including, but not limited to, common laboratory organic solvents. In particular embodiments, Form M can be obtained by crash cooling a solution comprising methanol and the HCl salt of Compound B1.

In certain embodiments, the chloride content of the Form M HCl salt is determined by analyzing a sample of Form M for chloride content, e.g., by performing elemental analysis, chloride titration, and/or ion chromatography. In certain embodiments, Form M has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form M has a chloride content corresponding to about 2 molar equivalents of HCl per mole of Compound B1. In certain embodiments, Form M is a bis-HCl salt of Compound B1.

A representative XRPD pattern of Form M of the HCl salt of Compound B1 is provided in FIG. 42. In certain embodiments, Form M of the HCl salt of Compound B1 is characterized by XRPD peaks located at one, two, three, four, five, six, seven, eight, nine, ten or more of the following approximate positions: 4.06, 5.2, 8.49, 11.05, 11.4, 12.92, 14.13, 14.96, 16.07, 16.7, 17.74, 19.02, 19.81, 20.96, 22.17, 23.0, 24.39, 25.15, 25.91, 27.06, 28.2, 28.65, 29.41, 29.9, 31.42, 34.65, 35.34 degrees 2θ. In certain embodiments, Form M of the HCl salt of Compound B1 is characterized by XRPD peaks located at one, two, three, four, five, six, seven, eight, nine, ten or more of the following approximate positions: 4.06, 5.2, 11.05, 11.4, 12.92, 16.07, 17.74, 19.81, 22.17, 23.0, 24.39, 25.15, 28.2, 28.65 degrees 2θ. In certain embodiments, Form M of the HCl salt of Compound B1 is characterized by XRPD peaks located at one or both of the following approximate positions: 28.2, 28.65 degrees 2θ. In certain embodiments, Form M of the HCl salt of Compound B1 is characterized by an XRPD pattern which matches the pattern exhibited in FIG. 42.

5.2.17 Form N of the HCl Salt of Compound B1

Certain embodiments herein provide the Form N crystal form of the HCl salt of Compound B1. In certain embodiments, Form N of the HCl salt of Compound B1 can be obtained by precipitation from a solution comprising the HCl salt of Compound B1 in ethanol, 2,2,2-trifluoroethanol, nitromethane, water, or a mixture of two or more thereof. In certain embodiments, Form N can be obtained by crystallization from solvent, water or solvent/water mixtures including, but not limited to, common laboratory organic solvents. In particular embodiments, Form N can be obtained by slow evaporation of a solution comprising 4:1 ethanol:2,2,2,-trifluoroethanol and the HCl salt of Compound B1. In particular embodiments, Form N can be obtained by slow evaporation of a solution comprising 4:1 nitromethane:2,2,2,-trifluoroethanol and the HCl salt of Compound B1. In particular embodiments, Form N can be obtained by crash precipitation by mixing THF with a solution comprising 2,2,2,-trifluoroethanol and the HCl salt of Compound B1. In particular embodiments, Form N can be obtained by vapor diffusion of p-dioxane into a solution comprising 2,2,2,-trifluoroethanol and the HCl salt of Compound B1.

In certain embodiments, the chloride content of the Form N HCl salt is determined by analyzing a sample of Form N for chloride content, e.g., by performing elemental analysis, chloride titration, and/or ion chromatography. In certain embodiments, Form N has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form N has a chloride content corresponding to about 2 molar equivalents of HCl per mole of Compound B1. In certain embodiments, Form N is a bis-HCl salt of Compound B1.

A representative XRPD pattern of Form N of the HCl salt of Compound B1 is provided in FIG. 43. In certain embodiments, Form N of the HCl salt of Compound B1 is characterized by XRPD peaks located at one, two, three, four, five, six, seven, eight, nine, ten or more of the following approximate positions: 3.47, 3.92, 4.41, 5.0, 6.66, 6.97, 7.97, 10.6, 11.99, 12.37, 13.27, 14.45, 15.93, 16.49, 18.32, 19.74, 22.24, 23.14, 24.39, 25.88, 26.29, 26.95 degrees 2θ. In certain embodiments, Form N of the HCl salt of Compound B1 is characterized by XRPD peaks located at one, two, three, four, five, six or seven of the following approximate positions: 3.47, 3.92, 10.6, 15.93, 18.32, 25.88, 26.29 degrees 2θ. In certain embodiments, Form N of the HCl salt of Compound B1 is characterized by an XRPD pattern which matches the pattern exhibited in FIG. 43.

5.2.18 Form O of the HCl Salt of Compound B1

Certain embodiments herein provide the Form O crystal form of the HCl salt of Compound B1. In certain embodiments, Form O of the HCl salt of Compound B1 can be obtained by precipitation from a solution comprising the HCl salt of Compound B1 in methanol, water, or a mixture thereof. In certain embodiments, Form O can be obtained by crystallization from solvent, water or solvent/water mixtures including, but not limited to, common laboratory organic solvents. In particular embodiments, Form O can be obtained by crash cooling a solution comprising methanol and the HCl salt of Compound B1.

In certain embodiments, the chloride content of the Form O HCl salt is determined by analyzing a sample of Form O for chloride content, e.g., by performing elemental analysis, chloride titration, and/or ion chromatography. In certain embodiments, Form O has a chloride content corresponding to between about 0.5 to about 1.0, about 1.0 to about 1.5, about 1.5 to about 2.0, or about 2.0 to about 2.5 molar equivalents of HCl per mole of Compound B1. In certain embodiments, Form O has a chloride content corresponding to about 2 molar equivalents of HCl per mole of Compound B1. In certain embodiments, Form O is a bis-HCl salt of Compound B1.

A representative XRPD pattern of Form O of the HCl salt of Compound B1 is provided in FIG. 44. In certain embodiments, Form O of the HCl salt of Compound B1 is characterized by XRPD peaks located at one, two, three, four, five, six, seven, eight, nine, ten or more of the following approximate positions: 2.95, 4.06, 6.41, 8.59, 9.53, 11.05, 11.5, 11.78, 12.89, 14.27, 14.79, 15.21, 16.25, 16.66, 17.46, 18.19, 19.4, 19.88, 20.54, 21.68, 22.17, 24.53, 25.25, 25.67, 27.12, 27.75, 28.68, 29.62, 31.56 degrees 2θ. In certain embodiments, Form O of the HCl salt of Compound B1 is characterized by XRPD peaks located at one, two, three, four, five, six, seven, eight, nine, ten or more of the following approximate positions: 2.95, 4.06, 6.41, 8.59, 9.53, 11.05, 12.89, 14.27, 15.21, 16.25, 18.19, 19.88, 21.68, 22.17, 25.25, 25.67, 27.12 degrees 2θ. In certain embodiments, Form O of the HCl salt of Compound B1 is characterized by XRPD peaks located at one, two, three, four or five of the following approximate positions: 2.95, 8.59, 9.53, 14.27, 15.21 degrees 2θ. In certain embodiments, Form O of the HCl salt of Compound B1 is characterized by an XRPD pattern which matches the pattern exhibited in FIG. 44.

5.2.19 Amorphous Form of the HCl Salt of Compound B1

Certain embodiments herein provide an amorphous form comprising the HCl salt of Compound B1. In certain embodiments, an amorphous form comprising the HCl salt of Compound B1 can be obtained by freeze drying a crystal form comprising the HCl salt of Compound B1 in a suitable solvent, such as, but not limited to, water. In certain embodiments, an amorphous form comprising the HCl salt of Compound B1 can be obtained by grinding a crystal form comprising the HCl salt of Compound B1. In certain embodiments, an amorphous form comprising the HCl salt of Compound B1 can be obtained by precipitation from solvent, water or solvent/water mixtures including, but not limited to, common laboratory organic solvents. In certain embodiments, an amorphous form comprising the HCl salt of Compound B1 can be obtained by slurrying the HCl salt of Compound B1 in isopropanol. In certain embodiments, an amorphous form comprising the HCl salt of Compound B1 can be obtained by evaporating a solution comprising the HCl salt of Compound B1 and water.

A representative XRPD pattern of an amorphous form of the HCl salt of Compound B1 is provided in FIG. 45. In certain embodiments, an amorphous form of the HCl salt of Compound B1 is characterized by an XRPD pattern which matches the pattern exhibited in FIG. 45.

In certain embodiments, an amorphous form of the HCl salt of Compound B1 is characterized by its behaviour under stress conditions. In certain embodiments, an amorphous form of the HCl salt of Compound B1 remains unchanged, as indicated by XRPD, after exposure to 75% RH at ambient temperature for 3 days. In certain embodiments, an amorphous form of the HCl salt of Compound B1, upon exposure to 75% RH at ambient temperature for 3 days, exhibits a weight gain of about 12.3%, corresponding to about 4.3 molar equivalents of water. In certain embodiments, an amorphous form of the HCl salt of Compound B1 remains unchanged, as indicated by XRPD, after exposure to 40° C. for 8 days.

A representative modulated DSC thermogram of an amorphous form of the HCl salt of Compound B1 obtained by grinding is presented in FIG. 46. In certain embodiments, the modulated DSC thermogram of an amorphous form of the HCl salt of Compound B1 comprises no observable glass transition event. In certain embodiments, an amorphous form of the HCl salt of Compound B1 is characterized by a modulated DSC thermogram which matches the thermogram exhibited in FIG. 46.

5.2.20 Form A of the HBr Salt of Compound B1

Certain embodiments herein provide the Form A crystal form of a HBr salt of Compound B1. In certain embodiments, Form A of the HBr salt of Compound B1 can be obtained by reacting Compound B1 with HBr in various solvents, including, but not limited to, methanol, water and mixtures thereof. In certain embodiments, the HBr may be charged to the reaction as a solution, e.g., as a concentrated aqueous solution. In certain embodiments, the HBr is reacted with Compound B1 in an amount suitable to generate the Form A HBr salt stoichiometry. In certain embodiments, at least about one molar equivalent of HBr is added per mole of Compound B1. In certain embodiments, at least about two molar equivalents of HBr are added per mole of Compound B1. In certain embodiments, about 2.5 molar equivalents of HBr are added per mole of Compound B1.

In certain embodiments, Form A of the HBr salt of Compound B1 can be obtained by precipitation from a solution comprising an HBr salt of Compound B1 in a solvent system comprising a solvent such as, but not limited to, methanol, water or a mixture thereof. In certain embodiments, Form A of the HBr salt of Compound B1 can be obtained by slurrying an HBr salt of Compound B1 in methanol, water or a mixture thereof. In certain embodiments, Form A of the HBr salt can be obtained by crystallization from solvent, water or solvent/water mixtures including, but not limited to, common laboratory organic solvents.

A representative XRPD pattern of Form A of the HBr salt of Compound B1 is provided in FIG. 47. In certain embodiments, Form A of the HBr salt of Compound B1 is characterized by XRPD peaks located at one, two, three, four, five, six, seven, eight, nine, ten or more of the following approximate positions: 6.84, 9.16, 9.4, 10.44, 11.34, 12.83, 13.14, 14.91, 15.39, 15.84, 16.47, 16.95, 17.23, 18.34, 19.83, 20.28, 20.66, 21.8, 22.22, 22.53, 23.05, 23.57, 24.15, 25.85, 26.61, 26.96, 27.44, 28.27, 28.72, 29.07, 30.21, 30.9, 32.08, 32.42, 34.36, 35.53, 37.57, 38.82 degrees 2θ. In certain embodiments, Form A of the HBr salt of Compound B1 is characterized by XRPD peaks located at one, two, three, four, five, six, seven, eight, nine, ten or more of the following approximate positions: 6.84, 9.16, 9.4, 10.44, 11.34, 14.91, 18.34, 20.28, 20.66, 22.22, 22.53, 26.96, 27.44, 28.27 degrees 2θ. In certain embodiments, Form A of the HBr salt of Compound B1 is characterized by an XRPD pattern which matches the pattern exhibited in FIG. 47.

In certain embodiments, the chemical profile of a sample of Form A of the HBr salt of Compound B1 can be characterized by solution NMR analysis. A representative $^1$H NMR spectrum of a sample of Form A dissolved in DMSO-d6 is provided as FIG. 48.

In certain embodiments, Form A of the HBr salt of Compound B1 may be characterized by its behavior upon storage at stress conditions. For example, in certain embodiments, when a sample of Form A is maintained at 75% RH for 4 days, the resulting material does not deliquesce. In certain embodiments, Form A of the HBr salt is physically stable with respect to humidity.

5.2.21 Form A of the Sulfate Salt of Compound B1

Certain embodiments herein provide the Form A crystal form of a sulfate salt of Compound B1. In certain embodiments, Form A of the sulfate salt of Compound B1 can be obtained by reacting Compound B1 with sulfuric acid in various solvents, including, but not limited to, water, acetonitrile, dioxane and mixtures of two or more thereof. In certain embodiments, the sulfuric acid is reacted with Compound B1 in an amount suitable to generate the Form A sulfate salt stoichiometry. In certain embodiments, at least about one molar equivalent of sulfuric acid is added per mole of Compound B1. In certain embodiments, at least about two molar equivalents of sulfuric acid are added per mole of Compound B1.

In certain embodiments, Form A of the sulfate salt of Compound B1 can be obtained by precipitation from a solution comprising a sulfate salt of Compound B1 in a suitable solvent system, such as, but not limited to, a solvent system comprising water, acetonitrile, dioxane, or mixtures of two or more thereof. In certain embodiments, Form A of the sulfate salt of Compound B1 can be obtained by precipitation from a solution comprising a sulfate salt of Compound B1 in a solvent system comprising water, acetonitrile and dioxane. In certain embodiments, Form A of the sulfate salt of Compound B1 can be obtained by crystallization from solvent, water or solvent/water mixtures including, but not limited to, common laboratory organic solvents.

A representative XRPD pattern of Form A of the sulfate salt of Compound B1 is provided in FIG. 49. In certain embodiments, Form A of the sulfate salt of Compound B1 is characterized by an XRPD pattern which matches the Form A pattern exhibited in FIG. 49.

5.2.22 Form B of the Sulfate Salt of Compound B1

Certain embodiments herein provide the Form B crystal form of a sulfate salt of Compound B1. In certain embodiments, Form B of the sulfate salt of Compound B1 can be obtained by reacting Compound B1 with sulfuric acid in various solvents, including, but not limited to, water. In certain embodiments, the sulfuric acid is reacted with Compound B1 in an amount suitable to generate the Form B sulfate salt stoichiometry. In certain embodiments, at least about one molar equivalent of sulfuric acid is added per mole of Compound B1. In certain embodiments, 1.5 molar equivalents of sulfuric acid is added per mole of Compound B1. In certain embodiments, at least about two molar equivalents of sulfuric acid are added per mole of Compound B1.

In certain embodiments, Form B of the sulfate salt of Compound B1 can be obtained by precipitation from a solution comprising a sulfate salt of Compound B1 in a suitable solvent system, such as, but not limited to, a solvent system comprising water. In certain embodiments, Form B of the sulfate salt of Compound B1 can be obtained from slurrying a sulfate salt of Compound B1 in a solvent system comprising water, at a suitable temperature (e.g., about 60° C.), for a suitable time period (e.g., about 30 minutes). In certain embodiments, Form B of the sulfate salt of Compound B1 can be obtained by crystallization from solvent, water or solvent/water mixtures including, but not limited to, common laboratory organic solvents.

A representative XRPD pattern of Form B of the sulfate salt of Compound B1 is provided in FIG. 49. In certain embodiments, Form B of the sulfate salt of Compound B1 is characterized by an XRPD pattern which matches the Form B pattern exhibited in FIG. 49.

5.2.23 Form C of the Sulfate Salt of Compound B1

Certain embodiments herein provide the Form C crystal form of a sulfate salt of Compound B1. In certain embodiments, Form C of the sulfate salt of Compound B1 can be obtained by reacting Compound B1 with sulfuric acid in various solvents, including, but not limited to, methanol, acetonitrile, acetone, water, and mixtures of two or more thereof. In certain embodiments, the sulfuric acid is reacted with Compound B1 in an amount suitable to generate the Form C sulfate salt stoichiometry. In certain embodiments, at least about one molar equivalent of sulfuric acid is added per mole of Compound B1. In certain embodiments, at least about two molar equivalents of sulfuric acid are added per mole of Compound B1.

In certain embodiments, Form C of the sulfate salt of Compound B1 can be obtained by precipitation from a solution comprising a sulfate salt of Compound B1 in a suitable solvent system, such as, but not limited to, a solvent system comprising methanol, acetonitrile, acetone, water, or mixtures of two or more thereof. In certain embodiments, Form C of the sulfate salt of Compound B1 can be obtained from slurrying a sulfate salt of Compound B1 in a solvent system comprising methanol, acetonitrile, acetone, water, or mixtures of two or more thereof. In certain embodiments, Form C of the sulfate salt of Compound B1 can be obtained by crystallization from solvent, water or solvent/water mixtures including, but not limited to, common laboratory organic solvents.

A representative XRPD pattern of Form C of the sulfate salt of Compound B1 is provided in FIG. 49. In certain embodiments, Form C of the sulfate salt of Compound B1 is characterized by XRPD peaks located at one, two, three, four, five, six, seven, eight, nine, ten or more of the following approximate positions: 3.2, 4.79, 5.87, 6.73, 7.81, 8.92, 9.89, 11.48, 12.59, 14.74, 16.19, 23.46, 26.33 degrees 2θ. In certain embodiments, Form C of the sulfate salt of Compound B1 is characterized by XRPD peaks located at one, two, three, four, five or six of the following approximate positions: 3.2, 4.79, 9.89, 11.48, 16.19, 26.33 degrees 2θ. In certain embodiments, Form C of the sulfate salt of Compound B1 is characterized by an XRPD pattern which matches the Form C pattern exhibited in FIG. 49.

In certain embodiments, the chemical profile of a sample of Form C of the sulfate salt of Compound B1 can be characterized by solution NMR analysis. A representative $^1$H NMR spectrum of a sample of Form C dissolved in DMSO-d6 is provided as FIG. 50.

In certain embodiments, Form C of the sulfate salt of Compound B1 may be characterized by its behavior upon storage at stress conditions. For example, in certain embodiments, when a sample of Form C is maintained at 75% RH for 7 days, the resulting material does not deliquesce. In certain embodiments, Form C of the sulfate salt is physically stable with respect to humidity.

5.2.24 Form A of the Mesylate Salt of Compound B1

Certain embodiments herein provide the Form A crystal form of a mesylate salt of Compound B1. In certain embodiments, Form A of the mesylate salt of Compound B1 can be obtained by reacting Compound B1 with methanesulfonic acid in various solvents, including, but not limited to, methanol. In certain embodiments, the methanesulfonic acid is reacted with Compound B1 in an amount suitable to generate the Form A mesylate salt stoichiometry. In certain embodiments, at least about one molar equivalent of methanesulfonic acid is added per mole of Compound B1. In certain embodiments, about 1.2 molar equivalents of methanesulfonic acid is added per mole of Compound B1. In certain embodiments, at least about two molar equivalents of methanesulfonic acid are added per mole of Compound B1.

In certain embodiments, Form A of the mesylate salt of Compound B11 can be obtained by precipitation from a solution comprising a mesylate salt of Compound B1 in a suitable solvent system, such as, but not limited to, a solvent system comprising methanol. In certain embodiments, Form A of the mesylate salt of Compound B1 can be obtained from crash cooling a solution comprising a mesylate salt of Compound B1 from a solvent system comprising methanol. In certain embodiments, Form A of the mesylate salt of Compound B1 can be obtained by crystallization from solvent, water or solvent/water mixtures including, but not limited to, common laboratory organic solvents.

A representative XRPD pattern of Form A of the mesylate salt of Compound B1 is provided in FIG. 51. In certain embodiments, Form A of the mesylate salt of Compound B1 is characterized by XRPD peaks located at one, two, three or four of the following approximate positions: 5.28, 7.74, 9.02, 26.2 degrees 2θ. In certain embodiments, Form A of the mesylate salt of Compound B1 is characterized by an XRPD pattern which matches the Form A pattern exhibited in FIG. 51.

In certain embodiments, the chemical profile of a sample of Form A of the mesylate salt of Compound B1 can be characterized by solution NMR analysis. A representative $^1$H NMR spectrum of a sample of Form A dissolved in DMSO-d6 is provided as FIG. 52. In certain embodiments, Form A of the mesylate salt of Compound B1 is characterized by a $^1$H NMR spectrum with proton integration indicative of a ratio of approximately 1:1 methanesulfonic acid:Compound B1.

In certain embodiments, Form A of the mesylate salt of Compound B1 may be characterized by its behavior upon storage at stress conditions. For example, in certain embodiments, when a sample of Form A is maintained at 75% RH and ambient temperature for 5 days, the resulting material does not deliquesce. In certain embodiments, Form A of the mesylate salt of Compound B1 is physically stable with respect to humidity.

5.2.25 Form B of the Mesylate Salt of Compound B1

Certain embodiments herein provide the Form B crystal form of a mesylate salt of Compound B1. In certain embodiments, Form B of the mesylate salt of Compound B1 can be obtained by reacting Compound B1 with methanesulfonic acid in various solvents, including, but not limited to, methanol. In certain embodiments, the methanesulfonic acid is reacted with Compound B1 in an amount suitable to generate the Form B mesylate salt stoichiometry. In certain embodiments, at least about one molar equivalent of methanesulfonic acid is added per mole of Compound B1. In certain embodiments, at least about two molar equivalents of methanesulfonic acid are added per mole of Compound B1. In certain embodiments, about 2.2 molar equivalents of methanesulfonic acid is added per mole of Compound B1.

In certain embodiments, Form B of the mesylate salt of Compound B1 can be obtained by precipitation from a solution comprising a mesylate salt of Compound B1 in a suitable solvent system, such as, but not limited to, a solvent system comprising methanol. In certain embodiments, Form B of the mesylate salt of Compound B1 can be obtained from crash cooling a solution comprising a mesylate salt of Compound B1 from a solvent system comprising methanol. In certain embodiments, Form B of the mesylate salt of Compound B1 can be obtained by crystallization from solvent, water or solvent/water mixtures including, but not limited to, common laboratory organic solvents.

A representative XRPD pattern of Form B of the mesylate salt of Compound B1 is provided in FIG. 51. In certain embodiments, Form B of the mesylate salt of Compound B1 is characterized by XRPD peaks located at one, two, three, four, five or six of the following approximate positions: 4.69, 5.18, 8.95, 19.34, 21.59, 26.3 degrees 2θ. In certain embodiments, Form B of the mesylate salt of Compound B1 is characterized by an XRPD pattern which matches the Form B pattern exhibited in FIG. 51.

In certain embodiments, the chemical profile of a sample of Form B of the mesylate salt of Compound B1 can be characterized by solution NMR analysis. A representative $^1$H NMR spectrum of a sample of Form B dissolved in DMSO-d6 is provided as FIG. 53. In certain embodiments, Form B of the mesylate salt of Compound B1 is characterized by $^1$H NMR spectrum with proton integration indicative of a ratio of approximately 1.5:1 methanesulfonic acid:Compound B1.

In certain embodiments, Form B of the mesylate salt of Compound B1 may be characterized by its behavior upon storage at stress conditions. For example, in certain embodiments, when a sample of Form B is maintained at 75% RH and ambient temperature for 4 days, the resulting material does not deliquesce. In certain embodiments, Form B of the mesylate salt of Compound B1 is physically stable with respect to humidity.

5.2.26 Form A of the Esylate Salt of Compound B1

Certain embodiments herein provide the Form A crystal form of an esylate salt of Compound B1. In certain embodiments, Form A of the esylate salt of Compound B1 can be obtained by reacting Compound B1 with ethanesulfonic acid in various solvents, including, but not limited to, methanol, ether and mixtures thereof. In certain embodiments, the ethanesulfonic acid is reacted with Compound B1 in an amount suitable to generate the Form A esylate salt stoichiometry. In certain embodiments, at least about one molar equivalent of ethanesulfonic acid is added per mole of Compound B1. In certain embodiments, at least about two molar equivalents of ethanesulfonic acid are added per mole of Compound B1.

In certain embodiments, Form A of the esylate salt of Compound B1 can be obtained by precipitation, including, e.g., crash precipitation, from a solution comprising an esylate salt of Compound B1 in a suitable solvent system, such as, but not limited to, a solvent system comprising methanol, ether or a mixture thereof. In certain embodiments, Form A of the esylate salt of Compound B1 can be obtained by crystallization from solvent, water or solvent/water mixtures including, but not limited to, common laboratory organic solvents.

A representative XRPD pattern of Form A of the esylate salt of Compound B1 is provided in FIG. 54. In certain embodiments, Form A of the esylate salt of Compound B1 is characterized by an XRPD pattern which matches the Form A pattern exhibited in FIG. 54.

5.2.27 Form B of the Esylate Salt of Compound B1

Certain embodiments herein provide the Form B crystal form of an esylate salt of Compound B1. In certain embodiments, Form B of the esylate salt of Compound B1 can be obtained by reacting Compound B1 with ethanesulfonic acid in various solvents, including, but not limited to, methanol, ether and mixtures thereof. In certain embodiments, the ethanesulfonic acid is reacted with Compound B1 in an amount suitable to generate the Form B esylate salt stoichiometry. In certain embodiments, at least about one molar equivalent of ethanesulfonic acid is added per mole of Compound B1. In certain embodiments, at least about two molar equivalents of ethanesulfonic acid are added per mole of Compound B1.

In certain embodiments, Form B of the esylate salt of Compound B1 can be obtained by precipitation, including, e.g., fast evaporation, from a solution comprising an esylate salt of Compound B1 in a suitable solvent system, such as, but not limited to, a solvent system comprising methanol, ether or a mixture thereof. In certain embodiments, Form B of the esylate salt of Compound B1 can be obtained by crystallization from solvent, water or solvent/water mixtures including, but not limited to, common laboratory organic solvents.

A representative XRPD pattern of Form B of the esylate salt of Compound B1 is provided in FIG. 54. In certain embodiments, Form B of the esylate salt of Compound B1 is characterized by XRPD peaks located at one, two, three, four, five, six, seven, eight, nine, ten or more of the following approximate positions: 5.38, 6.91, 7.57, 9.16, 9.47, 10.65, 12.94, 13.25, 13.73, 15.05, 15.78, 15.95, 16.36, 17.71, 18.3, 20.07, 22.6, 26.09 degrees 2θ. In certain embodiments, Form B of the esylate salt of Compound B1 is characterized by an XRPD pattern which matches the Form B pattern exhibited in FIG. 54.

In certain embodiments, the chemical profile of a sample of Form B of the esylate salt of Compound B1 can be characterized by solution NMR analysis. A representative $^1$H NMR spectrum of a sample of Form B dissolved in DMSO-d6 is provided as FIG. 55. In certain embodiments, Form B of the esylate salt of Compound B1 is characterized by a $^1$H NMR spectrum with proton integration indicative of a ratio of approximately 1:1 ethanesulfonic acid:Compound B1.

In certain embodiments, Form B of the esylate salt of Compound B1 may be characterized by its behavior upon storage at stress conditions. For example, in certain embodiments, when a sample of Form B is maintained at 75% RH and ambient temperature for 7 days, the resulting material does not deliquesce. In certain embodiments, Form B of the esylate salt of Compound B1 is physically stable with respect to humidity.

5.2.28 Form C of the Esylate Salt of Compound B1

Certain embodiments herein provide the Form C crystal form of an esylate salt of Compound B1. In certain embodiments, Form C of the esylate salt of Compound B1 can be obtained by reacting Compound B1 with ethanesulfonic acid in various solvents, including, but not limited to, methanol. In certain embodiments, the ethanesulfonic acid is reacted with Compound B1 in an amount suitable to generate the Form C esylate salt stoichiometry. In certain embodiments, at least about one molar equivalent of ethanesulfonic acid is added per mole of Compound B1. In certain embodiments, at least about two molar equivalents of ethanesulfonic acid are added per mole of Compound B1. In certain embodiments, about 2.5 molar equivalents of ethanesulfonic acid are added per mole of Compound B1.

In certain embodiments, Form C of the esylate salt of Compound B1 can be obtained by precipitation, including, e.g., crash cooling, from a solution comprising an esylate salt of Compound B1 in a suitable solvent system, such as, but not limited to, a solvent system comprising methanol. In certain embodiments, Form C of the esylate salt of Compound B1 can be obtained by crystallization from solvent, water or solvent/water mixtures including, but not limited to, common laboratory organic solvents.

A representative XRPD pattern of Form C of the esylate salt of Compound B1 is provided in FIG. 54. In certain embodiments, Form C of the esylate salt of Compound B1 is characterized by an XRPD pattern which matches the Form C pattern exhibited in FIG. 54.

5.2.29 Form A of the Edisylate Salt of Compound B1

Certain embodiments herein provide the Form A crystal form of an edisylate salt of Compound B1. In certain embodiments, Form A of the edisylate salt of Compound B1 can be obtained by reacting Compound B1 with 1,2-ethanedisulfonic acid in various solvents, including, but not limited to, methanol, ether and mixtures thereof. In certain embodiments, the 1,2-ethanedisulfonic acid is reacted with Compound B1 in an amount suitable to generate the Form A edisylate salt stoichiometry. In certain embodiments, at least about one molar equivalent of 1,2-ethanedisulfonic acid is added per mole of Compound B1. In certain embodiments, 1.5 molar equivalents of 1,2-ethanedisulfonic acid is added per mole of Compound B1. In certain embodiments, at least about two molar equivalents of 1,2-ethanedisulfonic acid are added per mole of Compound B1.

In certain embodiments, Form A of the edisylate salt of Compound B1 can be obtained by precipitation, including, e.g., crash cooling, from a solution comprising an edisylate salt of Compound B1 in a suitable solvent system, such as, but not limited to, a solvent system comprising methanol, ether or a mixture thereof. In certain embodiments, Form A of the edisylate salt of Compound B1 can be obtained by crystallization from solvent, water or solvent/water mixtures including, but not limited to, common laboratory organic solvents.

A representative XRPD pattern of Form A of the edisylate salt of Compound B1 is provided in FIG. 56. In certain embodiments, Form A of the edisylate salt of Compound B1 is characterized by XRPD peaks located at one, two, three, four, five, six, seven, eight, nine, ten or more of the following approximate positions: 5.28, 9.09, 10.37, 12.07, 14.15, 15.98, 16.75, 17.85, 19.62, 21.63, 22.11, 25.37, 26.26 degrees 2θ. In certain embodiments, Form A of the edisylate salt of Compound B1 is characterized by XRPD peaks located at one, two, three, four, five or six of the following approximate positions: 5.28, 9.09, 14.15, 15.98, 25.37, 26.26 degrees 2θ. In certain embodiments, Form A of the edisylate salt of Compound B1 is characterized by an XRPD pattern which matches the pattern exhibited in FIG. 56.

In certain embodiments, the chemical profile of a sample of Form A of the edisylate salt of Compound B1 can be characterized by solution NMR analysis. A representative $^1$H NMR spectrum of a sample of Form A dissolved in DMSO-d6 is provided as FIG. 57. In certain embodiments, Form A of the edisylate salt of Compound B1 is characterized by a $^1$H NMR spectrum with proton integration indicative of a ratio of approximately 1:1 ethanedisulfonic acid:Compound B1.

In certain embodiments, Form A of the edisylate salt of Compound B1 may be characterized by its behavior upon storage at stress conditions. For example, in certain embodiments, when a sample of Form A is maintained at 75% RH and ambient temperature for 7 days, the resulting material does not deliquesce. In certain embodiments, Form A of the edisylate salt of Compound B1 is physically stable with respect to humidity.

5.2.30 Form A of the Besylate Salt of Compound B1

Certain embodiments herein provide the Form A crystal form of a besylate salt of Compound B1. In certain embodiments, Form A of the besylate salt of Compound B1 can be obtained by reacting Compound B1 with benzenesulfonic acid in various solvents, including, but not limited to, methanol. In certain embodiments, the benzenesulfonic acid is reacted with Compound B1 in an amount suitable to generate the Form A besylate salt stoichiometry. In certain embodiments, at least about one molar equivalent of benzesulfonic acid is added per mole of Compound B1. In certain embodiments, one molar equivalent of benzenesulfonic acid is added per mole of Compound B1. In certain embodiments, at least about two molar equivalents of benzenesulfonic acid are added per mole of Compound B1.

In certain embodiments, Form A of the besylate salt of Compound B1 can be obtained by precipitation, including, e.g., crash cooling, from a solution comprising a besylate salt of Compound B1 in a suitable solvent system, such as, but not limited to, a solvent system comprising methanol. In certain embodiments, Form A of the besylate salt of Compound B1 can be obtained by crystallization from solvent, water or solvent/water mixtures including, but not limited to, common laboratory organic solvents.

A representative XRPD pattern of Form A of the besylate salt of Compound B1 is provided in FIG. 58. In certain embodiments, Form A of the besylate salt of Compound B1 is characterized by XRPD peaks located at one, two, three, four, five, six, seven, eight, nine, ten or more of the following approximate positions: 5.04, 7.08, 8.02, 8.43, 10.06, 10.41, 13.49, 15.08, 16.88, 18.82, 21.94, 25.92, 26.44, 27.1, 28.34 degrees 2θ. In certain embodiments, Form A of the besylate salt of Compound B1 is characterized by XRPD peaks located at one, two, three, four, five, six, seven, eight or nine of the following approximate positions: 5.04, 8.02, 8.43, 13.49, 15.08, 16.88, 25.92, 26.44, 27.1 degrees 2θ. In certain embodiments, Form A of the besylate salt of Compound B1 is characterized by an XRPD pattern which matches the Form A pattern exhibited in FIG. 58.

In certain embodiments, the chemical profile of a sample of Form A of the besylate salt of Compound B1 can be characterized by solution NMR analysis. A representative $^1$H NMR spectrum of a sample of Form A dissolved in DMSO-d6 is provided as FIG. 59. In certain embodiments, Form A of the besylate salt of Compound B1 is characterized by a $^1$H NMR spectrum with proton integration indicative of a ratio of approximately 1:1 benzenesulfonic acid:Compound B1.

In certain embodiments, Form A of the besylate salt of Compound B1 may be characterized by its behavior upon storage at stress conditions. For example, in certain embodiments, when a sample of Form A is maintained at 75% RH and ambient temperature for 3 days, the resulting material does not deliquesce. In certain embodiments, Form A of the besylate salt of Compound B1 is physically stable with respect to humidity.

5.2.31 Form B of the Besylate Salt of Compound B1

Certain embodiments herein provide the Form B crystal form of a besylate salt of Compound B1. In certain embodiments, Form B of the besylate salt of Compound B1 can be obtained by reacting Compound B1 with benzenesulfonic acid in various solvents, including, but not limited to, methanol. In certain embodiments, the benzenesulfonic acid is reacted with Compound B1 in an amount suitable to generate the Form B besylate salt stoichiometry. In certain embodiments, at least about one molar equivalent of benzesulfonic acid is added per mole of Compound B1. In certain embodiments, at least about two molar equivalents of benzenesulfonic acid are added per mole of Compound B1. In certain embodiments, 2.5 molar equivalents of benzenesulfonic acid is added per mole of Compound B1.

In certain embodiments, Form B of the besylate salt of Compound B1 can be obtained by precipitation, including, e.g., crash cooling, from a solution comprising a besylate salt of Compound B1 in a suitable solvent system, such as, but not limited to, a solvent system comprising methanol. In certain embodiments, Form B of the besylate salt of Compound B1 can be obtained by crystallization from solvent, water or solvent/water mixtures including, but not limited to, common laboratory organic solvents.

A representative XRPD pattern of Form B of the besylate salt of Compound B1 is provided in FIG. 58. In certain embodiments, Form B of the besylate salt of Compound B1 is characterized by XRPD peaks located at one, two, three, four, five, six, seven, eight, nine, ten or more of the following approximate positions: 5.14, 6.25, 8.78, 10.37, 13.21, 13.66, 15.01, 15.22, 16.92, 17.68, 18.62, 18.89, 19.31, 26.61, 27.06, 27.54, 28.51 degrees 2θ. In certain embodiments, Form B of the besylate salt of Compound B1 is characterized by XRPD peaks located at one, two, three or four of the following approximate positions: 5.14, 6.25, 16.92, 26.61 degrees 2θ. In certain embodiments, Form B of the besylate salt of Compound B1 is characterized by an XRPD pattern which matches the Form B pattern exhibited in FIG. 58.

In certain embodiments, the chemical profile of a sample of Form B of the besylate salt of Compound B1 can be characterized by solution NMR analysis. A representative $^1$H NMR spectrum of a sample of Form B dissolved in DMSO-d6 is provided as FIG. 60. In certain embodiments, Form B of the besylate salt of Compound B1 is characterized by a $^1$H NMR spectrum with proton integration indicative of a ratio of approximately 1.6:1 benzenesulfonic acid:Compound B1.

In certain embodiments, Form B of the besylate salt of Compound B1 may be characterized by its behavior upon storage at stress conditions. For example, in certain embodiments, when a sample of Form B is maintained at 75% RH and ambient temperature for 7 days, the resulting material does not deliquesce. In certain embodiments, Form B of the besylate salt of Compound B1 is physically stable with respect to humidity.

5.2.32 Form A of the Tosylate Salt of Compound B1

Certain embodiments herein provide the Form A crystal form of a tosylate salt of Compound B1. In certain embodiments, Form A of the tosylate salt of Compound B1 can be obtained by reacting Compound B1 with toluenesulfonic acid in various solvents, including, but not limited to, methanol. In certain embodiments, the toluenesulfonic acid is reacted with Compound B1 in an amount suitable to generate the Form A tosylate salt stoichiometry. In certain embodiments, at least about one molar equivalent of toluenesulfonic acid is added per mole of Compound B1. In certain embodiments, at least about two molar equivalents of toluenesulfonic acid are added per mole of Compound B1. In certain embodiments, one molar equivalent of toluenesulfonic acid is added per mole of Compound B1.

In certain embodiments, Form A of the tosylate salt of Compound B1 can be obtained by precipitation, including, e.g., crash cooling, from a solution comprising a tosylate salt of Compound B1 in a suitable solvent system, such as, but not limited to, a solvent system comprising methanol. In certain embodiments, Form A of the tosylate salt of Compound B1 can be obtained by crystallization from solvent, water or solvent/water mixtures including, but not limited to, common laboratory organic solvents.

A representative XRPD pattern of Form A of the tosylate salt of Compound B1 is provided in FIG. 61. In certain embodiments, Form A of the tosylate salt of Compound B1 is characterized by an XRPD pattern which matches the Form A pattern exhibited in FIG. 61.

5.2.33 Form B of the Tosylate Salt of Compound B1

Certain embodiments herein provide the Form B crystal form of a tosylate salt of Compound B1. In certain embodiments, Form B of the tosylate salt of Compound B1 can be obtained by reacting Compound B1 with toluenesulfonic acid in various solvents, including, but not limited to, methanol. In certain embodiments, the toluenesulfonic acid is reacted with Compound B1 in an amount suitable to generate the Form B tosylate salt stoichiometry. In certain embodiments, at least about one molar equivalent of toluenesulfonic acid is added per mole of Compound B1. In certain embodiments, at least about two molar equivalents of toluenesulfonic acid are added per mole of Compound B1. In certain embodiments, 1.5 molar equivalents of toluenesulfonic acid is added per mole of Compound B1.

In certain embodiments, Form B of the tosylate salt of Compound B1 can be obtained by precipitation, including, e.g., crash cooling, from a solution comprising a tosylate salt of Compound B1 in a suitable solvent system, such as, but not limited to, a solvent system comprising methanol. In certain embodiments, Form B of the tosylate salt of Compound B1 can be obtained by crystallization from solvent, water or solvent/water mixtures including, but not limited to, common laboratory organic solvents.

A representative XRPD pattern of Form B of the tosylate salt of Compound B1 is provided in FIG. 61. In certain embodiments, Form B of the tosylate salt of Compound B1 is characterized by XRPD peaks located at one, two, three, four, five, six, seven, eight, nine, ten or more of the following approximate positions: 4.93, 6.77, 7.95, 9.89, 10.79, 12.45, 12.8, 13.77, 14.91, 15.33, 16.75, 21.77, 22.6, 26.02, 26.92 degrees 2θ. In certain embodiments, Form B of the tosylate salt of Compound B1 is characterized by XRPD peaks located at one, two, three, four, five or six of the following approximate positions: 4.93, 7.95, 14.91, 16.75, 26.02, 26.92 degrees 2θ. In certain embodiments, Form B of the tosylate salt of Compound B1 is characterized by an XRPD pattern which matches the Form B pattern exhibited in FIG. 61.

In certain embodiments, the chemical profile of a sample of Form B of the tosylate salt of Compound B1 can be characterized by solution NMR analysis. A representative $^1$H NMR spectrum of a sample of Form B dissolved in DMSO-d6 is provided as FIG. 62. In certain embodiments, Form B of the tosylate salt of Compound B1 is characterized by a $^1$H NMR spectrum with proton integration indicative of a ratio of approximately 1:1 toluenesulfonic acid:Compound B1.

In certain embodiments, Form B of the tosylate salt of Compound B1 may be characterized by its behavior upon storage at stress conditions. For example, in certain embodiments, when a sample of Form B is maintained at 75% RH and ambient temperature for 5 days, the resulting material does not deliquesce. In certain embodiments, Form B of the tosylate salt of Compound B1 is physically stable with respect to humidity.

5.2.34 Form C of the Tosylate Salt of Compound B1

Certain embodiments herein provide the Form C crystal form of a tosylate salt of Compound B1. In certain embodiments, Form C of the tosylate salt of Compound B1 can be obtained by reacting Compound B1 with toluenesulfonic acid in various solvents, including, but not limited to, methanol. In certain embodiments, the toluenesulfonic acid is reacted with Compound B1 in an amount suitable to generate the Form C tosylate salt stoichiometry. In certain embodiments, at least about one molar equivalent of toluenesulfonic acid is added per mole of Compound B1. In certain embodiments, at least about two molar equivalents of toluenesulfonic acid are added per mole of Compound B1. In certain embodiments, 2.5 molar equivalents of toluenesulfonic acid is added per mole of Compound B1.

In certain embodiments, Form C of the tosylate salt of Compound B1 can be obtained by precipitation, including, e.g., crash cooling, from a solution comprising a tosylate salt of Compound B1 in a suitable solvent system, such as, but not limited to, a solvent system comprising methanol. In certain embodiments, Form C of the tosylate salt of Compound B1 can be obtained by crystallization from solvent, water or solvent/water mixtures including, but not limited to, common laboratory organic solvents.

A representative XRPD pattern of Form C of the tosylate salt of Compound B1 is provided in FIG. 61. In certain embodiments, Form C of the tosylate salt of Compound B1 is characterized by an XRPD pattern which matches the Form C pattern exhibited in FIG. 61.

5.2.35 Form A of the Napsylate Salt of Compound B1

Certain embodiments herein provide the Form A crystal form of a napsylate salt of Compound B1. In certain embodiments, Form A of the napsylate salt of Compound B1 can be obtained by reacting Compound B1 with napthalenesulfonic acid in various solvents, including, but not limited to, methanol. In certain embodiments, the naphthalene-2-sulfonic acid is reacted with Compound B1 in an amount suitable to generate the Form A napsylate salt stoichiometry. In certain embodiments, at least about one molar equivalent of naphthalene-2-sulfonic acid is added per mole of Compound B1. In certain embodiments, at least about two molar equivalents of naphthalene-2-sulfonic acid are added per mole of Compound B1. In certain embodiments, 1.5 molar equivalents of naphthalene-2-sulfonic acid is added per mole of Compound B1.

In certain embodiments, Form A of the napsylate salt of Compound B1 can be obtained by precipitation, including, e.g., crash cooling, from a solution comprising a napsylate salt of Compound B1 in a suitable solvent system, such as, but not limited to, a solvent system comprising methanol. In certain embodiments, Form A of the napsylate salt of Compound B1 can be obtained by crystallization from solvent, water or solvent/water mixtures including, but not limited to, common laboratory organic solvents.

A representative XRPD pattern of Form A of the napsylate salt of Compound B1 is provided in FIG. 63. In certain embodiments, Form A of the napsylate salt of Compound B1 is characterized by XRPD peaks located at one, two, three, four, five, six, seven, eight, nine, ten or more of the following approximate positions: 3.03, 4.76, 5.28, 7.74, 10.34, 11.06, 13.46, 14.39, 15.5, 16.71, 17.2, 17.68, 18.79, 21.87, 24.08, 24.88, 25.71 degrees 2θ. In certain embodiments, Form A of the napsylate salt of Compound B1 is characterized by XRPD peaks located at one, two, three, four or five of the following approximate positions: 3.03, 4.76, 5.28, 7.74, 25.71 degrees 2θ. In certain embodiments, Form A of the napsylate salt of Compound B1 is characterized by an XRPD pattern which matches the Form A pattern exhibited in FIG. 63.

In certain embodiments, the chemical profile of a sample of Form A of the napsylate salt of Compound B1 can be characterized by solution NMR analysis. A representative $^1$H NMR spectrum of a sample of Form A dissolved in DMSO-d6 is provided as FIG. 64. In certain embodiments, Form A of the napsylate salt of Compound B1 is characterized by a $^1$H NMR spectrum with proton integration indicative of a ratio of approximately 1:1 napthalenesulfonic acid:Compound B1.

In certain embodiments, Form A of the napsylate salt of Compound B1 may be characterized by its behavior upon storage at stress conditions. For example, in certain embodiments, when a sample of Form A is maintained at 75% RH and ambient temperature for 7 days, the resulting material does not deliquesce. In certain embodiments, Form A of the napsylate salt of Compound B1 is physically stable with respect to humidity.

5.2.36 Form B of the Napsylate Salt of Compound B1

Certain embodiments herein provide the Form B crystal form of a napsylate salt of Compound B1. In certain embodiments, Form B of the napsylate salt of Compound B1 can be obtained by reacting Compound B1 with naphthalene-2-sulfonic acid in various solvents, including, but not limited to, methanol. In certain embodiments, the napthalene-2-sulfonic acid is reacted with Compound B1 in an amount suitable to generate the Form B napsylate salt stoichiometry. In certain embodiments, at least about one molar equivalent of napthalene-2-sulfonic acid is added per mole of Compound B1. In certain embodiments, at least about two molar equivalents of napthalene-2-sulfonic acid are added per mole of Compound B1. In certain embodiments, 2.5 molar equivalents of napthalene-2-sulfonic acid is added per mole of Compound B1.

In certain embodiments, Form B of the napsylate salt of Compound B1 can be obtained by precipitation, including, e.g., crash cooling, from a solution comprising a napsylate salt of Compound B1 in a suitable solvent system, such as, but not limited to, a solvent system comprising methanol. In certain embodiments, Form B of the napsylate salt of Compound B1 can be obtained by crystallization from solvent, water or solvent/water mixtures including, but not limited to, common laboratory organic solvents.

A representative XRPD pattern of Form B of the napsylate salt of Compound B1 is provided in FIG. 63. In certain embodiments, Form B of the napsylate salt of Compound B1 is characterized by XRPD peaks located at one, two, three, four or five of the following approximate positions: 4.76, 7.77, 15.46, 21.94, 25.68 degrees 2θ. In certain embodiments, Form B of the napsylate salt of Compound B1 is characterized by an XRPD pattern which matches the Form B pattern exhibited in FIG. 63.

In certain embodiments, the chemical profile of a sample of Form B of the napsylate salt of Compound B1 can be characterized by solution NMR analysis. A representative $^1$H NMR spectrum of a sample of Form B dissolved in DMSO-d6 is provided as FIG. 65. In certain embodiments, Form B of the napsylate salt of Compound B1 is characterized by a $^1$H NMR spectrum with proton integration indicative of a ratio of approximately 2:1 napthalenesulfonic acid:Compound B1.

In certain embodiments, Form B of the napsylate salt of Compound B1 may be characterized by its behavior upon storage at stress conditions. For example, in certain embodiments, when a sample of Form B is maintained at 75% RH and ambient temperature for 7 days, the resulting material does not deliquesce. In certain embodiments, Form B of the napsylate salt of Compound B1 is physically stable with respect to humidity.

5.3 Methods of Use

Also provided herein are methods of using the solid forms comprising Compound B1 for the treatment, prevention, or amelioration of a disease or disorder that is mediated or otherwise affected via protein kinase activity or one or more symptoms of diseases or disorders that are mediated or otherwise affected via protein kinase activity (see, Krause and Van Etten, *N Engl J Med* (2005) 353(2):172-187, Blume-Jensen and Hunter, *Nature* (2001) 411(17): 355-365 and Plowman et al., DN&P, 7:334-339 (1994)). Such diseases or disorders include without limitation:

1) carcinomas, including Kit-mediated carcinomas, adenocarcinoma, squamous cell carcinoma, adenosquamous carcinoma, teratocarcinoma, head and neck cancer, cancers of mouth, throat, esophagus, bronchus, pharyx, chest, rectum, uterine, brain cancer, intracranial carcinoma, glioblastoma including PDGFR-mediated glioblastoma, glioblastoma multiforme including PDGFR-mediated glioblastoma multiforme, neuroblastoma, cancer of the larynx, multiple endocrine neoplasias 2A and 2B (MENS 2A and MENS 2B) including RET-mediated MENS, thyroid cancer, including sporadic and familial medullary thyroid carcinoma, papillary thyroid carcinoma, parathyroid carcinoma including any RET-mediated thyroid carcinoma, follicular thyroid cancer, anaplastic thyroid cancer, bronchial carcinoid, oat cell carcinoma, lung cancer, small-cell lung cancer including flt-3 and/or Kit-mediated small cell lung cancer, stomach/gastric cancer, gastrointestinal cancer, gastrointestinal stromal tumors (GIST) including Kit-mediated GIST and PDGFRα-mediated GIST, colon cancer, colorectal cancer, pancreatic cancer, islet cell carcinoma, hepatic/liver cancer, metastases to the liver, bladder cancer, kidney cancer, renal cell cancer including PDGFR-mediated renal cell cancer, cancers of the genitourinary tract, ovarian cancer including Kit-mediated and/or PDGFR-mediated ovarian cancer, endometrial cancer including CSF-1R-mediated endometrial cancer, cervical cancer, breast cancer including Flt-3-mediated and/or PDGFR-mediated breast cancer, prostate cancer including Kit-mediated prostate cancer, cancer of testicles, germ cell tumors including Kit-mediated germ cell tumors, seminomas including Kit-mediated seminomas, dysgerminomas, including Kit-mediated dysgerminomas, melanoma including PDGFR-mediated melanoma, metastases to the bone including CSF-1R-mediated bone metastatic breast, prostate and other cancers, metastatic tumors including VEGFR-mediated tumors, stromal tumors, neuroendocrine tumors, tumor angiogenesis including VEGFR-mediated tumor angiogenesis, mixed mesodermal tumors, VEGFR2 mediated intracranial tumors including glioblastoma multiforme and sporadic and von Hippel Landau (VHL) syndrome-associated capillary hemangioblastoma;

2) sarcomas, including PDGFR-mediated sarcomas, osteosarcoma, osteogenic sarcoma, bone cancer, glioma including PDGFR-mediated and/or CSF-1R-mediated glioma, astrocytoma, vascular tumors including VEGFR-mediated vascular tumors, Kaposi's sarcoma, carcinosarcoma, hemangiosarcomas including VEGFR3-mediated hemangiosarcomas, lymphangiosarcoma including VEGFR3-mediated lymphangiosarcoma, VEGFR3-mediated lymphangiogenesis;

3) myeloma, leukemia, myeloproliferative diseases, acute myelogenous leukemia (AML) including flt-3 mediated and/or KIT-mediated and/or CSF1R-mediated acute myeloid leukemia, chronic myelogenous leukemias (CML) including Flt-3-mediated and/or PDGFR-mediated chronic myeloid leukemia, myelodysplastic leukemias including Flt-3-mediated myelodysplastic leukemia, myelodysplastic syndrome, including Flt-3 mediated and/or Kit-mediated myelodysplastic syndrome, idiopathic hypereosinophilic syndrome (HES) including PDGFR-mediated HES, chronic eosinophilic leukemia (CEL) including PDGFR-mediated CEL, chronic myelomonocytic leukemia (CMML), mast cell leukemia including Kit-mediated mast cell leukemia, or systemic mastocytosis including Kit-mediated systemic mastocytosis;

c) lymphoma, lymphoproliferative diseases, acute lymphoblastic leukemia (ALL), B-cell acute lymphoblastic leukemias, T-cell acute lymphoblastic leukemias, natural killer (NK) cell leukemia, B-cell lymphoma, T-cell lymphoma, and natural killer (NK) cell lymphoma, any of which may be Flt-3 mediated and/or PDGFR-mediated, Langerhans cell histiocytosis including CSF-1R-mediated and flt-3-mediated Langerhans cell histiocytosis, mast cell tumors and mastocytosis;

4) Nonmalignant proliferation diseases; atherosclerosis including PDGFR-mediated atherosclerosis, restenosis following vascular angioplasty including PDGFR-mediated restenosis, and fibroproliferative disorders such as obliterative bronchiolitis and idiopathic myelofibrosis, both of which may be PDGFR-mediated;

5) Inflammatory diseases or disorders related to immune dysfunction, immunodeficiency, immunomodulation, autoimmune diseases, tissue transplant rejection, graft-versus-host disease, wound healing, kidney disease, multiple sclerosis, thyroiditis, type 1 diabetes, sarcoidosis, allergic rhinitis, inflammatory bowel disease including Crohn's disease and ulcerative colitis (UC), systemic lupus erythematosis (SLE), arthritis, osteoarthritis, rheumatoid arthritis, osteoporosis, asthma and chronic obstructive pulmonary disease (COPD), including any of the aforementioned diseases which are flt-3-mediated and/or CSF-1R-mediated; and 6) Infectious diseases mediated either via viral or bacterial pathogens and sepsis, including KIT-mediated sepsis.

Also provided are methods of modulating the activity, or subcellular distribution, of kinases in a cell, tissue or whole organism, using the compounds and compositions provided herein, or pharmaceutically acceptable derivatives thereof.

Kinases of high interest, i.e. those that mediate one or more of the aforementioned diseases or disorders, include without limitation class III receptor tyrosine kinases (RTKs), such as:

1) The platelet derived growth factor receptor (PDGFR) subfamily, which includes PDGFR α, PDGFR β, CSF-1R/FMS, Kit and Flt3;

2) The vascular endothelial growth factor (VEGF) receptor subfamily, which includes VEGFR1 (Flt1), VEGFR2 (KDR or Flk1) and VEGFR3 (Flt4);

3) The insulin receptor (IR) subfamily which includes insulin-like growth factor I receptor (IGF-1R);

4) Ret;

5) The HER (EGFR) subfamily;

6) The FGFR subfamily;

7) The HGFR (Met) subfamily;

8) The Abl protein tyrosine subfamily;

9) The Src subfamily, which includes Src, Yes1, Fyn, Lyn, Lck, Blk, Hck, Fgr and Yrk;

10) Frk, Btk, Csk, Abl, Fes, Fps, Fak, Jak and Ack, (and their respective subfamilies);

11) A kinase selected form the group consisting of prostate-derived sterile 20, sterile 11 and sterile 7;

12) the cam kinase subfamily (calmodulin regulated kinases and related kinases);

13) the AGC subfamily; and 14) the CMGC sub family (cdk, map kinase, glycogen synthetase kinase and clk).

Combination Therapy

Furthermore, it will be understood by those skilled in the art that the solid forms provided herein, including pharmaceutical compositions and formulations thereof, can be used in a wide variety of combination therapies to treat the conditions and diseases described above. Thus, also contemplated herein is the use of the solid forms provided herein in combination with other active pharmaceutical agents for the treatment of the disease/conditions described herein. It is believed that certain combinations may work synergistically in the treatment of particular types diseases or disorders, and conditions and symptoms associated with such diseases or disorders. The solid forms comprising compound B1 can also work to alleviate adverse effects associated with certain second active agents, and vice versa.

In one embodiment, such additional pharmaceutical agents include without limitation anti-cancer agents, and anti-inflammatory agents.

The solid forms or compositions provided herein may be administered simultaneously with, prior to, or after administration of one or more of the above agents.

Pharmaceutical compositions containing the solid forms, and one or more of the above agents are also provided.

5.4 Pharmaceutical Compositions and Routes of Administration

Provided herein are pharmaceutical compositions, which comprise the solid forms comprising Compound B1, or a pharmaceutically acceptable salt thereof, as an active ingredient, in combination with one or more a pharmaceutically acceptable excipients or carriers. In one embodiment, the pharmaceutical composition comprises at least one nonrelease controlling excipients or carrier. In another embodiment, the pharmaceutical composition comprises at least one release controlling and at least one nonrelease controlling excipient or carrier.

The solid forms comprising Compound B1 may be administered alone, or in combination with one or more other active ingredients (i.e., other therapeutic agents). The pharmaceutical compositions provided herein may be formulated in various dosage forms for oral, parenteral, and topical administration. The pharmaceutical compositions may also be formulated as modified release dosage forms, including delayed-, extended-, prolonged-, sustained-, pulsed-, controlled-, accelerated- and fast-, targeted-, programmed-release, and gastric retention dosage forms. These dosage forms can be prepared according to conventional methods and techniques known to those skilled in the art (see, *Remington: The Science and Practice of Pharmacy*, supra; *Modified-Release Drug Deliver Technology*, Rathbone et al., Eds., Drugs and the Pharmaceutical Science, Marcel Dekker, Inc.: New York, N.Y., 2003; Vol. 126).

In one embodiment, the pharmaceutical compositions are provided in a dosage form for oral administration. In another embodiment, the pharmaceutical compositions are provided in a dosage form for parenteral administration. In yet another embodiment, the pharmaceutical compositions are provided in a dosage form for topical administration.

The pharmaceutical compositions provided herein may be provided in a unit-dosage form or multiple-dosage form. A unit-dosage form, as used herein, refers to a physically discrete unit suitable for administration to human and animal subjects, and packaged individually as is known in the art. Each unit-dose contains a predetermined quantity of the active ingredient(s) sufficient to produce the desired therapeutic effect, in association with the required pharmaceutical carriers or excipients. Examples of a unit-dosage form include an ampoule, syringe, and individually packaged tablet and capsule. A unit-dosage form may be administered in fractions or multiples thereof. A multiple-dosage form is a plurality of identical unit-dosage forms packaged in a single container to be administered in segregated unit-dosage form. Examples of a multiple-dosage form include a vial, bottle of tablets or capsules, or bottle of pints or gallons.

The pharmaceutical compositions provided herein may be administered at once or multiple times at intervals of time. It is understood that the precise dosage and duration of treatment may vary with the age, weight, and condition of the patient being treated, and may be determined empirically using known testing protocols or by extrapolation from in vivo or in vitro test or diagnostic data. It is further understood that for any particular individual, specific dosage regimens should be adjusted over time according to the individual need and the professional judgment of the person administering or supervising the administration of the formulations.

A. Oral Administration

The pharmaceutical compositions provided herein may be provided in solid, semisolid, or liquid dosage forms for oral administration. As used herein, oral administration also includes buccal, lingual, and sublingual administration. Suitable oral dosage forms include, but are not limited to, tablets, capsules, pills, troches, lozenges, pastilles, cachets, pellets, medicated chewing gum, granules, bulk powders, effervescent or non-effervescent powders or granules, solutions, emulsions, suspensions, solutions, wafers, sprinkles, elixirs, and syrups. In addition to the active ingredient(s), the pharmaceutical compositions may contain one or more pharmaceutically acceptable carriers or excipients, including, but not limited to, binders, fillers, diluents, disintegrants, wetting agents, lubricants, glidants, coloring agents, dye-migration inhibitors, sweetening agents, and flavoring agents.

Suitable fillers and diluents include, but are not limited to, talc, calcium carbonate, microcrystalline cellulose, powdered cellulose, dextrates, kaolin, mannitol, silicic acid, sorbitol, starch, pre-gelatinized starch, dicalcium phosphate, calcium sulfate, lactose, sucrose, inositol, sodium chloride, dry starch, and powdered sugar and mixtures thereof. Certain diluents, such as mannitol, lactose, sorbitol, sucrose, and inositol, when present in sufficient quantity, can impart properties to some compressed tablets that permit disintegration in the mouth by chewing. Such compressed tablets can be used as chewable tablets. The filler and/or diluent may be present from about 20 to about 99% by weight in the pharmaceutical compositions provided herein.

Binders or granulators impart cohesiveness to a tablet to ensure the tablet remaining intact after compression. Suitable binders or granulators include, but are not limited to, starches, such as corn starch, potato starch, and pre-gelatinized starch (e.g., STARCH 1500); gelatin; sugars, such as sucrose, glucose, dextrose, molasses, and lactose; natural and synthetic gums, such as acacia, alginic acid, alginates, extract of Irish moss, panwar gum, ghatti gum, mucilage of isabgol husks, carboxymethylcellulose, methylcellulose, polyvinylpyrrolidone (PVP), Veegum, larch arabogalactan, powdered tragacanth, and guar gum; celluloses, such as ethyl cellulose, cellulose acetate, carboxymethyl cellulose calcium, sodium carboxymethyl cellulose, methyl cellulose, hydroxyethylcellulose (HEC), hydroxypropylcellulose (HPC), hydroxypropyl methyl cellulose (HPMC); microcrystalline celluloses, such as AVICEL-PH-101, AVICEL-PH-103, AVICEL RC-581, AVICEL-PH-105 (FMC Corp., Marcus Hook, Pa.); and mixtures thereof. The binder or granulator may be present from about 0.5 to about 20% by weight in the pharmaceutical compositions provided herein.

Suitable disintegrants include, but are not limited to, agar; bentonite; celluloses, such as methylcellulose and carboxymethylcellulose; wood products; natural sponge; cation-exchange resins; alginic acid; gums, such as guar gum and Veegum HV; citrus pulp; cross-linked celluloses, such as croscarmellose; cross-linked polymers, such as crospovidone; cross-linked starches; calcium carbonate; microcrystalline cellulose, such as sodium starch glycolate; polacrilin potassium; starches, such as corn starch, potato starch, tapioca starch, and pre-gelatinized starch; clays; aligns; and mixtures thereof. The amount of a disintegrant in the pharmaceutical compositions provided herein varies upon the type of formulation, and is readily discernible to those of ordinary skill in the art. The pharmaceutical compositions provided herein may contain from about 0.5 to about 15% or from about 1 to about 5% by weight of a disintegrant.

Suitable lubricants include, but are not limited to, calcium stearate; magnesium stearate; mineral oil; light mineral oil; glycerin; sorbitol; mannitol; glycols, such as glycerol behenate and polyethylene glycol (PEG); stearic acid; sodium lauryl sulfate; talc; hydrogenated vegetable oil, including peanut oil, cottonseed oil, sunflower oil, sesame oil, olive oil, corn oil, and soybean oil; zinc stearate; ethyl oleate; ethyl laureate; agar; starch; lycopodium; silica or silica gels, such as AEROSIL® 200 (W.R. Grace Co., Baltimore, Md.) and CAB-O-SIL® (Cabot Co. of Boston, Mass.); and mixtures thereof. The pharmaceutical compositions provided herein may contain about 0.1 to about 5% by weight of a lubricant. Suitable glidants include colloidal silicon dioxide, CAB-O-SIL® (Cabot Co. of Boston, Mass.), and asbestos-free talc. Coloring agents include any of the approved, certified, water soluble FD&C dyes, and water insoluble FD&C dyes suspended on alumina hydrate, and color lakes and mixtures thereof. A color lake is the combination by adsorption of a water-soluble dye to a hydrous oxide of a heavy metal, resulting in an insoluble form of the dye. Flavoring agents include natural flavors extracted from plants, such as fruits, and synthetic blends of compounds which produce a pleasant taste sensation, such as peppermint and methyl salicylate. Sweetening agents include sucrose, lactose, mannitol, syrups, glycerin, and artificial sweeteners, such as saccharin and aspartame. Suitable emulsifying agents include gelatin, acacia, tragacanth, bentonite, and surfactants, such as polyoxyethylene sorbitan monooleate (TWEEN® 20), polyoxyethylene sorbitan monooleate 80 (TWEEN® 80), and triethanolamine oleate. Suspending and dispersing agents include sodium carboxymethylcellulose, pectin, tragacanth, Veegum, acacia, sodium carbomethylcellulose, hydroxypropyl methylcellulose, and polyvinylpyrrolidone. Preservatives include glycerin, methyl and propylparaben, benzoic add, sodium benzoate and alcohol. Wetting agents include propylene glycol monostearate, sorbitan monooleate, diethylene glycol monolaurate, and polyoxyethylene lauryl ether. Solvents include glycerin, sorbitol, ethyl alcohol, and syrup. Examples of nonaqueous liquids utilized in emulsions include mineral oil and cottonseed oil. Organic acids include citric and tartaric acid. Sources of carbon dioxide include sodium bicarbonate and sodium carbonate.

It should be understood that many carriers and excipients may serve several functions, even within the same formulation.

The pharmaceutical compositions provided herein may be provided as compressed tablets, tablet triturates, chewable lozenges, rapidly dissolving tablets, multiple compressed tablets, or enteric-coating tablets, sugar-coated, or film-coated tablets. Enteric-coated tablets are compressed tablets coated with substances that resist the action of stomach acid but dissolve or disintegrate in the intestine, thus protecting the active ingredients from the acidic environment of the stomach. Enteric-coatings include, but are not limited to, fatty acids, fats, phenyl salicylate, waxes, shellac, ammoniated shellac, and cellulose acetate phthalates. Sugar-coated tablets are compressed tablets surrounded by a sugar coating, which may be beneficial in covering up objectionable tastes or odors and in protecting the tablets from oxidation. Film-coated tablets are compressed tablets that are covered with a thin layer or film of a water-soluble material. Film coatings include, but are not limited to, hydroxyethylcellulose, sodium carboxymethylcellulose, polyethylene glycol 4000, and cellulose acetate phthalate. Film coating imparts the same general characteristics as sugar coating. Multiple compressed tablets are compressed tablets made by more than one compression cycle, including layered tablets, and press-coated or dry-coated tablets.

The tablet dosage forms may be prepared from the active ingredient in powdered, crystalline, or granular forms, alone or in combination with one or more carriers or excipients described herein, including binders, disintegrants, controlled-release polymers, lubricants, diluents, and/or colorants. Flavoring and sweetening agents are especially useful in the formation of chewable tablets and lozenges.

The pharmaceutical compositions provided herein may be provided as soft or hard capsules, which can be made from gelatin, methylcellulose, starch, or calcium alginate. The hard gelatin capsule, also known as the dry-filled capsule (DFC), consists of two sections, one slipping over the other, thus completely enclosing the active ingredient. The soft elastic capsule (SEC) is a soft, globular shell, such as a gelatin shell, which is plasticized by the addition of glycerin, sorbitol, or a similar polyol. The soft gelatin shells may contain a preservative to prevent the growth of microorganisms. Suitable preservatives are those as described herein, including methyl- and propyl-parabens, and sorbic acid. The liquid, semisolid, and solid dosage forms provided herein may be encapsulated in a capsule. Suitable liquid and semisolid dosage forms include solutions and suspensions in propylene carbonate, vegetable oils, or triglycerides. Capsules containing such solutions can be prepared as described in U.S. Pat. Nos. 4,328,245; 4,409,239; and 4,410,545. The capsules may also be coated as known by those of skill in the art in order to modify or sustain dissolution of the active ingredient.

The pharmaceutical compositions provided herein may be provided in liquid and semisolid dosage forms, including emulsions, solutions, suspensions, elixirs, and syrups. An emulsion is a two-phase system, in which one liquid is dispersed in the form of small globules throughout another liquid, which can be oil-in-water or water-in-oil. Emulsions may include a pharmaceutically acceptable non-aqueous liquid or solvent, emulsifying agent, and preservative. Suspensions may include a pharmaceutically acceptable suspending agent and preservative. Aqueous alcoholic solutions may include a pharmaceutically acceptable acetal, such as a di(lower alkyl) acetal of a lower alkyl aldehyde, e.g., acetaldehyde diethyl acetal; and a water-miscible solvent having one or more hydroxyl groups, such as propylene glycol and ethanol. Elixirs are clear, sweetened, and hydroalcoholic solutions. Syrups are concentrated aqueous solutions of a sugar, for example, sucrose, and may also contain a preservative. For a liquid dosage form, for example, a solution in a polyethylene glycol may be diluted with a sufficient quantity of a pharmaceutically acceptable liquid carrier, e.g., water, to be measured conveniently for administration.

Other useful liquid and semisolid dosage forms include, but are not limited to, those containing the active ingredient(s) provided herein, and a dialkylated mono- or poly-alkylene glycol, including, 1,2-dimethoxymethane, diglyme, triglyme, tetraglyme, polyethylene glycol-350-dimethyl ether, polyethylene glycol-550-dimethyl ether, polyethylene glycol-750-dimethyl ether, wherein 350, 550, and 750 refer to the approximate average molecular weight of the polyethylene glycol. These formulations may further comprise one or more antioxidants, such as butylated hydroxytoluene (BHT), butylated hydroxyanisole (BHA), propyl gallate, vitamin E, hydroquinone, hydroxycoumarins, ethanolamine, lecithin, cephalin, ascorbic acid, malic acid, sorbitol, phosphoric acid, bisulfite, sodium metabisulfite, thiodipropionic acid and its esters, and dithiocarbamates.

The pharmaceutical compositions provided herein for oral administration may be also provided in the forms of liposomes, micelles, microspheres, or nanosystems. Micellar dosage forms can be prepared as described in U.S. Pat. No. 6,350,458.

The pharmaceutical compositions provided herein may be provided as non-effervescent or effervescent, granules and powders, to be reconstituted into a liquid dosage form. Pharmaceutically acceptable carriers and excipients used in the non-effervescent granules or powders may include diluents, sweeteners, and wetting agents. Pharmaceutically acceptable carriers and excipients used in the effervescent granules or powders may include organic acids and a source of carbon dioxide.

Coloring and flavoring agents can be used in all of the above dosage forms. The pharmaceutical compositions provided herein may be formulated as immediate or modified release dosage forms, including delayed-, sustained, pulsed-, controlled, targeted-, and programmed-release forms.

The pharmaceutical compositions provided herein may be co-formulated with other active ingredients which do not impair the desired therapeutic action, or with substances that supplement the desired action.

B. Parenteral Administration

The pharmaceutical compositions provided herein may be administered parenterally by injection, infusion, or implantation, for local or systemic administration. Parenteral administration, as used herein, includes intravenous, intraarterial, intraperitoneal, intrathecal, intraventricular, intraurethral, intrasternal, intracranial, intramuscular, intrasynovial, and subcutaneous administration.

The pharmaceutical compositions provided herein may be formulated in any dosage forms that are suitable for parenteral administration, including solutions, suspensions, emulsions, micelles, liposomes, microspheres, nanosystems, and solid forms suitable for solutions or suspensions in liquid prior to injection. Such dosage forms can be prepared according to conventional methods known to those skilled in the art of pharmaceutical science (see, *Remington: The Science and Practice of Pharmacy*, supra).

The pharmaceutical compositions intended for parenteral administration may include one or more pharmaceutically acceptable carriers and excipients, including, but not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, cryoprotectants, lyoprotectants, thickening agents, pH adjusting agents, and inert gases.

Suitable aqueous vehicles include, but are not limited to, water, saline, physiological saline or phosphate buffered saline (PBS), sodium chloride injection, Ringers injection, isotonic dextrose injection, sterile water injection, dextrose and lactated Ringers injection. Non-aqueous vehicles include, but are not limited to, fixed oils of vegetable origin, castor oil, corn oil, cottonseed oil, olive oil, peanut oil, peppermint oil, safflower oil, sesame oil, soybean oil, hydrogenated vegetable oils, hydrogenated soybean oil, and medium-chain triglycerides of coconut oil, and palm seed oil. Water-miscible vehicles include, but are not limited to, ethanol, 1,3-butanediol, liquid polyethylene glycol (e.g., polyethylene glycol 300 and polyethylene glycol 400), propylene glycol, glycerin, N-methyl-2-pyrrolidone, N,N-dimethylacetamide, and dimethyl sulfoxide.

Suitable antimicrobial agents or preservatives include, but are not limited to, phenols, cresols, mercurials, benzyl alcohol, chlorobutanol, methyl and propyl p-hydroxybenzoates, thimerosal, benzalkonium chloride (e.g., benzethonium chloride), methyl- and propyl-parabens, and sorbic acid. Suitable isotonic agents include, but are not limited to, sodium chloride, glycerin, and dextrose. Suitable buffering agents include, but are not limited to, phosphate and citrate. Suitable antioxidants are those as described herein, including bisulfite and sodium metabisulfite. Suitable local anesthetics include, but are not limited to, procaine hydrochloride. Suitable suspending and dispersing agents are those as described herein, including sodium carboxymethylcelluose, hydroxypropyl methylcellulose, and polyvinylpyrrolidone. Suitable emulsifying agents include those described herein, including polyoxyethylene sorbitan monolaurate, polyoxyethylene sorbitan monooleate 80, and triethanolamine oleate. Suitable sequestering or chelating agents include, but are not limited to EDTA. Suitable pH adjusting agents include, but are not limited to, sodium hydroxide, hydrochloric acid, citric acid, and lactic acid. Suitable complexing agents include, but are not limited to, cyclodextrins, including α-cyclodextrin, β-cyclodextrin, hydroxypropyl-β-cyclodextrin, sulfobutylether-β-cyclodextrin, and sulfobutylether 7-β-cyclodextrin (CAPTISOL®, CyDex, Lenexa, Kans.).

The pharmaceutical compositions provided herein may be formulated for single or multiple dosage administration. The single dosage formulations are packaged in an ampoule, a vial, or a syringe. The multiple dosage parenteral formulations must contain an antimicrobial agent at bacteriostatic or fungistatic concentrations. All parenteral formulations must be sterile, as known and practiced in the art.

In one embodiment, the pharmaceutical compositions are provided as ready-to-use sterile solutions. In another embodiment, the pharmaceutical compositions are provided as sterile dry soluble products, including lyophilized powders and hypodermic tablets, to be reconstituted with a vehicle prior to use. In yet another embodiment, the pharmaceutical compositions are provided as ready-to-use sterile suspensions. In yet another embodiment, the pharmaceutical compositions are provided as sterile dry insoluble products to be reconstituted with a vehicle prior to use. In still another embodiment, the pharmaceutical compositions are provided as ready-to-use sterile emulsions.

The pharmaceutical compositions provided herein may be formulated as immediate or modified release dosage forms, including delayed-, sustained, pulsed-, controlled, targeted-, and programmed-release forms.

The pharmaceutical compositions may be formulated as a suspension, solid, semi-solid, or thixotropic liquid, for administration as an implanted depot. In one embodiment, the pharmaceutical compositions provided herein are dispersed in a solid inner matrix, which is surrounded by an outer polymeric membrane that is insoluble in body fluids but allows the active ingredient in the pharmaceutical compositions diffuse through.

Suitable inner matrixes include polymethylmethacrylate, polybutyl-methacrylate, plasticized or unplasticized polyvinylchloride, plasticized nylon, plasticized polyethylene terephthalate, natural rubber, polyisoprene, polyisobutylene, polybutadiene, polyethylene, ethylene-vinyl acetate copolymers, silicone rubbers, polydimethylsiloxanes, silicone carbonate copolymers, hydrophilic polymers, such as hydrogels of esters of acrylic and methacrylic acid, collagen, cross-linked polyvinyl alcohol, and cross-linked partially hydrolyzed polyvinyl acetate.

Suitable outer polymeric membranes include polyethylene, polypropylene, ethylene/propylene copolymers, ethylene/ethyl acrylate copolymers, ethylene/vinyl acetate copolymers, silicone rubbers, polydimethyl siloxanes, neoprene rubber, chlorinated polyethylene, polyvinylchloride, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer.

C. Topical Administration

The pharmaceutical compositions provided herein may be administered topically to the skin, orifices, or mucosa. The topical administration, as used herein, includes (intra)dermal, conjunctival, intracorneal, intraocular, ophthalmic, auricular, transdermal, nasal, vaginal, urethral, respiratory, and rectal administration.

The pharmaceutical compositions provided herein may be formulated in any dosage forms that are suitable for topical administration for local or systemic effect, including emulsions, solutions, suspensions, creams, gels, hydrogels, ointments, dusting powders, dressings, elixirs, lotions, suspensions, tinctures, pastes, foams, films, aerosols, irrigations, sprays, suppositories, bandages, dermal patches. The topical formulation of the pharmaceutical compositions provided herein may also comprise liposomes, micelles, microspheres, nanosystems, and mixtures thereof.

Pharmaceutically acceptable carriers and excipients suitable for use in the topical formulations provided herein include, but are not limited to, aqueous vehicles, water-miscible vehicles, non-aqueous vehicles, antimicrobial agents or preservatives against the growth of microorganisms, stabilizers, solubility enhancers, isotonic agents, buffering agents, antioxidants, local anesthetics, suspending and dispersing agents, wetting or emulsifying agents, complexing agents, sequestering or chelating agents, penetration enhancers, cryoprotectants, lyoprotectants, thickening agents, and inert gases.

The pharmaceutical compositions may also be administered topically by electroporation, iontophoresis, phonophoresis, sonophoresis, or microneedle or needle-free injection, such as POWDERJECT™ (Chiron Corp., Emeryville, Calif.), and BIOJECT™ (Bioject Medical Technologies Inc., Tualatin, Oreg.).

The pharmaceutical compositions provided herein may be provided in the forms of ointments, creams, and gels. Suitable ointment vehicles include oleaginous or hydrocarbon vehicles, including lard, benzoinated lard, olive oil, cottonseed oil, and other oils, white petrolatum; emulsifiable or absorption vehicles, such as hydrophilic petrolatum, hydroxystearin sulfate, and anhydrous lanolin; water-removable vehicles, such as hydrophilic ointment; water-soluble ointment vehicles, including polyethylene glycols of varying molecular weight; emulsion vehicles, either water-in-oil (W/O) emulsions or oil-in-water (O/W) emulsions, including cetyl alcohol, glyceryl monostearate, lanolin, and stearic acid (see, *Remington: The Science and Practice of Pharmacy*, supra). These vehicles are emollient but generally require addition of antioxidants and preservatives.

Suitable cream base can be oil-in-water or water-in-oil. Cream vehicles may be water-washable, and contain an oil phase, an emulsifier, and an aqueous phase. The oil phase is also called the "internal" phase, which is generally comprised of petrolatum and a fatty alcohol such as cetyl or stearyl alcohol. The aqueous phase usually, although not necessarily, exceeds the oil phase in volume, and generally contains a humectant. The emulsifier in a cream formulation may be a nonionic, anionic, cationic, or amphoteric surfactant.

Gels are semisolid, suspension-type systems. Single-phase gels contain organic macromolecules distributed substantially uniformly throughout the liquid carrier. Suitable gelling agents include crosslinked acrylic acid polymers, such as carbomers, carboxypolyalkylenes, CARBOPOL®; hydrophilic polymers, such as polyethylene oxides, polyoxyethylene-polyoxypropylene copolymers, and polyvinylalcohol; cellulosic polymers, such as hydroxypropyl cellulose, hydroxyethyl cellulose, hydroxypropyl methylcellulose, hydroxypropyl methylcellulose phthalate, and methylcellulose; gums, such as tragacanth and xanthan gum; sodium alginate; and gelatin. In order to prepare a uniform gel, dispersing agents such as alcohol or glycerin can be added, or the gelling agent can be dispersed by trituration, mechanical mixing, and/or stirring.

The pharmaceutical compositions provided herein may be administered rectally, urethrally, vaginally, or perivaginally in the forms of suppositories, pessaries, bougies, poultices or cataplasm, pastes, powders, dressings, creams, plasters, contraceptives, ointments, solutions, emulsions, suspensions, tampons, gels, foams, sprays, or enemas. These dosage forms can be manufactured using conventional processes as described in *Remington: The Science and Practice of Pharmacy*, supra.

Rectal, urethral, and vaginal suppositories are solid bodies for insertion into body orifices, which are solid at ordinary temperatures but melt or soften at body temperature to release the active ingredient(s) inside the orifices. Pharmaceutically acceptable carriers utilized in rectal and vaginal suppositories include bases or vehicles, such as stiffening agents, which produce a melting point in the proximity of body temperature, when formulated with the pharmaceutical compositions provided herein; and antioxidants as described herein, including bisulfite and sodium metabisulfite. Suitable vehicles include, but are not limited to, cocoa butter (theobroma oil), glycerin-gelatin, carbowax (polyoxyethylene glycol), spermaceti, paraffin, white and yellow wax, and appropriate mixtures of mono-, di- and triglycerides of fatty acids, hydrogels, such as polyvinyl alcohol, hydroxyethyl methacrylate, polyacrylic acid; glycerinated gelatin. Combinations of the various vehicles may be used. Rectal and vaginal suppositories may be prepared by the compressed method or molding. The typical weight of a rectal and vaginal suppository is about 2 to about 3 g.

The pharmaceutical compositions provided herein may be administered ophthalmically in the forms of solutions, suspensions, ointments, emulsions, gel-forming solutions, powders for solutions, gels, ocular inserts, and implants.

The pharmaceutical compositions provided herein may be administered intranasally or by inhalation to the respiratory tract. The pharmaceutical compositions may be provided in the form of an aerosol or solution for delivery using a pressurized container, pump, spray, atomizer, such as an atomizer using electrohydrodynamics to produce a fine mist, or nebulizer, alone or in combination with a suitable propellant, such as 1,1,1,2-tetrafluoroethane or 1,1,1,2,3,3,3-heptafluoropropane. The pharmaceutical compositions may also be provided as a dry powder for insufflation, alone or in combination with an inert carrier such as lactose or phospholipids; and nasal drops. For intranasal use, the powder may comprise a bioadhesive agent, including chitosan or cyclodextrin.

Solutions or suspensions for use in a pressurized container, pump, spray, atomizer, or nebulizer may be formulated to contain ethanol, aqueous ethanol, or a suitable alternative agent for dispersing, solubilizing, or extending release of the active ingredient provided herein, a propellant as solvent; and/or a surfactant, such as sorbitan trioleate, oleic acid, or an oligolactic acid.

The pharmaceutical compositions provided herein may be micronized to a size suitable for delivery by inhalation, such as about 50 micrometers or less, or about 10 micrometers or less. Particles of such sizes may be prepared using a comminuting method known to those skilled in the art, such as spiral jet milling, fluid bed jet milling, supercritical fluid processing to form nanoparticles, high pressure homogenization, or spray drying.

Capsules, blisters and cartridges for use in an inhaler or insufflator may be formulated to contain a powder mix of the pharmaceutical compositions provided herein; a suitable powder base, such as lactose or starch; and a performance modifier, such as l-leucine, mannitol, or magnesium stearate. The lactose may be anhydrous or in the form of the monohydrate. Other suitable excipients or carriers include dextran, glucose, maltose, sorbitol, xylitol, fructose, sucrose, and trehalose. The pharmaceutical compositions provided herein for inhaled/intranasal administration may further comprise a suitable flavor, such as menthol and levomenthol, or sweeteners, such as saccharin or saccharin sodium.

The pharmaceutical compositions provided herein for topical administration may be formulated to be immediate release or modified release, including delayed-, sustained-, pulsed-, controlled-, targeted, and programmed release.

D. Modified Release

The pharmaceutical compositions provided herein may be formulated as a modified release dosage form. As used herein, the term "modified release" refers to a dosage form in which the rate or place of release of the active ingredient(s) is different from that of an immediate dosage form when administered by the same route. Modified release dosage forms include delayed-, extended-, prolonged-, sustained-, pulsed-, controlled-, accelerated- and fast-, targeted-, programmed-release, and gastric retention dosage forms. The pharmaceutical compositions in modified release dosage forms can be prepared using a variety of modified release devices and methods known to those skilled in the art, including, but not limited to, matrix controlled release devices, osmotic controlled release devices, multiparticulate controlled release devices, ion-exchange resins, enteric coatings, multilayered coatings, microspheres, liposomes, and combinations thereof. The release rate of the active ingredient(s) can also be modified by varying the particle sizes and polymorphorism of the active ingredient(s).

Examples of modified release include, but are not limited to, those described in U.S. Pat. Nos. 3,845,770; 3,916,899; 3,536,809; 3,598,123; 4,008,719; 5,674,533; 5,059,595; 5,591,767; 5,120,548; 5,073,543; 5,639,476; 5,354,556; 5,639,480; 5,733,566; 5,739,108; 5,891,474; 5,922,356; 5,972,891; 5,980,945; 5,993,855; 6,045,830; 6,087,324; 6,113,943; 6,197,350; 6,248,363; 6,264,970; 6,267,981; 6,376,461; 6,419,961; 6,589,548; 6,613,358; and 6,699,500.

1. Matrix Controlled Release Devices

The pharmaceutical compositions provided herein in a modified release dosage form may be fabricated using a matrix controlled release device known to those skilled in the art (see, Takada et al in "Encyclopedia of Controlled Drug Delivery," Vol. 2, Mathiowitz Ed., Wiley, 1999).

In one embodiment, the pharmaceutical compositions provided herein in a modified release dosage form is formulated using an erodible matrix device, which is water-swellable, erodible, or soluble polymers, including synthetic polymers, and naturally occurring polymers and derivatives, such as polysaccharides and proteins.

Materials useful in forming an erodible matrix include, but are not limited to, chitin, chitosan, dextran, and pullulan; gum agar, gum arabic, gum karaya, locust bean gum, gum tragacanth, carrageenans, gum ghatti, guar gum, xanthan gum, and scleroglucan; starches, such as dextrin and maltodextrin; hydrophilic colloids, such as pectin; phosphatides, such as lecithin; alginates; propylene glycol alginate; gelatin; collagen; and cellulosics, such as ethyl cellulose (EC), methylethyl cellulose (MEC), carboxymethyl cellulose (CMC), CMEC, hydroxyethyl cellulose (HEC), hydroxypropyl cellulose (HPC), cellulose acetate (CA), cellulose propionate (CP), cellulose butyrate (CB), cellulose acetate butyrate (CAB), CAP, CAT, hydroxypropyl methyl cellulose (HPMC), HPMCP, HPMCAS, hydroxypropyl methyl cellulose acetate trimellitate (HPMCAT), and ethylhydroxy ethylcellulose (EHEC); polyvinyl pyrrolidone; polyvinyl alcohol; polyvinyl acetate; glycerol fatty acid esters; polyacrylamide; polyacrylic acid; copolymers of ethacrylic acid or methacrylic acid (EUDRAGIT®, Rohm America, Inc., Piscataway, N.J.); poly(2-hydroxyethyl-methacrylate); polylactides; copolymers of L-glutamic acid and ethyl-L-glutamate; degradable lactic acid-glycolic acid copolymers; poly-D-(−)-3-hydroxybutyric acid; and other acrylic acid derivatives, such as homopolymers and copolymers of butylmethacrylate, methylmethacrylate, ethylmethacrylate, ethylacrylate, (2-dimethylaminoethyl)methacrylate, and (trimethylaminoethyl)methacrylate chloride.

In further embodiments, the pharmaceutical compositions are formulated with a non-erodible matrix device. The active ingredient(s) is dissolved or dispersed in an inert matrix and is released primarily by diffusion through the inert matrix once administered. Materials suitable for use as a non-erodible matrix device included, but are not limited to, insoluble plastics, such as polyethylene, polypropylene, polyisoprene, polyisobutylene, polybutadiene, polymethylmethacrylate, polybutylmethacrylate, chlorinated polyethylene, polyvinylchloride, methyl acrylate-methyl methacrylate copolymers, ethylene-vinyl acetate copolymers, ethylene/propylene copolymers, ethylene/ethyl acrylate copolymers, vinyl chloride copolymers with vinyl acetate, vinylidene chloride, ethylene and propylene, ionomer polyethylene terephthalate, butyl rubber epichlorohydrin rubbers, ethylene/vinyl alcohol copolymer, ethylene/vinyl acetate/vinyl alcohol terpolymer, and ethylene/vinyloxyethanol copolymer, polyvinyl chloride, plasticized nylon, plasticized polyethylene terephthalate, natural rubber, silicone rubbers, polydimethylsiloxanes, silicone carbonate copolymers, and; hydrophilic polymers, such as ethyl cellulose, cellulose acetate, crospovidone, and cross-linked partially hydrolyzed polyvinyl acetate; and fatty compounds, such as carnauba wax, microcrystalline wax, and triglycerides.

In a matrix controlled release system, the desired release kinetics can be controlled, for example, via the polymer type employed, the polymer viscosity, the particle sizes of the polymer and/or the active ingredient(s), the ratio of the active ingredient(s) versus the polymer, and other excipients or carriers in the compositions.

The pharmaceutical compositions provided herein in a modified release dosage form may be prepared by methods known to those skilled in the art, including direct compression, dry or wet granulation followed by compression, melt-granulation followed by compression.

2. Osmotic Controlled Release Devices

The pharmaceutical compositions provided herein in a modified release dosage form may be fabricated using an osmotic controlled release device, including one-chamber system, two-chamber system, asymmetric membrane technology (AMT), and extruding core system (ECS). In general, such devices have at least two components: (a) the core which contains the active ingredient(s); and (b) a semipermeable membrane with at least one delivery port, which encapsulates the core. The semipermeable membrane controls the influx of water to the core from an aqueous environment of use so as to cause drug release by extrusion through the delivery port(s).

In addition to the active ingredient(s), the core of the osmotic device optionally includes an osmotic agent, which creates a driving force for transport of water from the environment of use into the core of the device. One class of osmotic agents water-swellable hydrophilic polymers, which are also referred to as "osmopolymers" and "hydrogels," including, but not limited to, hydrophilic vinyl and acrylic polymers, polysaccharides such as calcium alginate, polyethylene oxide (PEO), polyethylene glycol (PEG), polypropylene glycol (PPG), poly(2-hydroxyethyl methacrylate), poly(acrylic) acid, poly(methacrylic) acid, polyvinylpyrrolidone (PVP), crosslinked PVP, polyvinyl alcohol (PVA), PVA/PVP copolymers, PVA/PVP copolymers with hydrophobic monomers such as methyl methacrylate and vinyl acetate, hydrophilic polyurethanes containing large PEO blocks, sodium croscarmellose, carrageenan, hydroxyethyl cellulose (HEC), hydroxypropyl cellulose (HPC), hydroxypropyl methyl cellulose (HPMC), carboxymethyl cellulose (CMC) and carboxyethyl, cellulose (CEC), sodium alginate, polycarbophil, gelatin, xanthan gum, and sodium starch glycolate.

The other class of osmotic agents is osmogens, which are capable of imbibing water to affect an osmotic pressure gradient across the barrier of the surrounding coating. Suitable osmogens include, but are not limited to, inorganic salts, such as magnesium sulfate, magnesium chloride, calcium chloride, sodium chloride, lithium chloride, potassium sulfate, potassium phosphates, sodium carbonate, sodium sulfite, lithium sulfate, potassium chloride, and sodium sulfate; sugars, such as dextrose, fructose, glucose, inositol, lactose, maltose, mannitol, raffinose, sorbitol, sucrose, trehalose, and xylitol, organic acids, such as ascorbic acid, benzoic acid, fumaric acid, citric acid, maleic acid, sebacic acid, sorbic acid, adipic acid, edetic acid, glutamic acid, p-toluenesulfonic acid, succinic acid, and tartaric acid; urea; and mixtures thereof.

Osmotic agents of different dissolution rates may be employed to influence how rapidly the active ingredient(s) is initially delivered from the dosage form. For example, amorphous sugars, such as MANNOGEM™ EZ (SPI Pharma, Lewes, Del.) can be used to provide faster delivery during the first couple of hours to promptly produce the desired therapeutic effect, and gradually and continually release of the remaining amount to maintain the desired level of therapeutic or prophylactic effect over an extended period of time. In this case, the active ingredient(s) is released at such a rate to replace the amount of the active ingredient metabolized and excreted.

The core may also include a wide variety of other excipients and carriers as described herein to enhance the performance of the dosage form or to promote stability or processing.

Materials useful in forming the semipermeable membrane include various grades of acrylics, vinyls, ethers, polyamides, polyesters, and cellulosic derivatives that are water-permeable and water-insoluble at physiologically relevant pHs, or are susceptible to being rendered water-insoluble by chemical alteration, such as crosslinking. Examples of suitable polymers useful in forming the coating, include plasticized, unplasticized, and reinforced cellulose acetate (CA), cellulose diacetate, cellulose triacetate, CA propionate, cellulose nitrate, cellulose acetate butyrate (CAB), CA ethyl carbamate, CAP, CA methyl carbamate, CA succinate, cellulose acetate trimellitate (CAT), CA dimethylaminoacetate, CA ethyl carbonate, CA chloroacetate, CA ethyl oxalate, CA methyl sulfonate, CA butyl sulfonate, CA p-toluene sulfonate, agar acetate, amylose triacetate, beta glucan acetate, beta glucan triacetate, acetaldehyde dimethyl acetate, triacetate of locust bean gum, hydroxylated ethylene-vinylacetate, EC, PEG, PPG, PEG/PPG copolymers, PVP, HEC, HPC, CMC, CMEC, HPMC, HPMCP, HPMCAS, HPMCAT, poly(acrylic) acids and esters and poly-(methacrylic) acids and esters and copolymers thereof, starch, dextran, dextrin, chitosan, collagen, gelatin, polyalkenes, polyethers, polysulfones, polyethersulfones, polystyrenes, polyvinyl halides, polyvinyl esters and ethers, natural waxes, and synthetic waxes.

Semipermeable membrane may also be a hydrophobic microporous membrane, wherein the pores are substantially filled with a gas and are not wetted by the aqueous medium but are permeable to water vapor, as disclosed in U.S. Pat. No. 5,798,119. Such hydrophobic but water-vapor permeable membrane are typically composed of hydrophobic polymers such as polyalkenes, polyethylene, polypropylene, polytetrafluoroethylene, polyacrylic acid derivatives, polyethers, polysulfones, polyethersulfones, polystyrenes, polyvinyl halides, polyvinylidene fluoride, polyvinyl esters and ethers, natural waxes, and synthetic waxes.

The delivery port(s) on the semipermeable membrane may be formed post-coating by mechanical or laser drilling. Delivery port(s) may also be formed in situ by erosion of a plug of water-soluble material or by rupture of a thinner portion of the membrane over an indentation in the core. In addition, delivery ports may be formed during coating process, as in the case of asymmetric membrane coatings of the type disclosed in U.S. Pat. Nos. 5,612,059 and 5,698,220.

The total amount of the active ingredient(s) released and the release rate can substantially by modulated via the thickness and porosity of the semipermeable membrane, the composition of the core, and the number, size, and position of the delivery ports.

The pharmaceutical compositions in an osmotic controlled-release dosage form may further comprise additional conventional excipients or carriers as described herein to promote performance or processing of the formulation.

The osmotic controlled-release dosage forms can be prepared according to conventional methods and techniques known to those skilled in the art (see, *Remington: The Science and Practice of Pharmacy*, supra; Santus and Baker, *J. Controlled Release* 1995, 35, 1-21; Verma et al., *Drug Development and Industrial Pharmacy* 2000, 26, 695-708; Verma et al., *J. Controlled Release* 2002, 79, 7-27).

In certain embodiments, the pharmaceutical compositions provided herein are formulated as AMT controlled-release dosage form, which comprises an asymmetric osmotic membrane that coats a core comprising the active ingredient(s) and other pharmaceutically acceptable excipients or carriers. See, U.S. Pat. No. 5,612,059 and WO 2002/17918. The AMT controlled-release dosage forms can be prepared according to conventional methods and techniques known to those skilled in the art, including direct compression, dry granulation, wet granulation, and a dip-coating method.

In certain embodiments, the pharmaceutical compositions provided herein are formulated as ESC controlled-release dosage form, which comprises an osmotic membrane that coats a core comprising the active ingredient(s), a hydroxylethyl cellulose, and other pharmaceutically acceptable excipients or carriers.

3. Multiparticulate Controlled Release Devices

The pharmaceutical compositions provided herein in a modified release dosage form may be fabricated a multiparticulate controlled release device, which comprises a multiplicity of particles, granules, or pellets, ranging from about 10 μm to about 3 mm, about 50 μm to about 2.5 mm, or from about 100 μm to about 1 mm in diameter. Such multiparticulates may be made by the processes know to those skilled in the art, including wet- and dry-granulation, extrusion/spheronization, roller-compaction, melt-congealing, and by spray-coating seed cores. See, for example, *Multiparticulate Oral Drug Delivery*; Marcel Dekker: 1994; and *Pharmaceutical Pelletization Technology*; Marcel Dekker: 1989.

Other excipients or carriers as described herein may be blended with the pharmaceutical compositions to aid in processing and forming the multiparticulates. The resulting particles may themselves constitute the multiparticulate device or may be coated by various film-forming materials, such as enteric polymers, water-swellable, and water-soluble polymers. The multiparticulates can be further processed as a capsule or a tablet.

4. Targeted Delivery

The pharmaceutical compositions provided herein may also be formulated to be targeted to a particular tissue, receptor, or other area of the body of the subject to be treated, including liposome-, resealed erythrocyte-, and antibody-based delivery systems. Examples include, but are not limited to, U.S. Pat. Nos. 6,316,652; 6,274,552; 6,271,359; 6,253,872; 6,139,865; 6,131,570; 6,120,751; 6,071,495; 6,060,082; 6,048,736; 6,039,975; 6,004,534; 5,985,307; 5,972,366; 5,900,252; 5,840,674; 5,759,542; and 5,709,874.

INCORPORATION BY REFERENCE

This application incorporates by reference in its entirety the U.S. Provisional Patent Application filed with the U.S. Patent Office on Sep. 19, 2008, entitled: METHODS OF ADMINISTERING N-(5-TERT-BUTYL-ISOXAZOL-3-YL)-N'-{4-[7-(2-MORPHOLIN-4-YL-ETHOXY)IMIDAZO[2,1-b][1,3]BENZOTHIAZOL-2-YL]PHENYL}UREA TO TREAT PROLIFERATIVE DISEASE, which discloses, inter alia, pharmaceutical compositions comprising Compound B1 and methods of administering Compound B1.

6. EXAMPLES

The following Examples are presented by way of illustration, not limitation.

6.1 Example 1

Synthesis of N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL}UREA ("Compound B1")

A. The intermediate 2-amino-1,3-benzothiazol-6-ol was prepared according to a slightly modified literature procedure by Lau and Gompf: *J. Org. Chem.* 1970, 35, 4103-4108. To a stirred solution of thiourea (7.6 g, 0.10 mol) in a mixture of 200 mL ethanol and 9 mL concentrated hydrochloric acid was added a solution of 1,4-benzoquinone (21.6 g, 0.20 mol) in 400 mL of hot ethanol. The reaction was stirred for 24 hours at room temperature and then concentrated to dryness. The residue was triturated with hot acetonitrile and the resulting solid was filtered and dried.

The free base was obtained by dissolving the hydrochloride salt in water, neutralizing with sodium acetate, and collecting the solid by filtration. The product (2-amino-1,3-benzothiazol-6-ol) was obtained as a dark solid that was pure by LCMS (M+H=167) and NMR. Yield: 13.0 g (78%). NMR (DMSO-$d_6$) 7.6 (m, 2H), 6.6 (d, 1H).

B. To prepare the 2-(4-nitrophenyl)imidazo[2,1-b][1,3]benzothiazol-7-ol intermediate, 2-amino-1,3-benzothiazol-6-ol (20.0 g, 0.12 mol) and 2-bromo-4'-nitroacetophenone (29.3 g, 0.12 mol) were dissolved in 600 mL ethanol and heated to reflux overnight. The solution was then cooled to 0° C. in an ice-water bath and the product was collected by vacuum filtration. After drying under vacuum with $P_2O_5$, the intermediate (2-(4-nitrophenyl)imidazo[2,1-b][1,3]benzothiazol-7-ol) was isolated as a yellow solid. Yield: 17.0 g (46%) NMR (DMSO-$d_6$) δ 10 (s, 1H), 8.9 (s, 1H), 8.3 (d, 2H), 8.1 (d, 2H), 7.8 (d, 1H), 7.4 (s, 1H), 6.9 (d, 1H).

C. To make the 7-(2-morpholin-4-yl-ethoxy)-2-(4-nitrophenyl)imidazo[2,1-b][1,3]benzothiazole intermediate: 2-(4-nitrophenyl)imidazo[2,1-b][1,3]benzothiazol-7-ol, (3.00 g, 9.6 mmol) was suspended in 100 mL dry DMF. To this mixture was added potassium carbonate (4.15 g, 30 mmol, 3 eq), chloroethyl morpholine hydrochloride (4.65 g, 25 mmol, 2.5 eq) and optionally tetrabutyl ammonium iodide (7.39 g, 2 mmol). The suspension was then heated to 90° C. for 5 hours or until complete by LCMS. The mixture was cooled to room temperature, poured into 800 mL water, and allowed to stand for 1 hour. The resulting precipitate was collected by vacuum filtration and dried under vacuum. The intermediate, (7-(2-morpholin-4-yl-ethoxy)-2-(4-nitro-phenyl)imidazo[2, 1-b][1,3]benzothiazole) was carried on without further purification. Yield: 3.87 g (95%) NMR (DMSO-d$_6$) δ 8.97 (s, 1H), 8.30 (d, 2H), 8.0 (d, 2H), 7.9 (d, 1H), 7.7 (s, 1H), 7.2 (d, 1H), 4.1 (t, 2H), 5.6 (m, 4H), 2.7 (t, 2H).

D. To make the intermediate 7-(2-morpholin-4-yl-ethoxy)-2-(4-amino-phenyl)imidazo[2,1-b][1,3]benzothiazole: To a suspension of 7-(2-morpholin-4-yl-ethoxy)-2-(4-nitro-phenyl)imidazo[2,1-b][1,3]benzothiazole (3.87 g, 9.1 mmol) in 100 mL isopropyl alcohol/water (3:1) was added ammonium chloride (2.00 g, 36.4 mmol) and iron powder (5.04 g, 90.1 mmol). The suspension was heated to reflux overnight with vigorous stirring, completion of the reaction was confirmed by LCMS. The mixture was filtered through Celite, and the filtercake was washed with hot isopropyl alcohol (150 mL). The filtrate was concentrated to approximately ⅓ of the original volume, poured into saturated sodium bicarbonate, and extracted 3 times with dichloromethane. The combined organic phases were dried over MgSO$_4$ and concentrated to give the product as an orange solid containing a small amount (4-6%) of starting material. (Yield: 2.75 g 54%). 80% ethanol/water may be used in the place of isopropyl alcohol/water—in which case the reaction is virtually complete after 3.5 hours and only traces of starting material are observed in the product obtained. NMR (DMSO-d$_6$) δ 8.4 (s, 1H), 7.8 (d, 1H), 7.65 (d, 1H), 7.5 (d, 2H), 7.1 (d, 1H), 6.6 (d, 2H), 4.1 (t, 2H), 3.6 (m, 4H), 2.7 (t, 2H).

E. A suspension of 7-(2-morpholin-4-yl-ethoxy)-2-(4-amino-phenyl)imidazo[2,1-b][1,3]benzothiazole (4.06 g, 10.3 mmol) and 5-tert-butylisoxazole-3-isocyanate (1.994 g, 12 mmol) in toluene was heated at 120° C. overnight. The reaction was quenched by pouring into a mixture of methylene chloride and water containing a little methanol and neutralized with saturated aqueous NaHCO$_3$ solution. The aqueous phase was extracted twice with methylene chloride, the combined organic extracts were dried over MgSO$_4$ and filtered. The filtrate was concentrated to about 20 ml volume and ethyl ether was added resulting in the formation of a solid. The precipitate was collected by filtration, washed with ethyl ether, and dried under vacuum to give the free base of Compound B1. Yield: 2.342 g (41%) NMR (DMSO-d$_6$) δ9.6 (br, 1H), 8.9 (br, 1H), 8.61 (s, 1H), 7.86 (d, 1H), 7.76 (d, 2H), 7.69 (d, 1H), 7.51 (d, 2H), 7.18 (dd, 1H), 6.52 (s, 1H), 4.16 (t, 2H), 3.59 (t, 4H), 3.36 (overlapping, 4H), 2.72 (t, 2H), 1.30 (s, 9H). NMR (CDCl$_3$) δ9.3 (br, 1H), 7.84 (m, 4H), 7.59 (d, 2H), 7.49 (d, 1H), 7.22 (d, 1H), 7.03 (dd, 1H), 5.88 (s, 1H), 4.16 (t, 2H), 3.76 (t, 4H), 2.84 (t, 2H), 2.61 (t, 4H), 1.37 (s, 9H).

6.2 Example 2

Alternative Synthesis of N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL}UREA ("Compound B1")

A. To a suspension of the intermediate 2-(4-Nitrophenyl)imidazo[2,1-b][1,3]benzothiazol-7-ol from Example 1B (2.24 g, 7.2 mmol) in ethanol (40 mL) was added SnCl$_2$.H$_2$O (7.90 g, 35 mmol) and heated to reflux. Concentrated HCl was added to the reaction mixture and the precipitate formed gradually. The reaction mixture was heated to reflux for 20 hours and then allowed to cool to room temperature. The solution was poured into ice and neutralized with 10% NaOH and adjusted to approximately pH 6. The organic phase was extracted three times with ethyl acetate (80 mL×3). Extracts were dried over MgSO$_4$ and concentrated to give a yellow solid. (1.621 g, 80%). The solid was recrystallized from methanol to give a pure product (1.355 g, 67%).

B. To a suspension of the intermediate from Step 2A (0.563 g, 2 mmol) in toluene (30 mL) was added 5-tert-butylisoxazole-3-isocyanate (0.332 g, 2 mmol) and heated to reflux overnight. LC-MS analysis showed presence of the intermediate but no trace of 5-tert-butylisoxazole-3-isocyanate and an additional 0.166 g of the isocyanate was added. The reaction was again heated to reflux overnight. Completion of reaction was verified by LC-MS. The solvent was removed and the resulting mixture was dissolved in methanol which was removed to give the second intermediate as a solid.

The mixture was dissolved in CH$_2$Cl$_2$ (150 mL) and washed with saturated NaHCO$_3$. The organic layer was dried over MgSO$_4$, concentrated, and purified by silica gel chromatography three times, first using a methanol/CH$_2$Cl$_2$ gradient, the second time using a hexane/ethyl acetate gradient followed by a methanol/ethyl acetate gradient, and a third time using a methanol/CH$_2$Cl$_2$ gradient.

C. To a suspension of the intermediate from Step 2B (0.110 g, 0.25 mmol) in THF (5 mL) was added Ph$_3$P (0.079 g, 0.3 mmol), diisopropylazodicarboxylate (0.061 g, 0.3 mmol) and 4-morpholinoethanol (0.039 g, 0.3 mmol). The reaction mixture was stirred at room temperature overnight. Completion of the reaction was verified by LC-MS. The solvent was removed and the final product was purified using silica gel chromatography, with methanol in CH$_2$Cl$_2$ (0.030 g, 21%).

6.3 Example 3

Bulk Synthesis of N-(5-TERT-BUTYL-ISOXAZOL-3-YL)-N'-{4-[7-(2-MORPHOLIN-4-YL-ETHOXY)IMIDAZO[2,1-B][1,3]BENZOTHIAZOL-2-YL]PHENYL}UREA ("Compound B1")

A multi-step reaction scheme that was used to prepare bulk quantities of Compound B1 is depicted in FIG. 66a and FIG. 66b, and is described further below.

Step 1: Preparation of 2-Amino-6-hydroxybenzothiazole (Intermediate 1)

2-Amino-6-methoxybenzothiazole is reacted with hot aqueous HBr for about 3 hrs and then the clear solution is cooled to ambient temperature overnight. The precipitated solids are collected, dissolved in hot water and the pH is adjusted to between 4.5-5.5. The resultant solids are collected, dried and recrystallized from Isopropanol. Second crop material is collected. The solids are vacuum dried to give Intermediate 1.

Step, 2: Preparation of 2-(4-Nitrophenyl)imidazo[2,1-b]benzothiazol-7-ol (Intermediate 2)

2-Amino-6-hydroxybenzothiazole, 2-Bromo-4-nitroacetophenone and absolute Ethanol are added together and heated to reflux for approximately 24 hours. Tetrabutylammonium iodide is added and the reaction is refluxed an additional 12 hours. The resulting yellow suspension is cooled and the solids collected and washed with Ethanol and Diethyl ether. The solids are dried under vacuum to give Intermediate 2.

Step 3: Preparation of 7-(2-Morpholin-4-yl-ethoxy)-2-(4-nitrophenyl)imidazo[2,1-b]benzothiazole (Intermediate 3)

Intermediate 2,4-(2-Chloroethyl)morpholine hydrochloride, Potassium carbonate and Tetrabutylammonium iodide are added to N,N-Dimethylformamide forming a yellow suspension that is heated for over 3 hours. The reaction is cooled and the solids are collected, slurried into water, filtered, slurried into acetone, filtered and washed with Acetone to give yellow solids that are dried under vacuum to give Intermediate 3.

Step 4: Preparation of 7-(2-Morpholin-4-yl-ethoxy)-2-(4-aminophenyl) imidazo[2,1-b]benzothiazole (Intermediate 4)

Intermediate 3 is dissolved into Methanol and THF and placed in a Hydrogenator. Raney Nickel is added and the vessel is pressurized with Hydrogen and stirred for >24 hrs. The reaction mixture is concentrated to a thick paste and diluted with Methyl tert-butyl ether. The resulting solids are filtered and washed with Methyl tert-butyl ether and dried under vacuum to give Intermediate 4.

Step 5: Preparation of {[5-(tert-Butyl)isoxazol-3-yl]amino}-N-{4-[7-(2-morpholin-4-yl-ethoxy)(4-hydroimidazolo[2,1-b]benzothiazol-2-yl)]phenyl}carboxamide (Compound B1)

3-Amino-5-tert-butyl isoxazole in Methylene chloride is added to a vessel containing toluene which is cooled to approx 0° C. Triphosgene is then added and the reaction mixture is cooled to below −15° C. Triethylamine is added, followed by Intermediate 4. The mixture is heated to distill off the Methylene chloride and then heated to over 60° C. for over 12 hours and cooled to 50-60° C. The resulting solids are filtered, washed with Heptane, slurried with 4% sodium hydroxide solution, and filtered. The solids are then washed with Methyl tert-butyl ether followed by Acetone and dried under vacuum to give Compound B1.

6.4 Example 4

Examples of Preparation of Compound B1 HCl Salt

Example A

For the preparation of a hydrochloride salt of Compound B1, N-(5-tert-butyl-isoxazol-3-yl)-N'-{4-[7-(2-morpholin-4-yl-ethoxy)imidazo[2,1-b][1,3]benzothiazol-2-yl]phenyl}urea hydrochloride, the free base was dissolved in a mixture of 20 ml methylene chloride and 1 ml methanol. A solution of 1.0 M HCl in ethyl ether (1.1 eq.) was added dropwise, followed by addition of ethyl ether. The precipitate was collected by filtration or centrifugation and washed with ethyl ether to give a hydrochloride salt of Compound B1. Yield: 2.44 g (98%) NMR (DMSO-$d_6$) δ1.0 (br, 1H), 9.68 (s, 1H), 9.26 (s, 1H), 8.66 (s, 1H), 7.93 (d, 1H), 7.78 (m, 3H), 7.53 (d, 2H), 7.26 (dd, 1H), 6.53 (s, 1H), 4.50 (t, 2H), 3.97 (m, 2H), 3.81 (t, 2H), 3.6 (overlapping, 4H), 3.23 (m, 2H), 1.30 (s, 9H).

Example B

Concentrated HCl is added to a suspension of Compound B1 in warm methanol forming a solution that slowly begins to precipitate. The reaction mixture is refluxed for over 2 hrs and then stirred overnight at ambient temperature. The HCl salt is collected and dried under vacuum.

Example C

Materials: {[5-(tert-Butyl)isoxazol-3-yl]amino}-N-{4-[7-(2-morpholin-4-yl-ethoxy)(4-hydroimidazolo[2,1-b]benzothiazol-2-yl)]phenyl}carboxamide (775 g, 1.38 mol, 1.0 eq); HCl 37% aqueous (288 mL, 3.46 mol, 2.5 eq); Methanol (MeOH, AR) (40 L). Procedure: (Step 1) Equipped a 50 L 3-neck round bottom flask with a mechanical agitator, thermocouple probe, Nitrogen inlet, drying tube, reflux condenser, addition funnel and in a heating mantle. (Step 2) Charged the flask with {[5-(tert-Butyl)isoxazol-3-yl]amino}-N-{4-[7-(2-morpholin-4-yl-ethoxy)(4-hydroimidazolo[2,1-b]benzothiazol-2-yl)]phenyl}carboxamide (775 g) and MeOH, AR (40 L). Heat the resulting off-white suspension to reflux (68° C.). A clear solution did not form. (Step 3) Added HCl (37% aqueous) (228 mL) over 5 minutes at 68° C. The reaction mixture turned into a clear solution and then a new precipitate formed within approximately 3 minutes. Continued heating at reflux for approximately 5 hours. Allowed the reaction mixture to cool to ambient temperature overnight. (Step 4) Collected the off-white solids by filtration onto a polypropylene filter, washing the solids with MeOH, AR (2×1 L). (Step 5) Combined two lots of material prepared in this manner (740 g and 820 g). Slurried the combined solids in Methanol (30 L) over 30 minutes at reflux and cool to the room temperature. (Step 6) Collected the solids by filtration onto a polypropylene filter, rinsing with Methanol (2×1.5 L). (Step 7) Dried the solids in a vacuum oven (<10 mmHg) at 40° C. Yield: 1598 g (84%), off-white solid; HPLC: 98.2% (area); MS: 561.2 (M+1); $^1$H NMR: conforms (300 MHz, DMSO-d6); Elemental Analysis (EA): Theory=54.97% C, 5.41% H, 13.26% N, 5.06% S; 11.19% Cl; Actual 54.45% C, 5.46% H, 13.09% N, 4.99% S; 10.91% Cl.

| Examples of Compound B1 HCl salt synthesis | | | | |
|---|---|---|---|---|
| Compound B1 Free Base | HCl (conc.) | Yield | Purity | Yield % |
| 5.0 g | 0.82 g | 4.7 g | EA, conforms | 83.0% |
| 5.0 g | 0.82 g | 4.86 g | EA, conforms | 85.0% |
| 5.0 g | 0.82 g | 4.65 g | EA, conforms | 82.0% |
| 50 g | 8.2 g | 46 g | 99.2% (A %) | 82.0% |
| 50 g | 8.2 g | 47 g | 98.4% (A %) | 82.0% |
| 775 g | 125 g | 740 g | 98.9% (A %) | 85.0% |
| 900 g | 145 g | 820 g | 97.2% (A %) | 83.0% |
| | | 1598 g | 98.2% (A %) | 100% |

Example D

In a 50-L 3-neck round bottom flask equipped with a mechanical stirrer, heating mantle, condenser and nitrogen inlet was charged Compound B1 (1052.4 g, 1.877 mol, 1.00 equiv.) and methanol (21 L). The reactor was heated and stirred. At an internal temperature >50° C., conc. HCl (398.63 mL, 4.693 mol, 2.5 equiv.) was charged over 5 minutes through an addition funnel. With the addition, the reaction changed from a pale yellow suspension to a white suspension. The internal temperature was 55° C. at the conclusion of the addition. The reaction was heated to reflux for 1 hour, then heating discontinued and the reaction allowed to cool to room temperature. The reaction was filtered in two portions, each filter cake washed with methanol (2×1 L), transferred to trays and dried in a vacuum oven (45° C.) to constant weight. The dried trays were combined to produce 1141.9 g, 96% yield, 99.1% HPLC purity, 10.9% chloride by titration.

6.5 Example 5

Methods and Techniques for Solid Form Synthesis and Analysis 6.5.1 Solubility Measurements A weighed sample was treated with aliquots of the test solvent at room temperature or elevated temperature. Complete dissolution of the test material was determined by visual inspection. Solubility was estimated based on the total solvent used to provide complete dissolution. The actual solubility may be greater than the value calculated because of the use of solvent aliquots that were too large or due to a slow rate of dissolution. The solubility is expressed as "less than" if dissolution did not occur during the experiment. If complete dissolution was achieved as a result of only one aliquot addition, the solubility is expressed as "greater than."

6.5.2 Crystal Form Screen

Both thermodynamic and kinetic crystallization techniques were employed. These techniques are described in more detail below. Once solid samples were harvested from crystallization attempts, they were either examined under a microscope for birefringence and morphology or observed with the naked eye. Any crystalline shape was noted, but sometimes the solid exhibited unknown morphology, due to small particle size. Solid samples were then analyzed by XRPD, and the crystalline patterns compared to each other to identify new crystal forms.

Cold Precipitation (CP).

Solutions were prepared in various solvents at elevated temperature (about 60° C.). The solutions were then filtered through a 0.2-μm nylon filter into an antisolvent at sub-ambient temperature. If there were no solids present, or if the amount of solids was judged too small for XRPD analysis, the vial was placed in a freezer. The resulting solids were isolated by filtration and analyzed.

Crash Cool (CC).

Saturated solutions were prepared in various solvents at elevated temperatures (about 60° C.) and filtered through a 0.2-μm nylon filter into a vial while still warm. Vials were then placed in a refrigerator or a dry ice/acetone bath. The resulting solids were isolated by filtration and analyzed.

Fast Evaporation (FE).

Solutions were prepared in various solvents and sonicated between aliquot additions to assist in dissolution. Once a mixture reached complete dissolution, as judged by visual observation, the solution was filtered through a 0.2-μm nylon filter. The filtered solution was allowed to evaporate at ambient in an uncapped vial. The solids that formed were isolated and analyzed.

Freeze Dry (FD).

Dilute water solution was prepared, filtered through a 0.2-μm nylon filter, and frozen. The frozen sample was lyophilized using an FTSsystems Flexi-Dry.

Slow Evaporation (SE).

Solutions were prepared in various solvents and sonicated between aliquot additions to assist in dissolution. Once a mixture reached complete dissolution, as judged by visual observation, the solution was filtered through a 0.2-μm nylon filter. The filtered solution was allowed to evaporate at ambient in a vial covered with aluminum foil perforated with pinholes. The solids that formed were isolated and analyzed.

Grinding.

A solid sample was placed into a stainless steel milling rotor with a small metal ball. The sample was ground at 30 Hz on a ball mill for a given amount of time. The solids were isolated and analyzed.

Slow Cool (SC).

Saturated solutions were prepared in various solvents at elevated temperatures (about 60° C.) and filtered through a 0.2-μm nylon filter into an open vial while still warm. The vial was covered and allowed to cool slowly to room temperature. The presence or absence of solids was noted. If there were no solids present, or if the amount of solids was judged too small for XRPD analysis, the vial was placed in a refrigerator overnight. Again, the presence or absence of solids was noted and if there were none, the vial was placed in a freezer overnight. Solids that formed were isolated by filtration and allowed to dry prior to analysis.

Slurry Experiments.

Solutions were prepared by adding enough solids to a given solvent so that excess solids were present. The mixture was then agitated in a sealed vial at either ambient or elevated temperature. After a given amount of time, the solids were isolated by vacuum filtration.

Stress Experiments.

Solids were stressed under different temperature or relative humidity (RH) environments for a measured time period. Specific RH values were achieved by placing the sample inside sealed chambers containing saturated salt solutions. The salt solutions were selected and prepared following an ASTM standard procedure. Samples were analyzed by XRPD immediately after removal from the stress environment.

6.5.3 Salt Screen

Experimental conditions included different guests, solvents, stoichiometries and crystallization techniques. These techniques are described in more detail below. Once solid samples were harvested from salt attempts, they were either examined under a microscope for birefringence and morphology or observed with the naked eye. Any crystalline shape was noted, but sometimes the solid exhibited unknown morphology, due to small particle size. Solid samples were then analyzed by XRPD.

Crash Precipitation.

A solution containing the free base and an acid was prepared at elevated temperature (about 60° C.). The solution was then filtered through a 0.2-μm nylon filter into an antisolvent at ambient temperature. The resulting solids were isolated and analyzed.

Crash Cool (CC).

Solutions containing the free base and an acid were prepared in various solvents at elevated temperature (about 60° C.) and may or may not have been filtered through a 0.2 μm nylon filter into a vial while still warm. Vials were then placed in a refrigerator or a freezer. The resulting solids were isolated by vacuum filtration and analyzed by XRPD.

Fast Evaporation (FE).

A solution containing free base and an acid was prepared and filtered through a 0.2-μm nylon filter. The filtered solution was allowed to evaporate at ambient in an uncapped vial. The solids that formed were isolated and analyzed.

Slow Cool.

A solution of the free base and an acid was prepared at elevated temperature. The mixture was then allowed to cool down to room temperature. The presence or absence of solids was noted. If there were no solids present, the vial was placed in a refrigerator. The presence or absence of solids was noted and the resulting solid was isolated and analyzed.

Slurry.

Solutions were prepared by adding an acid solution to a solution of free base with excess solids present. The mixture was then agitated in a sealed vial at ambient or elevated temperature for a given amount of time. The solids were isolated and analyzed.

6.5.4 Instrumental Techniques 6.5.4.1 Differential Scanning Calorimetry (DSC)

Analyses were carried out on a TA Instruments differential scanning calorimeter 2920. The instrument was calibrated using indium as the reference material. The sample was placed into a standard aluminum DSC pan with an uncrimped or a crimped lid configuration, and the weight accurately recorded. The sample cell was equilibrated at about 25° C. and heated under a nitrogen purge at a rate of about 10° C./min, up to a final temperature of about 300° C. To determine the glass transition temperature (Tg) of amorphous material, the sample cell was cycled several times between about −40 and about 70° C. The Tg is reported from the inflection point of the transitions as the average value.

6.5.4.2 Dynamic Vapor Sorption/Desorption (DVS)

Data were collected on a VTI SGA-100 moisture balance system. For sorption isotherms, a sorption range of about 5 to about 95% relative humidity (RH) and a desorption range of about 95 to about 5% RH in 10% RH increments were used for analysis. The samples were not dried prior to analysis. Equilibrium criteria used for analysis were less than 0.0100% weight change in 5 minutes with a maximum equilibration time of 3 hours if the weight criterion was not met. Data were not corrected for the initial moisture content of the samples.

6.5.4.3 Modulated Differential Scanning Calorimetry (MDSC)

Modulated differential scanning calorimetry data were obtained on a TA Instruments differential scanning calorimeter 2920 equipped with a refrigerated cooling system (RCS). The sample was placed into an aluminum DSC pan, and the weight accurately recorded. The pan was covered with a lid and crimped. MDSC data were obtained using a modulation amplitude of +/−0.8° C. and a 60 second period with an underlying heating rate of about 2° C./min from about −30 to about 150° C. The temperature and the heat capacity were calibrated using indium metal and sapphire as the calibration standards, respectively. The reported glass transition temperature is obtained from the inflection of the step change in the reversible heat flow versus temperature curve.

6.5.4.4 Nuclear Magnetic Resonance (NMR)

The solution phase $^1$H NMR spectra acquisition parameters are printed on each spectrum. Spectra were referenced to internal tetramethylsilane at 0.0 ppm.

6.5.4.5 Optical Microscopy

Observations made by optical microscopy were collected on a Wolfe polarizing optical microscope at a magnification of 4×. Crossed polarizers (CP) were used to observe birefringence in the samples.

6.5.4.6 Thermogravimetry (TG)

Analyses were carried out on a TA Instruments 2950 thermogravimetric analyzer. The calibration standards were nickel and Alumel™. Each sample was placed in an aluminum sample pan and inserted into the TG furnace. Samples were first equilibrated at about 25° C. or started directly from ambient conditions, then heated under a stream of nitrogen at a heating rate of about 10° C./min, up to a final temperature of about 300 or about 350° C. unless specified otherwise.

6.5.4.7 Thermogravimetric Infrared (TG-IR)

Thermogravimetric infrared (TG-IR) analyses were acquired on a TA Instruments thermogravimetric (TG) analyzer model 2050 interfaced to a Magna 560® Fourier transform infrared (FT-IR) spectrophotometer (Thermo Nicolet) equipped with an Ever-Glo mid/far IR source, a potassium bromide (KBr) beamsplitter, and a deuterated triglycine sulfate (DTGS) detector. The TG instrument was operated under a flow of helium at 90 and 10 cc/min for the purge and balance, respectively. Each sample was placed in a platinum sample pan, inserted into the TG furnace, accurately weighed by the instrument, and the furnace was heated from ambient temperature to about 275 or about 325° C. at a rate of about 20° C./min. The TG instrument was started first, immediately followed by the FT-IR instrument. Each IR spectrum represents 8 co-added scans collected at a spectral resolution of 4 cm$^{-1}$. IR spectra were collected every 1 seconds for 8 minutes. A background scan was collected before the beginning of the experiment. Wavelength calibration was performed using polystyrene. The TG calibration standards were nickel and Alumel™. Volatiles were identified from a search of the High Resolution Nicolet TGA Vapor Phase spectral library

6.5.4.8 X-Ray Powder Diffraction (XRPD)

X-ray powder diffraction analyses were performed on an Inel XRG-3000 diffractometer, equipped with a curved position-sensitive detector with a 2θ range of 120°. Real time data was collected using Cu Kα radiation starting at approximately 4° 2θ at a resolution of 0.03° 2θ. The tube voltage and amperage were set to 40 kV and 30 mA, respectively. Patterns are displayed from 2.5 to 40° 2θ. Samples were prepared for analysis by packing them into thin-walled glass capillaries. Each capillary was mounted onto a goniometer head that is motorized to permit spinning of the capillary during data acquisition. Instrument calibration was performed daily using a silicon reference standard.

Listings of XRPD peak positions were obtained either by visual inspection of XRPD patterns or using the software Pattern Match version 2.3.5 (see Ivanisevic, I. et al., System and method for matching diffraction patterns, U.S. Patent App. Pub. No. 20040103130, May 2004). In general, positions of XRPD peaks are expected to vary by about ±0.2° 2θ. Determination of whether an XRPD pattern matched a second XRPD pattern was performed either by visual inspection of the two XRPD patterns or using the software Pattern Match version 2.3.5. In general, as understood in the art, two XRPD patterns match one another if the characteristic peaks of the first pattern are located at approximately the same positions as the characteristic peaks of the second pattern. As understood in the art, determining whether two XRPD patterns match may require consideration of individual variables and parameters such as, but not limited to, preferred orientation, phase impurities, degree of crystallinity, particle size, variation in diffractometer instrument setup, variation in XRPD data collection parameters, and variation in XRPD data processing, among others.

6.5.4.9 Single Crystal X-Ray Diffraction

The crystal structure of the Form B crystal form of the HCl salt of Compound B1 was solved by single-crystal X-ray diffraction according to the procedure described below.

Sample Preparation.

The HCl salt of Compound B1 was dissolved in 10 mL methanol and filtered through a 0.2 mm nylon filter into a 20 mL glass vial. The vial was covered with aluminum foil with 7 pin-holes and left at ambient to evaporate. Single crystals were observed prior to complete evaporation.

Data Collection.

A colorless needle of $C_{29}H_{34}Cl_2N_6O_4S$ having approximate dimensions of 0.35×0.13×0.04 mm, was isolated and mounted on a glass fiber in random orientation. Preliminary examination and data collection were performed with Mo $K_\alpha$ radiation ($\lambda$=0.71073 Å) on a Nonius KappaCCD diffractometer. Refinements were performed on an LINUX PC using SHELX97 (see reference i, infra). Cell constants and an orientation matrix for data collection were obtained from least-squares refinement using the setting angles of 16934 reflections in the range 2°<θ<24°. The refined mosaicity from DENZO/SCALEPACK was 0.70° indicating moderate crystal quality. The space group was determined by the program XPREP (see reference i, infra). From the systematic presence of the following conditions: h0l h+l=2n, 0k0 k=2n and from subsequent least-squares refinement, the space group was determined to be $P2_1/n$ (no. 14). The data were collected to a maximum 2θ value of 48.32°, at a temperature of 150±1 K.

Data Reduction.

A total of 16934 reflections were collected, of which 4937 were unique. The frames were integrated with DENZO-SMN (see reference ii, infra). Lorentz and polarization corrections were applied to the data. The linear absorption coefficient is 0.316 mm$^{-1}$ for Mo $K_\alpha$ radiation. An empirical absorption correction using SCALEPACK was applied (see reference ii, infra). Transmission coefficients ranged from 0.889 to 0.988. Intensities of equivalent reflections were averaged. The agreement factor for the averaging was 7.6% based on intensity.

Structure Solution and Refinement.

The structure was solved by direct methods using SIR2004 (see reference iv, infra). The remaining atoms were located in succeeding difference Fourier syntheses. Hydrogen atoms were included in the refinement but restrained to ride on the atom to which they are bonded. The structure was refined in full-matrix least-squares by minimizing the function: $\Sigma w(|F_o|^2-|F_c|^2)^2$, where the weight w is defined as $1/[\sigma^2(F_o^2)+(0.0866P)^2+(0.0000P)]$, where $P=(F_o^2+2F_c^2)/3$.

Scattering factors were taken from the "International Tables for Crystallography" (see reference v, infra). Of the 4937 reflections used in the refinements, only the reflections with $F_o^2>2\sigma(F_o^2)$ were used in calculating R. A total of 3413 reflections were used in the calculation. The final cycle of refinement included 398 variable parameters and converged (largest parameter shift was <0.01 times its estimated standard deviation) with unweighted and weighted agreement factors of: $R=\Sigma|F_o-F_c|/\Sigma F_o=0.055$ and $$R_w = \sqrt{(\Sigma w(F_o^2 - F_c^2)^2 / \Sigma w(F_o^2)^2)} = 0.134.$$

The standard deviation of an observation of unit weight was 1.007. The highest peak in the final difference Fourier had a height of 0.47 e/Å$^3$. The minimum negative peak had a height of −0.48 e/Å$^3$.

Simulated X-Ray Powder Diffraction (XRPD) Pattern.

A simulated XRPD pattern was generated for Cu radiation using PowderCell 2.3 (see reference vi, infra) and the atomic coordinates, space group, and unit cell parameters from the single crystal data.

ORTEP and Packing Diagrams.

ORTEP diagrams were prepared using ORTEP III (see reference vii, infra). Atoms are represented by 50% probability anisotropic thermal ellipsoids. Packing diagrams were prepared using CAMERON modeling software (see reference viii, infra). Hydrogen bonding is represented as dashed lines. Additional figures were generated using Mercury version 1.4.1. Hydrogen bonding is represented as dashed lines.

Results from the Single Crystal Structure of the Form B Crystal Form of the HCl Salt of Compound B1.

The monoclinic approximate cell parameters and approximate calculated volume were determined to be: a=15.6089 (11) Å, b=11.9443 (6) Å, c=16.9448 (12) Å, α=90.00, β=101.249 (3)°, γ=90.00, V=3098.5 (3) Å$^3$. For the di-HCl salt of Compound B1 the formula weight is 633.60 g/mol with Z=4 and a calculated density of 1.358 g cm$^{-3}$. The space group was determined to be $P2_1/n$ (no. 14). Crystal data and crystallographic data collection parameters are summarized in Table 1.

An ORTEP drawing of the di-HCl salt of Compound B1 is shown in FIG. 19. The single crystal structure is in agreement with the Compound B1 structure, depicted above as structure (I). The asymmetric unit shown in contains one divalent Compound B1 molecule and two chloride anions. Salt formation was confirmed by locating the protons at N1 and N84 from the Fourier map. The labeling scheme was arbitrarily assigned.

Packing diagrams were prepared, such as the packing diagram depicted in FIG. 20. Hydrogen atoms are included in the figures and hydrogen bonding is represented with dashed lines. The structure can be described as layers of Compound B1 molecules separated by chloride ions. The two chloride ions are closely associated with the two protonated nitrogen atoms on the Compound B1 molecule. While one chloride ion (Cl2) is interacting with fused imidazole and the two amide nitrogen N27 and N29, the other halide ion does not appear to have additional interactions within the van der Waals radii of its nearest neighbors.

Slight shifts in peak location between the simulated XRPD pattern and experimental XRPD patterns relate to the fact that the experimental powder pattern was collected at ambient temperature, while the single crystal data was collected at 150 K. Low temperatures are used in single crystal analysis to improve the quality of the structure.

References and Citations for Single-Crystal XRD Data Collection:

(i) Sheldrick, G. M. *SHELX97, A Program for Crystal Structure Refinement*, University of Gottingen, Germany, 1997; (ii) Otwinowski, Z.; Minor, W. *Methods Enzymol.* 1997, 276, 307; (iii) Bruker, XPREP in SHELXTL v.6.12, Bruker AXS Inc., Madison, Wis., USE, 2002; (iv) Burla, M. C., et al., *J. Appl. Cryst.* 2005, 38, 381; (v) International Tables for Crystallography, Vol. C, Kluwer Academic Publishers: Dordrecht, The Netherlands, 1992, Tables 4.2.6.8 and 6.1.1.4; (vi) PowderCell for Windows v.2.3 Kraus, W.; Nolze, G. Federal Institute for Materials Research and Testing, Berlin Germany, EU, 1999; (vii) Johnson, C. K. ORTEPIII, Report ORNL-6895, Oak Ridge National Laboratory, TN, U.S.A. 1996. ORTEP-3 for Windows v.1.05, Farrugia, L. J., *J. Appl. Cryst.* 1997, 30, 565; (viii) Watkin, D. J.; et al. CAMERON, Chemical Crystallography Laboratory, University of Oxford, Oxford, 1996.

TABLE 1

Crystal Data and Data Collection Parameters for Form B Compound B1 HCl salt

| | |
|---|---|
| formula | $C_{29}H_{34}Cl_2N_6O_4S$ |
| formula weight | 633.60 |
| space group | P 21/n (No. 14) |
| a, Å | 15.6089(11) |
| b, Å | 11.9443(6) |
| c, Å | 16.9448(12) |
| b, deg | 101.249(3) |

TABLE 1-continued

Crystal Data and Data Collection Parameters for
Form B Compound B1 HCl salt

| | |
|---|---|
| V, Å$^3$ | 3098.5(3) |
| Z | 4 |
| $d_{calc}$, g cm$^{-3}$ | 1.358 |
| crystal dimensions, mm | 0.35 × 0.13 × 0.04 |
| temperature, K | 150. |
| radiation (wavelength, Å) | Mo K$_\alpha$ (0.71073) |
| monochromator | graphite |
| linear abs coef, mm$^{-1}$ | 0.316 |
| absorption correction applied | empirical |
| transmission factors: min, max | 0.889, 0.988 |
| diffractometer | Nonius Kappa CCD |
| h, k, l range | −17 to 17 −13 to 12 −19 to 19 |
| 2θrange, deg | 4.20-48.32 |
| mosaicity, deg | 0.70 |
| programs used | SHELXTL |
| F$_{000}$ | 1328.0 |
| weighting | 1/[σ$^2$(F$_o^2$) + (0.0866P)$^2$ + 0.0000P] where P = (F$_o^2$ + 2F$_c^2$)/3 |
| data collected | 16934 |
| unique data | 4937 |
| R$_{int}$ | 0.076 |
| data used in refinement | 4937 |
| cutoff used in R-factor calculations | F$_o^2$ > 2.0σ(F$_o^2$) |
| data with I > 2.0σ(I) | 3413 |
| number of variables | 398 |
| largest shift/esd in final cycle | 0.00 |
| R(F$_o$) | 0.055 |
| R$_w$(F$_o^2$) | 0.134 |
| goodness of fit | 1.007 |

6.6 Example 6

Preparation of Solid Forms Comprising Compound B1

6.6.1 Solid Forms Comprising the Free Base of Compound B1

6.6.1.1 Form A of the Free Base of Compound B1

Form A of the free base of Compound B1 was formed by dissolution of crude Compound B1 (160 g) in hot dimethylformamide (DMF; 1.3 L), followed by hot filtration, followed by stirring at about 15° C. to obtain a white solid. Another lot of crude Compound B1 (118 g) was dissolved in hot DMF (0.8 L) followed by filtration and combination with the first lot. The combined materials in DMF were stirred for over 2 hours at about 15° C. A white solid was filtered off, rinsed twice with two 500 mL portions of diethyl ether, and air dried. The resulting solid was determined by XRPD to be the Form A crystal form of the free base of Compound B1. XRPD data for Form A of the free base of Compound B1 is provided as FIG. 2.

6.6.1.2 Form B of the Free Base of Compound B1

Form B of the free base of Compound B1 was formed by fast evaporation of a 1:1 hippuric acid:Compound B1 mixture in a solvent system comprising methanol and hexanes. This sample of Form B material was a white solid, appearing by optical microscopy to be fibers with birefringence and extinguishment. Form B of the free base of Compound B1 was also formed by crash precipitation of a 1:1 maleic acid:Compound B1 mixture in a solvent system comprising methanol, tetrahydrofuran and hexanes. This sample of Form B material was an off-white solid, appearing by optical microscopy to be small, thin blades with birefringence and extinguishment. The Form B material was crystalline as observed by XRPD. XRPD data for Form B of the free base of Compound B1 is provided as FIG. 5.

6.6.1.3 Methanol Solvate of the Free Base of Compound B1

A methanol solvate of the free base of Compound B1 was formed by crash cooling a 1:1 fumaric acid:Compound B1 mixture in a solvent system comprising methanol and ether. The resulting material was a white solid, appearing by optical microscopy to be fibers with birefringence and extinguishment. This methanol solvate of the free base of Compound B1 was crystalline as observed by XRPD. XRPD data for this methanol solvate of the free base of Compound B1 is provided as FIG. 6.

6.6.2 Solid Forms Comprising the HCl Salt of Compound B1

6.6.2.1 Preparation of Solid Forms

| Solvent | Conditions | Habit/Description | XRPD Result |
|---|---|---|---|
| ACN/water (1:1) | Crash cool (~60° C. to refrigerator) | Off-white solid, irregular particles with birefringence and extinguishment | Amorphous + peaks |
| EtOH | Fast Evaporation | Fibers with birefringence and extinguishment | F |
| EtOH/water (4:1) | Slow cool (~60° C. to ambient) | Off-white solid, fibers with birefringence and extinguishment | F |
| MeOH | Slow evaporation | Blades with birefringence and extinguishment | B |
| MeOH | Slow evaporation | Needles and blades with birefringence and extinguishment | B |
| MeOH | Slow cool (~60° C. to freezer) | Fibers with birefringence and extinguishment | Amorphous |
| TFE | Slow evaporation | Light-yellow solid, fibers with birefringence and extinguishment | Disordered A |
| Water | Slow evaporation | Glass with birefringence | C |
| Water | Slow evaporation | Glass with birefringence | Amorphous |
| Water | Freeze drying | Fluffy white solid, irregular particles and aggregates | Amorphous |
| — | Grinding | Off-white solid, irregular particles | Amorphous |

6.6.2.2 Cold Precipitation Experiments

| Solvent | Antisolvent | Habit/Description | XRPD Result |
|---|---|---|---|
| Methanol | Acetone | White solid, rosette and needles with birefringence and extinguishment | H |
| | EtOAc | White solid, chunks | I |

6.6.2.3 Slurry Experiments

| Solvent | Conditions | Habit/Description | XRPD Result |
|---|---|---|---|
| Acetone | Slurry, 13 days | Yellow solid, chunks and irregular particles with some birefringence | D |
| ACN | Slurry, 13 days | Light-brown solid, chunks | D |
| 2-Butanone | Slurry, 13 days | Orange solid, chunks | A |
| DCM | Slurry, 13 days | Off-white solid, chunks | E |
| DCM | Slurry, 19 days | Off-white solid, chunks | E |
| 1,4-Dioxane | Slurry, 13 days | Off-white solid, chunks | A |
| 1,4-Dioxane/water (9:1) | Slurry, 13 days | Off-white solid, chunks | G |
| EtOAc | Slurry, 13 days | Off-white solid, chunks | D |
| EtOH | Slurry, 15 days | Light-yellow solid, small blades with birefringence and extinguishment | B |
| EtOH/water (24:1) | Slurry, 1 day (~60° C.) | Off-white solid, irregular particles with some birefringence and extinguishment | B |
| IPA | Slurry, 13 days | Light-yellow solid, chunks and irregular particles | Amorphous |
| IPA/water (24:1) | Slurry, 1 day (~60° C.) | White solid, irregular particles with some birefringence and extinguishment | H |
| Nitromethane | Slurry, 15 days | Yellow solid, chunks | A + peaks |
| THF | Slurry, 13 days | Light-yellow solid, chunks | A |
| TFT | Slurry, 13 days | Off-white solid, chunks and irregular particles | D |

6.6.2.4 Additional Preparation of Solid Forms Comprising the HCl Salt of Compound B1

| Solvent[a] | Conditions[a] | Habit/Description | XRPD Result |
|---|---|---|---|
| acetone | slurry, RT, 7 days | white, tiny needles, birefringent | B |
| | slurry, ~50° C., 5 days | white, small needles, birefringent | B |
| acetonitrile | slurry, RT, 7 days | white, tiny needles, birefringent | B |
| | slurry, RT, 18 days | light yellow; morphology unknown, partial birefringence; very small needles, birefringent | B |
| | slurry, ~60° C., 5 days | white, small needles, birefringent | B |
| 2-butanone (MEK) | slurry, RT, 7 days | white, tiny needles, birefringent | B |
| | slurry, ~60° C., 5 days | white, small needles, birefringent | B |
| Dichloromethane | slurry, RT, 7 days | white, small needles, birefringent | B |
| Dichloromethane:TFE 6:1 | SE under N$_2$ | off-white, dendridic needles and morphology unknown, birefringent | low crystalline I |
| p-dioxane | slurry, RT, 7 days | white, tiny needles, birefringent | B |
| | slurry, ~60° C., 5 days | white, needles and morphology unknown, birefringent | B |
| ethanol | slurry, RT, 7 days | white, tiny needles, birefringent | B |
| | slurry, 57° C., 2 days | white, tiny needles, birefringent | B |
| ethanol:TFE 4:1 | SE under N$_2$ | white, morphology unknown, partially birefringent | L |
| | SE under N$_2$, scale- | white, morphology unknown, | N with peak |

| Solvent[a] | Conditions[a] | Habit/Description | XRPD Result |
|---|---|---|---|
| | up | partially birefringent | shifts |
| | SE under N₂, scale-up | white, morphology unknown, partially birefringent | low crystalline, peaks from K or L |
| ethyl acetate | slurry, RT, 7 days | off-white, tiny needles, birefringent | B |
| isopropanol | slurry, RT, 7 days | white, tiny needles, birefringent | B |
| | slurry, ~60° C., 5 days | white, small needles, birefringent | B |
| methanol | FE under N₂ | white, thin needles and morphology unknown, birefringent | lower crystallinity J + F |
| | slurry, RT, 7 days | white, needles and morphology unknown, birefringent | B |
| | CC | white, small needles, birefringent; morphology unknown, not birefringent | J (possibly contains F) |
| | CC, scale-up | white, needles, birefringent | M |
| | CC, scale-up | white, morphology unknown, partially birefringent | F, l.c. |
| | filtrate from 2794-31-01, freezer 6 days | white, needles, birefringent; morphology unknown, partially birefringent | F (peak shifts) + J (minor) |
| | CC, scale-up | white, morphology unknown, partially birefringent | F |
| | CC, scale up | white, morphology unknown, partially birefringent | F, peak shifts |
| | CC, scale-up | white, morphology unknown, partially birefringent | Form O (might contain minor J) |
| methanol:TFE 50:1 | CC | white, needles, birefringent; morphology unknown, partially birefringent | F + J (minor) |
| Nitromethane | slurry, RT, 7 days | white, tiny needles, birefringent | B |
| | slurry, ~60° C., 5 days | white, small needles, birefringent | B |
| Nitromethane:TFE 6:1 | cold crash ppt, left for SE | off-white; morphology unknown, partial birefringence | low crystalline |
| | cold crash ppt., left for SE | white; morphology unknown, partial birefringence | two peaks from I + one peak at ~8.9° 2θ |
| | cold crash ppt., left for SE | light yellow; morphology unknown, birefringence; morphology unknown, partial birefringence | low crystalline (small sample) |
| | cold crash ppt., left for SE | white; morphology unknown, partial birefringence | low crystalline I (might contain minor D) |
| Nitromethane:TFE 4:1 | SE under N₂ | white, morphology unknown, partially birefringent | N minus peak at ~3.5° 2θ |
| Tetrahydrofuran | slurry, RT, 7 days | white, small needles, birefringent | B |
| | slurry, ~60° C., 5 days | white, small needles, birefringent | B |
| 2,2,2-trifluoroethanol | FE under N₂ | yellow, spherulites of needles, birefringent | low crystalline |
| | SE under N₂ | off-white, morphology unknown, birefringent | I |
| | CP w/acetone | white, flaky solid, not birefringent | low crystalline I |
| | CP w/ACN | white and translucent, morphology unknown, partially birefringent | possibly amorphous with 2 peaks |
| | CP w/MEK | white, flaky solid, partially birefringent | low crystalline I |
| | CP w/p-dioxane | off-white, morphology unknown, partially birefringent | K |
| | CP w/p-dioxane, scale-up | off-white, morphology unknown, not birefringent | K |
| | CP w/p-dioxane, scale-up | off-white, morphology unknown, partially birefringent | K |
| | CP w/EtOAc | white, flaky solid, not birefringent | low crystalline |

-continued

| Solvent[a] | Conditions[a] | Habit/Description | XRPD Result |
|---|---|---|---|
| | CP w/IPA | off-white, morphology unknown, not birefringent | low crystalline |
| | CP w/THF | white, morphology unknown, partially birefringent | N |
| 2,2,2-trifluoro-ethanol | VD w/acetone | white and yellow, small needles and morphology unknown, partially birefringent | low crystalline I + D |
| | VD w/ACN | white, morphology unknown, partially birefringent | likely low crystalline L |
| | VD w/MEK | white, morphology unknown, partially birefringent | I |
| | VD w/ p-dioxane | off-white, needles, birefringent; morphology unknown, partially birefringent | D (peak shifts) |
| | VD w/ p-dioxane, scale-up | white, morphology unknown, partially birefringent | N |
| | VD w/EtOH | off-white, morphology unknown, partially birefringent | similar to low crystalline I |
| 2,2,2-trifluoro-ethanol | VD w/EtOAc | white, morphology unknown, partially birefringent | I |
| | VD w/EtOAc, scale-up | white, morphology unknown, partially birefringent | I (peak at ~4° 2θ) |
| | VD w/IPA | white, morphology unknown, partially birefringent | I |
| | VD w/nitromethane | white, morphology unknown, partially birefringent | small sample; low signal/noise ratio, difficult to interpret |
| | VD w/THF | off-white, needles and morphology unknown, birefringent | low crystalline I |
| TFE: 2-butanone 4:1 | SE | off-white; morphology unknown, partial birefringence | low crystalline I + D, similar to 229632 |
| TFE:acetone 4:1 | SE | light yellow; morphology unknown, partial birefringence | F |
| TFE:acetonitrile 4:1 | SE | light yellow; morphology unknown, partial birefringence | F |
| TFE:ethyl acetate 4:1 | SE | off-white; morphology unknown, partial birefringence; needle-like morphology, partial birefringence | low crystalline I with peak shifts + one peak at ~3° 2θ |
| TFE:p-dioxane 5:1 | SE | off-white; morphology unknown, partial birefringence | low crystalline I; similar to 229634 |
| TFE:isopropanol 5:3 | SE | off-white; morphology unknown, partial birefringence | crystalline I + minor D |
| TFE:tetrahydro-furan 5:1 | SE | light yellow; needle-like, partial birefringence; morphology unknown, partial birefringence | low crystalline I + minor D |
| Trifluoro-toluene | slurry, RT, 7 days | white, tiny needles, birefringent | B |
| | SE under $N_2$ | off-white, flaky solid, not birefrigence | I |
| Trifluoro-toluene:TFE 5:1 | cold crash ppt., left for SE | off-white; morphology unknown, slight birefringence | low crystalline I (might contain minor D), |
| water | RE | off-white, glassy solid and morphology unknown, partially birefringent | low crystalline |
| acetone:water 50:50 | SE | off-white, aggregates of spherical particles and morphology unknown, partially birefringent | low signal/noise ratio, difficult to interpret |

| Solvent[a] | Conditions[a] | Habit/Description | XRPD Result |
|---|---|---|---|
| acetone:water 80:20 | slurry, RT, 7 days | white, needles and morphology unknown, birefringent | B |
| acetonitrile:water 50:50 | SE | white, morphology unknown, birefringent | low crystalline |
| p-dioxane:water 50:50 | dried under N₂ | yellow, glassy solid and morphology unknown, birefringent | very low crystalline |
|  | SC | white, thin needles and spherulites, birefringent; morphology unknown, not birefringent | possibly low crystalline A |
|  | CC | white, morphology unknown, partially birefringent | F |
| p-dioxane:water 80:20 | slurry, RT, 7 days | white, small needles, birefringent | B |
| ethanol:water 50:50 | SE | white, needles and morphology unknown, birefringent; clear, jelly-like solid, not birefringent | very low crystalline |
| ethanol:water 80:20 | slurry, RT, 7 days | white, needles and morphology unknown, birefringent | B |
| isopropanol:water 20:80 | SE | white, morphology unknown, partially birefringent | low crystalline |
|  | SC | translucent, spherical particles and morphology unknown, partially birefringent | very low crystalline |
|  | CC | off-white, morphology unknown, birefringent | low signal/noise ratio, difficult to interpret |
| isopropanol:water 80:20 | slurry, RT, 7 days | white, morphology unknown, partially birefringent | B |
| Tetrahydrofuran:water 50:50 | SE | yellow, morphology unknown, birefringent | very low crystalline |

[a] Abbreviations in Table: CC = crash cool, CP = crash precipitation, EtOAc = ethyl acetate, FE = fast evaporation, VD = vapor diffusion, IPA = isopropanol, MEK = methyl ethyl ketone (2-butanone), RE = rotary evaporation, RT = room (ambient) temperature, SC = slow cool, SE = slow evaporation, THF = tetrahydrofuran, TFE = 2,2,2 = trifluoroethanol.

6.6.2.5 Scale-up Experiments of Involving Crystal Forms Comprising the HCl Salt of Compound B1

| Starting Form | Solvent | Conditions | Habit/Description | XRPD Result |
|---|---|---|---|---|
| B | TFE | SE | yellow/light yellow; morphology unknown, not birefringent; sperulites, birefringent | low crystalline |
| B | methanol | SE | light yellow; needles, birefringent; morphology unknown, very partial birefringence | F + B |
| B | water | SE under N₂ | light yellow; morphology unknown, birefringent; morphology unknown, partial birefringence | low crystalline |
|  | water | SE | light yellow; morphology unknown, birefringence; morphology unknown, partial birefringence | low crystalline |
|  | water | SE | light yellow; morphology unknown, partial birefringence; morphology unknown, birefringence | low crystalline, peaks from D and I |
| B | acetone | slurry RT, 7 days | white/yellow; morphology unknown, partial birefringence; morphology unknown, birefringent | B |
| B | methylene chloride | slurry RT, 7 days | white/light yellow; morphology unknown, partial birefringence; morphology unknown, birefringent | B |
| B | EtOH:Water (4:1) | slow cool, ~63° C. to ambient, freezer X days | off-white; morphology unknown, birefringence; morphology unknown, partial birefringence | F |
|  | EtOH:water (4:1) | slow cool, ~63° C. to | white; morphology unknown, partial birefringence; morphology | F |

-continued

| Starting Form | Solvent | Conditions | Habit/Description | XRPD Result |
|---|---|---|---|---|
| | | ambient | unknown, partial birefringence; thin needles, birefringent | |
| | EtOH:water (4:1) | slow cool, ~63° C. to ambient, freezer 6 days | white; morphology unknown, partial birefringence | F |
| B | dioxane:water (9:1) | rotating wheel, 7 days | light yellow or pale white; morphology unknown, not birefringent; morphology unknown, birefringent | B |
| B | methanol/acetone | cold precipitation, freezer X days | white; needles, birefringence; morphology unknown, partial birefringence | some H and B |
| | IPA:water (24:1) | slurry, 1 day, ~60° C. | white/yellowish; morphology unknown, not birefringent; small needles, birefringent | B |
| | IPA:water (24:1) | slurry, 7 days, ~60° C. | Light yellow, very small needles, birefringent; Light brown, morphology unknown, partial birefringence; Light yellow, morphology unknown, partial birefringence | B + minor H |
| | methanol/acetone | cold precipitation, freezer 11 days | white; needles, birefringent; morphology unknown, partial birefringence | similar to H (minus peak at ~4° 2Theta, peak shifts) |
| A | water | gel; FE using nitrogen | light yellow; morphology unknown, birefringence; morphology unknown, partial birefringence | low crystalline |
| A | IPA/water (24:1) | Slurry, 1 day, ~60° C. | white; needles, birefringence; morphology unknown, partial birefringence | similar to H (peak shifts, missing peaks) |
| | IPA/water (24:1) | Slurry, 2 days, ~60° C. | off-white; unknown morphology, partial birefringence | low angle 2θ shoulder |

Abbreviations in Table:
CC = crash cool,
CP = crash precipitation,
EtOAc = ethyl acetate,
FE = fast evaporation,
IPA = isopropanol,
MEK = methyl ethyl ketone (2-butanone),
RE = rotary evaporation,
RT = room (ambient) temperature,
SC = slow cool,
SE = slow evaporation,
THF = tetrahydrofuran,
TFE = 2,2,2 = trifluoroethanol.

6.6.2.6 Stress Studies

Humidity Stress Studies

| Starting Form | Conditions | Habit/Description | XRPD Result |
|---|---|---|---|
| A | 75% RH 4 days: 3.4% weight gain | White solid, irregular particles | D |
| A | 75% RH 1 day: 4.2% weight gain 2 days: 3.8% weight gain 4 days: 3.8% weight gain | Off-white solid, irregular particles | D |
| A | Oven: 40° C. 4 days: 3.0% weight loss | White solid, irregular particles | A + E |
| B | 75% RH 2 and 4 days: no weight change | Light-yellow solid, small blades with birefringence and extinguishment | B |
| D | Oven: 80° C., 3 days | Light-yellow solid, irregular particles | D |
| F | Oven: 80° C., 3 days | Off-white solid, fibers | Disordered + F |

-continued

| Starting Form | Conditions | Habit/Description | XRPD Result |
|---|---|---|---|
| Amorphous | 75% RH, 3 days | white solid, irregular particles, 11.8% weight gain | Amorphous |
| Amorphous | Oven: 40° C., 8 days | White solid, irregular particles | Amorphous |

Abbreviations in Table:
RH = Relative Humidity

Mechanical Stress Studies Involving Crystal Forms Comprising the HCl Salt of Compound B1

| Starting Form | Method | XRPD Result |
|---|---|---|
| Form B | compression, ~3 metric tons, 1 min | B |
| Form B | grind with mortar and pestle, dry, 1 min | B |
| Form B | grind with mortar and pestle, acetone, 1 min | B |
| Form B | grind with mortar and pestle, 2,2,2-trifluoroethanol, 1 min | B |
| Form B | grind with mortar and pestle, water, 1 min | B + small peak at approx. 3° 2θ |
| Form B | milling, dry, 10 min | B |
| Form B | milling, acetone, 10 min | B |
| Form B | milling, 2,2,2-trifluoroethanol, 10 min | B + large peak at approx. 3° 2θ |
| Form B | milling, water, 10 min | B |

6.6.2.7 Solubility Data for Forms A and B of the HCl Salt of Compound B1

Solubility Data for Form A of the HCl Salt of Compound B1

| Solvent System | Temperature (° C.) | Approximate Solubility (mg/mL) |
|---|---|---|
| Acetone | Ambient | <2 |
| Acetonitrile (ACN) | Ambient | <2 |
| 2-Butanone | Ambient | <2 |
| Dichloromethane (DCM) | Ambient | <2 |
| 1,4-Dioxane | Ambient | <2 |
| Ethyl Acetate (EtOAc) | Ambient | <2 |
| Ethanol (EtOH) | Ambient | 1 |
| Isopropanol (IPA) | Ambient | <2 |
| Methanol (MeOH) | Ambient | 3 |
| Nitromethane | Ambient | <2 |
| Tetrahydrofuran (THF) | Ambient | <2 |
| Trifluoroethanol (TFE) | Ambient | >72 |
| Trifluorotoluene (TFT) | Ambient | <2 |
| Water | Ambient | 36[a] |
| ACN/water (1:1) | 60° C. | ≥110 |
| Ethanol/water (24:1) | 60° C. | <2 |
| Ethanol/water (4:1) | 60° C. | ≥39 |
| Isopropanol/water (24:1) | 60° C. | <2 |

[a] Certain samples formed a gel upon addition of water; actual solubility may differ substantially from reported value.

Solubility Data for Form B of the HCl salt of Compound B1

| Solvent System | Temperature (° C.) | Approximate Solubility (mg/mL) |
|---|---|---|
| acetone | Ambient | <1 |
| acetonitrile | Ambient | <1 |
| 2-butanone (MEK) | Ambient | <1 |
| dichloromethane | Ambient | <1 |
| p-dioxane | Ambient | <1 |
| ethanol | Ambient | <1 |
| ethyl acetate | Ambient | <1 |
| isopropanol | Ambient | <1 |
| methanol | Ambient | 1 |
| nitromethane | Ambient | <1 |
| tetrahydrofuran | Ambient | <1 |
| 2,2,2-trifluoroethanol | Ambient | 52 |
| trifluorotoluene | Ambient | <1 |
| water | Ambient | 1 |
| acetone:water 50:50 | Ambient | 13 |
| acetonitrile:water 50:50 | Ambient | 51 |
| p-dioxane:water 50:50 | Ambient | 6 |
| ethanol:water 50:50 | Ambient | 13 |
| isopropanol:water 20:80 | Ambient | 5 |
| tetrahydrofuran:water 50:50 | Ambient | 24 |
| acetone | 54 | <1 |
| acetonitrile | 60 | <1 |
| 2-butanone (MEK) | 62 | <1 |
| p-dioxane | 63 | <1 |
| ethanol | 60 | <2 |
| isopropanol | 63 | <1 |
| methanol | 62 | 2 |
| nitromethane | 64 | <1 |
| tetrahydrofuran | 64 | <1 |
| 2,2,2-trifluoroethanol | 67 | 53 |
| water | 68 | <3 |
| dioxane:water 50:50 | 62 | 23 |
| isopropanol:water 20:80 | 62 | 54 |

6.6.2.8 Characterization Data of Solid Forms Comprising the HCl Salt of Compound B1

| Solid Form | Analytical Technique | Results |
|---|---|---|
| A | XRPD | See FIG. 8. |
| A | DSC | Endotherm at ~77, ~143, ~190, ~242 and ~272° C. |
| A | TGA | ~5.2% weight loss up to ~95° C. |
| A | TGIR-TGA | ~6.1% weight loss up to ~90° C., volatilization of THF<br>~6.2% weight loss from ~90 to ~200° C., loss of HCl<br>~9.0% weight loss from ~200 to ~250° C., loss of HCl + decomposition |

| Solid Form | Analytical Technique | Results |
|---|---|---|
| A | TGIR-IR | Volatilization of THF (~100° C.), loss of HCl and decomposition (>~200° C.) |
| A | NMR | Consistent with the structure of Compound B1 HCl, solvent THF (~1.76 and ~3.60 ppm) |
| A | Moisture Balance | ~3.9% weight loss upon equilibrium at 5% RH. ~16.7% weight gain from 5 to 95% RH, corresponding to 6.5 moles of water. ~16.6% weight loss from 95 to 5% RH. |
| A | Post-Moisture Balance XRPD | Form D |
| B | XRPD | See FIG. 13 |
| B | DSC | Endotherms with signal maxima at ~58, ~178 and ~284° C. (onset temperature at ~260° C.) |
| B | TGA | ~1.0% weight loss up to ~200° C. ~41.8% weight loss from ~200 to ~347° C. |
| B | Moisture Balance | ~3.6% weight gain, corresponding to ~1.2 moles of water from ~5 to ~95% RH, ~3.2% weight loss from ~95 to ~5% RH |
| B | Post-Moisture Balance XRPD | Form B |
| B | NMR | Intact structure of Compound B1 HCl, peak shift, residual methanol (~3.17 ppm) |
| B (lot 2) | XRPD | See FIG. 13 |
| B (lot 2) | DSC | Endotherms with signal maxima at ~56, 285° C. (onset temperature at ~259° C.) |
| B (lot 2) | TGIR-TGA | ~1.0% weight loss up to ~200° C., volatilization of water ~32.4% weight loss from ~200 to ~300° C., loss of HCl and decomposition |
| B (lot 2) | TGIR-IR | Volatilization of water (~80° C.) loss of HCl and decomposition (>~200° C.) |
| B (lot 3) | XRPD | See FIG. 13 |
| B (lot 3) | DSC | Endotherm with signal maxima at ~64, ~288° C. (onset temperature at ~260° C.) |
| D | XRPD | See FIG. 23 |
| D | DSC | Endotherms at ~62, ~228, ~268° C. |
| D | TGA | ~4.1% weight loss up to ~100° C. |
| E | XRPD | See FIG. 26 |
| E | DSC | Endotherms at ~82, ~240 and ~269° C. |
| E | TGA | Weight loss in four steps up to ~300° C., ~2.6% weight loss up to ~85° C. |
| F | XRPD | See FIG. 29 |
| F | DSC | Endotherms at ~85, ~237 and ~272° C. |
| F | TGA | Weight loss in four steps, 4.6% weight loss up to ~110° C. |
| G | XRPD | See FIG. 32 |
| G | DSC | Endotherms at ~67, ~115, ~241 and ~267° C. |
| G | TGA | ~13.7% weight loss up to ~85° C. |
| H | XRPD | See FIG. 35 |
| H | DSC | Endotherms at ~86, ~178, ~248 and ~273° C. |
| H | TGA | ~2.7% weight loss up to ~150° C., ~5.3% weight loss from ~150 to ~200° C. |
| Amorphous | XRPD | See FIG. 45 |
| Amorphous | MDSC | No observed Tg |

6.6.3 Solid Forms of the HBr Salt of Compound B1

Form A of the HBr salt of Compound B1 was formed by a slurrying a 2.5:1 hydrobromic acid:Compound B1 mixture in a solvent system of methanol/water, in which the water was a minor component. The reaction was slurried at about 60° C. for about 30 minutes, and Form A of the HBr salt was isolated. The Form A HBr material was a white solid, appearing by optical microscopy to be fibers with birefringence and extinguishment. $^1$H NMR indicated that the parent Compound B1 structure was intact. The material was crystalline as observed by XRPD. The isolated white solid did not deliquesce upon storage at 75% RH for 4 days. XRPD and $^1$H NMR data for Form A of the HBr salt of Compound B1 are provided as FIG. 47 and FIG. 48.

6.6.4 Solid Forms of the Sulfate Salt of Compound B1

Form A of the sulfate salt of Compound B1 was formed by crash precipitation of a 1:1 sulfuric acid:Compound B1 mixture in a solvent system of water/acetonitrile/dioxane. The isolated Form A sulfate material appeared to be a pink solid comprising chunks. The material was crystalline as observed by XRPD. XRPD data for Form A of the sulfate salt of Compound B1 is provided in FIG. 49.

Form B of the sulfate salt of Compound B1 was formed by slurrying a 1.5:1 sulfuric acid:Compound B1 mixture in water. The reaction was slurried at about 60° C. for about 30 minutes, and Form B of the sulfate salt was isolated. The isolated Form B sulfate material appeared to be an off-white solid comprising irregular particles with some birefringence. The material was crystalline as observed by XRPD. XRPD data for Form B of the sulfate salt of Compound B1 is provided in FIG. 49.

Form C of the sulfate salt of Compound B1 was formed by slurrying a 1:1 sulfuric acid:Compound B1 mixture in a solvent system comprising methanol, acetonitrile, acetone and water, in which water was a minor component. The reaction was slurried for about 17 days, and Form C of the sulfate salt was isolated. The isolated Form C sulfate material appeared to be a pink solid comprising chunks with some birefringence. The material was crystalline as observed by XRPD. $^1$H NMR indicated that the parent Compound B1 structure was intact. The isolated solid did not deliquesce upon storage at 75% RH for 7 days. XRPD and $^1$H NMR data for Form C of the sulfate salt of Compound B1 are provided in FIG. 49 and FIG. 50.

6.6.5 Solid Forms of the Mesylate Salt of Compound B1

Form A of the mesylate salt of Compound B1 was formed by crash cooling a 1.2:1 methanesulfonic acid:Compound B1 mixture in methanol. The isolated Form A mesylate material appeared to be an off-white solid comprising irregular particles with some birefringence and extinguishment, and chunks. The material was crystalline as observed by XRPD. $^1$H NMR indicated that the parent Compound B1 structure was intact, and integration of a peak at approximately 2.34 ppm, assigned to methanesulfonic acid, indicated about 1 molar equivalent of acid per mole of Compound B1. The isolated solid did not deliquesce upon storage at 75% RH for 5 days. XRPD and $^1$H NMR data for Form A of the mesylate salt of Compound B1 are provided in FIG. 51 and FIG. 52.

Form B of the mesylate salt of Compound B1 was formed by crash cooling a 2.2:1 methanesulfonic acid:Compound B1 mixture in methanol. The isolated Form B mesylate material appeared to be a white solid comprising small particles with some birefringence and extinguishment. The material was crystalline as observed by XRPD. $^1$H NMR indicated that the parent Compound B1 structure was intact, and integration of a peak at approximately 2.34 ppm, assigned to methanesulfonic acid, indicated about 1.5 molar equivalents of acid per mole of Compound B1. The isolated solid did not deliquesce upon storage at 75% RH for 4 days. XRPD and $^1$H NMR data for Form B of the mesylate salt of Compound B1 are provided in FIG. 51 and FIG. 53.

6.6.6 Solid Forms of the Esylate Salt of Compound B1

Form A of the esylate salt of Compound B1 was formed by crash precipitating a 1:1 ethanesulfonic acid:Compound B1 mixture in a solvent system of methanol/ether. The isolated Form A mesylate material appeared to be a white solid comprising chunks. The material was crystalline as observed by XRPD. XRPD data for Form A of the esylate salt of Compound B1 is provided in FIG. 54.

Form B of the esylate salt of Compound B1 was formed by fast evaporation of a 1:1 ethanesulfonic acid:Compound B1 mixture in a methanol/ether solvent system. The isolated Form B esylate material appeared to be a light yellow solid comprising fibers with birefringence and extinguishment. The material was crystalline as observed by XRPD. $^1$H NMR indicated that the parent Compound B1 structure was intact, and integration of peaks at about 1.07 and about 2.41 ppm, assigned to ethanesulfonic acid, indicated about 1 molar equivalent of acid per mole of Compound B1. The isolated solid did not deliquesce upon storage at 75% RH for 7 days. XRPD and $^1$H NMR data for Form B of the esylate salt of Compound B1 are provided in FIG. 54 and FIG. 55.

Form C of the esylate salt of Compound B1 was formed by crash cooling a 2.5:1 ethanesulfonic acid:Compound B1 mixture in a methanol solvent system. The isolated Form C esylate material appeared to be a white solid comprising fibers and small particles with some birefringence and extinguishment. The material was crystalline as observed by XRPD. XRPD data for Form C of the esylate salt of Compound B1 is provided in FIG. 54.

6.6.7 Solid Forms of the Edisylate Salt of Compound B1

Form A of the edisylate salt of Compound B1 was formed by crash cooling a 1.5:1 ethanedisulfonic acid:Compound B1 mixture in a methanol/ether solvent system. The isolated Form A edisylate material appeared to be an off-white solid comprising chunks and irregular particles with some birefringence. The material was crystalline as observed by XRPD. $^1$H NMR indicated that the parent Compound B1 structure was intact, and integration of a peak at about 2.69 ppm, assigned to ethanedisulfonic acid, indicated about 1 molar equivalent of acid per mole of Compound B1. The isolated solid did not deliquesce upon storage at 75% RH for 7 days. XRPD and $^1$H NMR data for Form A of the edisylate salt of Compound B1 are provided in FIG. 56 and FIG. 57.

6.6.8 Solid Forms of the Besylate Salt of Compound B1

Form A of the besylate salt of Compound B1 was formed by crash cooling a 1:1 benzenesulfonic acid:Compound B1 mixture in methanol. The isolated Form A besylate material appeared to be a white solid comprising irregular particles with some birefringence and extinguishment. The material was crystalline as observed by XRPD. $^1$H NMR indicated that the parent Compound B1 structure was intact, and integration of peaks at about 7.3 and about 7.6 ppm, assigned to benzenesulfonic acid, indicated about 1 molar equivalent of acid per mole of Compound B1. The isolated solid did not deliquesce upon storage at 75% RH for 3 days. XRPD and $^1$H NMR data for Form A of the besylate salt of Compound B1 are provided in FIG. 58 and FIG. 59

Form B of the besylate salt of Compound B1 was formed by crash cooling a 2.5:1 benzenesulfonic acid:Compound B1 mixture in methanol. The isolated Form B besylate material appeared to be a white solid comprising irregular particles with some birefringence and extinguishment. The material was crystalline as observed by XRPD. $^1$H NMR indicated that the parent Compound B1 structure was intact, and integration of peaks at about 7.3 and 7.6 ppm, assigned to benzenesulfonic acid, indicated about 1.6 molar equivalent of acid per mole of Compound B1. The isolated solid did not deliquesce upon storage at 75% RH for 7 days. XRPD and $^1$H NMR data for Form B of the besylate salt of Compound B1 are provided in FIG. 58 and FIG. 60.

6.6.9 Solid Forms of the Tosylate Salt of Compound B1

Form A of the tosylate salt of Compound B1 was formed by crash cooling a 1:1 toluenesulfonic acid:Compound B1 mixture in methanol. The isolated Form A tosylate material appeared to be a white solid comprising chunks. The material was crystalline as observed by XRPD. XRPD data for Form A of the tosylate salt of Compound B1 are provided in FIG. 61.

Form B of the tosylate salt of Compound B1 was formed by crash cooling a 1.5:1 toluenesulfonic acid:Compound B1 mixture in methanol. The isolated Form B tosylate material appeared to be a white solid comprising irregular particles and chunks. The material was crystalline as observed by XRPD. $^1$H NMR indicated that the parent Compound B1 structure was intact, and integration of peaks at about 2.29, 7.11 and 7.48 ppm, assigned to toluenesulfonic acid, indicated about 1 molar equivalent of acid per mole of Compound B1. The isolated solid did not deliquesce upon storage at 75% RH for 5 days. XRPD and $^1$H NMR of Form B of the tosylate salt of Compound B1 are provided as in FIG. 61 and FIG. 62.

Form C of the tosylate salt of Compound B1 was formed by crash cooling a 2.5:1 toluenesulfonic acid:Compound B1 mixture in methanol. The isolated Form C tosylate material appeared to be a white solid comprising irregular particles and chunks. The material was crystalline as observed by XRPD. XRPD data for Form C of the tosylate salt of Compound B1 are provided in FIG. 61.

6.6.10 Solid Forms of the Napsylate Salt of Compound B1

Form A of the napsylate salt of Compound B1 was formed by crash cooling a 1.5:1 napthalene-2-sulfonic acid:Compound B1 mixture in methanol. The isolated Form A napsylate material appeared to be a white solid comprising chunks. The material was crystalline as observed by XRPD. $^1$H NMR indicated that the parent Compound B1 structure was intact, and integration of a peak at about 8.14 ppm, assigned to naphthalene-2-sulfonic acid, indicated about 1 molar equivalent of acid per mole of Compound B1. The isolated solid did not deliquesce upon storage at 75% RH for 7 days. XRPD and $^1$H NMR of Form A of the napsylate salt of Compound B1 are provided in FIG. 63 and FIG. 64.

Form B of the napsylate salt of Compound B1 was formed by crash cooling a 2.5:1 napthalene-2-sulfonic acid:Compound B1 mixture in methanol. The isolated Form B napsylate material appeared to be an off-white solid comprising granular particles. The material was crystalline as observed by XRPD. $^1$H NMR indicated that the parent Compound B1 structure was intact, and integration of a peak at about 8.14 ppm, assigned to naphthalene-2-sulfonic acid, indicated about 2 molar equivalent of acid per mole of Compound B1. The isolated solid did not deliquesce upon storage at 75% RH for 7 days. XRPD and $^1$H NMR of Form B of the napsylate salt of Compound B1 are provided in FIG. 63 and FIG. 65.

Applicants incorporate by reference herein the entire contents of each of the documents cited herein.

What is claimed is:

1. A solid form comprising a salt of the compound of formula (I):

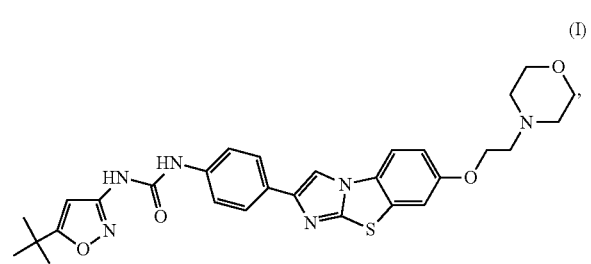 [SMILES: CC(C)(C)c1cc(NC(=O)Nc2ccc(-c3cn4c(n3)sc3cc(OCCN5CCOCC5)ccc34)cc2)no1]

wherein the salt is selected from the group consisting of: hydrobromide, besylate, esylate, edisylate, mesylate, napsylate, sulfate and tosylate salts.

2. The solid form of claim 1 which further comprises a solvent.

3. The solid form of claim 1 which further comprises water.

4. A solid form comprising a bis-HCl salt of the compound of formula (I):

5. The solid form of claim 4 which is substantially free of solvent.

6. The solid form of claim 4 which is substantially free of water.

7. The solid form of claim 4 which is anhydrous.

8. The solid form of claim 4 which is the Form B crystal form of the bis-HCl salt of the compound of formula (I).

9. The solid form of claim 4 having an XRPD pattern comprising peaks at approximately 6.98, 10.7, 20.82 and 27.6 ° 2θ when analyzed using copper Kα radiation.

10. The solid form of claim 9 having an XRPD pattern further comprising peaks at approximately 15.78, 18.48, 22.62 and 27.08 ° 2θ when analyzed using copper Kα radiation.

11. The solid form of claim 10 having an XRPD pattern further comprising peaks at approximately 13.04, 18.8, 24.38 and 26.16 ° 2θ when analyzed using copper Kα radiation.

12. The solid form of claim 4 having an XRPD pattern which matches the XRPD patterns presented in FIG. 13a.

13. The solid form of claim 4 having an XRPD pattern which matches the XRPD pattern presented in FIG. 13b.

14. The solid form of claim 4 having a DSC thermogram comprising an endothermic event with an onset temperature of approximately 260° C.

15. The solid form of claim 4 having unit cell parameters consistent with the following approximate unit cell parameters: a=15.6089 Å, b=11.9443 Å, c=16.9448 Å, β=101.249°, V=3098.5 Å$^3$ and Z=4.

16. The solid form of claim 4 which is physically stable at about 75% RH at about ambient temperature.

17. The solid form of any of claim 5, 6, 7 or 8 which is substantially pure.

18. The solid form of claim 5, 6, 7 or 8 which is substantially free of chemical impurities.

19. The solid form of claim 5, 6, 7 or 8 which is substantially free of physical impurities.

20. A pharmaceutical composition comprising the solid form of any of claim 5, 6, 7 or 8.

21. An amorphous form comprising the compound of the following formula, or a pharmaceutically acceptable salt thereof:

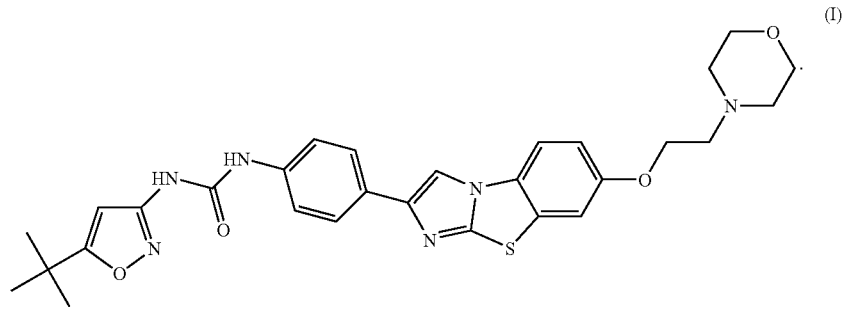 [SMILES: CC(C)(C)c1cc(NC(=O)Nc2ccc(-c3cn4c(n3)sc3cc(OCCN5CCOCC5)ccc34)cc2)no1]

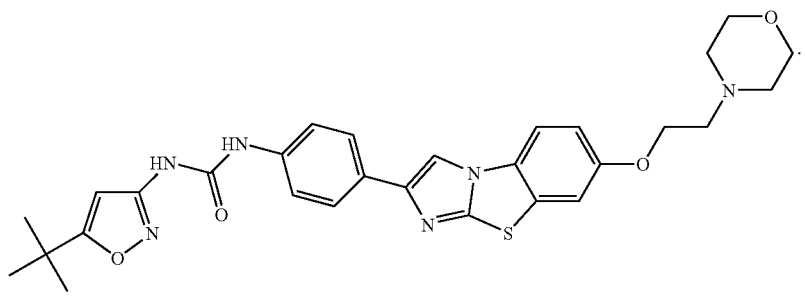 [SMILES: CC(C)(C)c1cc(NC(=O)Nc2ccc(-c3cn4c(n3)sc3cc(OCCN5CCOCC5)ccc34)cc2)no1]

22. A crystal form comprising the compound of the following formula:

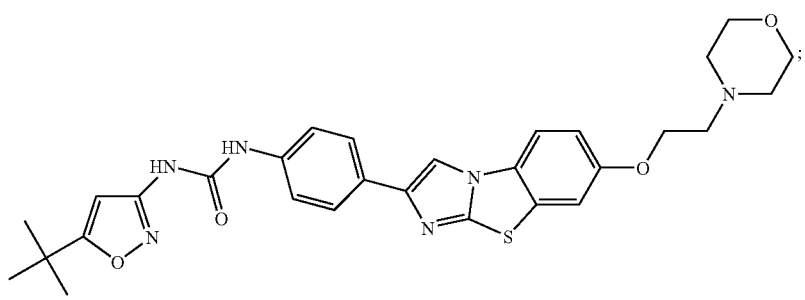 [SMILES: CC(C)(C)c1cc(NC(=O)Nc2ccc(-c3cn4c(n3)sc3cc(OCCN5CCOCC5)ccc34)cc2)no1]

which is selected from the group consisting of:
a. Form A of the HCl salt;
b. Form B of the HCl salt;
c. Form C of the HCl salt,
d. Form D of the HCl salt;
e. Form E of the HCl salt;
f. Form F of the HCl salt;
g. Form G of the HCl salt;
h. Form H of the HCl salt;
i. Form I of the HCl salt;
j. Form J of the HCl salt;
k. Form K of the HCl salt;
l. Form L of the HCl salt;
m. Form N of the HCl salt;
n. Form O of the HCl salt;
o. Form A of the HBr salt;
P. Form A of the sulfate salt;
q. Form B of the sulfate salt;
r. Form C of the sulfate salt;
s. Form A of the mesylate salt;
t. Form B of the mesylate salt;
u. Form A of the esylate salt;
v. Form B of the esylate salt;
w. Form C of the esylate salt;
x. Form A of the edisylate salt;
y. Form A of the besylate salt;
z. Form B of the besylate salt;
aa. Form A of the tosylate salt;
bb. Form B of the tosylate salt;
cc. Form C of the tosylate salt;
dd. Form A of the napsylate salt; and
ee. Form B of the napsylate salt.

23. A pharmaceutical composition comprising the crystal form of claim 22.

* * * * *